United States Patent [19]
Budhu et al.

[11] Patent Number: 6,166,037
[45] Date of Patent: Dec. 26, 2000

[54] PYRROLIDINE AND PIPERIDINE MODULATORS OF CHEMOKINE RECEPTOR ACTIVITY

[75] Inventors: Richard J. Budhu, Monmouth Junction, N.J.; Edward Holson, New York, N.Y.; Jeffrey J. Hale, Westfield, N.J.; Christopher Lynch, Scotch Plains, N.J.; Malcolm Maccoss, Freehold, N.J.; Scott C. Berk, Maplewood, N.J.; Sander G. Mills, Scotch Plains, N.J.; Christopher A. Willoughby, Clark, N.J.

[73] Assignee: Merck & Co., Inc., Rahway, N.J.

[21] Appl. No.: 09/141,227

[22] Filed: Aug. 27, 1998

Related U.S. Application Data

[60] Provisional application No. 60/057,743, Aug. 28, 1997.
[51] Int. Cl.$^7$ ........................ A61K 31/445; C07D 401/06
[52] U.S. Cl. .......................... 514/326; 514/212; 514/213; 514/255; 514/278; 514/307; 514/316; 540/595; 540/602; 544/372; 546/18; 546/148; 546/186; 546/187; 546/191; 546/208
[58] Field of Search ..................... 540/595, 602; 544/372; 546/18, 148, 186, 187, 191, 208; 514/212, 213, 255, 278, 307, 316, 326

[56] References Cited

U.S. PATENT DOCUMENTS 5,635,510 6/1997 Burkholder et al. ..................... 514/278
5,686,424 11/1997 Connell et al. ........................... 514/19

FOREIGN PATENT DOCUMENTS 639568 2/1995 European Pat. Off. .
WO 98/25604 6/1998 WIPO .
WO 98/25605 6/1998 WIPO .
WO 98/25617 6/1998 WIPO .

OTHER PUBLICATIONS

Setoi et al. "1-Arylsulfonyl2-carboxypiperidino or carboxyphenyl amino . . . " CA 113:40445, 1990.

Weiss et al. "Effects of amino acid amides and aminothiols on . . . " CA 114:94966, 1990.

Caldwell, et al., USSN 09/241,486 (filed Feb. 1, 1999).

*Primary Examiner*—Ceila Chang
*Attorney, Agent, or Firm*—J. Eric Thies; David L. Rose

[57] ABSTRACT

The present invention is directed to pyrrolidine and piperidine compounds of the formula I:

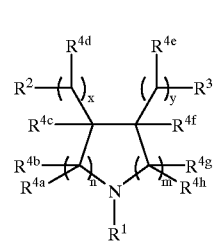

(wherein $R^1$, $R^2$, $R^3$, $R^{4a}$, $R^{4b}$, $R^{4c}$, $R^{4d}$, $R^{4e}$, $R^{4f}$, $R^{4g}$, $R^{4h}$, m, n, x and y are defined herein) which are useful as modulators of chemokine receptor activity. In particular, these compounds are useful as modulators of the chemokine receptors CCR-1, CCR-2, CCR-2A, CCR-2B, CCR-3, CCR-4, CCR-5, CXCR-3, and/or CXCR-4.

25 Claims, No Drawings

PYRROLIDINE AND PIPERIDINE MODULATORS OF CHEMOKINE RECEPTOR ACTIVITY

This application is a Provisional of application No. 60/057,743 Aug. 28, 1997.

BACKGROUND OF THE INVENTION

Chemokines are chemotactic cytokines that are released by a wide variety of cells to attract macrophages, T cells, eosinophils, basophils and neutrophils to sites of inflammation (reviewed in Schall, *Cytokine*, 3, 165–183 (1991) and Murphy, *Rev. Immun.*, 12, 593–633 (1994)). There are two classes of chemokines, C-X-C ($\alpha$) and C-C ($\beta$), depending on whether the first two cysteines are separated by a single amino acid (C-X-C) or are adjacent (C-C). The $\alpha$-chemokines, such as interleukin-8 (IL-8), neutrophil-activating protein-2 (NAP-2) and melanoma growth stimulatory activity protein (MGSA) are chemotactic primarily for neutrophils, whereas $\beta$-chemokines, such as RANTES, MIP-1$\alpha$, MIP-1$\beta$, monocyte chemotactic protein-1 (MCP-1), MCP-2, MCP-3 and eotaxin are chemotactic for macrophages, T-cells, eosinophils and basophils (Deng, et al., *Nature* 381, 661–666 (1996)).

The chemokines bind specific cell-surface receptors belonging to the family of G-protein-coupled seven-transmembrane-domain proteins (reviewed in Horuk, *Trends Pharm. Sci.*, 15, 159–165 (1994)) which are termed "chemokine receptors." On binding their cognate ligands, chemokine receptors transduce an intracellular signal though the associated trimeric G protein, resulting in a rapid increase in intracellular calcium concentration. There are at least seven human chemokine receptors that bind or respond to $\beta$-chemokines with the following characteristic pattern: CCR-1 (or "CKR-1" or "CC-CKR-1") [MIP-1$\alpha$, MIP-1$\beta$, MCP-3, RANTES] (Ben-Barruch, et al.,*J. Biol. Chem.*, 270, 22123–22128 (1995); Beote, et al, *Cell*, 72, 415–425 (1993)); CCR-2A and CCR-2B (or "CKR-2A"/"CKR-2A" or "CC-CKR-2A"/"CC-CKR-2A") [MCP-1, MCP-3, MCP-4]; CCR-3 (or "CKR-3" or "CC-CKR-3") [eotaxin, RANTES, MCP-3] (Combadiere, et al.,*J. Biol. Chem.*, 270, 16491–16494 (1995); CCR-4 (or "CKR-4" or "CC-CKR-4") [MIP-1$\alpha$, RANTES, MCP-1] (Power, et al., *J. Biol. Chem.*, 270, 19495–19500 (1995)); CCR-5 (or "CKR-5" or "CC-CKR-5") [MIP-1$\alpha$, RANTES, MIP-1$\beta$] (Sanson, et al., *Biochemistry*, 35, 3362–3367 (1996)); and the Duffy blood-group antigen [RANTES, MCP-1] (Chaudhun, et al.,*J. Biol. Chem.*, 269, 7835–7838 (1994)). The $\beta$-chemokines include eotaxin, MIP ("macrophage inflammatory protein"), MCP ("monocyte chemoattractant protein") and RANTES ("regulation-upon-activation, normal T expressed and secreted").

Chemokine receptors, such as CCR-1, CCR-2, CCR-2A, CCR-2B, CCR-3, CCR-4, CCR-5, CXCR-3, CXCR-4, have been implicated as being important mediators of inflammatory and immunoregulatory disorders and diseases, including asthma and allergic diseases, as well as autoimmune pathologies such as rheumatoid arthritis and atherosclerosis. Accordingly, agents which modulate chemokine receptors would be useful in such disorders and diseases.

A retrovirus designated human immunodeficiency virus (HIV-1) is the etiological agent of the complex disease that includes progressive destruction of the immune system (acquired immune deficiency syndrome; AIDS) and degeneration of the central and peripheral nervous system. This virus was previously known as LAV, HTLV-III, or ARV.

Certain compounds have been demonstrated to inhibit the replication of HIV, including soluble CD4 protein and synthetic derivatives (Smith, et al., *Science*, 238, 1704–1707 (1987)), dextran sulfate, the dyes Direct Yellow 50, Evans Blue, and certain azo dyes (U.S. Pat. No. 5,468,469). Some of these antiviral agents have been shown to act by blocking the binding of gp120, the coat protein of HIV, to its target, the CD4 gyycoprotein of the cell.

Entry of HIV-1 into a target cell requires cell-surface CD4 and additional host cell cofactors. Fusin has been identified as a cofactor required for infection with virus adapted for growth in transformed T-cells, however, fusin does not promote entry of macrophagetropic viruses which are believed to be the key pathogenic strains of HIV in vivo. It has recently been recognized that for efficient entry into target cells, human immunodeficiency viruses require the chemokine receptors CCR-5 and CXCR-4, as well as the primary receptor CD4 (Levy, *N. Engl. J. Med.*, 335(20), 1528–1530 (Nov. 14, 1996). The principal cofactor for entry mediated by the envelope glycoproteins of primary macrophage-trophic strains of HIV-1 is CCR5, a receptor for the $\beta$-chemokines RANTES, MIP-1$\alpha$ and MIP-1$\beta$ (Deng, et al., *Nature*, 381, 661–666 (1996)). HIV attaches to the CD4 molecule on cells through a region of its envelope protein, gp120. It is believed that the CD-4 binding site on the gp120 of HIV interacts with the CD4 molecule on the cell surface, and undergoes conformational changes which allow it to bind to another cell-surface receptor, such as CCR5 and/or CXCR-4. This brings the viral envelope closer to the cell surface and allows interaction between gp41 on the viral envelope and a fusion domain on the cell surface, fusion with the cell membrane, and entry of the viral core into the cell. It has been shown that $\beta$-chemokine ligands prevent HIV-1 from fusing with the cell (Dragic, et al., *Nature*, 381, 667–673 (1996)). It has further been demonstrated that a complex of gp120 and soluble CD4 interacts specifically with CCR-5 and inhibits the binding of the natural CCR-5 ligands MIP-1$\alpha$ and MIP-1$\beta$ (Wu, et al., *Nature*, 384, 179–183 (1996); Trkola, et al., *Nature* 384, 184–187 (1996)).

Humans who are homozygous for mutant CCR-5 receptors which do not serve as co-receptors for HIV-1 in vitro appear to be unusually resistant to HIV-1 infection and are not immunocompromised by the presence of this genetic variant (*Nature*, 382, 722–725 (1996)). Absence of CCR-5 appears to confer protection from HIV-1 infection (*Nature*, 382, 668–669 (1996)). Other chemokine receptors may be used by some strains of HIV-1 or may be favored by non-sexual routes of transmission. Although most HIV-1 isolates studied to date utilize CCR-5 or fusin, some can use both as well as the related CCR-2B and CCR-3 as co-receptors (*Nature Medicine*, 2(11), 1240–1243 (1996)). Nevertheless, drugs targeting chemokine receptors may not be unduly compromised by the genetic diversity of HIV-1 (Zhang, et al., *Nature*, 383, 768 (1996)). Accordingly, an agent which could block chemokine receptors in humans who possess normal chemokine receptors should prevent infection in healthy individuals and slow or halt viral progression in infected patients. By focusing on the host's cellular immune response to HIV infection, better therapies towards all subtypes of HIV may be provided. These results indicate that inhibition of chemokine receptors presents a viable method for the prevention or treatment of infection by HIV and the prevention or treatment of AIDS.

The peptides eotaxin, RANTES, MIP-1$\alpha$, MIP-1$\beta$, MCP-1, and MCP-3 are known to bind to chemokine receptors. As noted above, the inhibitors of HIV-1 replication present in supernatants of CD8+ T cells have been characterized as the β-chemokines RANTES, MIP-1α and MIP-1β. PCT Patent Publication WO 97/10211 and EPO Patent Publication EP 0,673,928 disclose certain piperidines as tachykinin antagonists.

SUMMARY OF THE INVENTION

The present invention is directed to compounds which are modulators of chemokine receptor activity and are useful in the prevention or treatment of certain inflammatory and immunoregulatory disorders and diseases, including asthma and allergic diseases, as well as autoimmune pathologies such as rheumatoid arthritis and atherosclerosis. The invention is also directed to pharmaceutical compositions comprising these compounds and the use of these compounds and compositions in the prevention or treatment of such diseases in which chemokine receptors are involved.

The present invention is further concerned with compounds which inhibit the entry of human immunodeficiency virus (HIV) into target cells and are of value in the prevention of infection by HIV, the treatment of infection by HIV and the prevention and/or treatment of the resulting acquired immune deficiency syndrome (AIDS). The present invention also relates to pharmaceutical compositions containing the compounds and to a method of use of the present compounds and other agents for the prevention and treatment of AIDS and viral infection by HIV.

DETAILED DESCRIPTION OF THE INVENTION

The present invention is directed to compounds of formula I:

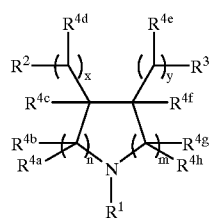

wherein:

$R^1$ is -X-$R^8$, wherein X is selected from the group consisting of:

(1) —$CH_2$—,
(2) —$CH_2CH_2$—,
(3) —$CH_2CH_2CH_2$—,
(4) —CH($C_{1-6}$ alkyl)-,
(5) —CO—,
(6) —$SO_2$—,
(7) —$CONH_2$—, and
(8) —CONH($C_{1-6}$ alkyl)-, and wherein $R^8$ is a selected from:
phenyl, naphthyl, biphenyl, fluorenyl, dihydronaphthyl, tetrahydronaphthyl, octahydronaphthyl, $C_{1-6}$ alkyl, $C_{5-8}$ cycloalkyl, cyclohexenyl, adamantyl, and heteroaryl, which may be unsubstituted or substituted, where the substituents are independently selected from:
(a) hydroxy,
(b) $C_{1-3}$alkyl,
(c) —O—$C_{1-3}$alkyl,
(d) halogen,
(e) trifluoromethyl,
(f) phenyl
(g) —$CO_2$($C_{1-6}$ alkyl), and
(h) —$CONH_2$;

$R^2$ is selected from the group consisting of:

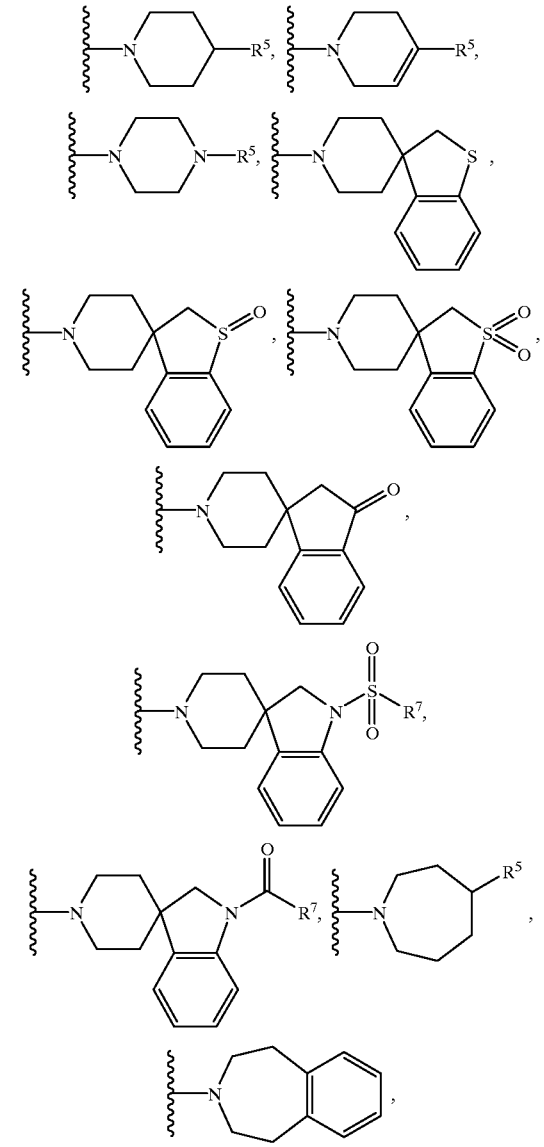

wherein $R^5$ is a selected from:
(1) —$NR^6CO$—O—$R^7$, wherein $R^6$ is hydrogen, $C_{1-6}$ alkyl or $C_{1-6}$ alkyl-$C_{5-6}$ cycloalkyl, and $R^7$ is $C_{1-6}$ alkyl, $C_{5-6}$ cycloalkyl, benzyl or phenyl, which is unsubsituted or substituted with halo, $C_{1-3}$alkyl, $C_{1-3}$alkoxy or trifluoromethyl,
(2) -phenyl, which is unsubstituted or substituted with halo, $C_{1-3}$alkyl, $C_{1-3}$alkoxy or trifluoromethyl,
(3) —$C_{1-6}$alkyl-phenyl, which is unsubstituted or substituted with halo, $C_{1-3}$alkyl, $C_{1-3}$alkoxy or trifluoromethyl,
(4) —O—$C_{1-6}$alkyl-phenyl, which is unsubstituted or substituted with halo, $C_{1-3}$alkyl, $C_{1-3}$alkoxy or trifluoromethyl, (5) —C$_{1-4}$alkyl-O—C$_{1-4}$alkyl-phenyl, which is unsubsituted or substituted with halo, C$_{1-3}$alkyl, C$_{1-3}$alkoxy or trifluoromethyl,
(6) -hydrogen,
(7) —C$_{1-6}$alkyl,
(8) —OH,
(9) —CO$_2$(C$_{1-6}$ alkyl), and
(10) —CO—NR$^6$—(C$_{0-3}$ alkyl)-R$^7$;

R$^3$ is selected from the group consisting of:
  phenyl, naphthyl, biphenyl, fluorenyl, dihydronaphthyl, tetrahydronaphthyl, octahydronaphthyl, C$_{1-6}$ alkyl, C$_{5-8}$ cycloalkyl, cyclohexenyl, adamantyl, and heteroaryl, which may be unsubstituted or substituted, where the substituents are independently selected from:
  (a) hydroxy,
  (b) C$_{1-3}$alkyl,
  (c) —O—C$_{1-3}$alkyl,
  (d) halogen,
  (e) trifluoromethyl,
  (f) phenyl
  (g) —CO$_2$(C$_{1-6}$ alkyl), and
  (h) —CONH$_2$;

R$^{4a}$, R$^{4b}$, R$^{4c}$, R$^{4d}$, R$^{4e}$, R$^{4f}$, R$^{4g}$, and R$^{4h}$ are independently selected from the group consisting of:
  (1) hydrogen, and
  (2) C$_{1-6}$ alkyl;

m is an integer selected from 0, 1 and 2, and n is an integer selected from 0, 1 and 2, wherein the sum of m+n is 1, 2, 3 or 4;

x is an integer selected from 0, 1, 2 and 3;
y is an integer selected from 0, 1 and 2;

and pharmaceutically acceptable salts thereof and individual diastereomers thereof.

Preferred compounds of the present invention include those of formula Ia:

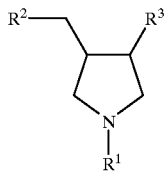

Ia wherein:

R$^1$, R$^2$ and R$^3$ are defined above;

and pharmaceutically acceptable salts and individual diastereomers thereof.

Preferred compounds of the present invention include those of formula Ib:

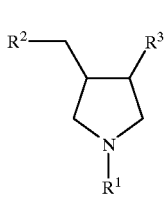

Ib wherein:
R$^1$ is -X-R$^8$, wherein X is selected from the group consisting of:

(1) —CH$_2$—,
(2) —CH$_2$CH$_2$—,
(3) —CH(C$_{1-6}$ alkyl)-,
(4) —CO—,
(5) —SO$_2$—,
(6) —CONH$_2$—, and
(7) —CONH(C$_{1-6}$ alkyl)-, and wherein R$^8$ is a selected from:
  phenyl, naphthyl, biphenyl, fluorenyl, dihydronaphthyl, tetrahydronaphthyl, octahydronaphthyl, C$_{1-6}$ alkyl, C$_{5-8}$ cycloalkyl, cyclohexenyl, adamantyl, and heteroaryl, which may be unsubstituted or substituted, where the substituents are independently selected from:
  (a) hydroxy,
  (b) C$_{1-3}$alkyl,
  (c) —O—C$_{1-3}$alkyl,
  (d) halogen,
  (e) trifluoromethyl,
  (f) phenyl
  (g) —CO$_2$(C$_{1-6}$ alkyl), and
  (h) —CONH$_2$;

R$^2$ is selected from the group consisting of:

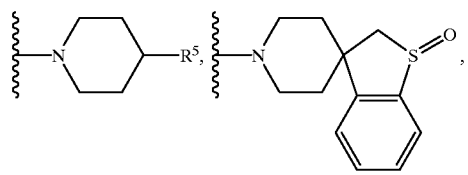

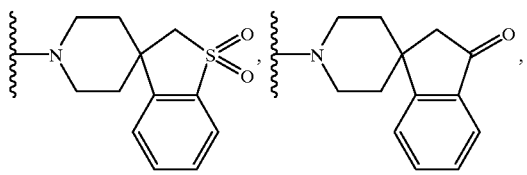

wherein R$^5$ is a selected from:
(1) —NR$^6$CO—O—R$^7$, wherein R$^6$ is hydrogen, C$_{1-6}$ alkyl or C$_{1-6}$ alkyl-C$_{5-6}$ cycloalkyl, and R$^7$ is C$_{1-6}$ alkyl, C$_{5-6}$ cycloalkyl, benzyl or phenyl, which is unsubsituted or substituted with halo, C$_{1-3}$alkyl, C$_{1-3}$alkoxy or trifluoromethyl,
(2) -phenyl, which is unsubstituted or substituted with halo, C$_{1-3}$alkyl, C$_{1-3}$alkoxy or trifluoromethyl,
(3) —C$_{1-6}$alkyl-phenyl, which is unsubstituted or substituted with halo, C$_{1-3}$alkyl, C$_{1-3}$alkoxy or trifluoromethyl,
(4) -hydrogen,
(5) —C$_{1-6}$alkyl,
(6) —OH,
(7) —CO$_2$(C$_{1-6}$ alkyl), and
(8) —CO—NR$^6$—(C$_{0-3}$ alkyl)-R$^7$;

R$^3$ is selected from the group consisting of:
  phenyl, naphthyl, biphenyl, fluorenyl, dihydronaphthyl, tetrahydronaphthyl, octahydronaphthyl, C$_{1-6}$ alkyl, C$_{5-8}$ cycloalkyl, cyclohexenyl, adamantyl, and heteroaryl, which may be unsubstituted or substituted, where the substituents are independently selected from:
  (a) hydroxy,
  (b) C$_{1-3}$alkyl,
  (c) —O—C$_{1-3}$alkyl,
  (d) halogen, (e) trifluoromethyl,
(f) phenyl
(g) —CO$_2$(C$_{1-6}$ alkyl), and
(h) —CONH$_2$;

and pharmaceutically acceptable salts thereof and individual diastereomers thereof.

More preferred compounds of the present invention include those of formula Ic:

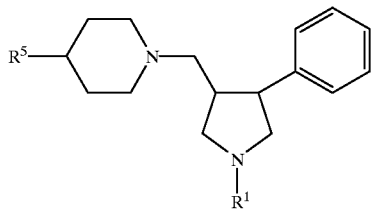

Ic wherein

R$^1$ is -X-R$^8$, wherein X is selected from the group consisting of:
(1) —CH$_2$—, and
(2) —CO—,
and wherein R$^8$ is a selected from cyclohexyl, cyclopentyl, naphthyl, unsubstituted phenyl or substituted phenyl, where the substituents on phenyl are independently selected from halogen and methyl;

R$^5$ is a selected from:
(1) -phenyl, which is unsubsituted or substituted with halo, C$_{1-3}$alkyl, C$_{1-3}$alkoxy or trifluoromethyl, and
(3) —C$_{1-6}$alkyl-phenyl, which is unsubsituted or substituted with halo, C$_{1-3}$alkyl, C$_{1-3}$alkoxy or trifluoromethyl.

Highly preferred compounds of the present invention include those of formula Id:

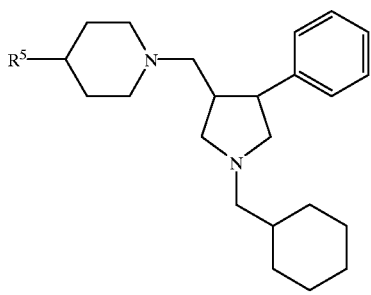

wherein R$^5$ is a selected from:
(1) -phenyl, which is unsubsituted or substituted with halo, C$_{1-3}$alkyl, C$_{1-3}$alkoxy or trifluoromethyl, and
(3) —C$_{3-4}$alkyl-phenyl, which is unsubsituted or substituted with halo, C$_{1-3}$alkyl, C$_{1-3}$alkoxy or trifluoromethyl.

In the present invention it is preferred that R$^1$ is -X-R$^8$, wherein X is selected from the group consisting of:
(1) —CH$_2$—,
(2) —CH$_2$CH$_2$—,
(3) —CH(C$_{1-6}$ alkyl)-,
(4) —CO—,
(5) —SO$_2$—,
(6) —CONH$_2$—, and
(7) —CONH(C$_{1-6}$ alkyl)-,
and wherein R$^8$ is a selected from:
phenyl, naphthyl, biphenyl, fluorenyl, dihydronaphthyl, tetrahydronaphthyl, octahydronaphthyl, C$_{1-6}$ alkyl, C$_{5-8}$ cycloalkyl, cyclohexenyl, adamantyl, and heteroaryl, which may be unsubstituted or substituted, where the substituents are independently selected from:
(a) hydroxy,
(b) C$_{1-3}$alkyl,
(c) —O—C$_{1-3}$alkyl,
(d) halogen,
(e) trifluoromethyl,
(f) phenyl
(g) —CO$_2$(C$_{1-6}$ alkyl), and
(h) —CONH$_2$.

In the present invention it is more preferred that R$^1$ is -X-R$^8$, wherein X is selected from the group consisting of:
(1) —CH$_2$—, and
(2) —CO—,
and wherein R$^8$ is a selected from:
phenyl, naphthyl, C$_{1-6}$ alkyl, cyclohexyl, cyclopentyl, pyridyl, quinolyl, thiophenyl, indolyl, benzoxazolyl and benzthiazolyl, which may be unsubstituted or substituted, where the substituents are independently selected from:
(a) chloro,
(b) fluoro,
(c) —O—CH$_3$,
(d) —CH$_3$,
(e) trifluoromethyl,
(f) —CO$_2$CH$_3$, and
(g) —CONH$_2$.

In the present invention it is highly preferred that R$^1$ is selected from the group consisting of:
(1) —CH$_2$-phenyl,
(2) —CO-phenyl,
(3) —CH$_2$-(2-chlorophenyl),
(4) —CO-(2-chlorophenyl),
(5) —CH$_2$-(2-naphthyl),
(6) —CO-(2-naphthyl),
(7) —CH$_2$-cyclopentyl,
(8) —CO-cyclopentyl,
(9) —CH$_2$-cyclohexyl, and
(10) —CO-cyclohexyl.

In the present invention it is most preferred that R$^1$ is selected from the group consisting of:
(1) —CH$_2$-cyclopentyl,
(2) —CO-cyclopentyl,
(3) —CH$_2$-cyclohexyl, and
(4) —CO-cyclohexyl.

In the present invention it is preferred that R$^2$ is selected from the group consisting of:

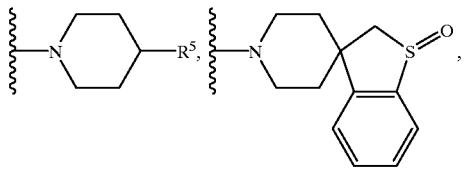

-continued

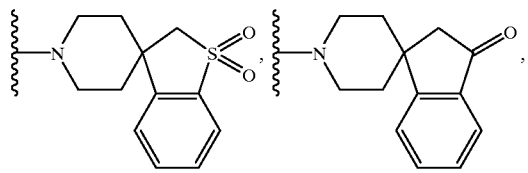

wherein R⁵ is a selected from:

(1) —NR⁶CO—O—R⁷, wherein R⁶ is hydrogen, $C_{1-6}$ alkyl or $C_{1-6}$ alkyl-$C_{5-6}$ cycloalkyl, and R⁷ is $C_{1-6}$ alkyl, $C_{5-6}$ cycloalkyl, benzyl or phenyl, which is unsubsituted or substituted with halo, $CF_3$, $C_{1-3}$alkyl, $C_{1-3}$alkoxy or trifluoromethyl, (2) -phenyl, which is unsubsituted or substituted with halo, $CF_3$, $C_{1-3}$alkyl, $C_{1-3}$alkoxy or trifluoromethyl, (3) —$C_{1-6}$alkyl, (4) —$C_{1-6}$alkyl-phenyl, which is unsubsituted or substituted with halo, $CF_3$, $C_{1-3}$alkyl, $C_{1-3}$alkoxy or trifluoromethyl, (5) —$CO_2$($C_{1-6}$ alkyl), and (6) —CO—NR⁶—($C_{0-3}$ alkyl)-R⁷.

In the present invention it is more preferred that R² is:

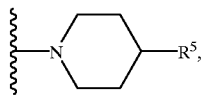

wherein R⁵ is selected from:

(1) —NR⁶CO—O—R⁷, wherein R⁶ is hydrogen, $C_{1-6}$ alkyl or $C_{1-6}$ alkyl-$C_{5-6}$ cycloalkyl, and R⁷ is $C_{1-6}$ alkyl, $C_{5-6}$ cycloalkyl, benzyl or phenyl, which is unsubsituted or substituted with halo, $CF_3$, $C_{1-3}$alkyl, $C_{1-3}$alkoxy or trifluoromethyl, (2) -phenyl, which is unsubsituted or substituted with halo, $CF_3$, $C_{1-3}$alkyl, $C_{1-3}$alkoxy or trifluoromethyl, (3) —$C_{1-6}$alkyl-phenyl, which is unsubsituted or substituted with halo, $CF_3$, $C_{1-3}$alkyl, $C_{1-3}$alkoxy or trifluoromethyl, and (4) —CO—NR⁶—($C_{0-3}$ alkyl)-R⁷.

In the present invention it is still more preferred that R² is:

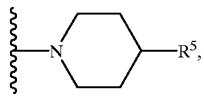

wherein R⁵ is selected from:

(1) -phenyl, which is unsubsituted or substituted with halo, $CF_3$, $C_{1-3}$alkyl, $C_{1-3}$alkoxy or trifluoromethyl, and (2) —$C_{1-6}$alkyl-phenyl, which is unsubsituted or substituted with halo, $CF_3$, $C_{1-3}$alkyl, $C_{1-3}$alkoxy or trifluoromethyl.

In the present invention it is even more preferred that R² is:

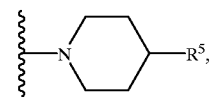

wherein R⁵ is a selected from:

(1) -phenyl, which is unsubsituted or substituted with halo, $C_{1-3}$alkyl, $C_{1-3}$alkoxy or trifluoromethyl, and (3) —$C_{3-4}$alkyl-phenyl, which is unsubsituted or substituted with halo, $C_{1-3}$alkyl, $C_{1-3}$alkoxy or trifluoromethyl.

In the present invention it is highly preferred that R² is:

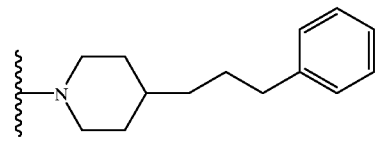

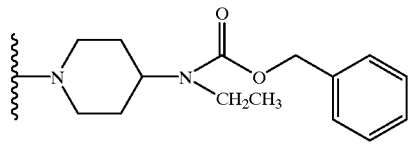

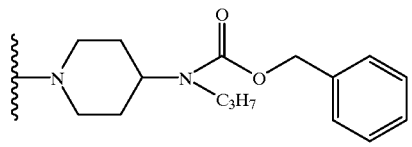

or

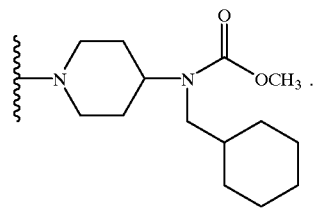

In the present invention it is preferred that R³ is selected from the group consisting of:

phenyl, naphthyl, biphenyl, fluorenyl, dihydronaphthyl, tetrahydronaphthyl, octahydronaphthyl, $C_{1-6}$ alkyl, $C_{5-8}$ cycloalkyl, cyclohexenyl, adamantyl, and thienyl, which may be unsubstituted or substituted, where the substituents are independently selected from:
(a) hydroxy,
(b) $C_{1-3}$alkyl,
(c) —O—$C_{1-3}$alkyl,
(d) halogen,
(e) trifluoromethyl,
(f) phenyl
(g) —$CO_2$($C_{1-6}$ alkyl), and
(h) —$CONH_2$.

In the present invention it is more preferred that R³ is phenyl or thienyl, which may be unsubstituted or substituted, where the substituents are independently selected from:
(a) chloro,
(b) fluoro,
(c) bromo,
(d) trifluoromethyl, and
(e) —O—$CH_3$.

In the present invention it is most preferred that $R^3$ is phenyl or thienyl.

In the present invention it is preferred that $R^{4a}$, $R^{4b}$, $R^{4c}$, $R^{4d}$, $R^{4e}$, $R^{4f}$, $R^{4g}$, and $R^{4h}$ are independently selected from the group consisting of:

(1) hydrogen, and (2) $C_{1-6}$ alkyl.

In the present invention it is more preferred that $R^{4a}$, $R^{4b}$, $R^{4c}$, $R^{4e}$, $R^{4f}$, $R^{4g}$, and $R^{4h}$ are each hydrogen and wherein $R^{4d}$ is selected from the group consisting of:

(1) hydrogen, and (2) $CH_3$.

In the present invention it is most preferred that $R^{4a}$, $R^{4b}$, $R^{4c}$, $R^{4e}$, $R^{4f}$, $R^{4g}$, and $R^{4h}$ are each hydrogen.

In the present invention it is most preferred that $R^{4d}$ is selected from the group consisting of:

(1) hydrogen, and (2) $CH_3$.

In the present invention it is preferred that m is 1 and n is 1.

In the present invention it is preferred that x is 1.

In the present invention it is preferred that y is 0.

The compounds of the instant invention have at least two asymmetric centers at the ring junction of the substitutents bearing $R^2$ and $R^3$. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The relative configurations of the most preferred compounds of this invention are of the trans orientation, i.e. as depicted:

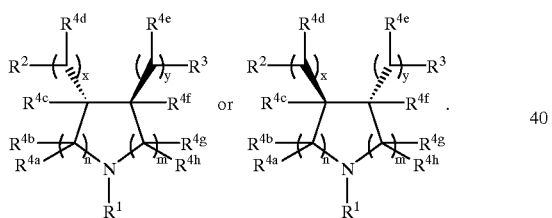

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

As appreciated by those of skill in the art, halo or halogen as used herein are intended to include chloro, fluoro, bromo and iodo. Similarly, $C_{1-6}$, as in $C_{1-6}$alkyl is defined to identify the group as having 1, 2, 3, 4, 5, or 6 carbons, such that $C_{1-6}$alkyl specifically includes methyl, ethyl, propyl, butyl, pentyl, hexyl, and cyclohexyl. The term "heteroaryl" as used herein is intended to include the following groups: benzimidazolyl, benzofuranyl, benzoxazolyl, furanyl, imidazolyl, indolyl, isooxazolyl, isothiazolyl, oxadiazolyl, oxazolyl, pyrazinyl, pyrazolyl, pyridyl, pyrimidyl, pyrrolyl, quinolyl, tetrazolyl, thiadiazolyl, thiazolyl, thienyl, and triazolyl.

Exemplifying the invention is the use of the compounds disclosed in the Examples and herein.

Specific compounds within the present invention include a compound which selected from the group consisting of:

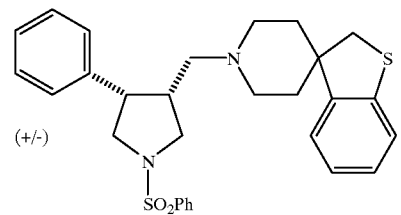

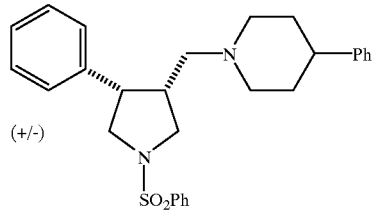

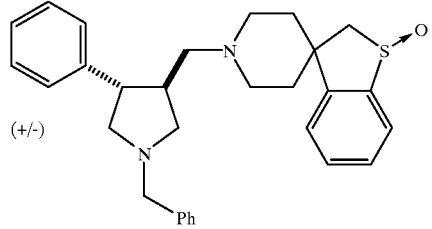

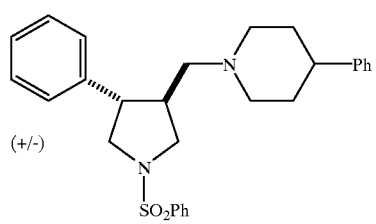

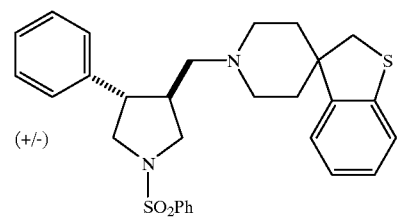

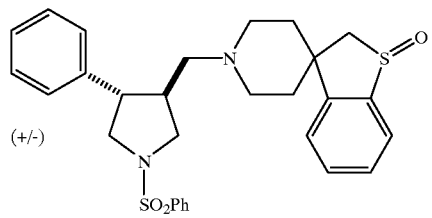

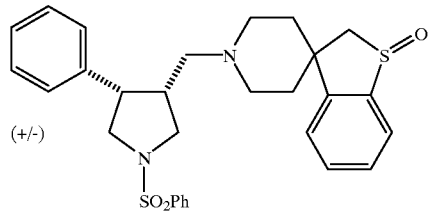

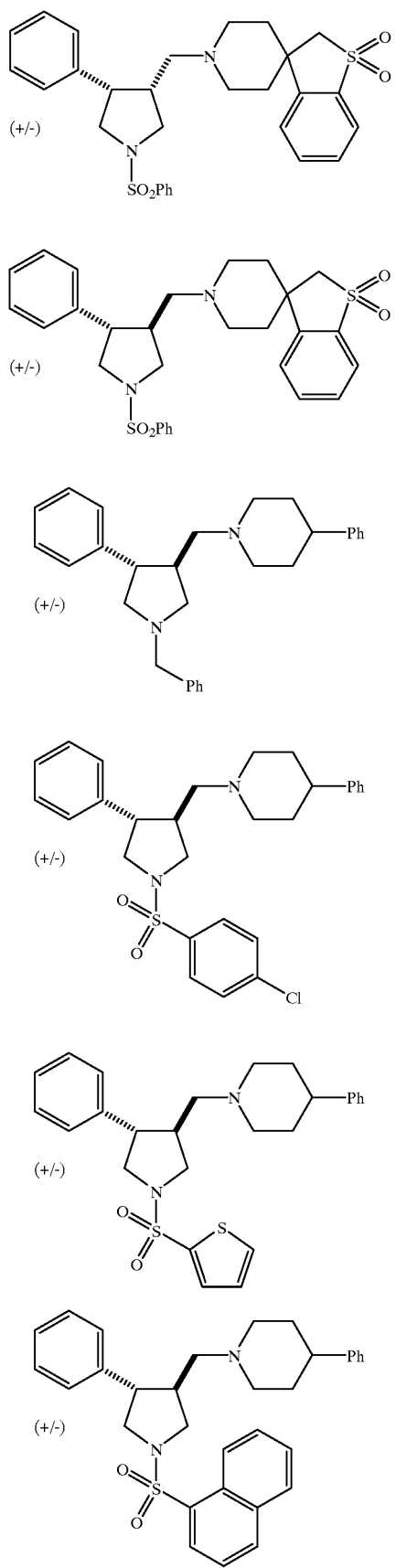
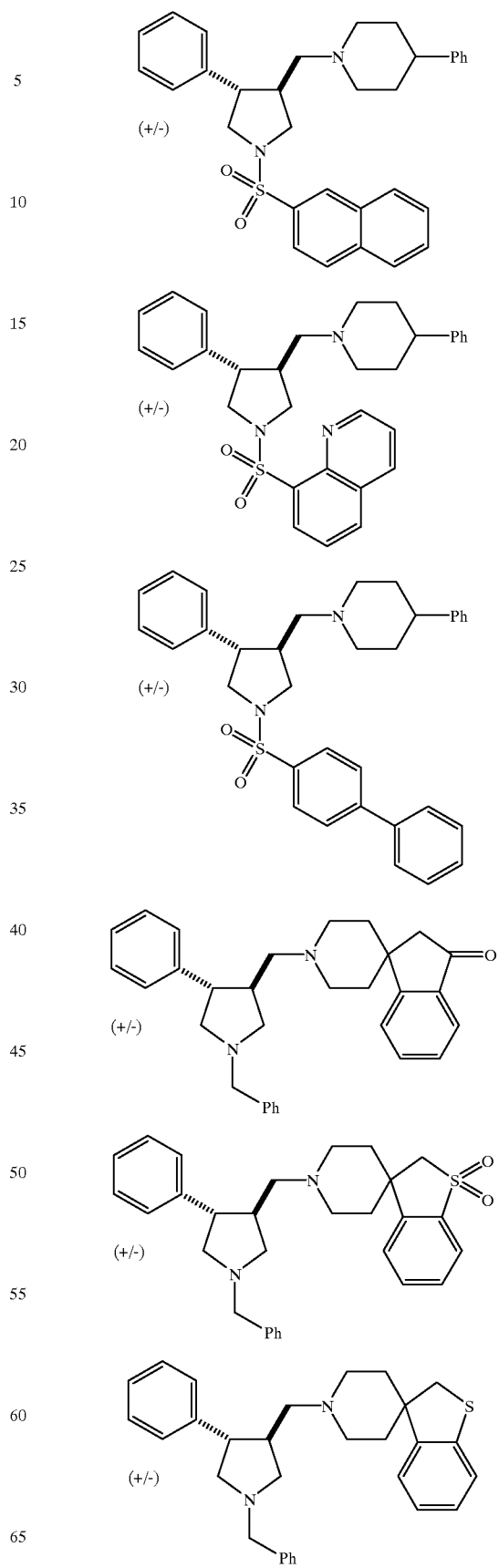

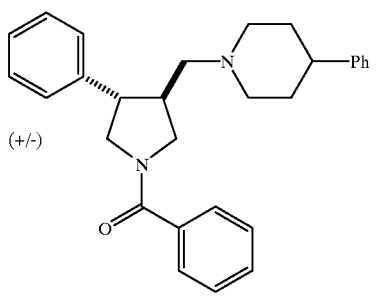
(+/-)
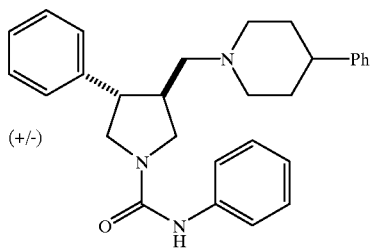
(+/-)
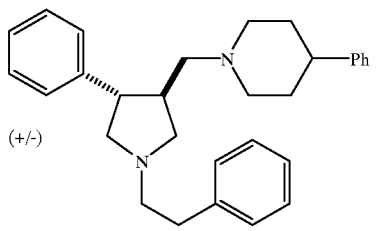
(+/-)
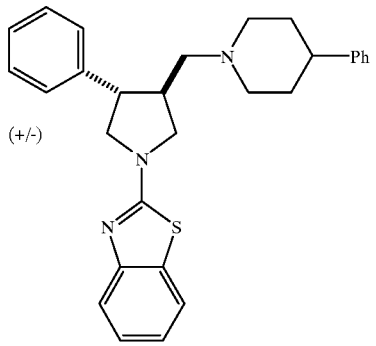
(+/-)
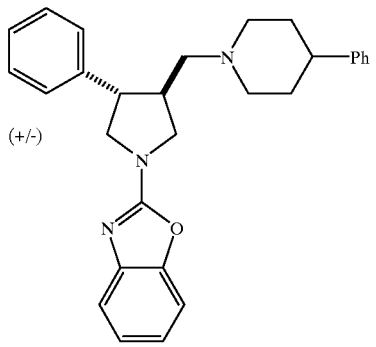
(+/-)
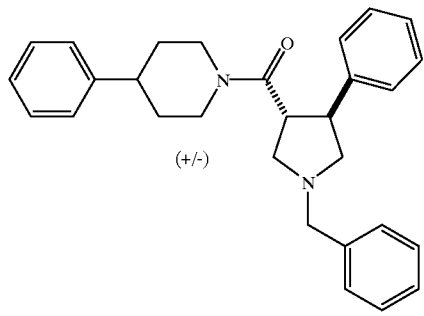
(+/-)
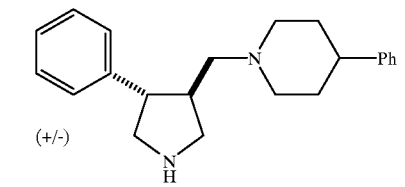
(+/-)
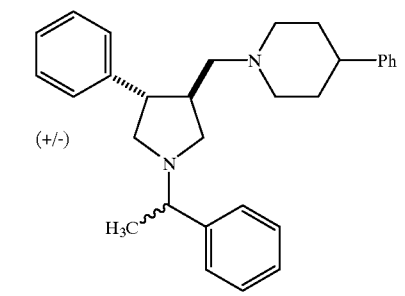
(+/-)
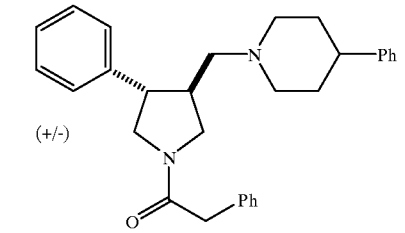
(+/-)
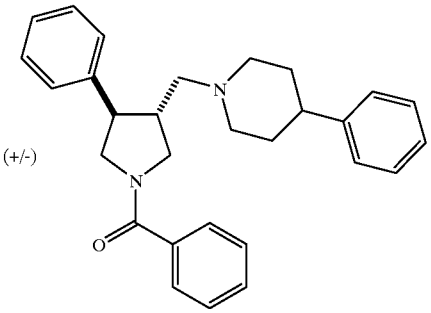
(+/-)
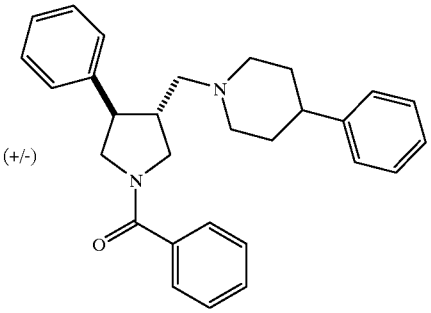
(+/-)

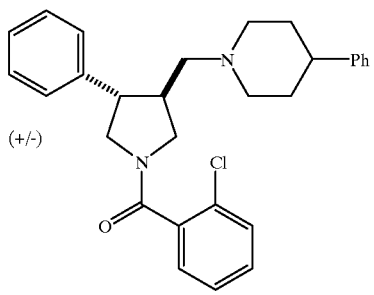
(+/-)
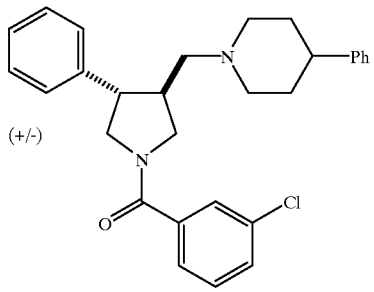
(+/-)
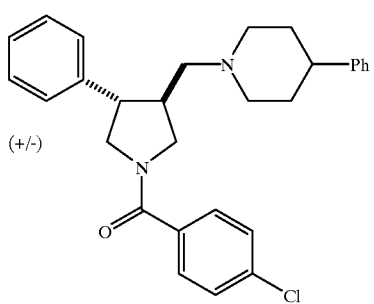
(+/-)
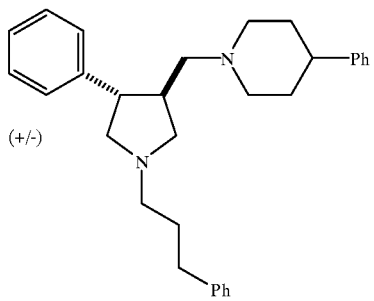
(+/-)
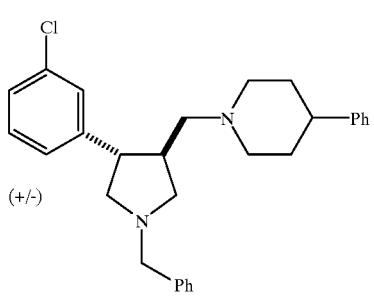
(+/-)
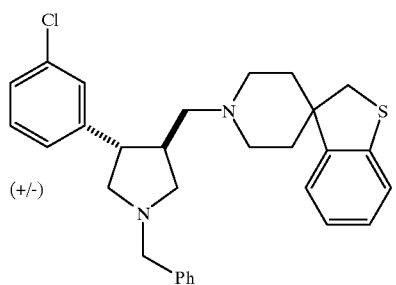
(+/-)
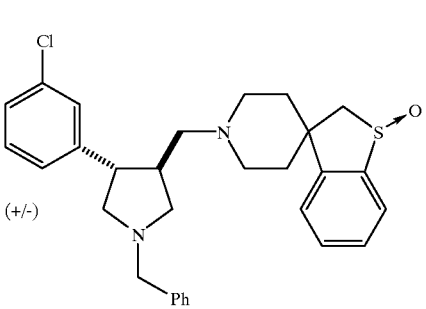
(+/-)
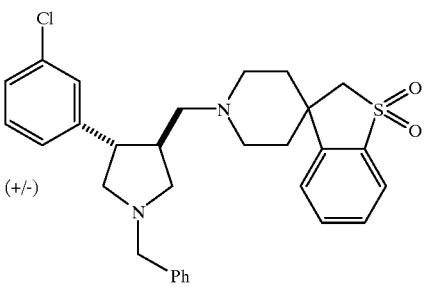
(+/-)
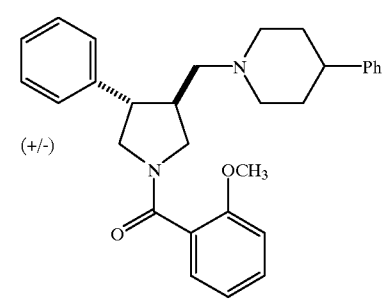
(+/-)
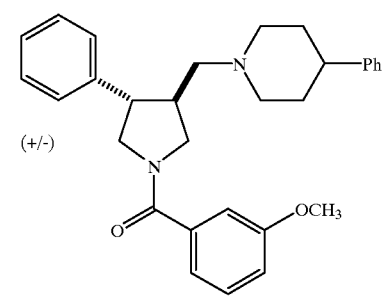
(+/-)

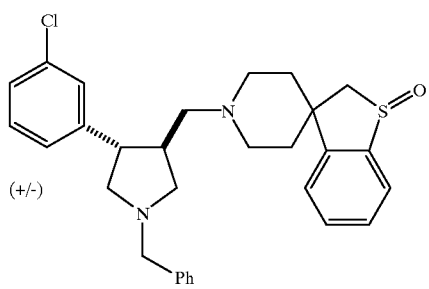
(+/-)
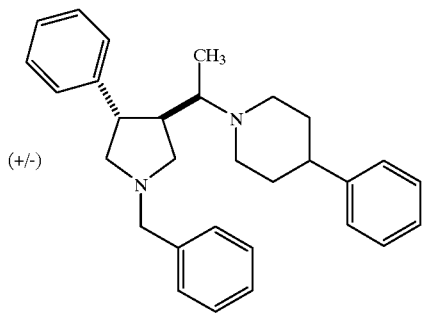
(+/-)
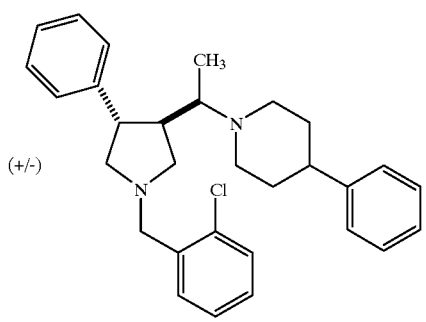
(+/-)
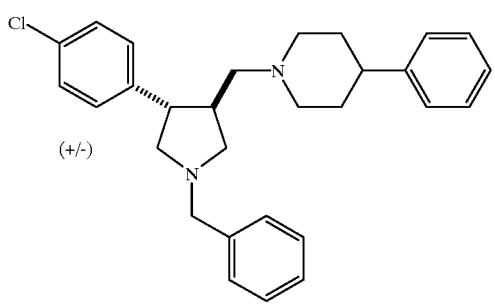
(+/-)
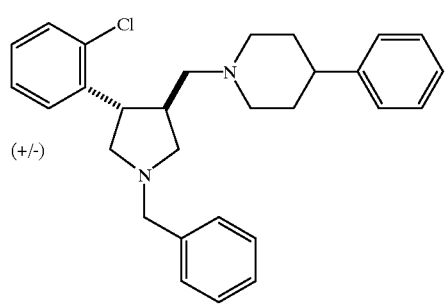
(+/-)
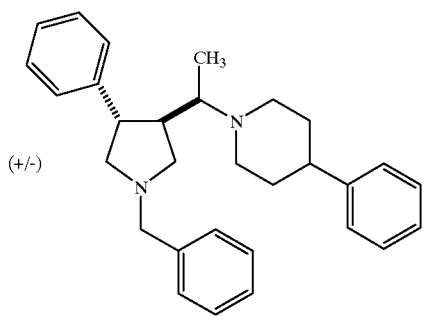
(+/-)
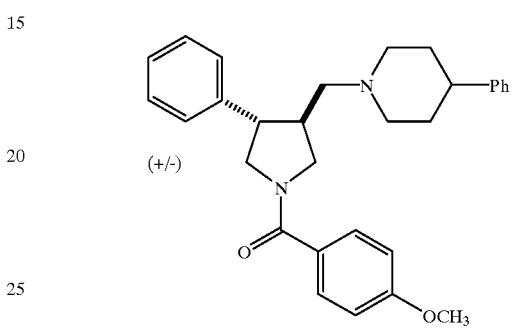
(+/-)
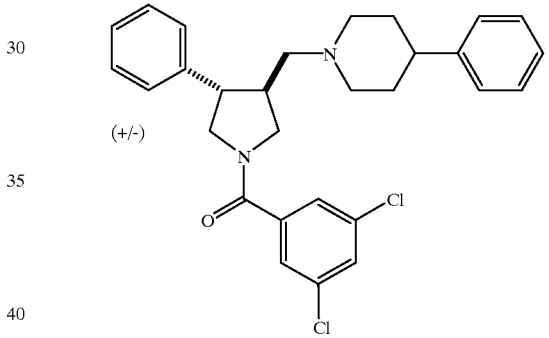
(+/-)
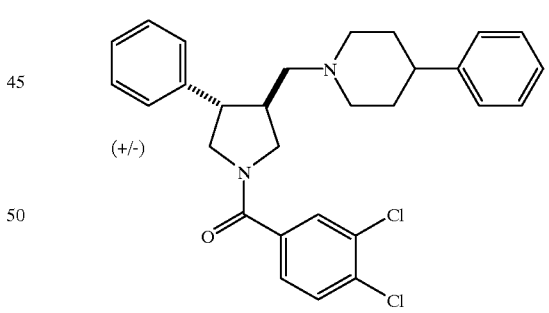
(+/-)
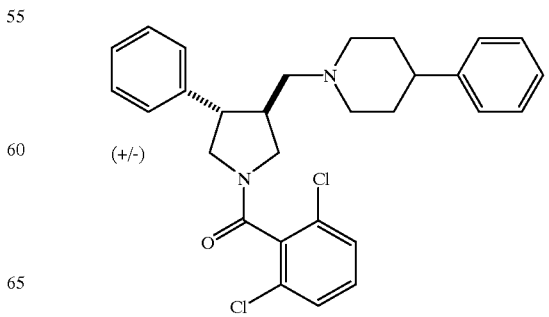
(+/-)

-continued
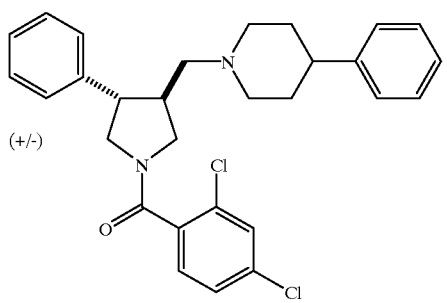
(+/-)
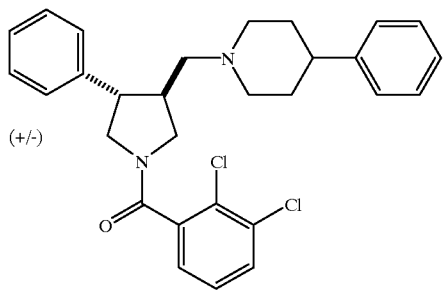
(+/-)
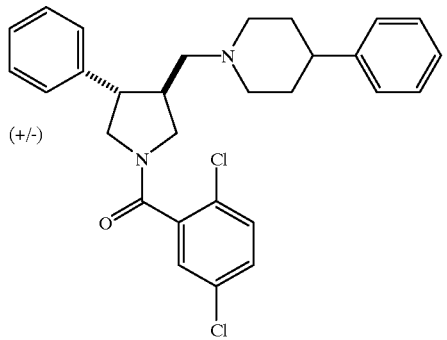
(+/-)
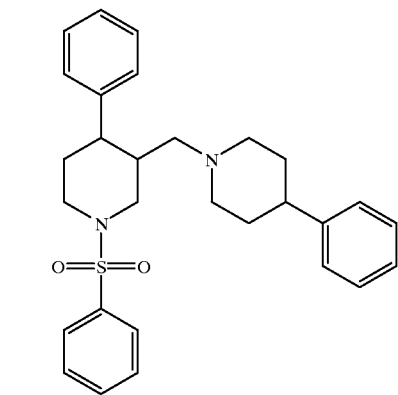
-continued
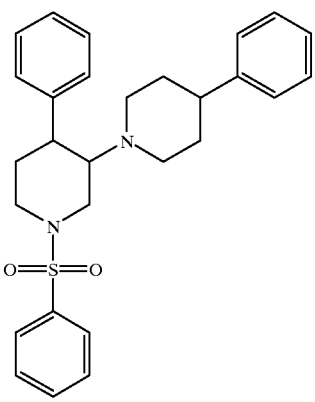
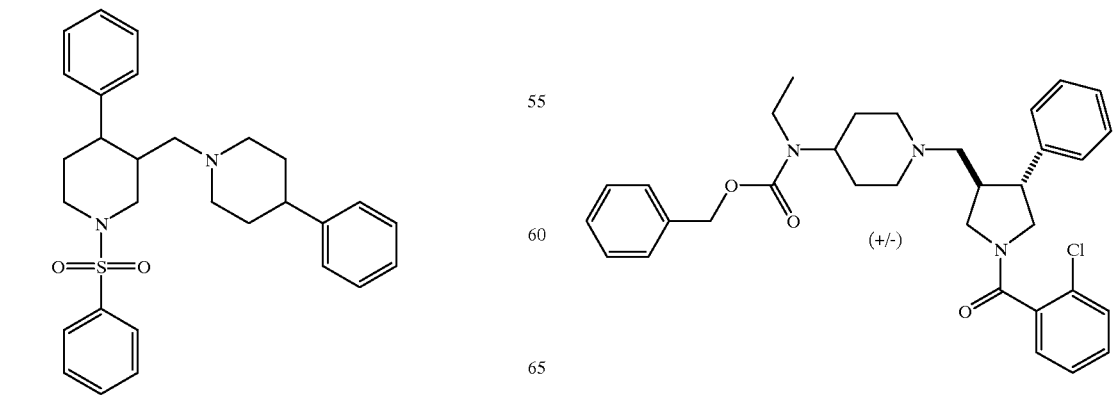
(+/-)
(+/-)
(+/-)

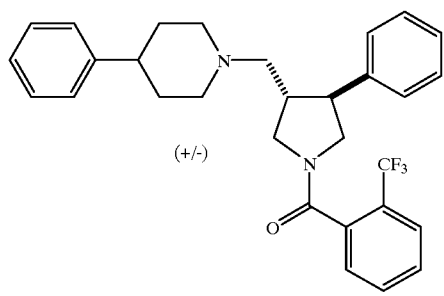
(+/-)
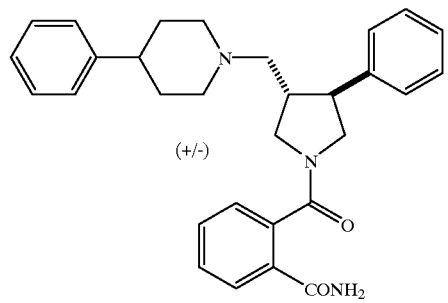
(+/-)
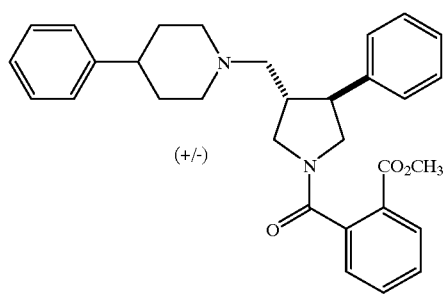
(+/-)
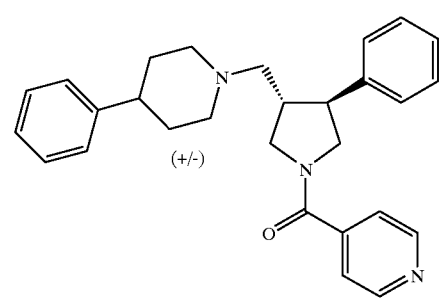
(+/-)
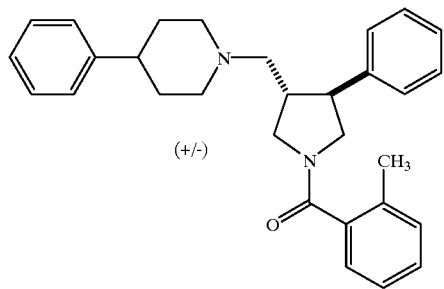
(+/-)
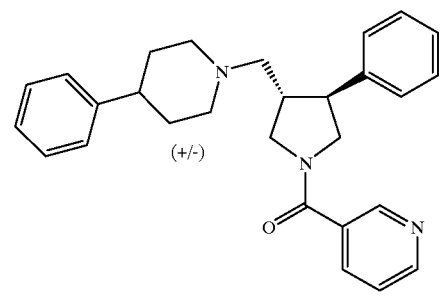
(+/-)
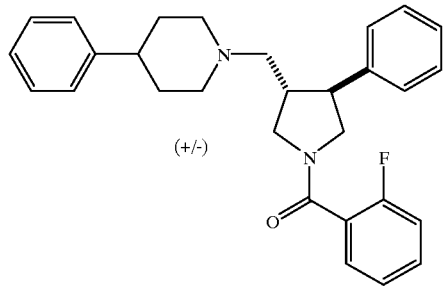
(+/-)
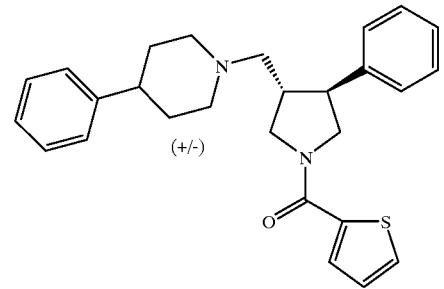
(+/-)
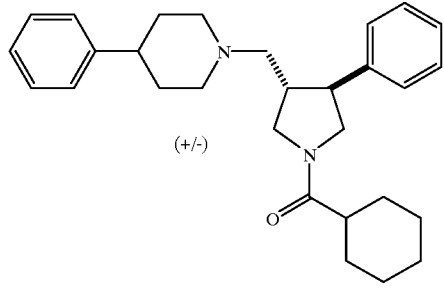
(+/-)
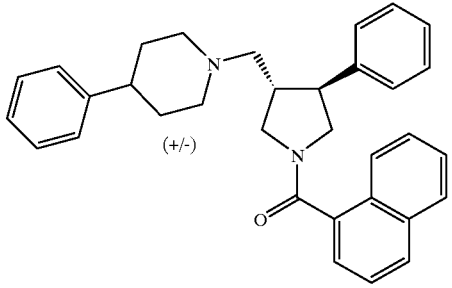
(+/-)

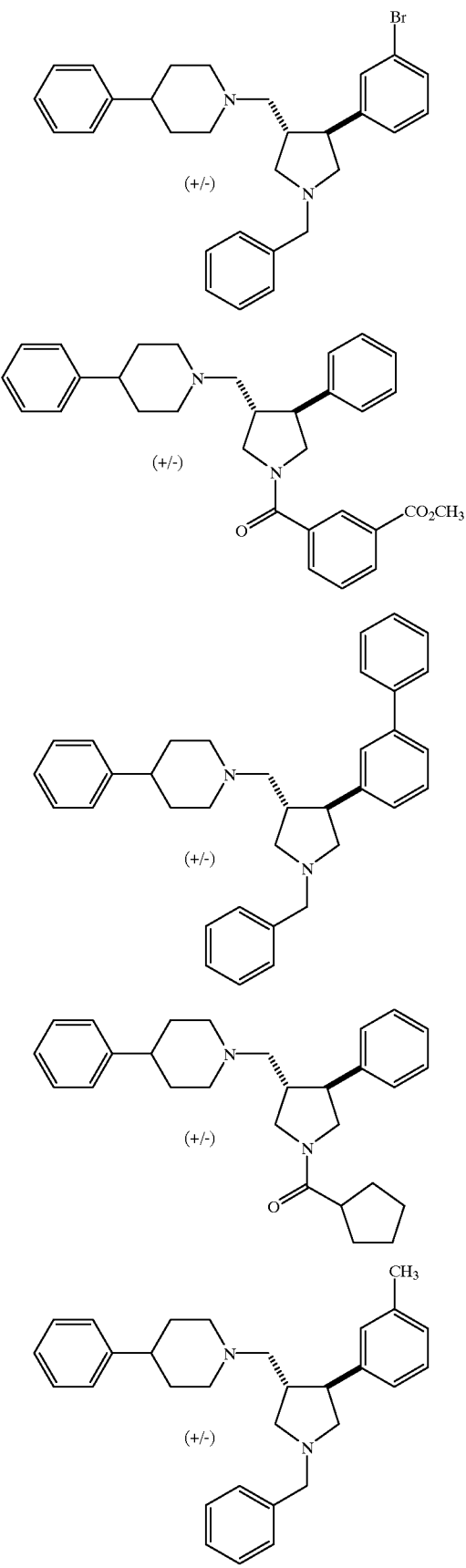
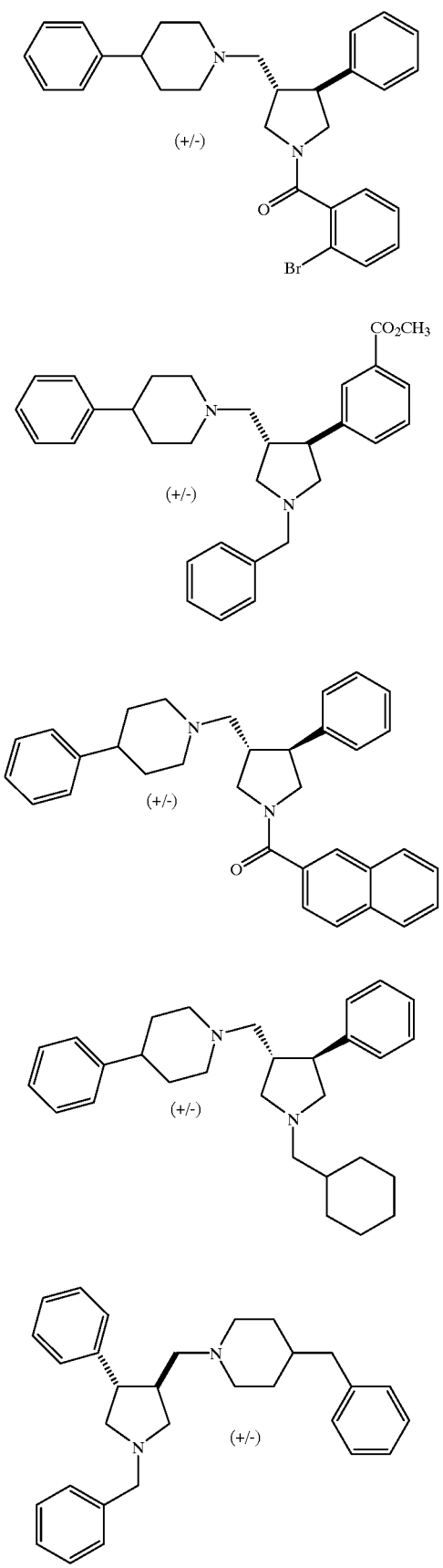

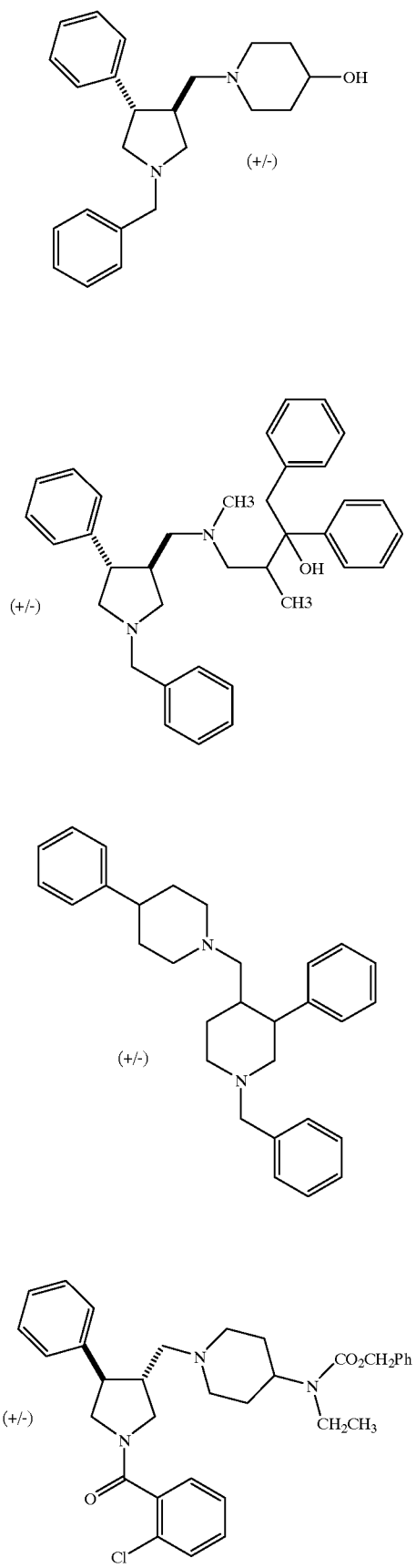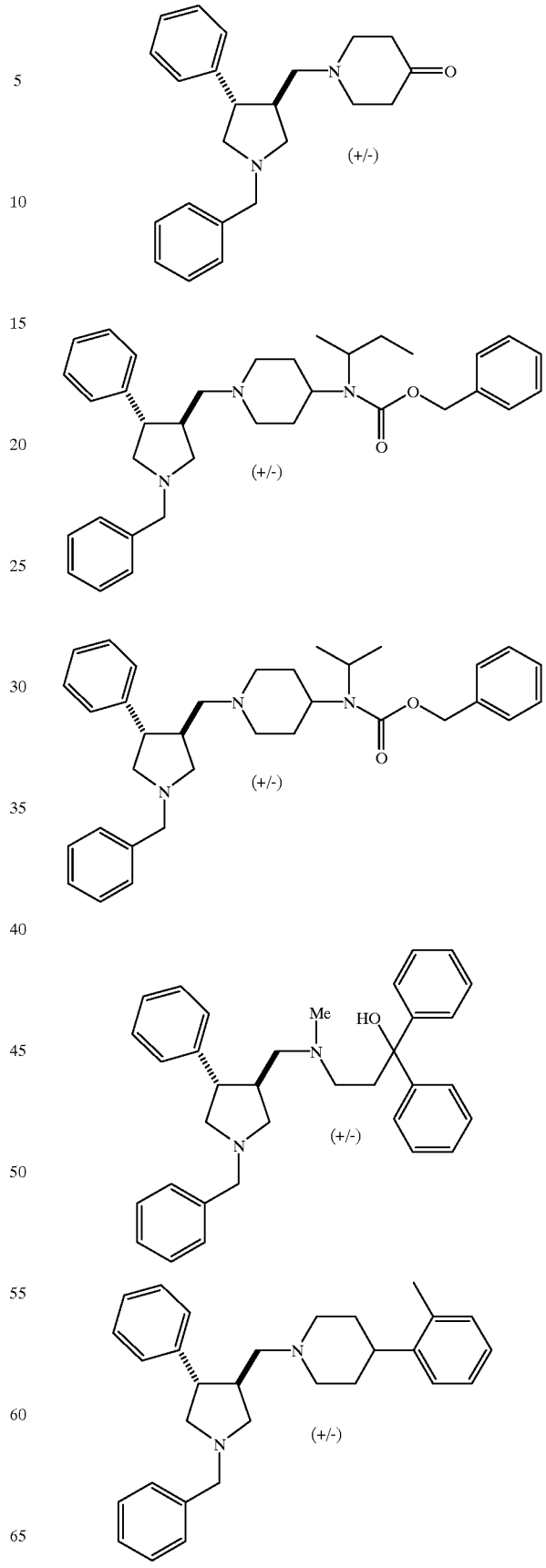

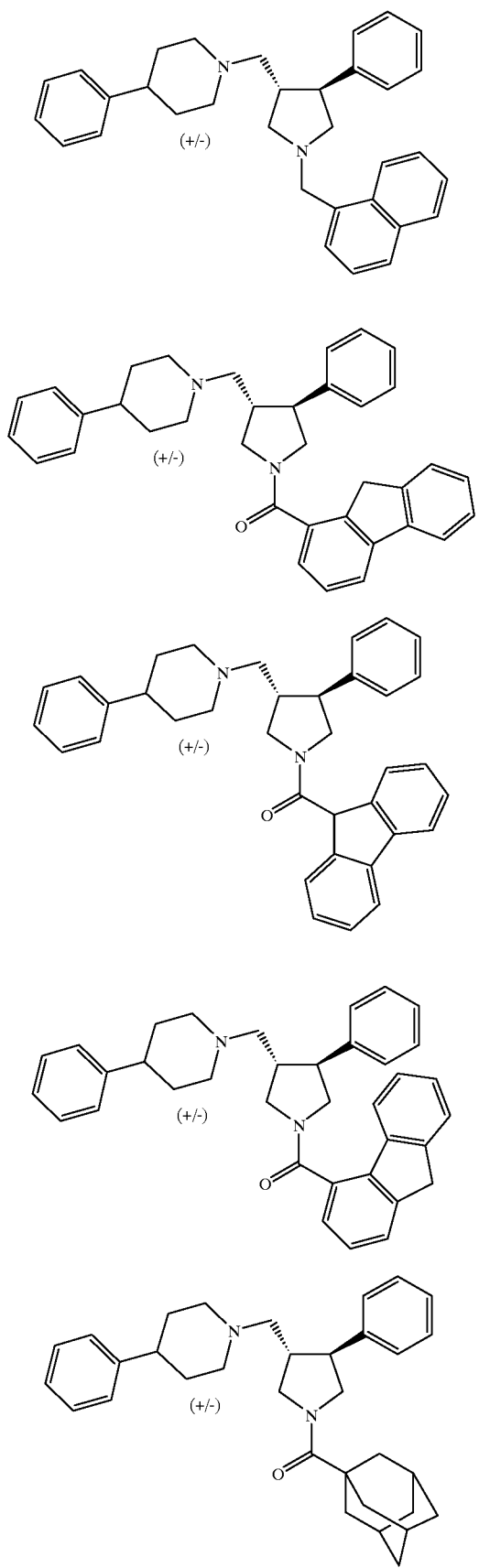
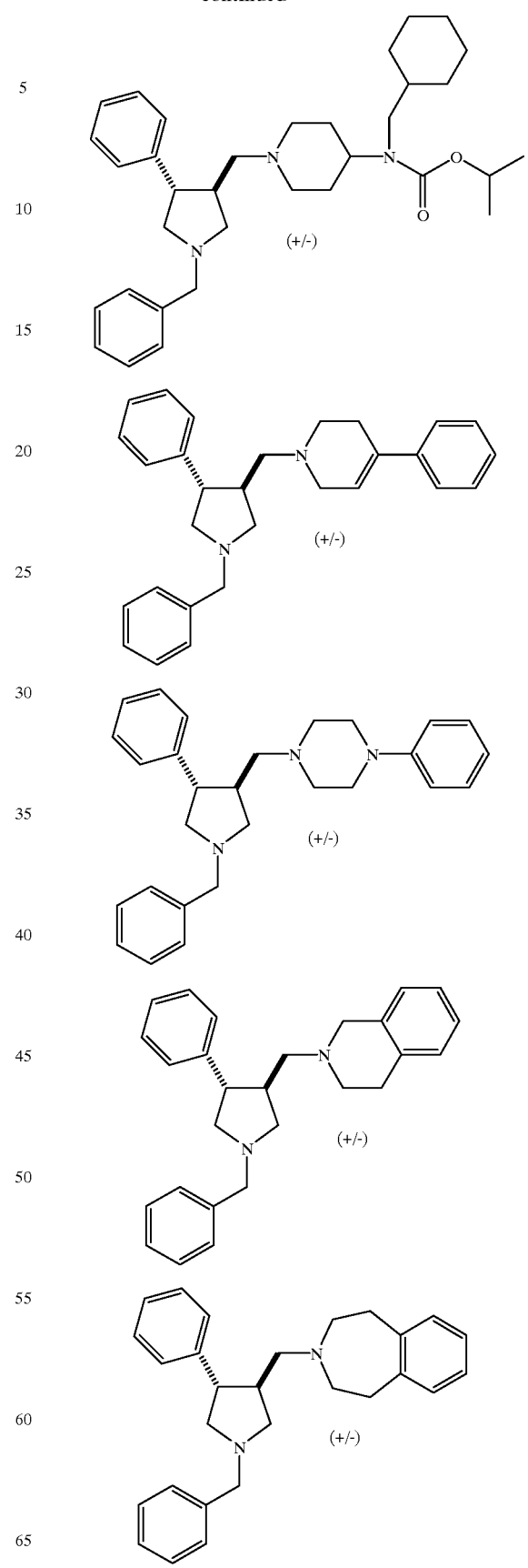

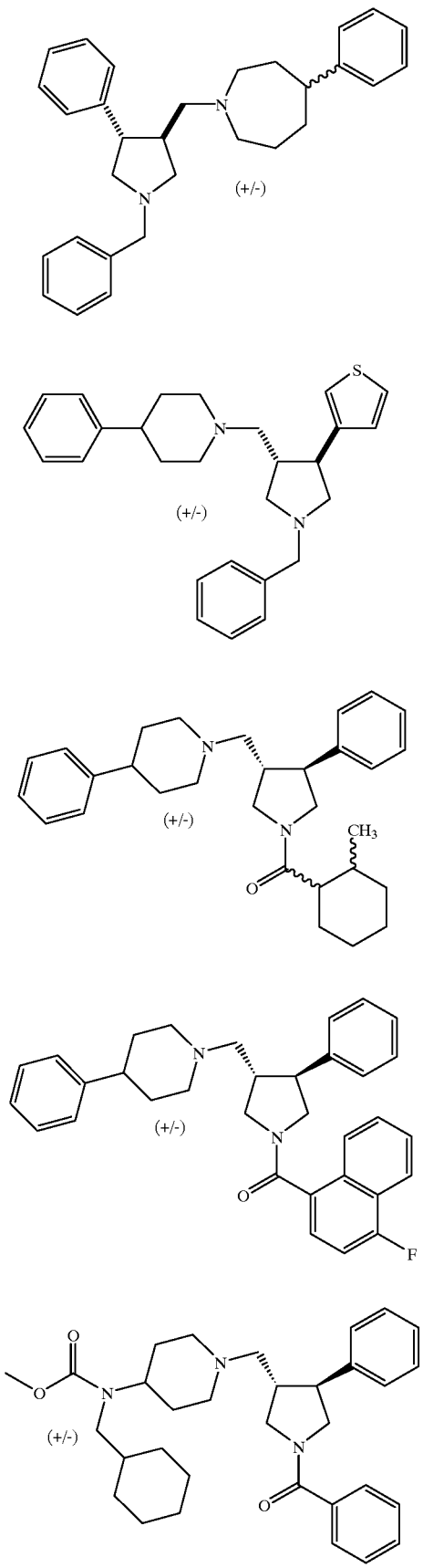
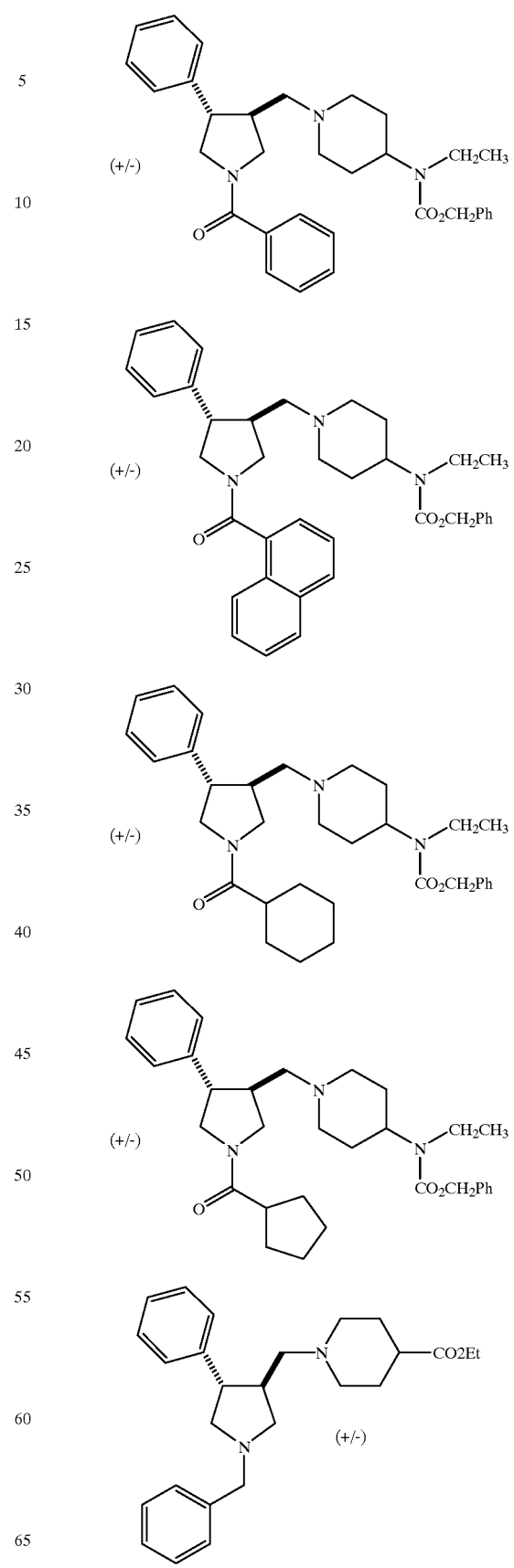

33
-continued
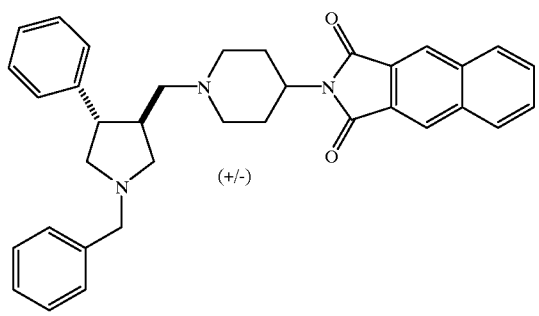
(+/-)
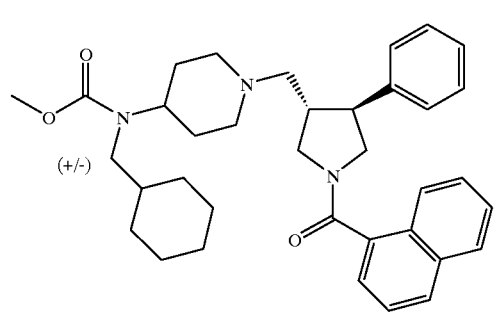
(+/-)
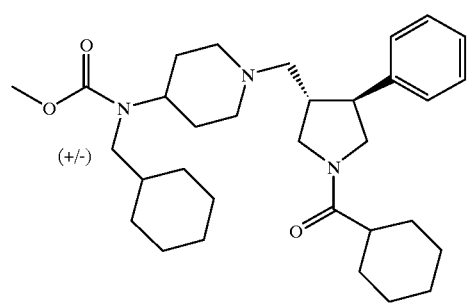
(+/-)
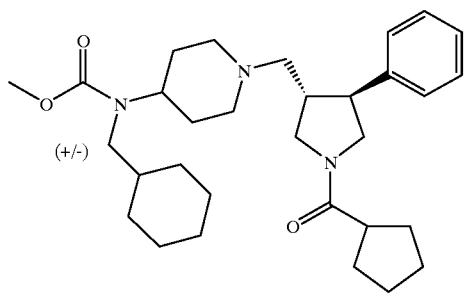
(+/-)
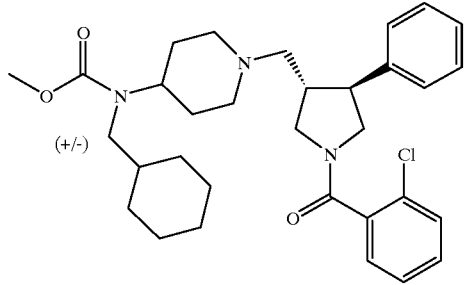
(+/-)
34
-continued
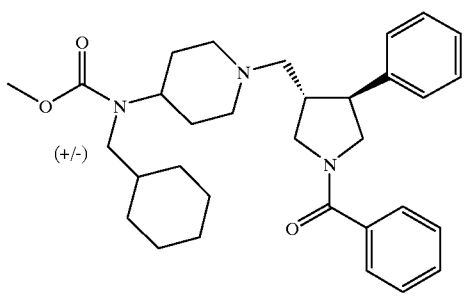
(+/-)
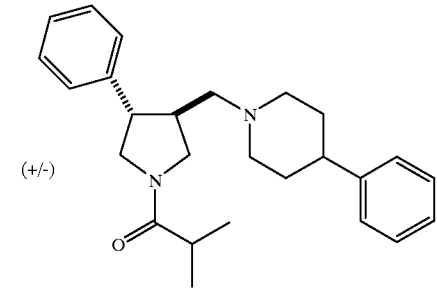
(+/-)
(+/-)
(+/-)
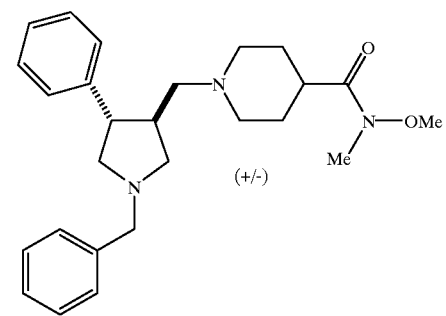
(+/-)

35
-continued
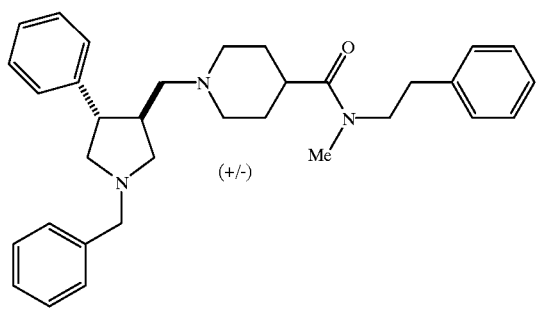
(+/-)
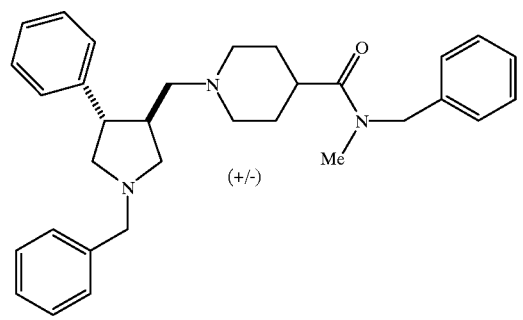
(+/-)
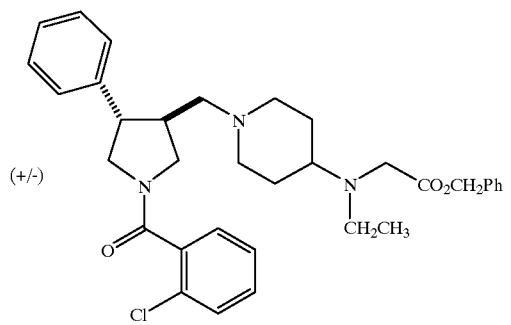
(+/-)
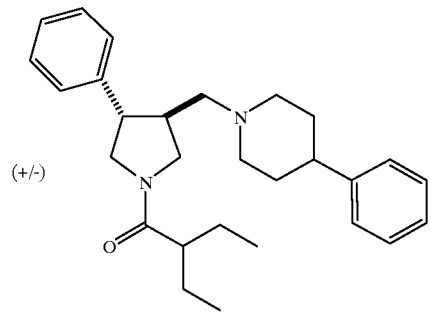
(+/-)
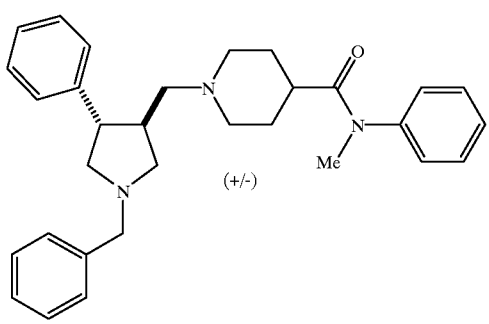
(+/-)
36
-continued
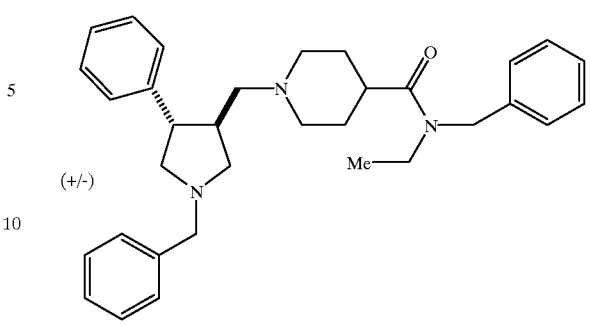
(+/-)
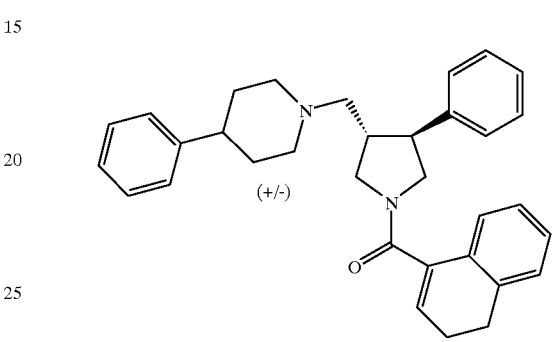
(+/-)
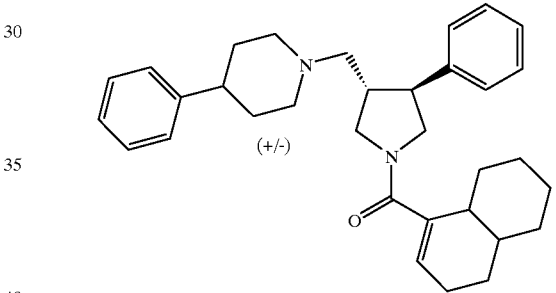
(+/-)
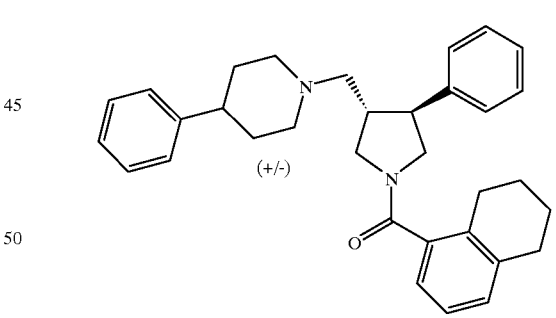
(+/-)
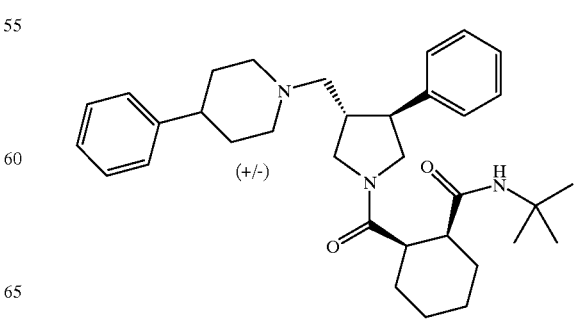
(+/-)

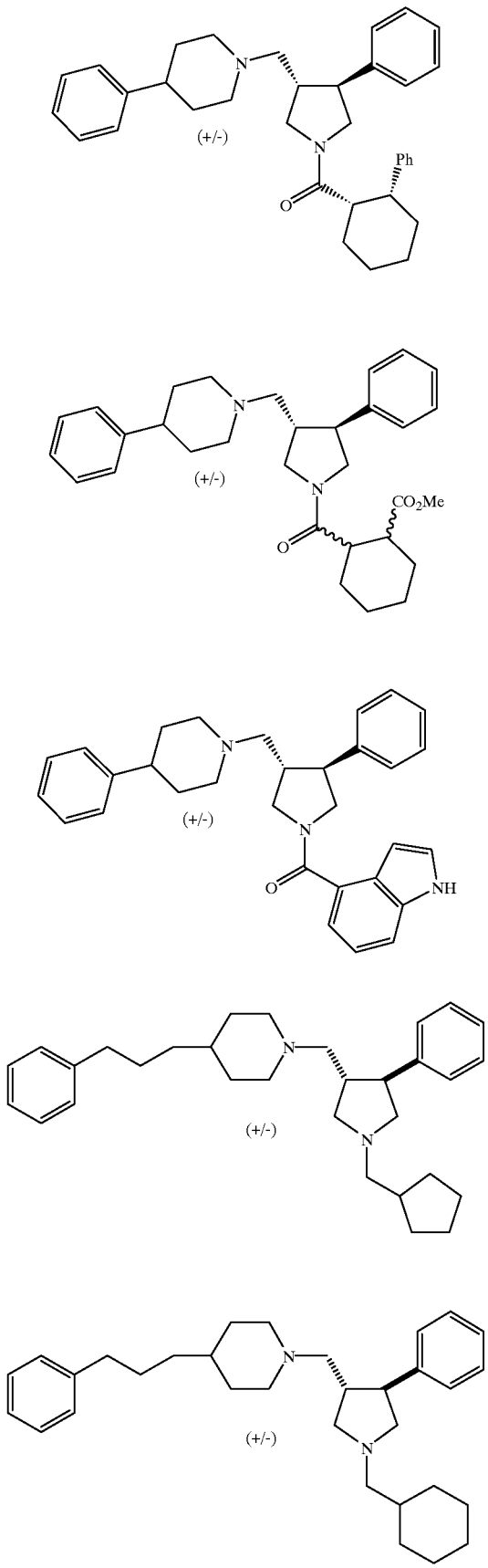

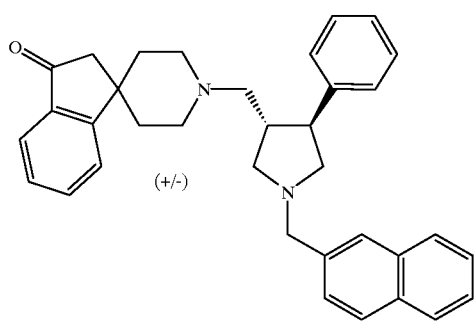
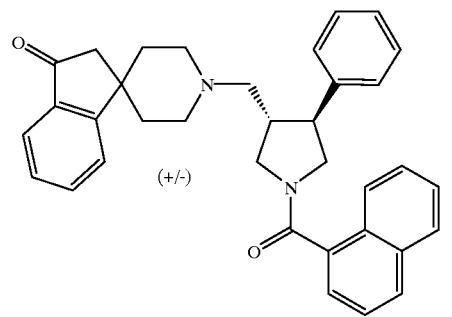
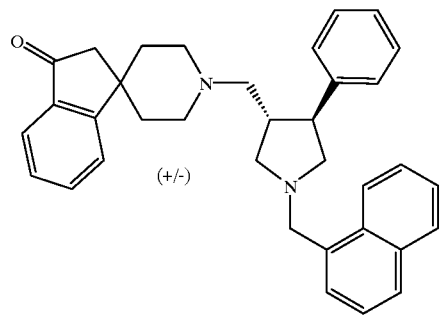
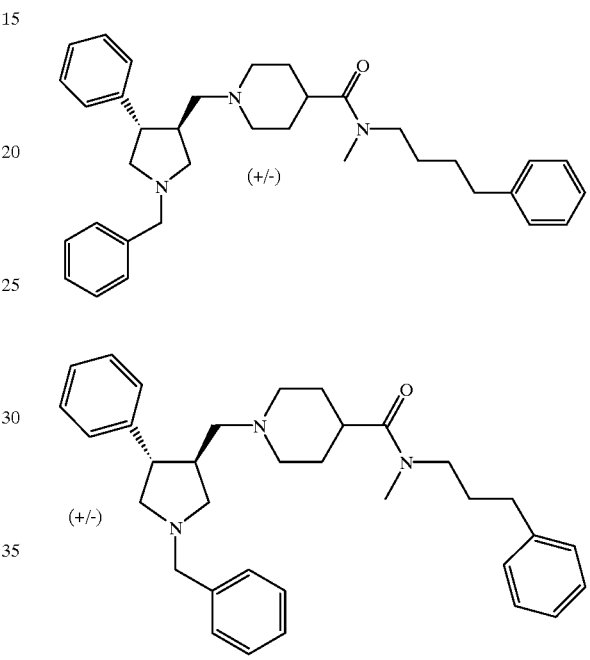
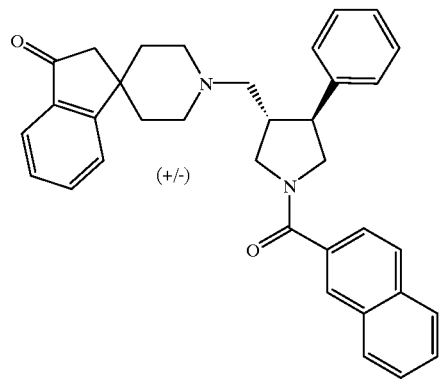
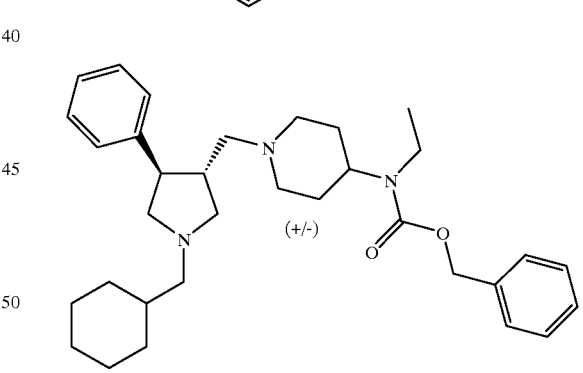
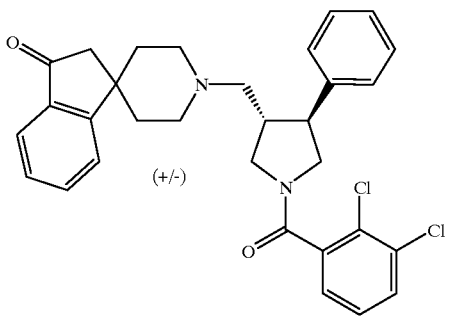
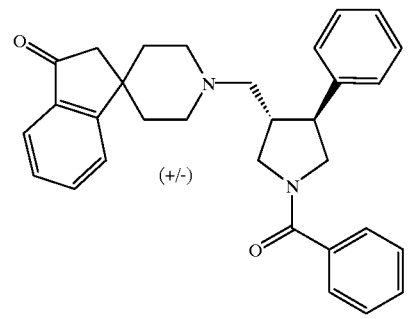
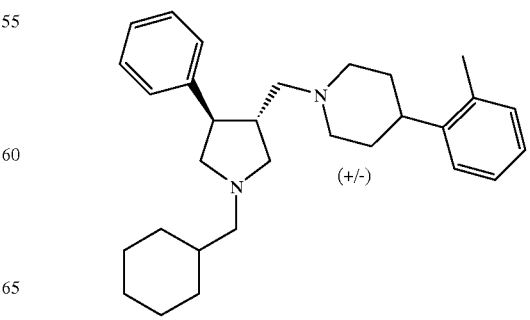

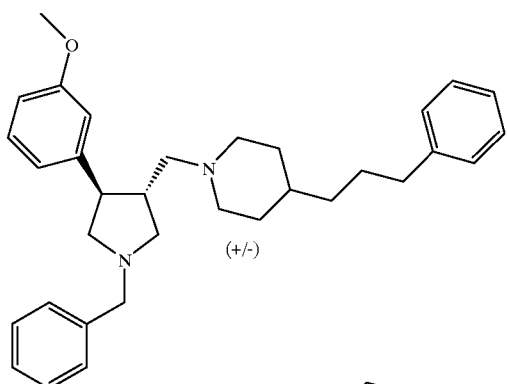
(+/-)
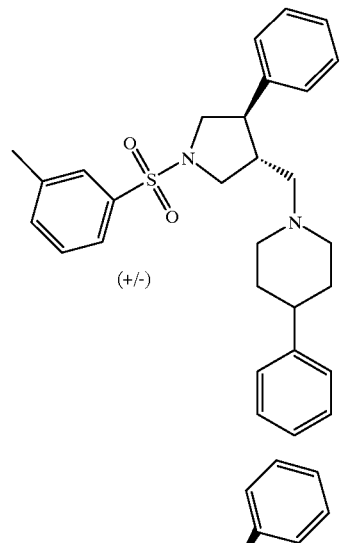
(+/-)
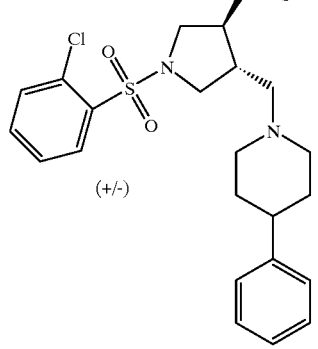
(+/-)
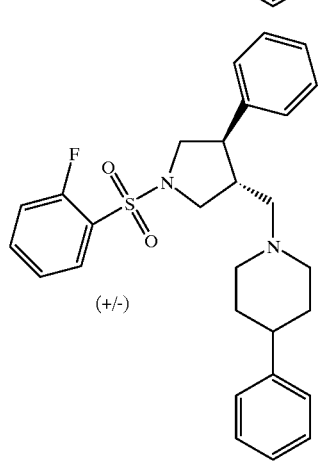
(+/-)
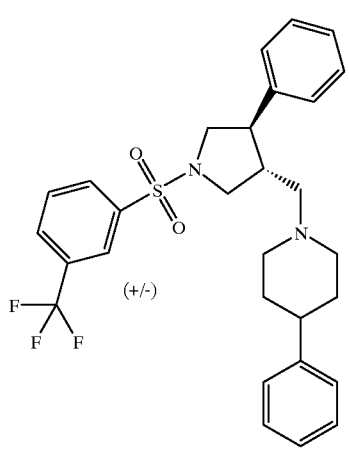
(+/-)
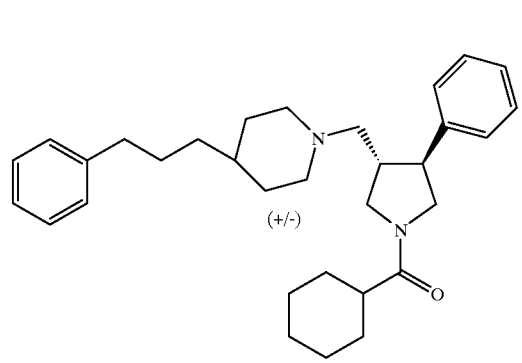
(+/-)
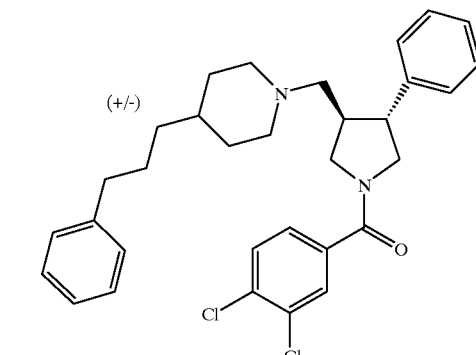
(+/-)
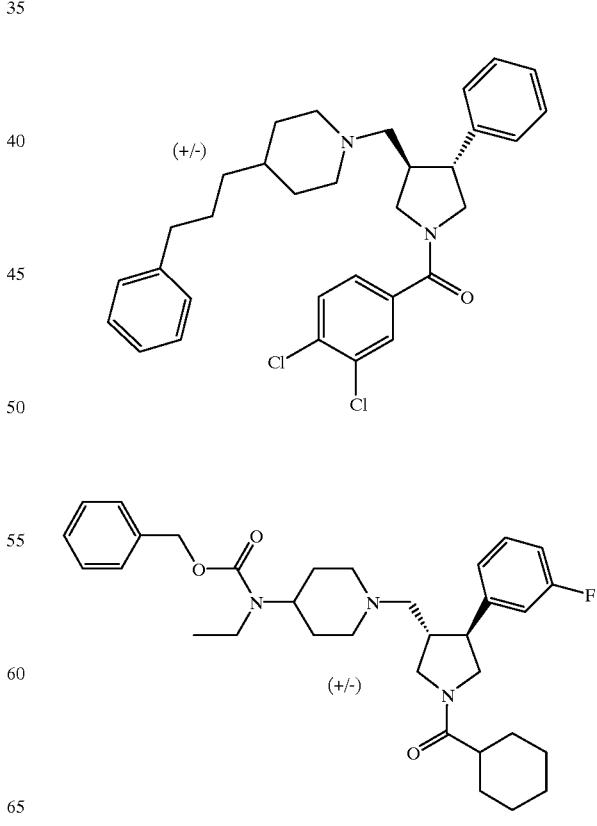
(+/-)
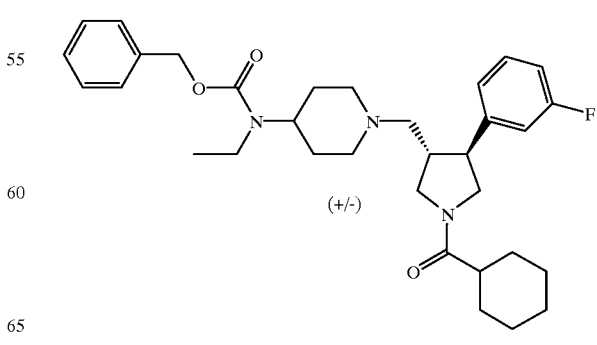
(+/-)

-continued
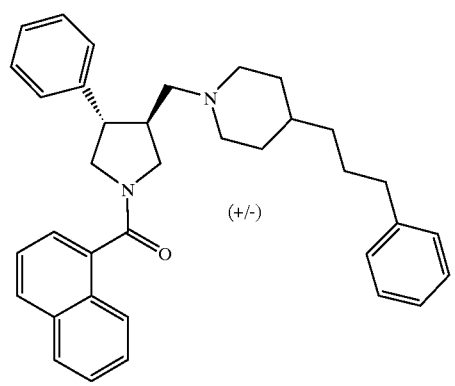
(+/-)
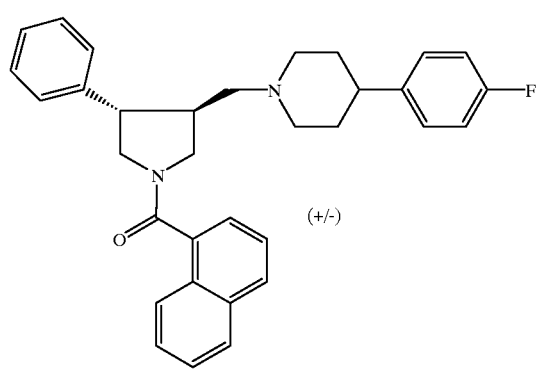
(+/-)
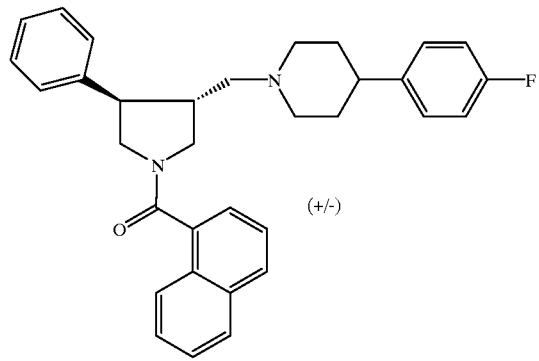
(+/-)
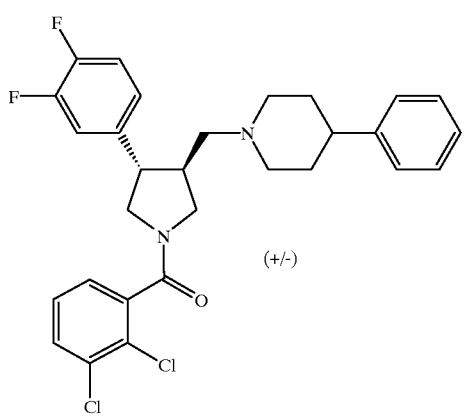
(+/-)
-continued
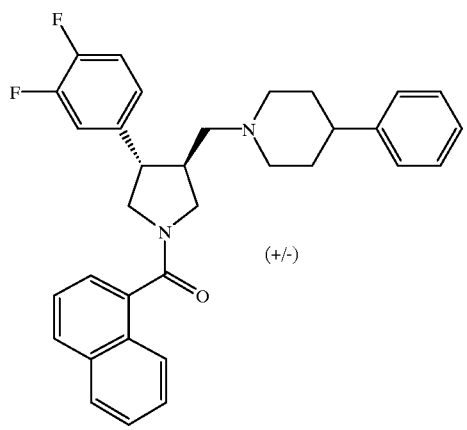
(+/-)
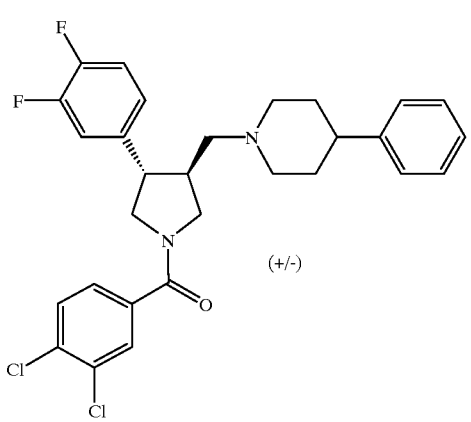
(+/-)
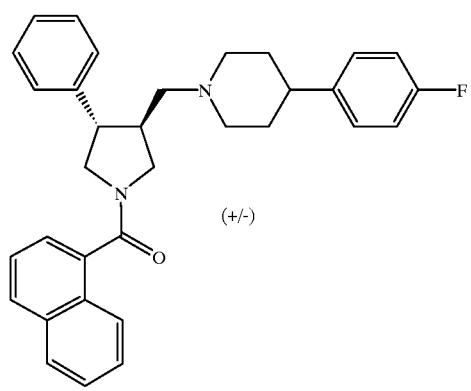
(+/-)
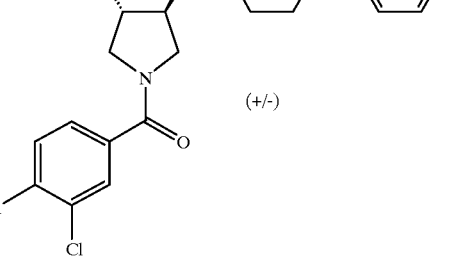
(+/-)

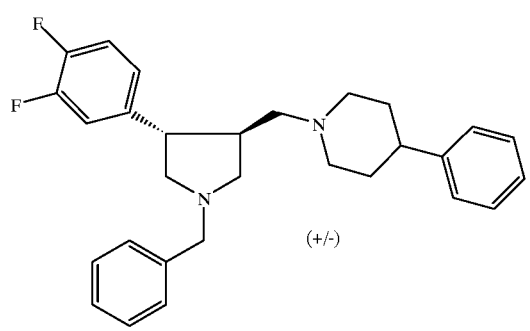
(+/-)
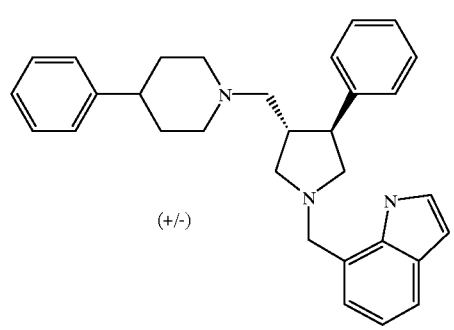
(+/-)
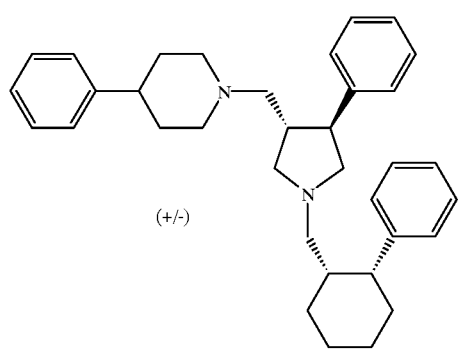
(+/-)
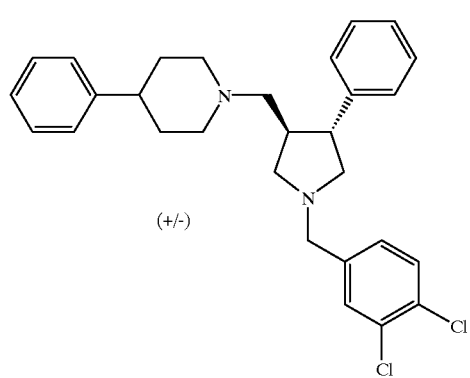
(+/-)
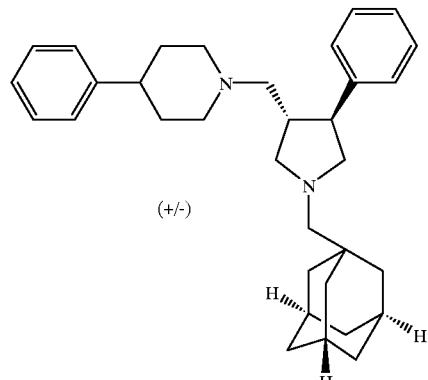
(+/-)
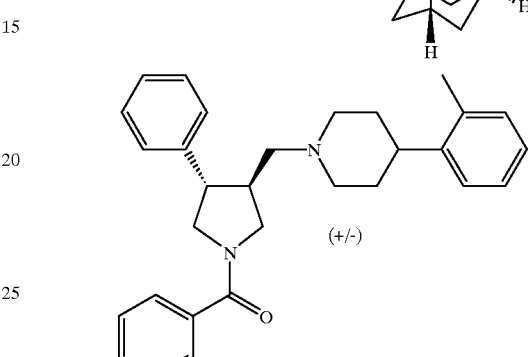
(+/-)
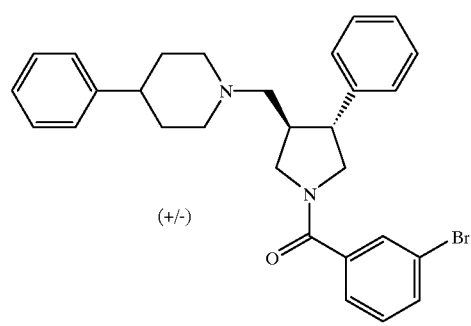
(+/-)
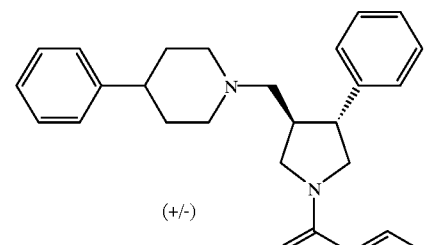
(+/-)
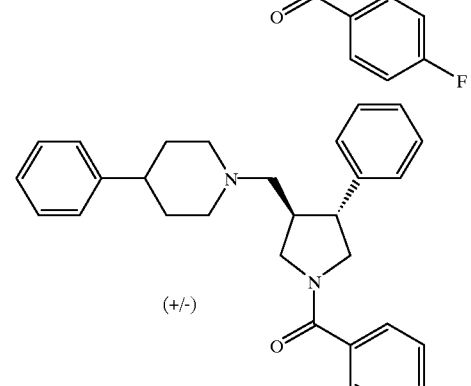
(+/-)

6,166,037
47
-continued
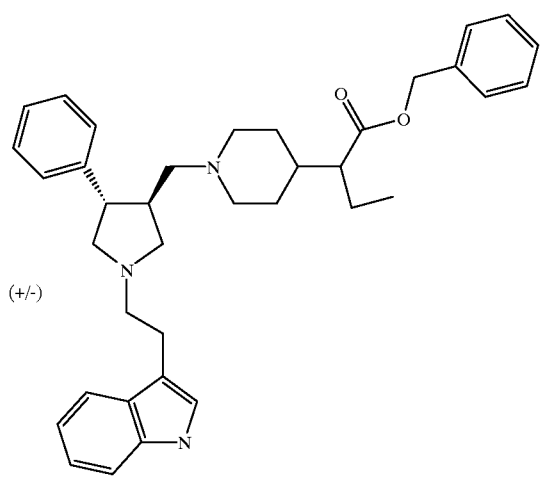
(+/-)
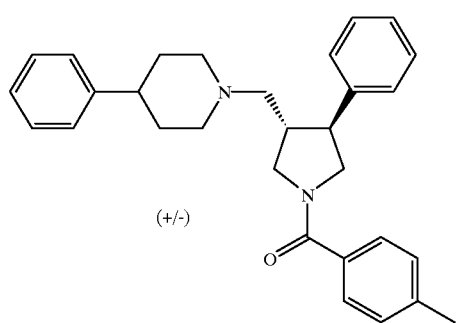
(+/-)
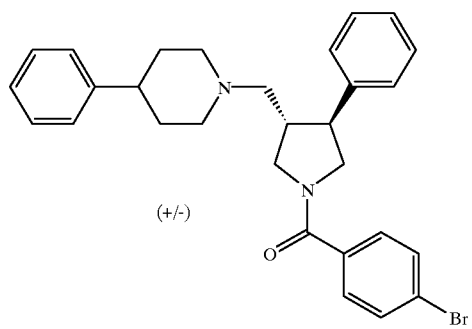
(+/-)
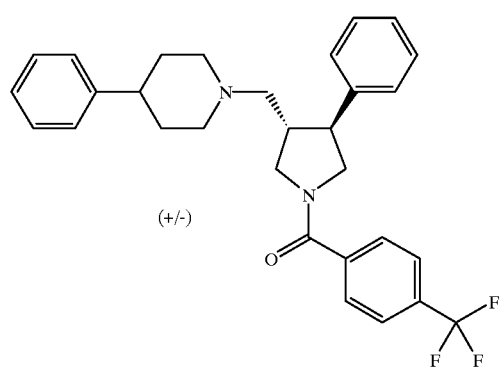
(+/-)
48
-continued
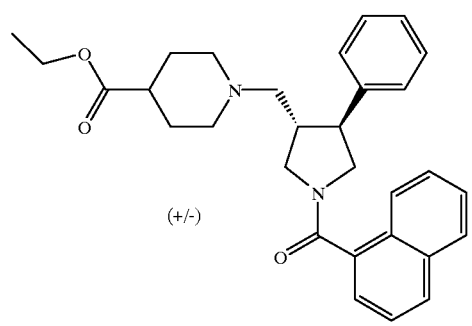
(+/-)
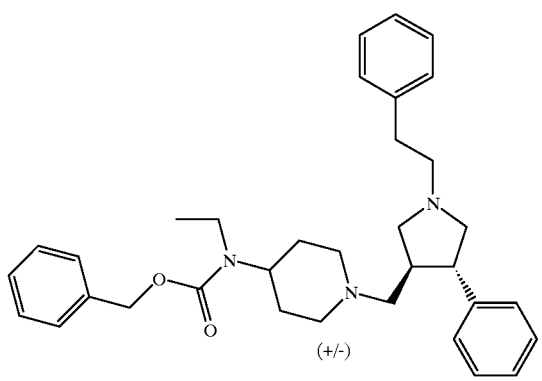
(+/-)
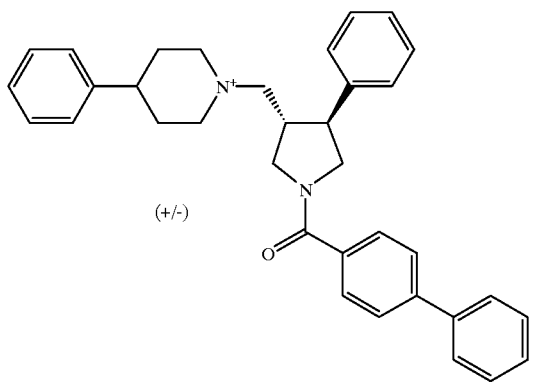
(+/-)
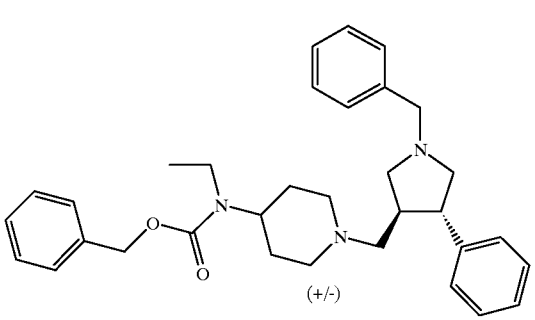
(+/-)

-continued
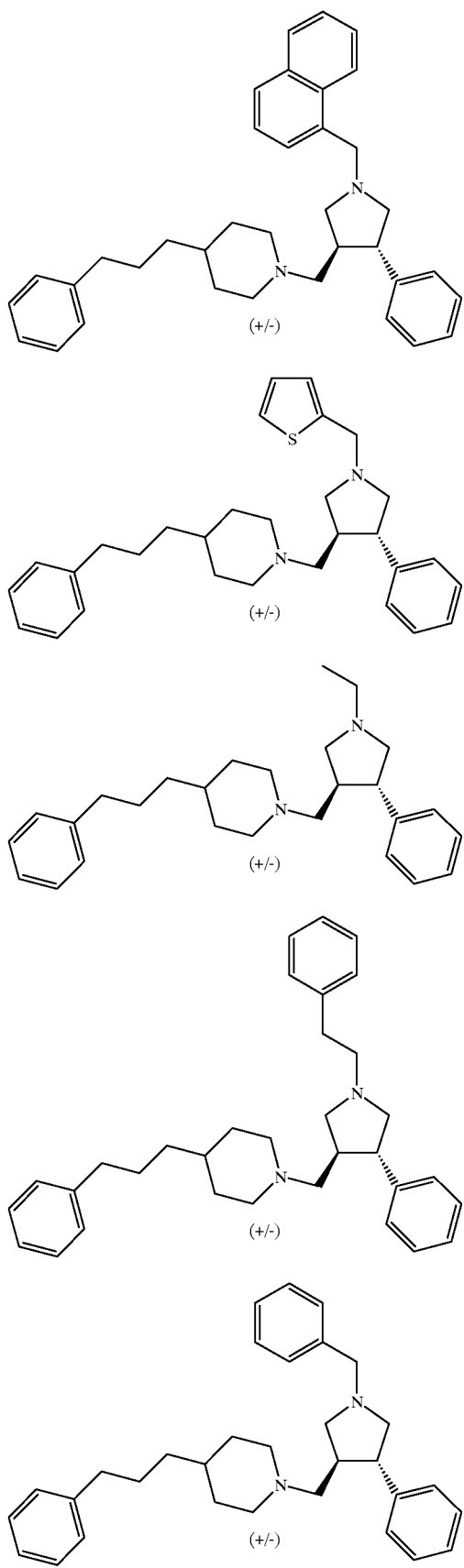
-continued
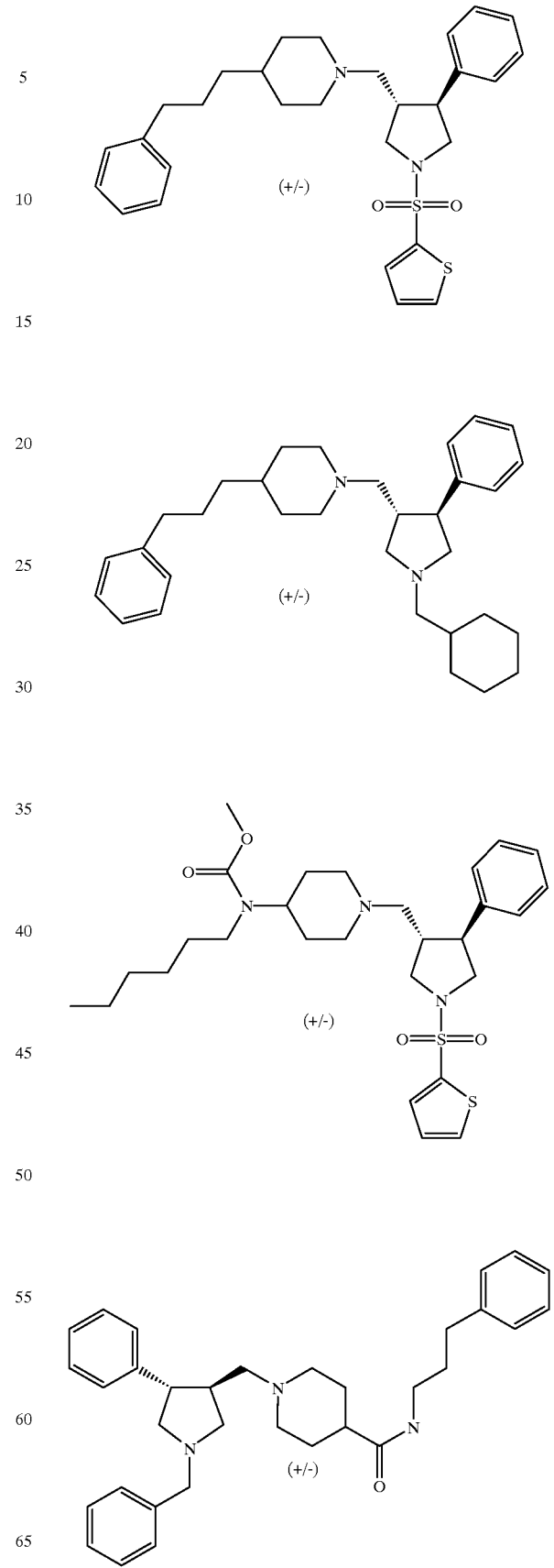

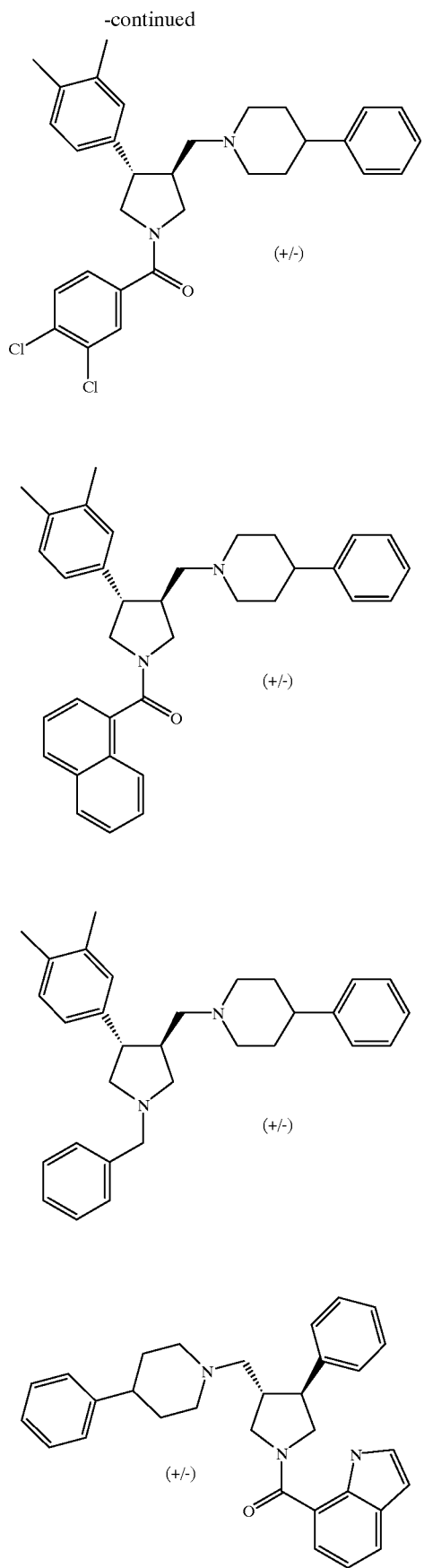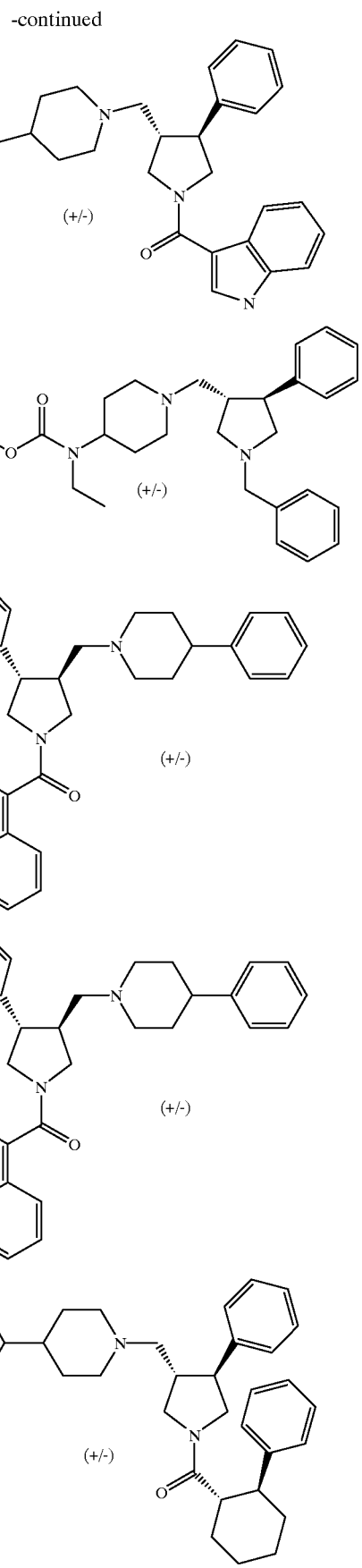

53
-continued
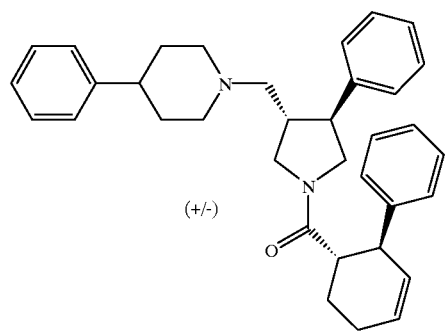
(+/-)
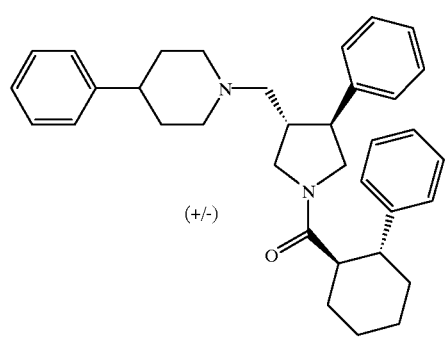
(+/-)
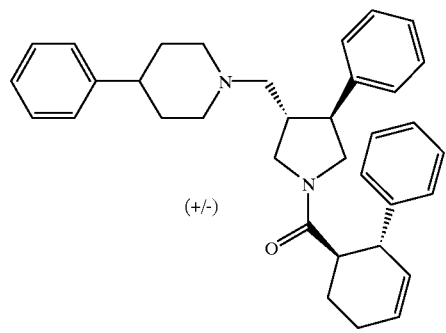
(+/-)
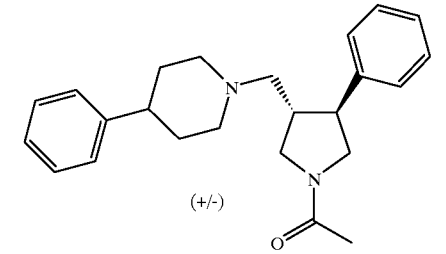
(+/-)
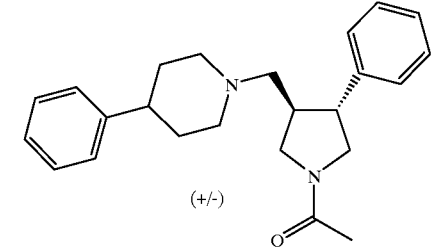
(+/-)
54
-continued
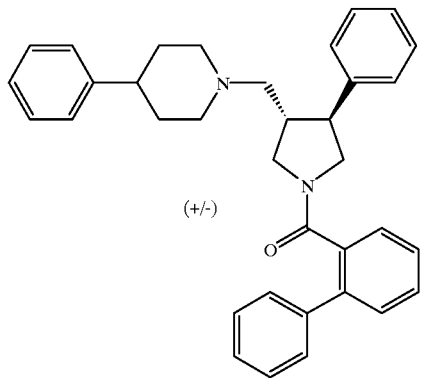
(+/-)
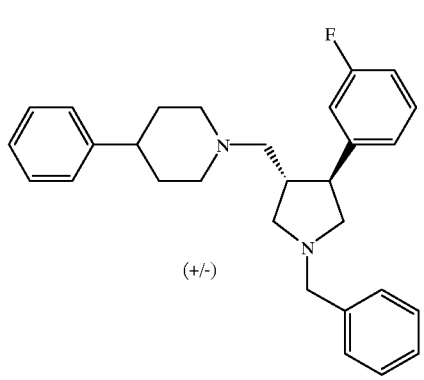
(+/-)
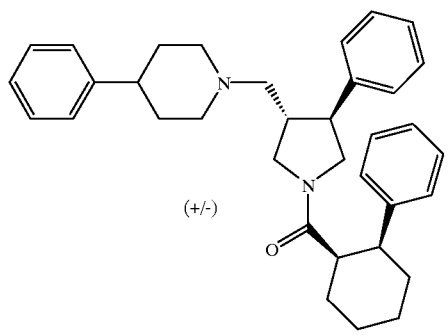
(+/-)
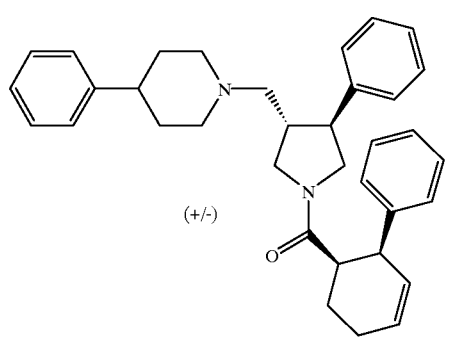
(+/-)

55
-continued
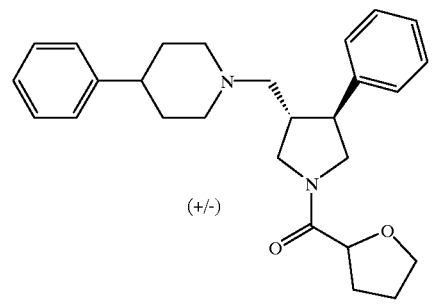
(+/-)
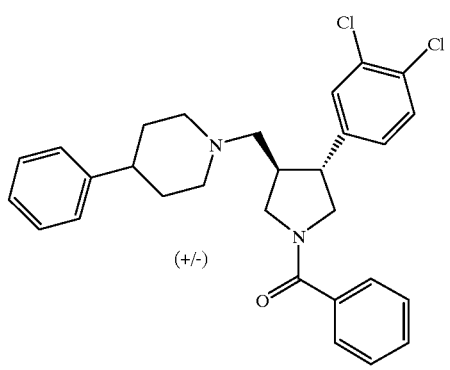
(+/-)
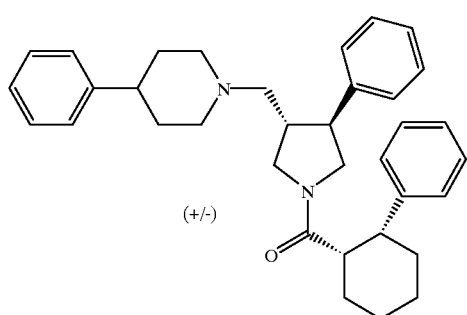
(+/-)
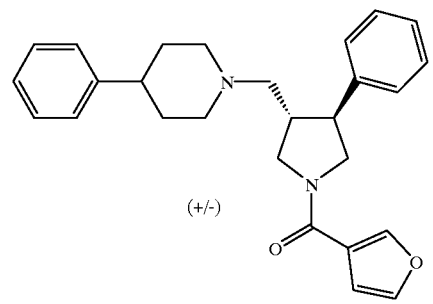
(+/-)
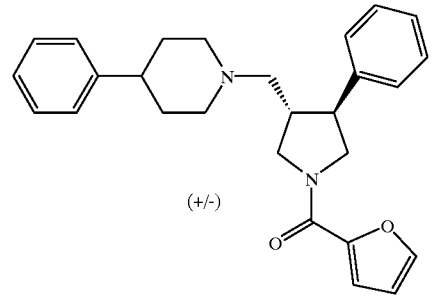
(+/-)
56
-continued
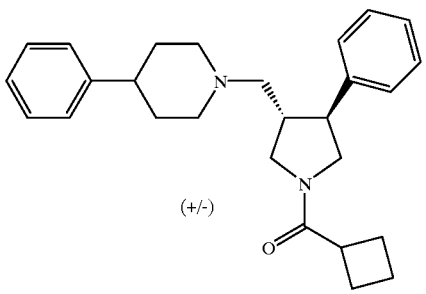
(+/-)
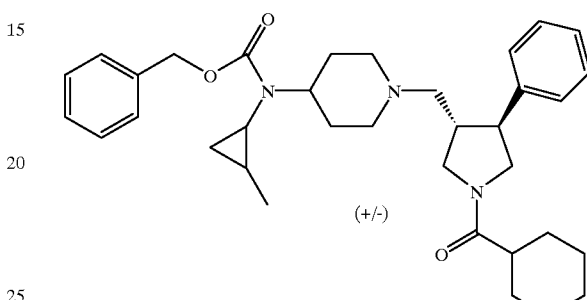
(+/-)
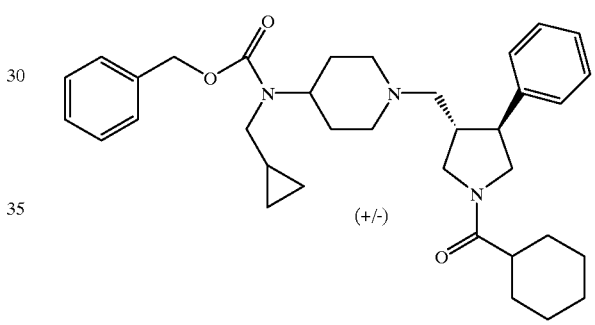
(+/-)
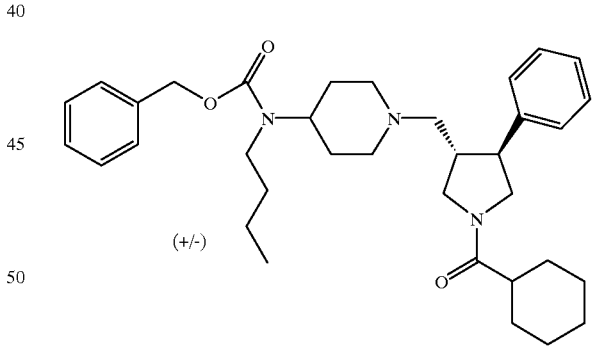
(+/-)
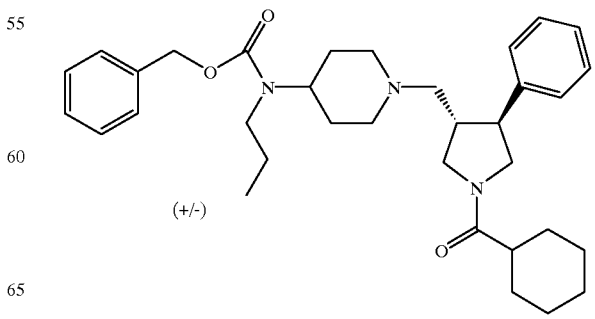
(+/-)

-continued

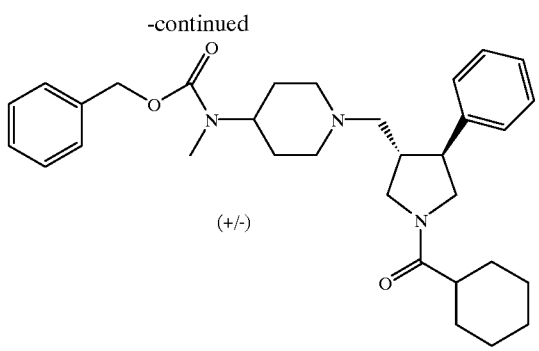

(+/-)

and pharmaceutically acceptable salts thereof and individual diastereomers thereof.

The subject compounds are useful in a method of modulating chemokine receptor activity in a patient in need of such modulation comprising the administration of an effective amount of the compound.

The present invention is directed to the use of the foregoing spiro-substituted azacycles as modulators of chemokine receptor activity. In particular, these compounds are useful as modulators of the chemokine receptors, including CCR-1, CCR-2, CCR-2A, CCR-2B, CCR-3, CCR-4, CCR-5, CXCR-3, and/or CXCR-4.

The utility of the compounds in accordance with the present invention as modulators of chemokine receptor activity may be demonstrated by methodology known in the art, such as the assay for CCR-1 and/or CCR-5 binding as disclosed by Van Riper, et al., *J. Exp. Med.*, 177, 851–856 (1993), and the assay for CCR-2 and/or CCR-3 binding as disclosed by Daugherty, et al., *J. Exp. Med.*, 183, 2349–2354 (1996). Cell lines for expressing the receptor of interest include those naturally expressing the receptor, such as EOL-3 or THP-1, or a cell engineered to express a recombinant receptor, such as CHO, RBL-2H3, HEK-293. For example, a CCR3 transfected AML14.3D10 cell line has been placed on restricted deposit with American Type Culture Collection in Rockville, Md. as ATCC No. CRL-12079, on Apr. 5, 1996. The utility of the compounds in accordance with the present invention as inhibitors of the spread of HIV infection in cells may be demonstrated by methodology known in the art, such as the HIV quantitation assay disclosed by Nunberg, et al., *J. Virology,* 65 (9), 4887–4892 (1991).

In particular, the compounds of the following examples had activity in binding to the CCR-5 receptor or to the CCR-3 receptor in the aforementioned assays, generally with an $IC_{50}$ of less than about 10 $\mu$M. Such a result is indicative of the intrinsic activity of the compounds in use as modulators of chemokine receptor activity.

Mammalian chemokine receptors provide a target for interfering with or promoting eosinophil and/or lymphocyte function in a mammal, such as a human. Compounds which inhibit or promote chemokine receptor function, are particularly useful for modulating eosinophil and/or lymphocyte function for therapeutic purposes. Accordingly, the present invention is directed to compounds which are useful in the prevention and/or treatment of a wide variety of inflammatory and immunoregulatory disorders and diseases, including asthma and allergic diseases, as well as autoimmune pathologies such as rheumatoid arthritis and atherosclerosis.

For example, an instant compound which inhibits one or more functions of a mammalian chemokine receptor (e.g., a human chemokine receptor) may be administered to inhibit (i.e., reduce or prevent) inflammation. As a result, one or more inflammatory processes, such as leukocyte emigration, chemotaxis, exocytosis (e.g., of enzymes, histamine) or inflammatory mediator release, is inhibited. For example, eosinophilic infiltration to inflammatory sites (e.g., in asthma) can be inhibited according to the present method.

Similarly, an instant compound which promotes one or more functions of a mammalian chemokine receptor (e.g., a human chemokine) is administered to stimulate (induce or enhance) an inflammatory response, such as leukocyte emigration, chemotaxis, exocytosis (e.g., of enzymes, histamine) or inflammatory mediator release, resulting in the beneficial stimulation of inflammatory processes. For example, eosinophils can be recruited to combat parasitic infections.

In addition to primates, such as humans, a variety of other mammals can be treated according to the method of the present invention. For instance, mammals including, but not limited to, cows, sheep, goats, horses, dogs, cats, guinea pigs, rats or other bovine, ovine, equine, canine, feline, rodent or murine species can be treated. However, the method can also be practiced in other species, such as avian species (e.g., chickens).

Diseases and conditions associated with inflammation and infection can be treated using the method of the present invention. In a preferred embodiment, the disease or condition is one in which the actions of eosinophils and/or lymphocytes are to be inhibited or promoted, in order to modulate the inflammatory response.

Diseases or conditions of humans or other species which can be treated with inhibitors of chemokine receptor function, include, but are not limited to: inflammatory or allergic diseases and conditions, including respiratory allergic diseases such as asthma, allergic rhinitis, hypersensitivity lung diseases, hypersensitivity pneumonitis, eosinophilic pneumonias (e.g., Loeffler's syndrome, chronic eosinophilic pneumonia), delayed-type hypersentitivity, interstitial lung diseases (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies (e.g., to penicillin, cephalosporins), insect sting allergies; autoimmune diseases, such as rheumatoid arthritis, psoriatic arthritis, multiple sclerosis, systemic lupus erythematosus, myasthenia gravis, juvenile onset diabetes; glomerulonephritis, autoimmune thyroiditis, Behcet's disease; graft rejection (e.g., in transplantation), including allograft rejection or graft-versus-host disease; inflammatory bowel diseases, such as Crohn's disease and ulcerative colitis; spondyloarthropathies; scleroderma; psoriasis (including T-cell mediated psoriasis) and inflammatory dermatoses such an dermatitis, eczema, atopic dermatitis, allergic contact dermatitis, urticaria; vasculitis (e.g., necrotizing, cutaneous, and hypersensitivity vasculitis); eosinphilic myositis, eosinophilic fasciitis; cancers with leukocyte infiltration of the skin or organs. Other diseases or conditions in which undesirable inflammatory responses are to be inhibited can be treated, including, but not limited to, reperfusion injury, atherosclerosis, certain hematologic malignancies, cytokine-induced toxicity (e.g., septic shock, endotoxic shock), polymyositis, dermatomyositis.

Diseases or conditions of humans or other species which can be treated with promoters of chemokine receptor function, include, but are not limited to: immunosuppression, such as that in individuals with immunodeficiency syndromes such as AIDS, individuals undergoing radiation therapy, chemotherapy, therapy for autoimmune disease or other drug therapy (e.g., corticosteroid therapy), which causes immunosuppression; immunosuppression due congenital deficiency in receptor function or other causes; and infectious diseases, such as parasitic diseases, including, but not limited to helminth infections, such as nematodes (round worms); (Trichuriasis, Enterobiasis, Ascariasis, Hookworm, Strongyloidiasis, Trichinosis, filariasis); trematodes (flukes) (Schistosomiasis, Clonorchiasis), cestodes (tape worms) (Echinococcosis, Taeniasis saginata, Cysticercosis); visceral worms, visceral larva migrans (e.g., Toxocara), eosinophilic gastroenteritis (e.g., Anisaki spp., Phocanema ssp.), cutaneous larva migrans (Ancylostona braziliense, Ancylostoma caninum).

The compounds of the present invention are accordingly useful in the prevention and treatment of a wide variety of inflammatory and immunoregulatory disorders and diseases.

In another aspect, the instant invention may be used to evaluate putative specific agonists or antagonists of chemokine receptors, including CCR-1, CCR-2, CCR-2A, CCR-2B, CCR-3, CCR-4, CCR-5, CXCR-3, and CXCR-4. Accordingly, the present invention is directed to the use of these compounds in the preparation and execution of screening assays for compounds which modulate the activity of chemokine receptors. For example, the compounds of this invention are useful for isolating receptor mutants, which are excellent screening tools for more potent compounds. Furthermore, the compounds of this invention are useful in establishing or determining the binding site of other compounds to chemokine receptors, e.g., by competitive inhibition. The compounds of the instant invention are also useful for the evaluation of putative specific modulators of the chemokine receptors, including CCR-1, CCR-2, CCR-2A, CCR-2B, CCR-3, CCR-4, CCR-5, CXCR-3, and CXCR-4. As appreciated in the art, thorough evaluation of specific agonists and antagonists of the above chemokine receptors has been hampered by the lack of availability of non-peptidyl (metabolically resistant) compounds with high binding affinity for these receptors. Thus the compounds of this invention are commercial products to be sold for these purposes.

The present invention is further directed to a method for the manufacture of a medicament for modulating chemokine receptor activity in humans and animals comprising combining a compound of the present invention with a pharmaceutical carrier or diluent.

The present invention is further directed to the use of these compounds in the prevention or treatment of infection by a retrovirus, in particular, the human immunodeficiency virus (HIV) and the treatment of, and delaying of the onset of consequent pathological conditions such as AIDS. Treating AIDS or preventing or treating infection by HIV is defined as including, but not limited to, treating a wide range of states of HIV infection: AIDS, ARC (AIDS related complex), both symptomatic and asymptomatic, and actual or potential exposure to HIV. For example, the compounds of this invention are useful in treating infection by HIV after suspected past exposure to HIV by, e.g., blood transfusion, organ transplant, exchange of body fluids, bites, accidental needle stick, or exposure to patient blood during surgery.

In a preferred aspect of the present invention, a subject compound may be used in a method of inhibiting the binding of a human immunodeficiency virus to a chemokine receptor, such as CCR-5 and/or CXCR-4, of a target cell, which comprises contacting the target cell with an amount of the compound which is effective at inhibiting the binding of the virus to the chemokine receptor.

The subject treated in the methods above is a mammal, preferably a human being, male or female, in whom modulation of chemokine receptor activity is desired. "Modulation" as used herein is intended to encompass antagonism, agonism, partial antagonism and/or partial agonism. The term "therapeutically effective amount" means the amount of the subject compound that will elicit the biological or medical response of a tissue, system, animal or human that is being sought by the researcher, veterinarian, medical doctor or other clinician.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the invention or a prodrug of a compound of the invention to the individual in need of treatment.

Combined therapy to modulate chemokine receptor activity and thereby prevent and treat inflammatory and immunoregulatory disorders and diseases, including asthma and allergic diseases, as well as autoimmune pathologies such as rheumatoid arthritis and atherosclerosis, and those pathologies noted above is illustrated by the combination of the compounds of this invention and other compounds which are known for such utilities.

For example, in the treatment or prevention of inflammation, the present compounds may be used in conjunction with an antiinflammatory or analgesic agent such as an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non-steroidal antiinflammatory agent, or a cytokine-suppressing antiinflammatory agent, for example with a compound such as acetaminophen, asprin, codiene, fentanyl, ibuprofen, indomethacin, ketorolac, morphine, naproxen, phenacetin, piroxicam, a steroidal analgesic, sufentanyl, sunlindac, tenidap, and the like. Similarly, the instant compounds may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levo-desoxy-ephedrine; an antitussive such as codeine, hydrocodone, caramiphen, carbetapentane, or dextramethorphan; a diuretic; and a sedating or non-sedating antihistamine.

The present invention is further directed to combinations of the present compounds with one or more agents useful in the prevention or treatment of AIDS. For example, the compounds of this invention may be effectively administered, whether at periods of pre-exposure and/or post-exposure, in combination with effective amounts of the AIDS antivirals, immunomodulators, anti-infectives, or vaccines known to those of ordinary skill in the art.

| Drug Name | Manufacturer | Indication |
|---|---|---|
| ANTIVIRALS | | |
| 097 | Hoechst/Bayer | HIV infection, AIDS, ARC (non-nucleoside reverse transcriptase inhibitor) |

-continued

| Drug Name | Manufacturer | Indication |
|---|---|---|
| 141 W94 | Glaxo Wellcome | HIV infection, AIDS, ARC (protease inhibitor) |
| 1592U89 | Glaxo Wellcome | HIV infection, AIDS, ARC |
| Acemannan | Carrington Labs (Irving, TX) | ARC |
| Acyclovir | Burroughs Wellcome | HIV infection; AIDS, ARC, in combination with AZT |
| AD-439 | Tanox Biosystems | HIV infection, AIDS, ARC |
| AD-519 | Tanox Biosystems | HIV infection, AIDS, ARC |
| Adefovir dipivoxil | Gilead Sciences | HIV infection |
| AL-721 | Ethigen (Los Angeles, CA) | ARC, PGL HIV positive, AIDS |
| Alpha Interferon | Glaxo Wellcome | Kaposi's sarcoma, HIV in combination w/Retrovir |
| Ansamycin LM 427 | Adria Laboratories (Dublin, OH) Erbamont (Stamford, CT) | ARC |
| Antibody which neutralizes pH labile alpha aberrant Interferon | Advanced Biotherapy Concepts (Rockville, MD) | AIDS, ARC |
| AR177 | Aronex Pharm | HIV infection, AIDS, ARC |
| beta-fluoro-ddA | Nat'l Cancer Institute | AIDS-associated diseases |
| (−) 6-Chloro-4(S)-cyclopropylethynyl-4(S)-trifluoro-methyl-1,4-dihydro-2H-3,1-benzoxazin-2-one | Merck | HIV infection, AIDS, ARC (non-nucleoside reverse transcriptase inhibitor) |
| CI-1012 | Warner-Lambert | HIV-1 infection |
| Cidofovir | Gilead Science | CMV retinitis, herpes, papillomavirus |
| Curdlan sulfate | AJI Pharma USA | HIV infection |
| Cytomegalovirus immune globin | MedImmune | CMV retinitis |
| Cytovene Ganciclovir | Syntex | sight threatening CMV peripheral CMV retinitis |
| Delaviridine | Pharmacia-Upjohn | HIV infection, AIDS, ARC (protease inhibitor) |
| Dextran Sulfate | Ueno Fine Chem. Ind. Ltd. (Osaka, Japan) | AIDS, ARC, HIV positive asymptomatic |
| ddC Dideoxycytidine | Hoffman-La Roche | HIV infection, AIDS, ARC |
| ddI Dideoxyinosine | Bristol-Myers Squibb | HIV infection, AIDS, ARC; combination with AZT/d4T |
| DMP-450 | AVID (Camden, NJ) | HIV infection, AIDS, ARC (protease inhibitor) |
| EL10 | Elan Corp, PLC (Gainesville, GA) | HIV infection |
| Efavirenz, DMP-266 | DuPont-Merck Pharmaceuticals | HIV infection, AIDS, ARC (non-nucleoside reverse transcriptase inhibitor) |
| Famciclovir | Smith Kline | herpes zoster, herpes simplex |
| FTC | Emory University | HIV infection, AIDS, ARC (reverse transcriptase inhibitor) |

-continued

| Drug Name | Manufacturer | Indication |
|---|---|---|
| GS 840 | Gilead | HIV infection, AIDS, ARC (reverse transcriptase inhibitor) |
| GW 141 | Glaxo Welcome | HIV infection, AIDS, ARC (protease inhibitor) |
| GW 1592 | Glaxo Welcome | HIV infection, AIDS, ARC (reverse transcriptase inhibitor) |
| HBY097 | Hoechst Marion Roussel | HIV infection, AIDS, ARC (non-nucleoside reverse transcriptase inhibitor) |
| Hypericin | VIMRx Pharm. | HIV infection, AIDS, ARC |
| Recombinant Human Interferon Beta | Triton Biosciences (Almeda, CA) | AIDS, Kaposi's sarcoma, ARC |
| Interferon alfa-n3 | Interferon Sciences | ARC, AIDS |
| Indinavir | Merck | HIV infection, AIDS, ARC, asymptomatic HIV positive, also in combination with AZT/ddI/ddC |
| ISIS 2922 | ISIS Pharmaceuticals | CMV retinitis |
| KNI-272 | Nat'l Cancer Institute | HIV-assoc. diseases |
| Lamivudine, 3TC | Glaxo Wellcome | HIV infection, AIDS, ARC (reverse transcriptase inhibitor); also with AZT |
| Lobucavir | Bristol-Myers Squibb | CMV infection |
| Nelfinavir | Agouron Pharmaceuticals | HIV infection, AIDS, ARC (protease inhibitor) |
| Nevirapine | Boeheringer Ingleheim | HIV infection, AIDS, ARC (protease inhibitor) |
| Novapren | Novaferon Labs, Inc. (Akron, OH) | HIV inhibitor |
| Peptide T Octapeptide Sequence | Peninsula Labs (Belmont, CA) | AIDS |
| Trisodium Phosphonoformate | Astra Pharm. Products, Inc | CMV retinitis, HIV infection, other CMV infections |
| PNU-140690 | Pharmacia Upjohn | HIV infection, AIDS, ARC (protease inhibitor) |
| Probucol | Vyrex | HIV infection, AIDS |
| RBC-CD4 | Sheffield Med. Tech (Houston TX) | HIV infection, AIDS, ARC |
| Ritonavir | Abbott | HIV infection, AIDS, ARC (protease inhibitor) |
| Saquinavir | Hoffmann-LaRoche | HIV infection, AIDS, ARC (protease inhibitor) |
| Stavudine; d4T Didehydrodeoxy-thymidine | Bristol-Myers Squibb | HIV infection, AIDS, ARC |
| Valaciclovir | Glaxo Wellcome | genital HSV & CMV infections |
| Virazole Ribavirin | Viratek/ICN (Costa Mesa, CA) | asymptomatic HIV positive, LAS, ARC |
| VX-478 | Vertex | HIV infection, AIDS, ARC |
| Zalcitabine | Hoffmann-La Roche | HIV infection, AIDS, ARC, with AZT |

| Drug Name | Manufacturer | Indication |
|---|---|---|
| Zidovudine; AZT | Glaxo Wellcome | HIV infection, AIDS, ARC, Kaposi's sarcoma, in combination with other therapies |
| IMMUNO-MODULATORS | | |
| AS-101 | Wyeth-Ayerst | AIDS |
| Bropirimine | Pharmacia Upjohn | advanced AIDS |
| Acemannan | Carrington Labs, Inc. (Irving, TX) | AIDS, ARC |
| CL246,738 | American Cyanamid Lederle Labs | AIDS, Kaposi's sarcoma |
| EL10 | Elan Corp, PLC (Gainesville, GA) | HIV infection |
| Gamma Interferon | Genentech | ARC, in combination w/TNF (tumor necrosis factor) |
| Granulocyte Macrophage Colony Stimulating Factor | Genetics Institute Sandoz | AIDS |
| Granulocyte Macrophage Colony Stimulating Factor | Hoeschst-Roussel Immunex | AIDS |
| Granulocyte Macrophage Colony Stimulating Factor | Schering-Plough | AIDS, combination w/AZT |
| HIV Core Particle Immunostimulant | Rorer | seropositive HIV |
| IL-2 Interleukin-2 | Cetus | AIDS, in combination w/AZT |
| IL-2 Interleukin-2 | Hoffman-La Roche Immunex | AIDS, ARC, HIV, in combination w/AZT |
| IL-2 Interleukin-2 (aldeslukin) | Chiron | AIDS, increase in CD4 cell counts |
| Immune Globulin Intravenous (human) | Cutter Biological (Berkeley, CA) | pediatric AIDS, in combination w/AZT |
| IMREG-1 | Imreg (New Orleans, LA) | AIDS, Kaposi's sarcoma, ARC, PGL |
| IMREG-2 | Imreg (New Orleans, LA) | AIDS, Kaposi's sarcoma, ARC, PGL |
| Imuthiol Diethyl Dithio Carbamate | Merieux Institute | AIDS, ARC |
| Alpha-2 Interferon | Schering Plough | Kaposi's sarcoma w/AZT, AIDS |
| Methionine-Enkephalin | TNI Pharmaceutical (Chicago, IL) | AIDS, ARC |
| MTP-PE Muramyl-Tripeptide | Ciba-Geigy Corp. | Kaposi's sarcoma |
| Granulocyte Colony Stimulating Factor | Amgen | AIDS, in combination w/AZT |
| Remune | Immune Response Corp. | immunotherapeutic |
| rCD4 Recombinant Soluble Human CD4 | Genentech | AIDS, ARC |
| rCD4-IgG hybrids | | AIDS, ARC |
| Recombinant Soluble Human CD4 | Biogen | AIDS, ARC |
| Interferon Alfa 2a | Hoffman-La Roche | Kaposi's sarcoma AIDS, ARC, in combination w/AZT |
| SK&F106528 Soluble T4 | Smith Kline | HIV infection |
| Thymopentin | Immunobiology Research Institute | HIV infection |
| Tumor Necrosis Factor; TNF | Genentech | ARC, in combination w/gamma Interferon |

| Drug Name | Manufacturer | Indication |
|---|---|---|
| ANTI-INFECTIVES | | |
| Clindamycin With Primaquine | Pharmacia Upjohn | PCP |
| Fluconazole | Pfizer | cryptococcal meningitis, candidiasis |
| Pastille Nystatin Pastille | Squibb Corp. | prevention of oral candidiasis |
| Ornidyl Eflornithine | Merrell Dow | PCP |
| Pentamidine Isethionate (IM & Iv) | LyphoMed (Rosemont, IL) | PCP treatment |
| Trimethoprim | | antibacterial |
| Trimethoprim/sulfa | | antibacterial |
| Piritrexim | Burroughs Wellcome | PCP treatment |
| Pentamidine isethionate for inhalation | Fisons Corporation | PCP prophylaxis |
| Spiramycin | Rhone-Poulenc | cryptosporidial diarrhea |
| Intraconazole-R51211 | Janssen Pharm. | histoplasmosis; cryptococcal meningitis |
| Trimetrexate | Warner-Lambert | PCP |
| OTHER | | |
| Daunorubicin | NeXstar, Sequus | Karposi's sarcoma |
| Recombinant Human Erythropoietin | Ortho Pharm. Corp. | severe anemia assoc. with AZT therapy |
| Recombinant Human Growth Hormone | Serono | AIDS-related wasting, cachexia |
| Leukotriene B4 Receptor Antagonist | — | HIV infection |
| Megestrol Acetate | Bristol-Myers Squibb | treatment of anorexia assoc. w/AIDS |
| Soluble CD4 Protein and Derivatives | — | HIV infection |
| Testosterone | Alza, Smith Kline | AIDS-related wasting |
| Total Enteral Nutrition | Norwich Eaton Pharmaceuticals | diarrhea and malabsorption related to AIDS |

It will be understood that the scope of combinations of the compounds of this invention with AIDS antivirals, immunomodulators, anti-infectives or vaccines is not limited to the list in the above Table, but includes in principle any combination with any pharmaceutical composition useful for the treatment of AIDS.

Preferred combinations are simultaneous or alternating treatments of with a compound of the present invention and an inhibitor of HIV protease and/or a non-nucleoside inhibitor of HIV reverse transcriptase. An optional fourth component in the combination is a nucleoside inhibitor of HIV reverse transcriptase, such as AZT, 3TC, ddC or ddI. Preferred agents for combination therapy include: Zidovudine, Lamivudine, Stavudine, Efavirenz, Ritonavir, Nelfinavir, Abacavir, Indinavir, 141-W94 (4-amino-N-((2 syn,3S)-2-hydroxy-4-phenyl-3-((S)-tetrahydrofuran-3-yloxycarbonylamino)-butyl)-N-isobutyl-benzenesulfonamide), N-(2(R)-hydroxy-1(S)-indanyl)-2(R)-phenylmethyl-4-(S)-hydroxy-5-(1-(4-(2-benzo[b]furanylmethyl)-2(S)-N'(t-butylcarboxamido)-piperazinyl))-pentaneamide, and Delavirdine. A preferred inhibitor of HIV protease is indinavir, which is the sulfate salt of N-(2(R)-hydroxy-1(S)-indanyl)-2(R)-phenylmethyl-4-(S)-hydroxy-5-(1-(4-(3-pyridyl-methyl)-2(S)-N'-(t-butylcarbo-xamido)-piperazinyl))-pentaneamide ethanolate, and is synthesized according to U.S. Pat. No. 5,413,999. Indinavir is generally administered at a dosage of 800 mg three times a day. Other preferred inhibitors of HIV protease include nelfinavir and ritonavir. Preferred non-nucleoside inhibitors of HIV reverse transcriptase include (−) 6-chloro-4(S)-cyclopropylethynyl-4(S)-trifluoromethyl-1,4-dihydro-2H-3,1-benzoxazin-2-one, which may be prepared by methods disclosed in EP 0,582,455. The preparation of ddC, ddI and AZT are also described in EPO 0,484,071. These combinations may have unexpected effects on limiting the spread and degree of infection of HIV. Preferred combinations with the compounds of the present invention include the following: (1) Zidovudine and Lamivudine; (2) Stavudine and Lamivudine; (3) Efavirenz; (4) Ritoavir; (5) Nelfinavir; (6) Abacavir; (7) Indinavir; (8) 141-W94; and (9) Delavirdine. Preferred combinations with the compounds of the present invention further include the following (1) indinavir, with efavirenz or (−) 6-chloro-4(S)-cyclopropylethynyl-4(S)-trifluoromethyl-1,4-dihydro-2H-3,1-benzoxazin-2-one, and, optionally, AZT and/or 3TC and/or ddI and/or ddC; (2) indinavir, and any of AZT and/or ddI and/or ddC.

In such combinations the compound of the present invention and other active agents may be administered separately or in conjunction. In addition, the administration of one element may be prior to, concurrent to, or subsequent to the administration of other agent(s).

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of The present invention are employed. (For purposes of this application, topical application shall include mouth washes and gargles.)

The pharmaceutical composition and method of the present invention may further comprise other therapeutically active compounds as noted herein which are usually applied in the treatment of the above mentioned pathological conditions.

In the treatment or prevention of conditions which require chemokine receptor modulation an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Several methods for preparing the compounds of this invention are illustrated in the following Schemes and Examples. Starting materials are made from known procedures or as illustrated.

Several methods for preparing the compounds of this invention are illustrated in the following Schemes and Examples.

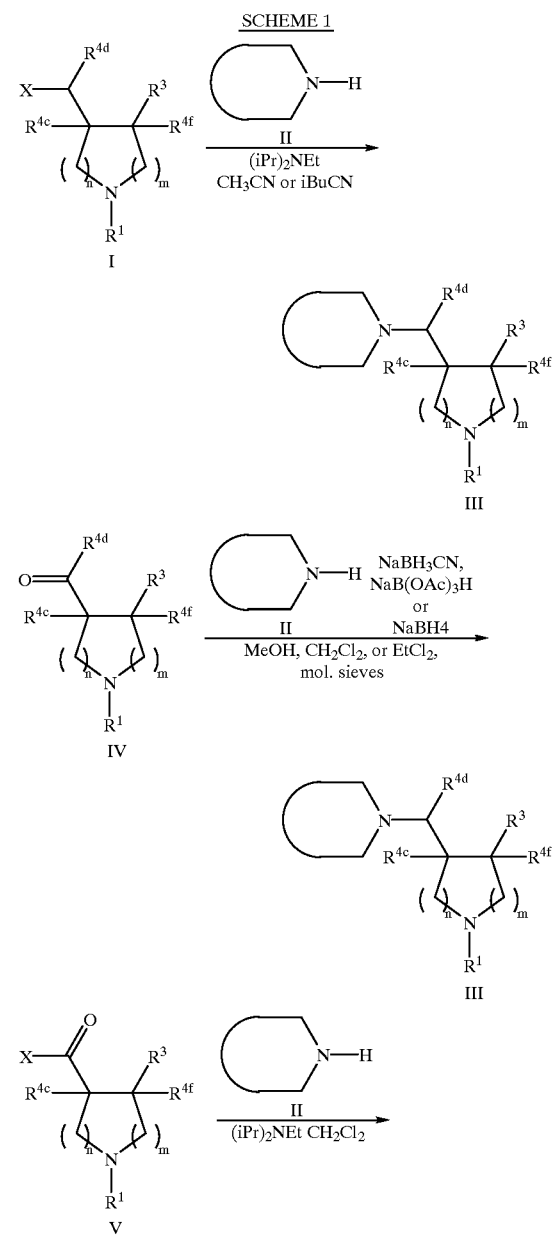

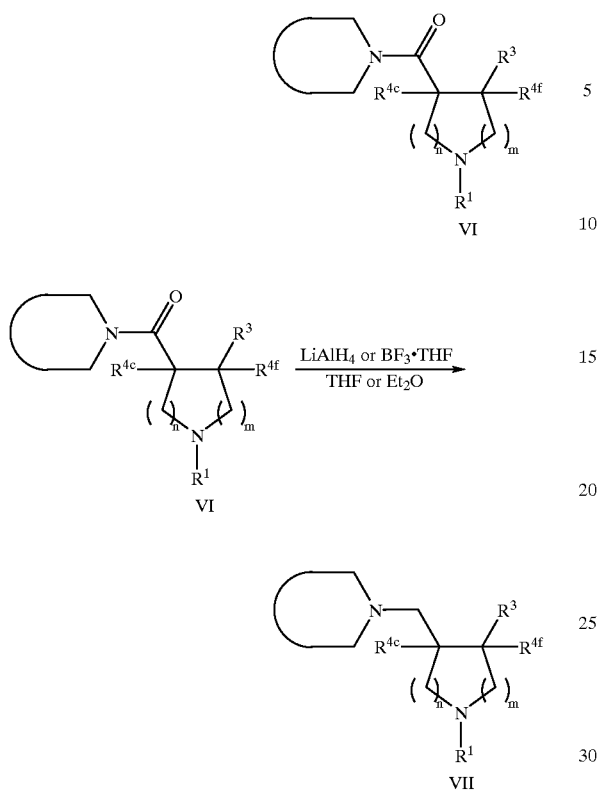

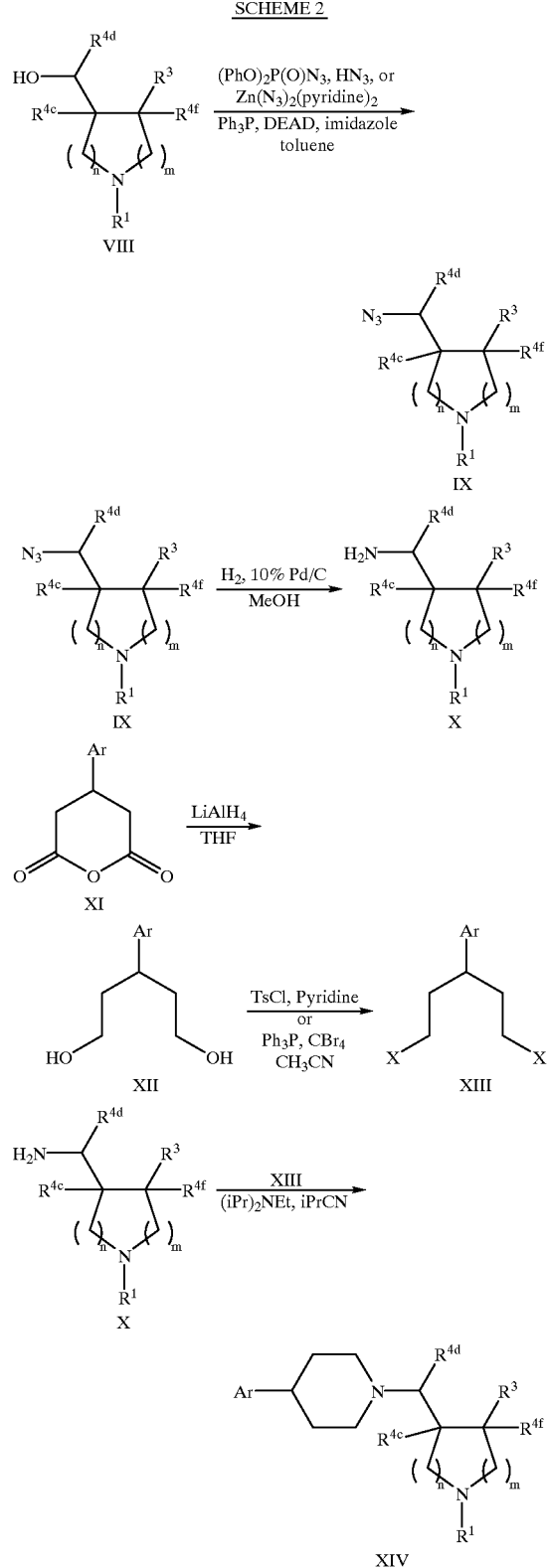

SCHEME 2

In one protocol, the compounds of the present invention are prepared by alkylating heterocycle I (wherein X is a leaving group such as, for example, bromide, iodide, methanesulfonate, p-toluenesulfonate, trifluoromethanesulfonate) with cyclic amine II under appropriate conditions to provide compound III (Scheme 1). Cyclic amine II is available commercially or can be prepared using the methods given below.

Alternatively, heterocycle IV, bearing a carbonyl group, can be combined with the cyclic amine II and the intermediate imine or iminium species is reduced to tertiary amine III under homogenous conditions (e.g. using sodium cyanoborohydride, sodium borohydride, or sodium triacetoxyborohydride) or in the presence of hydrogen and a heterogeneous catalyst (e.g. palladium on carbon or Raney nickel).

In an alternative embodiment of the present invention, heterocycle V, bearing an activated acyl side chain (wherein X', for example, is a chloride or bromide atom, or is a hydroxybenzotriazole residue from activation of the corresponding carboxylic acid with HOBt in the presence of a suitable carbodiimide) is allowed to react with cyclic amine II to provide the corresponding tertiary amide VI (Scheme 1). Compound VI can then be treated with a suitable reducing agent (e.g. diborane; borane in THF; borane dimethylsulfide, or lithium aluminum hydride) to provide the desired product VII.

An alternative preparation of the target compounds is carried out as shown in Scheme 2. Treatment of alcohol VIII with zinc azide bis(pyridine) complex in the presence of triphenylphosphine and diethyl azodicarboxylate, or with diphenylphosphoryl azide, or with hydrazoic acid, provides azide IX. Reduction of IX, for example, with hydrogen and palladium on carbon, affords primary amine X. This amine can be doubly alkylated with a bis-electrophile such as XIII under basic conditions, to provide the desired chemokine receptor modulator XIV. Bis-electrophiles can be prepared from substituted glutaric anhydride derivatives such as XI by reduction to diol XII followed by double activation, using, for example, p-toluenesulfonyl chloride in pyridine, or triphenylphosphine carbon tetrabromide in acetonitrile, to provide XIII (where X=Br or OTs).

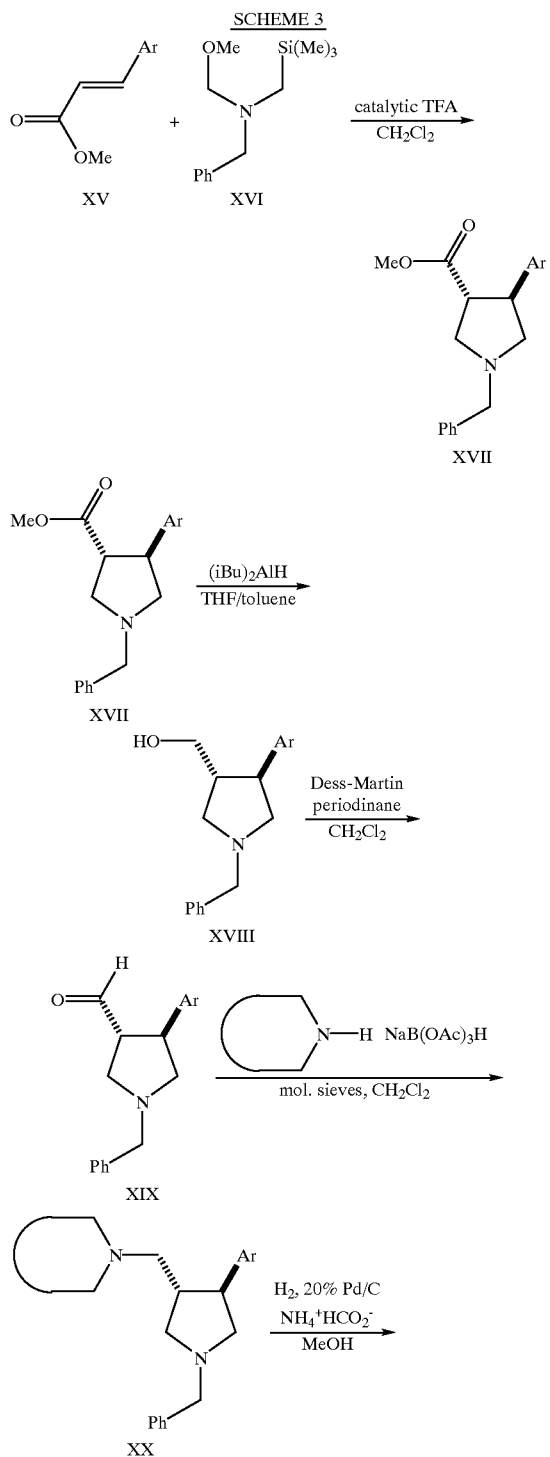

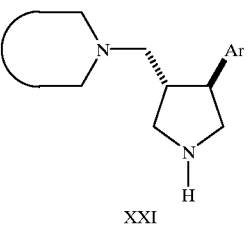

The preparation of compounds within the scope of the instant invention which bear a 1,3,4-trisubstituted pyrrolidine framework is detailed in Scheme 3. Treatment of a trans-cinnamic ester such as XV with N-benzyl-N-methoxymethyl-N-(trimethylsilyl)-methylamine (XVI) in the presence of a substoichiometric amount of an acid such as TFA, titanium tetrafluoride lithium fluoride or cesium fluoride according to the procedure of Padwa et al (*J. Org. Chem.* 1987, 52, 235) preferentially affords the 3,4-trans pyrrolidine XVII. Executing this sequence starting from the cis-cinnamic- ester results in preferential formation of the 3,4-cis pyrrolidine. Reduction of ester XVII, for example, with diisobutylaluminum hydride, lithium aluminium hydride, or sodium bis(2-methoxyethoxy)aluminum hydride, provides the primary alcohol XVIII. Oxidation to the aldehyde XIX can be carried out under numerous conditions, such as with the Dess-Martin periodinane, with DMSO and oxalyl chloride at low temperature, followed by triethylamine (Swern oxidation), or with various chromium trioxide-based reagents (see March J. "Advanced Organic Chemistry", 4th ed., John Wiley & Sons, New York, pp. 1167–1171 (1992)). Reductive amination with cyclic amine II then provides diamine XX, which can itself be a chemokine receptor modulator. Alternatively, The N-benzyl group is cleaved in a hydrogen atmosphere in the presence of 20% palladium on carbon to provide the secondary amine XXI.

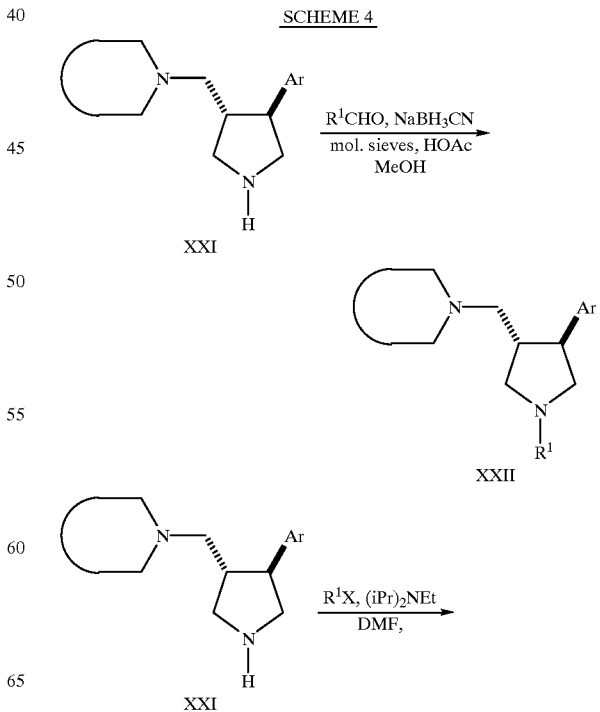

-continued

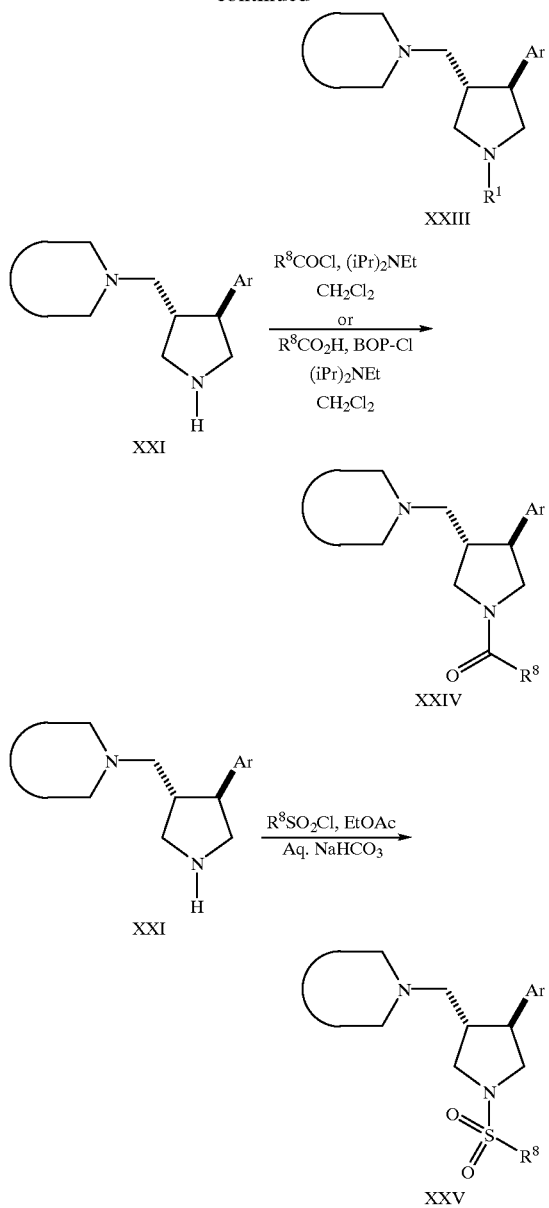

SCHEME 5

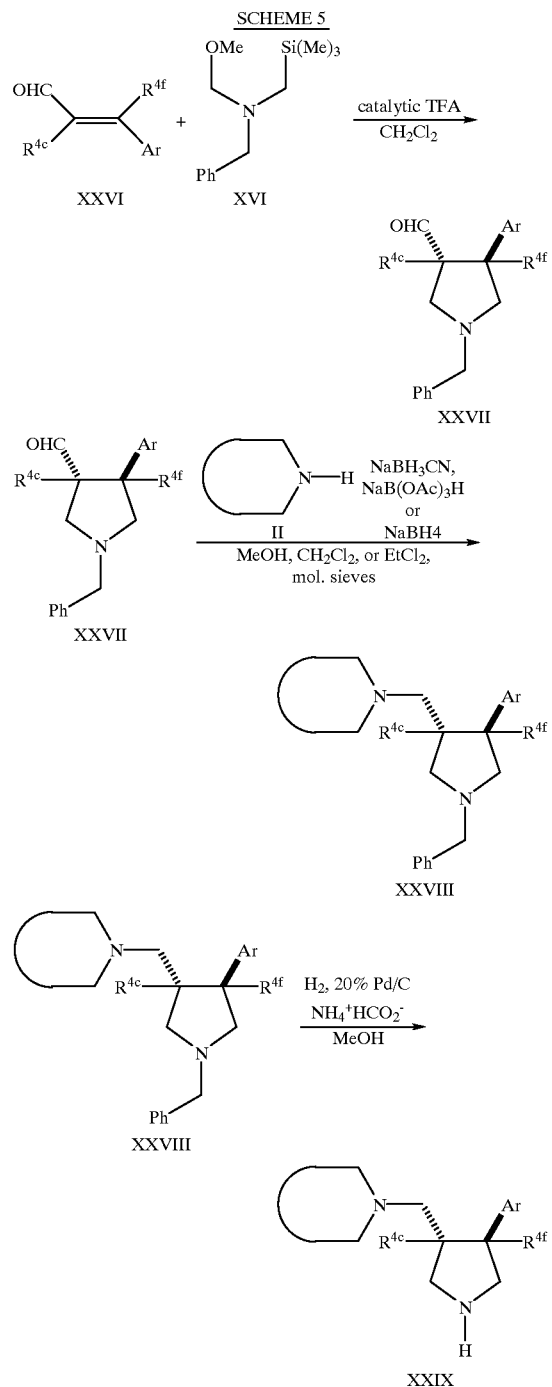

The 1-unsubstituted pyrrolidine XXI may be further functionalized as shown in Scheme 4. Reductive amination with suitable aldehydes under standard conditions provides the tertiary amine XXII. For subunits with a primary or secondary aliphatic carbon linked to nitrogen, alkylation with a suitable halide, methanesulfonate, p-toluene-sulfonate, etc. is carried out under standard conditions to provide N-alkylated pyrrolidine XXIII. Alternatively, secondary amine XXI are acylated with, for example, acid chlorides or bromides, or activated esters such as HOBt esters (prepared by treating the precursor carboxylic acid with a suitable carbodiimide in the presence of HOBt) or a symmetrical or mixed anhydride, to give amide XXIV. The sulfonamide XXV is prepared under standard conditions by exposing XXI to an alkyl or aryl sulfonyl chloride in the presence of a suitable base to neutralize the formed hydrogen chloride.

Compounds possessing geminal substituents on positions 3 or 4 (or on both C3 and C4) of the pyrrolidine ring are prepared by the method shown in Scheme 5. Cycloaddition of unsaturated aldehyde XXVI with reagent XVI in the presence of a substoichiometric amount of an acid such as TFA or titanium tetrafluoride according to the procedure of Padwa et al (*J. Org. Chem.* 1987, 52, 235) provides pyrrolidine aldehyde XXVII. Reductive amination with cyclic amine II under standard conditions provides diamine XXVIII, which is debenzylated in a hydrogen atmosphere with palladium on charcoal catalyst, to afford the secondary pyrrolidine XXIX. Compound XXIX is further functionalized according to the chemistry detailed in Scheme 4 for compound XXI.

SCHEME 6

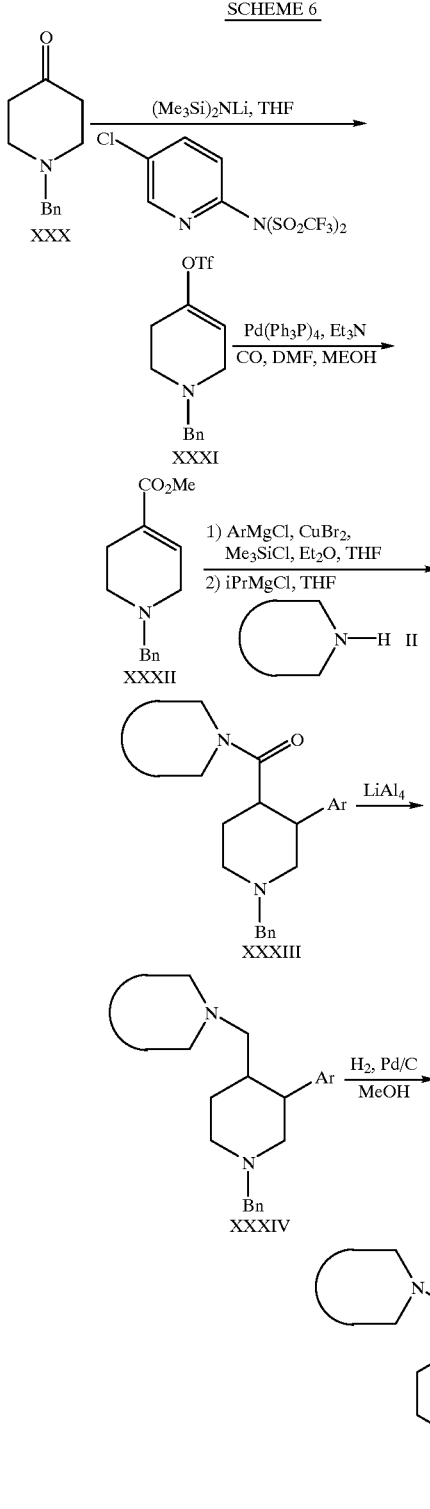

catalysed carbonylation in the presence of methanol then affords unsaturated ester XXII. Conjugate addition of an aryl magnesiu-m halide reagent in the presence of a copper catalyst and chlorotrimethylsilane to this species, followed by treatment with the magnesium salt of a suitable cyclic amine, then yields amide XXXIII. Reduction with lithium aluminum hydride or borane-THF affords the tertiary amine IV, which is hydrogenated under standard conditions to the secondary piperidine XKXV. This compound is alkylated, acylated or sulfonated by analogy to the conditions described for compound XXI in Scheme 4.

SCHEME 7

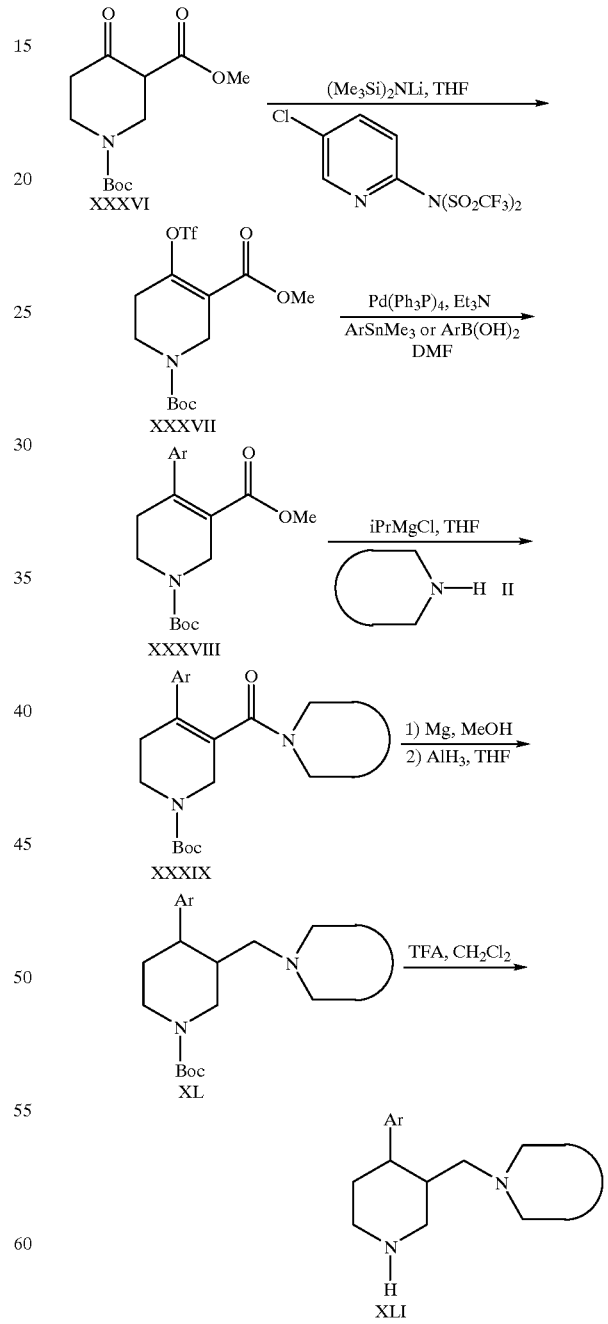

The synthesis of one framework for piperidine-based chemokine receptor modulators is given in Scheme 6. Enolate formation of the 4-piperidone derivative XXX followed by formation of the vinyl triflate with either 2-[N,N-bis(trifluoromethylsulfonyl)amino]-5-chloropyridine or with N-phenyltriflimide provides compound XI. Palladium- Synthesis of a piperidine derivative with an alternate presentation of the 3- and 4-substituents is given in Scheme 7. Formation of the enolate of ketoester X)=VI (prepared from commercially available 3-carbomethoxy-4-oxopiperidine and Boc anhydride) followed by addition of either 2-[N,N-bis(trifluoro-methylsulfonyl)amino]-5-chloropyridine or N-phenyltriflimide provides vinyl triflate XII. Palladium-mediated. coupling with a suitable aryl stannane or aryl boronic acid provides unsaturated ester XXXVIII. Treatment of this compound with the magnesium salt of a suitable cyclic amine then affords amide X)=, which can be reduced successively with magnesium metal in methanol followed by alane in THF, to provide the tertiary amine XL. Removal of the Boc group under standard acidic conditions yields secondary amine XLI, which can be alkylated, acylated or sulfonated by analogy to the conditions described for compound XXI in Scheme 4.

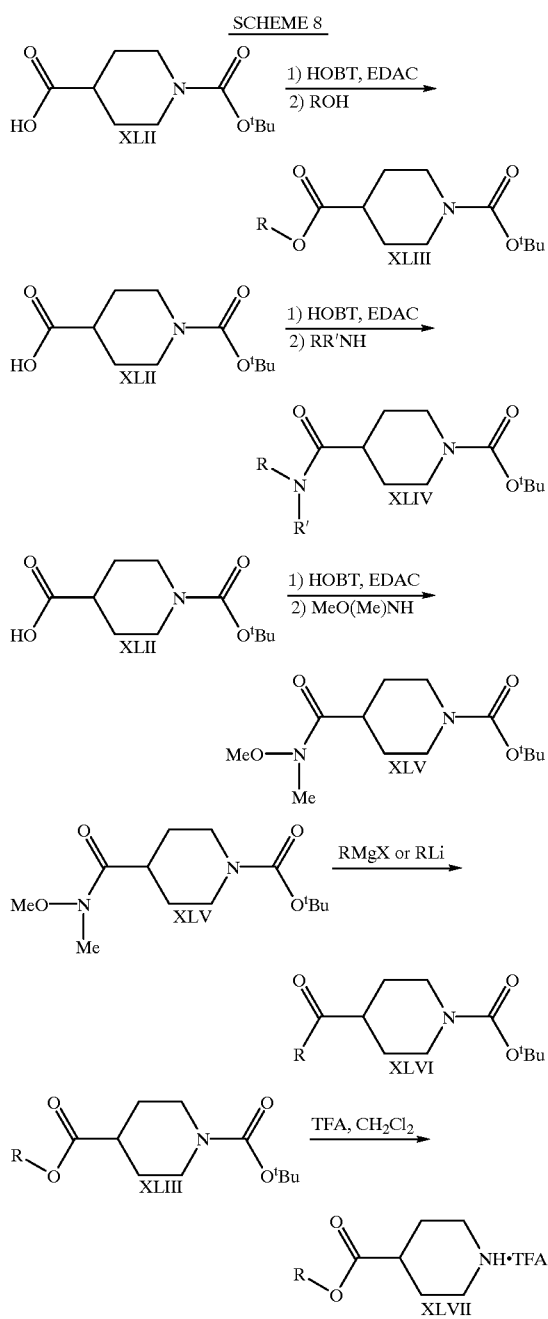

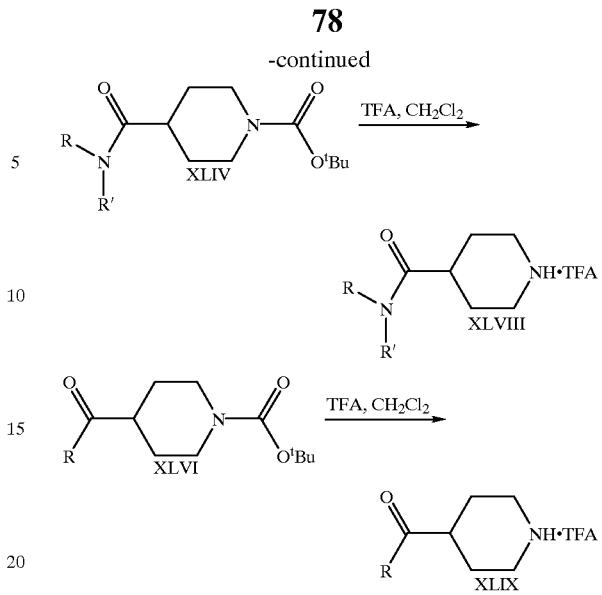

The cyclic amine II employed in the preceding Schemes can be obtained commercially in many cases or is prepared by a number of procedures. For example, as shown in Scheme 8, compound XLII, the N-t-butoxycarbonyl protected form of isonipecotic acid (4-piperidine-2carboxylic acid) is activated under standard conditions, for example with a carbodiimide, and converted into ester XLIII or amide XLIV. Alternatively, acid XLII is converted into the N-methyl-N-methoxy amide, XLV, which upon reaction with organomagnesium and organolithium reagents forms the ketone XLVI. The Boc group of XLIII, XLIV and XLVI is removed under acidic conditions to provide secondary amines XLVII, XLVIII and XLIX, respectively.

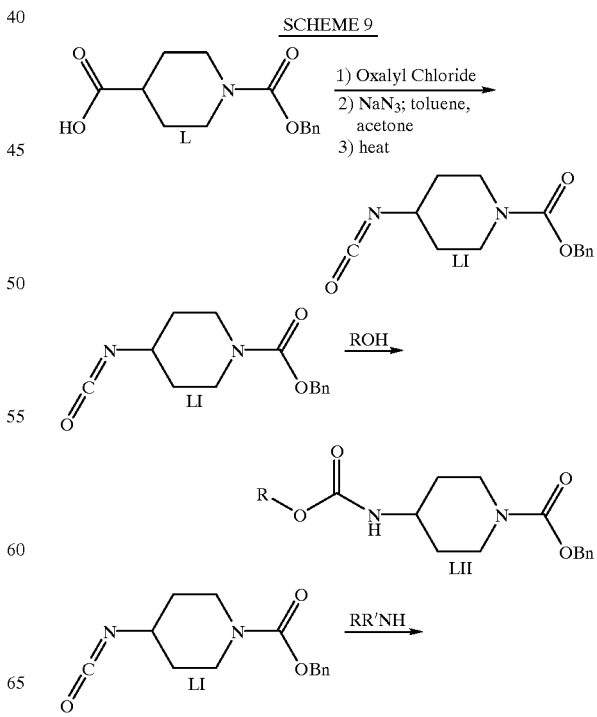

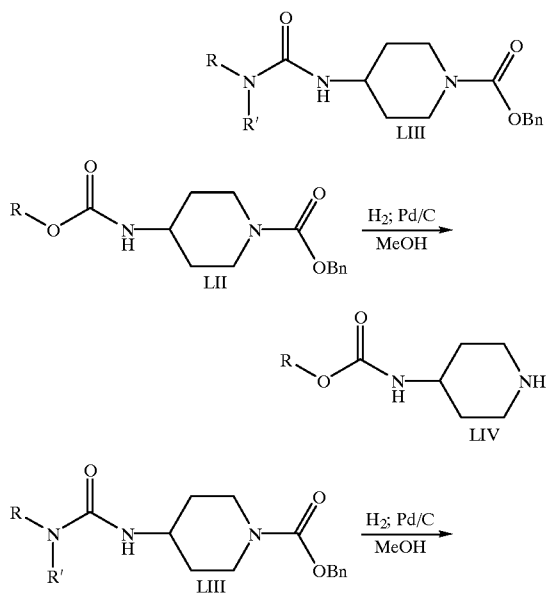

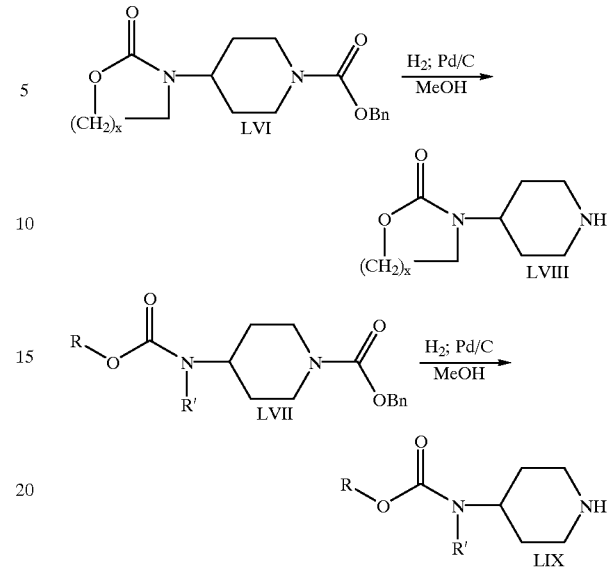

Alternatiely, CBZ-protected piperidine L is allowed to react with oxalyl chloride and then sodium azide, to provide the corresponding acyl azide, which can then be thermally rearranged to isocyanate LI (Scheme 9). Compound LI is treated with an alcohol ROH or an amine RR'NH to form carbamate LII or urea LIII, respectively, each of which is deprotected with hydrogen in the presence of palladium on carbon to secondary amines LIV or LV.

If the carbamate LII has R =-(CH$_2$)xCH$_2$Cl, where x=1–3, then treatment with a suitable base, such as sodium hydride, lithium 5 hexamethyldisilazide or potassium t-butoxide, can induce cyclization to compound LVI (Scheme 10). For other R groups, carbamate LII is treated with an alkylating agent R'X, where R'=primary or secondary alkyl, allyl, propargyl or benzyl, while X=bromide, iodide, tosylate, mesylate or trifluoromethanesulfonate, in the presence of a suitable base, such as sodium hydride, lithium hexamethyldisilazide or potassium t-butoxide, to give derivative LVII; a similar process can be employed for urea LIII. In each case, removal of the CBZ protecting group under standard conditions provides the secondary amines LVIII and LIX.

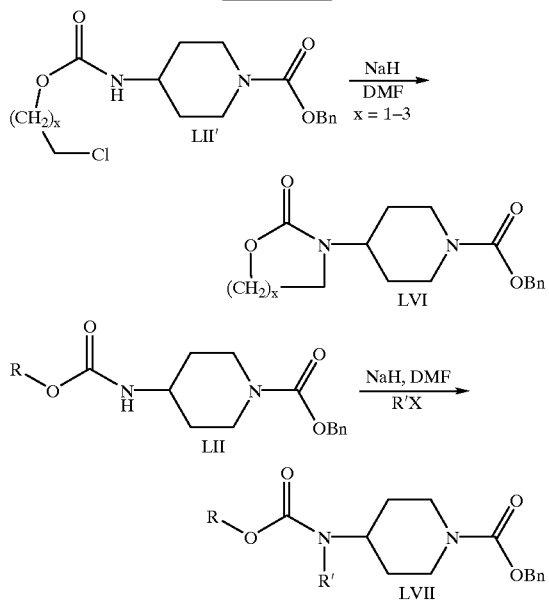

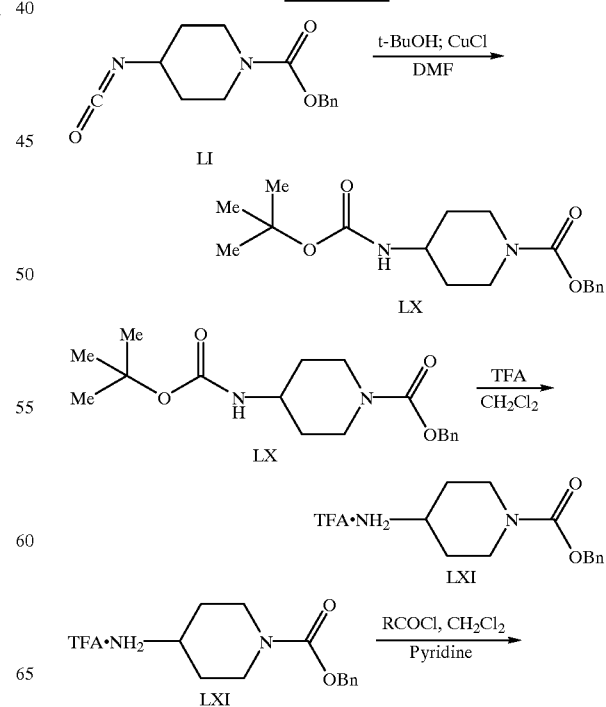

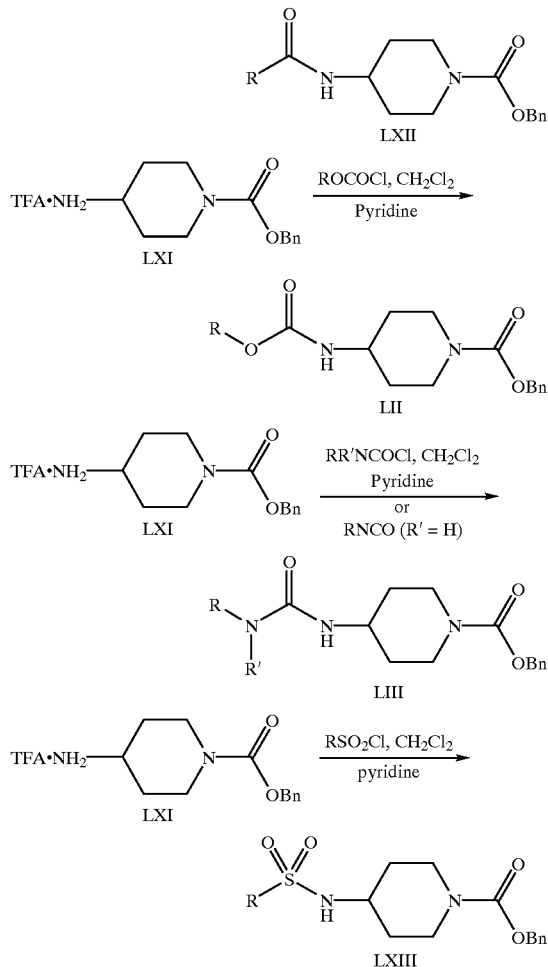

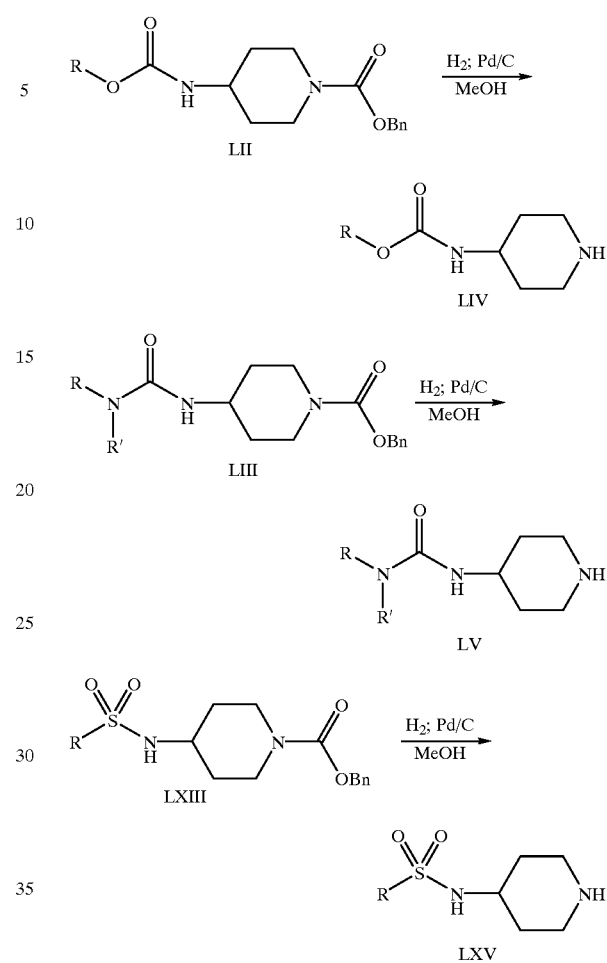

Additional derivatization of a piperidine with nitrogen functionality at C4 is carried out as shown in Scheme 11. For example, if the ring nitrogen is protected with a CBZ group, as with isocyanate LI, treatment with tert-butyl alcohol in the presence of copper(I) chloride, provides Boc derivative LX. This compound is selectively deprotected to the free amine LXI. This amine is acylated with an acid chloride, a chloroformate, an isocyanate, or a carbamyl chloride, to provide compounds LXII, LII or LIII. Alternatively, amine LXI is sulfonated with an alkyl or arylsulfonyl chloride, to give sulfonamide LXIII. Compounds LXII and LXIII optionally is alkylated under the conditions given above for the preparation of LVII from LII.

As shown in Scheme 12, removal of the CBZ group under reductive conditions gives the desired secondary amines LIV, LYIV, LV, and LXV.

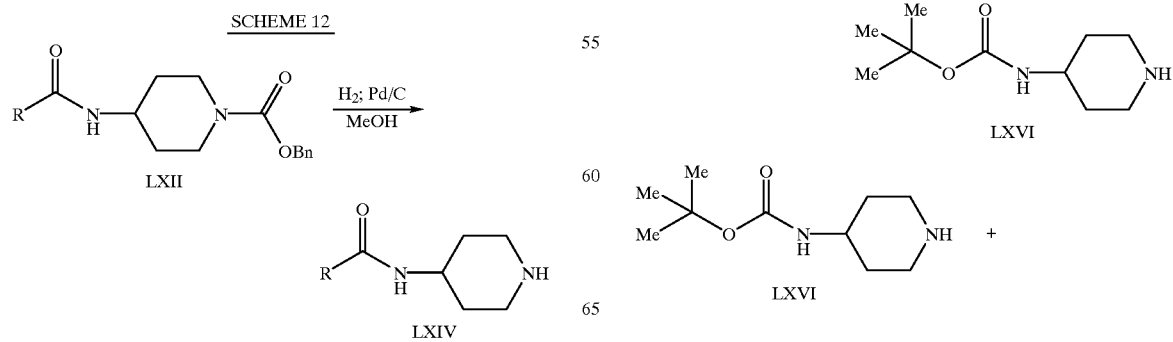

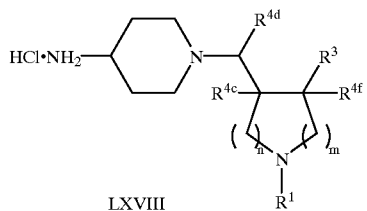

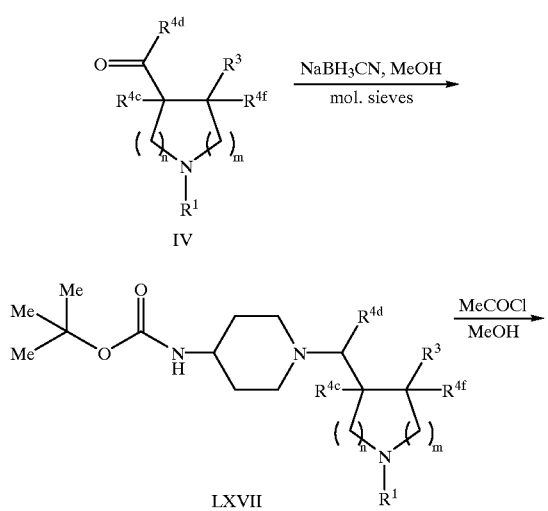

Functionalization of the piperidine also is carried out after it has been coupled with an Ni substituent. For example, as shown in Scheme 13, reductive deprotection of CBZ derivative IL yields secondary amine LXVI. Reductive amination with an appropriate aldehyde or ketone fragment (such as IV) provides piperidine ILVII. Removal of the Boc group under acidic conditions then gives primary amine LXVIII. This primary amine is then functionalized by analogy to the chemistry given in Scheme 11. Cyclic amines (compound II) with spirocyclic functionality are prepared in some cases using methods described in the literature; more specifically, as described in Ong, H. H. et al, Journal of Medicinal Chemistry, 1983,26, 981–986, and Chen et al, U.S. Pat. No. 5,536,716. None of the compounds in these references are disclosed to be chemokine receptor modulators.

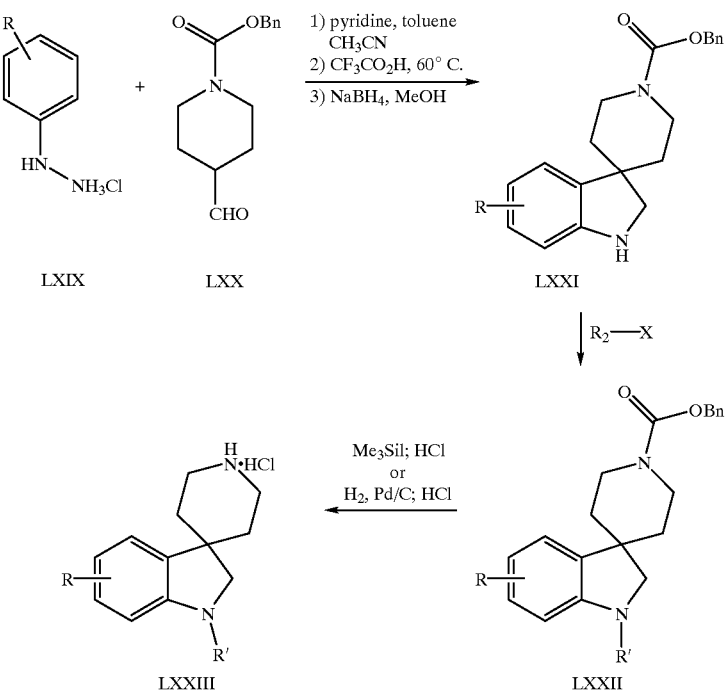

Substituted spiro(indoline-3,4'-piperidine) derivatives can be prepared as shown in Scheme 14 starting from the substituted phenylhydrazine LXIX and the aldyhyde LXX. Following the Fischer indole reaction and reduction of the intermediate imine with a mild reducing agent such as sodium borohydride, the indoline LXXI can be combined with an electrophile such as an acyl chloride or a sulfonyl chloride. The protecting group on compound LXXII, for example a benzyloxycarbonyl group, can be removed by treatment with hydrogen in the presence of palladium on carbon or by exposure to trimethylsilyl iodide, to give the deprotected substituted spiro(indoline-3,4'-piperidine) LXXIII.

of the chloride with the 2-bromothiophenol IVIII provides allylic sulfide LXXIX, which can be cyclized under radical conditions to give spiro(2,3-dihydrobenzothiophene-3,4'-piperidine) LXXX. Cleavage of the t-butoxycarbonyl group under standard conditions, such as trifluoroacetic acid, then provides the desired spirocycle LXXXI.

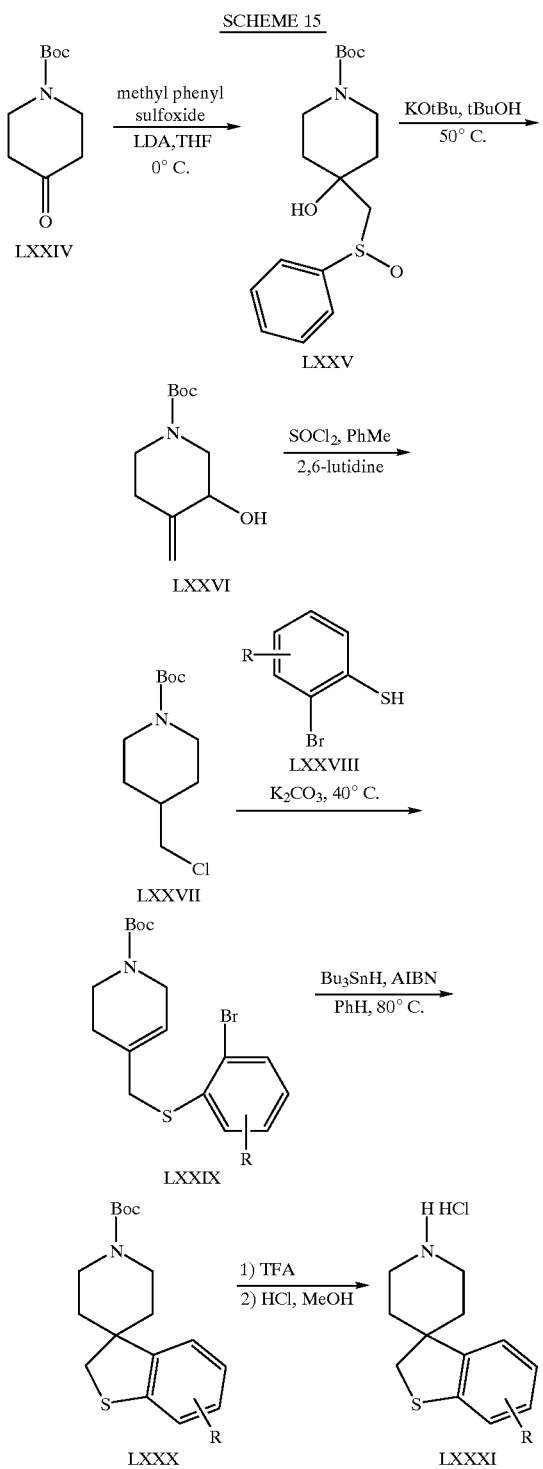

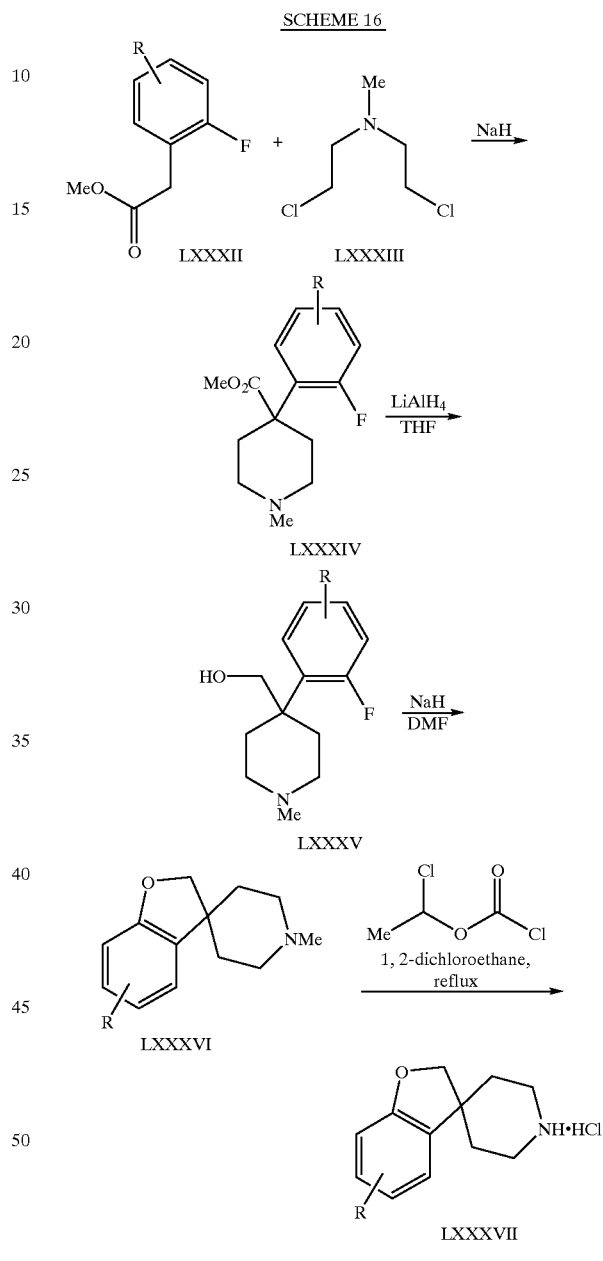

Preparation of spiro(2,3-dihydrobenzothiophene-3,4'-piperidine) derivatives is shown in Scheme 15. Reaction piperidone LXXIV with the lithium salt of methyl phenyl sulfoxide affords adduct DLXV. Base-mediated elimination-rearrangement and basic cleavage provides the allylic alcohol LXXVI. The alcohol is converted to rearranged allylic chloride LXXVII with thionyl chloride in toluene in the presence of 2,6-lutidine as a proton scavenger. Displacement Spiro(2,3-dihydrobenzofiiran-3,4'-piperidine) derivatives are prepared as illustrated in Scheme 16. Treatment of an appropiately substituted ester of 2-fluorophenylacetate (LXXXII) with mechiorethamine hydrochloride (LXXXIII) under basic conditions provides piperidine LXXXIV, which on treatment with a strong reducing agent such as lithium aluminum hydride produces the corresponding 4-(hydroxymethyl) compound LXXXV. Cyclization with base provides benzofuiran LXXXVI, and cleavage of the N-methyl group is then carried out using 1-chloroethyl chloroformate or other suitable N-demethylating agents, to provide the desired intermediate LXXXVII.

SCHEME 17

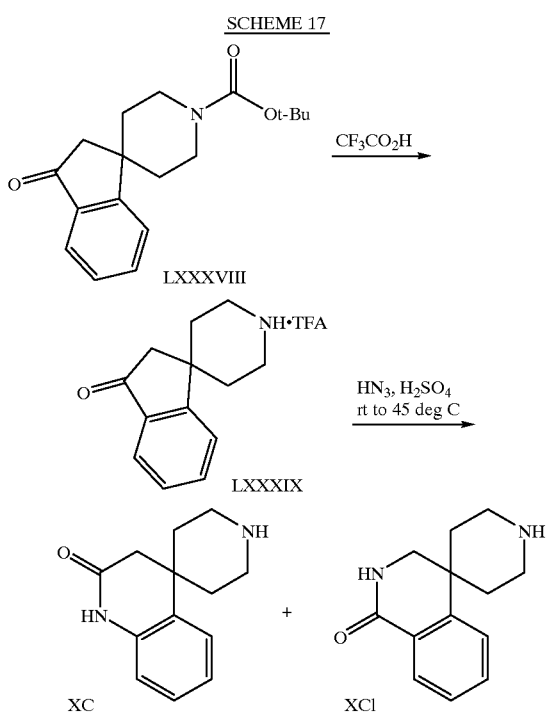

Spiro(2-oxo-1,2,3,4-tetrahydroquinoline-4,4'-piperidine) and spiro(1-oxo-1,2,3,4-tetrahydroisoquinoline-4,4'-piperidine) are prepared as shown in Scheme 17. Starting from the spiro(2-oxoindane-3,4'-piperidine) LXVIII (described in Claremon, D. A. et al, European Patent 0 431943 943 A2, Evans, B. E. et al, U.S. Pat. No. 5,091,387, Davis, L. et al, U.S. Pat. No. 4,420,485, all of which are incorporated by reference, and Parham et al, *Journal of Organic Chemistry*, 41,2628 (1976)), deprotection of the piperidine nitrogen is carried out by treatment with acid, for example trifluoroacetic acid, to provide ketone LXXXIX. After protection as the trifluoroacetamide, the product is exposed to hydrazoic acid in the presence of sulfuric acid. Heating of this mixture effects a Schmidt rearrangement, to provide both tetrahydroquinoline XC and the tetrahydroisoquinoline XCI. These spiro compounds are then separated and coupled to functionalized aldehydes by the methodology given above.

Cyclic amines (compound II) which are 4-arylpiperazines functionality are prepared using methods described in the following Schemes. Starting materials are made from known procedures or as illustrated. Substituted purines are prepared as disclosed in U.S. Pat. No. 5,057,517; imidazo(1.2-a) pyrazinyl, as disclosed in U.S. Pat. No. 4,242,344; (1,2,4)-triazolo(1.5-a)pyrazinyl as disclosed in *J. Org. Chem*, 1974, 39, 2143 and *J. C. S. Perkin I*, 1980, 506; 1,7-naphthyridinyl as disclosed in *J. Org. Chem.* 1963,28, 1753; furo(3.2-c) pyridinyl as disclosed in *J. Heterocyclic Chem.*, 1982,19, 1207; and substituted 6-H-7,8-dihydro-thiopyrano(3.2-d) pyrimidyl as disclosed in *Arch. Int. Pharmacodyn.* 1986, 280, pp302–313.

Optionally, Compound III formed in the alkylation step is further modified in subsequent reactions. In one illustration of such an approach, the piperazine fragment may contain a nitro group, which is reduced to the amine after the coupling step. The resulting amine is further modified by acylation to provide the desired compounds. The piperazine fragment may also contain a protecting group such as a benzyl ester or a t-butyl ester. After reductive amination the protecting group is removed and the resulting acid is further reacted to provide additional analogs. Alternatively, the aldehyde portion may also contain a protecting group such as a t-butoxycarbonyl for an amino function. After reductive amination, the t-butoxycarbonyl group is removed by treatment with a strong acid such as trifluoroacetic acid, formic acid or hydrochloric acid and the resulting amine may be acylated to provide other analogs.

The piperazine starting materials used in the coupling reaction are prepared using methods described in the literature; more specifically as described in U.S. Pat. No. 5,057, 517; U.S. Pat. No. 4,242,344; *J. Org. Chem*, 1974, 39, 2143 and J. C. S. Perkin I, 1980, 506; *J. Org. Chem.* 1963,28, 1753; J. Heterocyclic Chem., 1982,19, 1207; *Arch. Int. Pharmacodyn.* 1986, 280, pp302–313 ; Meurer, L.. C. et al., *J. Med. Chem.*, 1992, 35, 3845–3857. None of these published compounds are disclosed to be chemokine receptor modulators. Alternatively, the piperazine substrates is prepared as illustrated in Schemes 18–21.

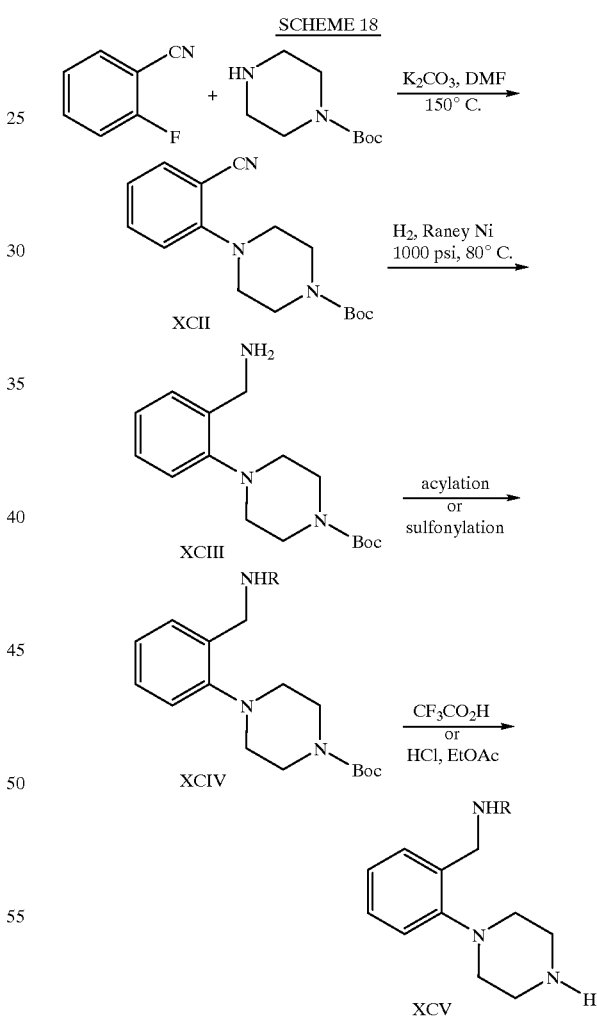

Substituted 4-arylpiperazines are prepared from appropriate fluorobenzene derivative as shown in Scheme 18. Thus, reaction of 2-fluorobenzonitrile with 1-t-butoxycarbonylpiperazine in the presence of a base such as $K_2CO_3$ gives 1-t-butoxycarbonyl-4-(2-cyanophenyl)-piperazine (compound XCII). Reduction of the cyano group by hydrogenation in the presence of Raney nickel or by other known methods gives benzyl amine XCIII, which is acylated or sulfonylated, to provide piperazine XCIV. The t-butoxycarbonyl protecting group is removed under acidic conditions, for example by treatment with trifluoroacetic acid or anhydrous HCl to give 1-unsubstituted piperazine XCV which can be used in the reductive amination or alkylation steps described in Scheme 1. Similar reactions using 2-chloro-nitrobenzene in the place of 2-fluorobenzonitrile provides compounds containing a substituted aniline. Analogs containing a benzoic acid or its derivatives are prepared by substituting 2-fluorobenzoic acid in this sequence.

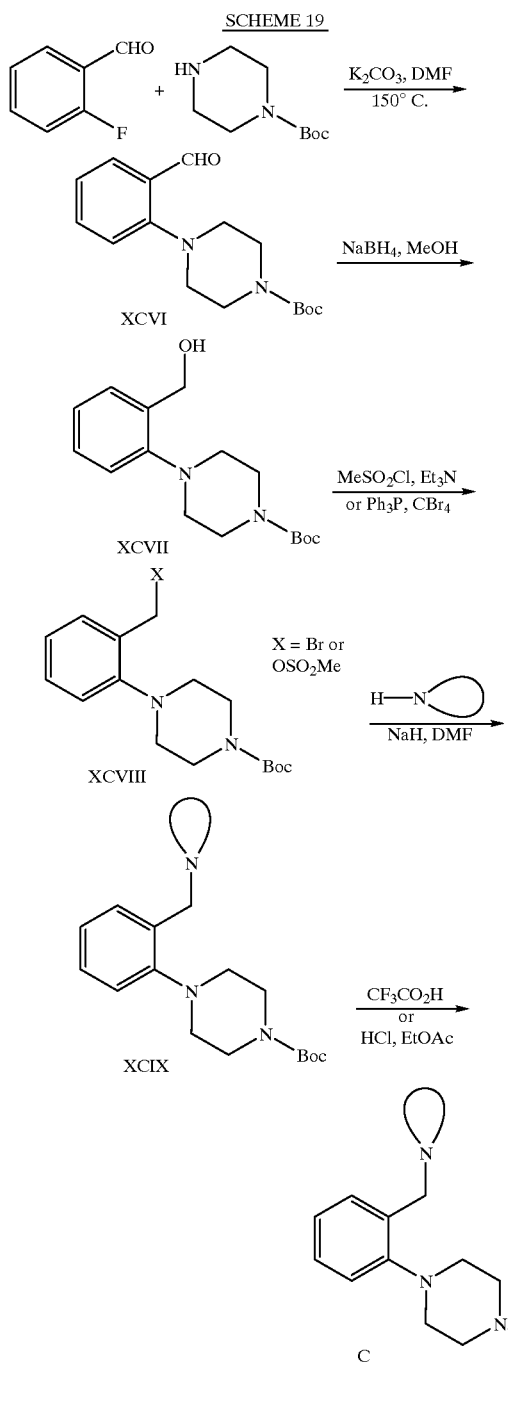

Arylpiperazine derivatives containing heterocyclic substituents are synthesized as shown in Scheme 19. Reaction between 2-fluorobenzaldehyde and 1-t-butoxycarbonylpiperazine gives 1-t-butoxycarbonyl-4-(2-formylphenyl)-piperazine (compound XCVI). Reduction of this aldehyde and treatment of the alcohol XCVII with methanesulfonyl chloride gives XCVIII (X=mesylate), while treatment of XCVII with triphenylphosphine and carbon tetrabromide gives XCVIII (X=bromide). Displacement of the leaving group by a heterocycle such as imidazole in the presence of a base provides piperazine XCIX. Removal of the t-butoxycarbonyl protecting group under standard anhydrous acidic conditions furnishes compound C which is used in the coupling reactions described in Scheme I.

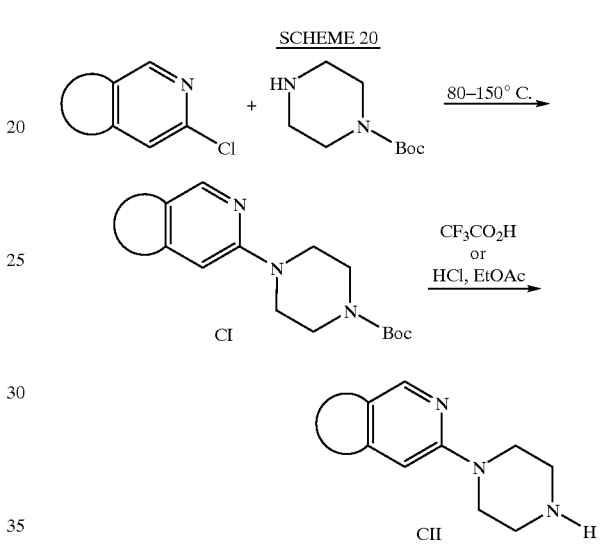

Preparation of piperazines containing a heteroaryl substituent is outlined in Scheme 20, Reaction of 1-t-butoxycarbonyl-piperazine with a chloro substituted heteroaromatic compound such as 8-chloro-1,7-naphthyridine or 8-chloro-(1,2,4)-triazolo(1,5-a)pyrazine gives N-protected piperazine CI. Removal of the t-butoxycarbonyl protecting group under standard conditions by treatment with acid provides piperazine CII for use in the coupling steps outlined in Scheme 1.

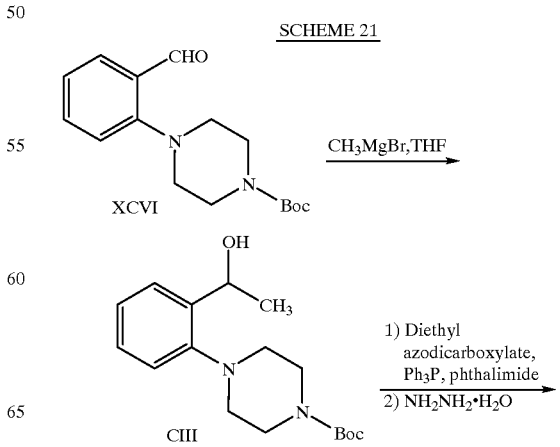

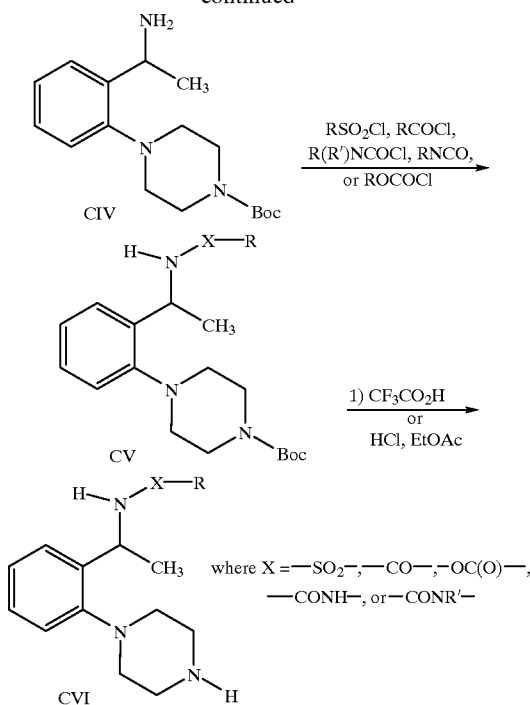

Preparation of piperazines containing a heteroaryl substituent on a branched side chain is outlined in Scheme 21. Reaction of aldehyde XCVI whose synthesis is described in Scheme 19 with a carbon nucleophile such as a Grignard reagent, for example methyl magnesium bromide, provides the benzylic alcohol CIII. Conversion to the benzylic amine can be carried out by treatment of the alcohol with potassium phthalimide in the presence of diethyl azodicarboxylate and triphenyl phosphine, followed by heating with hydrazine hydrate, to give the free primary amine CIV. Conversion to CIV can also be carried out by activation of the hydroxyl group with a alkyl- or arylsulfonyl chloride, such as p-toluenesulfonyl chloride, to give a benzylic sulfonate ester. The sulfonate ester is then displaced with ammonia or a primary or secondary amine. Alternatively, the sulfonate ester can be displaced with a suitable salt of the azide anion, such as sodium azide, zinc azide, or tetrabutylammonium azide, and the resulting alkyl azide can be reduced to primary amine CIV with hydrogen gas in the presence of a suitable catalyst, such as 5% palladium on carbon. Alternatively, the alkyl azide can be reduced by treatment with triphenyl phosphine followed by hydrolysis to afford CIV. Benzylic amine CIV can then be derivatized with a number of electrophilic reagents, such as alkyl or aryl sulfonyl chlorides, carboxylic acid chlorides, carboxylic acid anhydrides, alkyl chloroformates, carbamyl chlorides or alkyl or aryl isocyanates to provide sulfonamides, carboxamides, ureas, or carbamates CV. These intermediates can then be deprotected under acidic conditions to remove the Boc group to provide free piperazine CVI for use in the coupling reactions described in Scheme I.

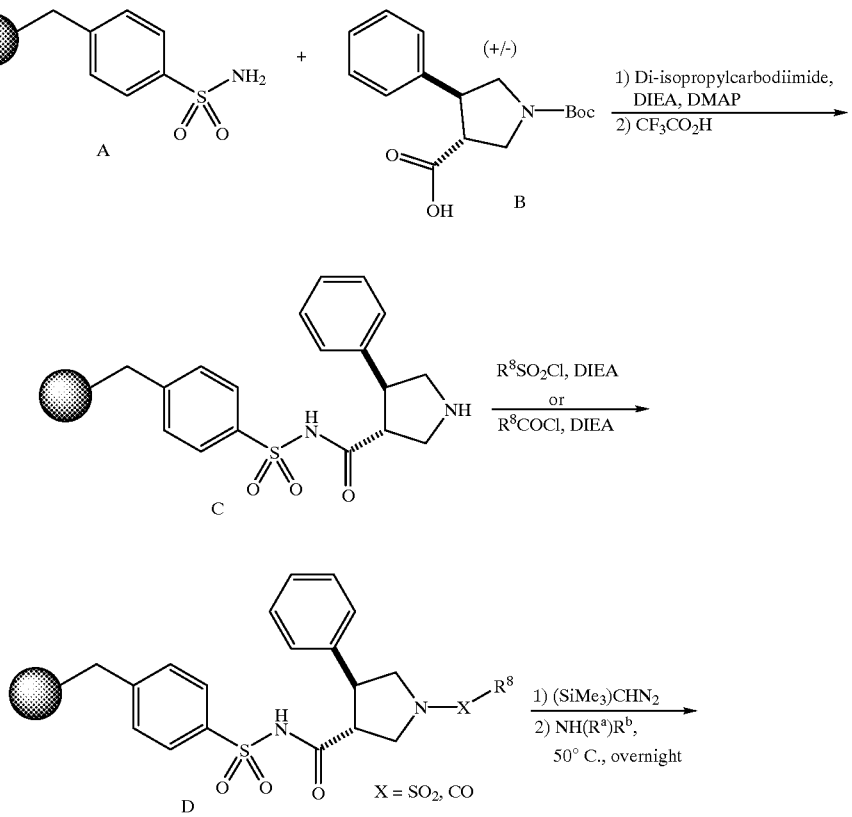

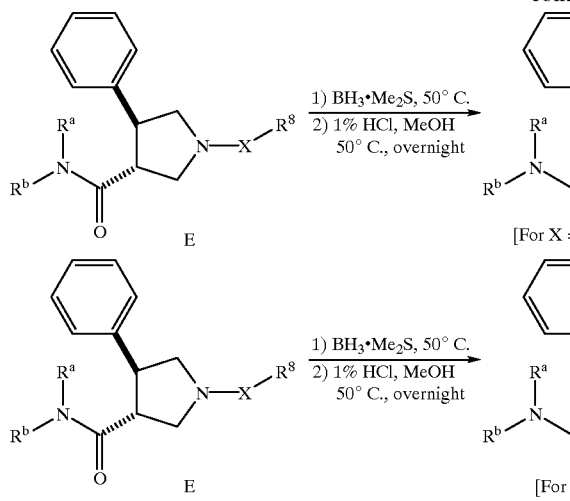

Preparation of target pyrrolidines using solid support technology is outlined in Scheme 22. Coupling of intermediate B to a commercially available 4-sulfamylbenzoyl polystyrene resin A (or a alkyl sulfamyl resin) is carried out with di-isopropylcarbodiimide or with other activating agents, for example dicyclohexylcarbodiimide, EDAC, oxalyl chloride, etc. Agents that result in the formation of the symmetrical anhydride from B (which then serves as the acylating agent) are also suitable for this purpose. Removal of the Boc group is carried out with trifluoroacetic acid or other acidic reagents, to give resin-bound pyrrolidine C. This intermediate is then coupled with sulfonyl chlorides or carbonyl chlorides in the presence of a suitable amine, preferably a hindered tertiary amine such as diisopropylethylamine (DIEA), lutidine, DBU, etc., to provide the N-functionalized pyrrolidine D. Alkylation of the acyl sulfonamide nitrogen can be carried out with trimethylsilyldiazomethane, diazomethane, with bromoacetonitrile in the presence of DBU and DMF, or under Mitsunobu conditions with a phenol such as pentafluorophenol. Reaction of the resulting N-alkylated intermediate with an amine NH(Ra)Rb at a temperature between 0 and 140° C., preferably around 50° C., for 4–24 hr, preferably about 14 hr, then cleaves the pyrrolidine from the resin as amide E. Reduction of the newly formed amide (and other amide functionality, if present) with borane methyl sulfide complex (or other hydride reducing agents, such as borane-pyridine, borane-THF, lithium aluminum hydride, lithium di-(sec) butyl borohydride, etc) followed by hydrolysis with dilute hydrogen chloride in methanol at a temperature between 0 and 140° C., preferably around 50°0 C., for 4–24 hr, preferably about 14 hr, provides either sulfonamide F or amine G.

Cyclic amines (compound II) from Scheme 1 which are spirocyclic piperidines are prepared using azacyclic starting materials prepared using methods described in the literature; more specifically, as described in Claremon, D. A. et al, European Patent Publication 0 431 943, Evans, B. E. et al U.S. Pat. No. 5,091,387, Davis, L. et al, U.S. Pat. No. 4,420,485, and Parham et al, *Journal of Organic Chemistry*, 41, 2628 (1976). None of the compounds in the foregoing references are alleged to be chemokine receptor modulators.

In some cases the order of carrying out the foregoing reaction schemes may be varied to facilitate the reaction or to avoid unwanted reaction products. The following examples are provided for the purpose of further illustration only and are not intended to be limitations on the disclosed invention.

EXAMPLE 1

1-Benzenesulfonyl-3-(RS)-(spiro[2,3-dihydrobenzothiophene-3,4'-piperidin-1'-yl])methyl-4-(SR)-phenylpyrrolidine Step A: 1-Phenylmethyl-3-(SR)-carbomethoxy-4-(SR)-phenylpyrrolidine A solution of 1.98 g (12.2 mmol) of methyl (Z)-cinnamate and 5.80 g (24.4 mmol) N-(methoxymethyl)-N-(trimethylsilylmethyl)-benzylamine in 30 mL of $CH_2Cl_2$ at 0° C. was treated with 20 drops of trifluoroacetic acid and stirred cold for 1 h. The reaction mixture was partitioned between 200 mL of ether and 100 mL of sat'd $NaHCO_3$ and the layers were separated. The organic layer was washed with 100 mL of sat'd NaCl, dried over $MgSO_4$ and concentrated in vacuo. Flash chromatography on 150 g of silica gel using 20:1 v/v CH2Cl2/ether as the eluant afforded 2.61 g (72%) of the title compound as an oil. 1H NMR (500 MHz, CDCl3): δ2.83 (t, J=8.7, 1H), 3.09–3.19 (m, 6H), 3.16 (s, 3H), 3.46–3.51 (m, 1H), 3.73–3.79 (m, 3H), 7.19–7.42 (10H). Mass Spectrum ($NH_3$-CI): m/z 296 (M+1).

Step B: 1-Phenylmethyl-3-(SR)-hydroxymethyl-4-(SR)-phenylpyrrolidine

A solution of 2.61 g (8.8 mmol) of 1-phenylmethyl-3-(SR)-carbomethoxy-4-(SR)-phenylpyrrolidine (from Example 1, Step A) in 100 mL of THF at −78 ° C. was treated with 9.2 mL of 1.5 M diisobutyl-aluminum hydride solution in toluene. The reaction was warmed to 0 ° C. and stirred for 1 h. The reaction was quenched with 50 mL of sat'd sodium potassium tartrate solution, diluted with 100 mL of ether and stirred at rt for 20 h. The layers were separated and the organic layer was washed with 75 mL of $H_2O$, dried over $MgSO_4$ and concentrated in vacuo. Flash chromatography on 100 g of silica gel using 1:1 v/v, then 3:2 v/v EtOAc/hexanes as the eluant afforded 1.99 g (84%) of the title compound as a solid. $^1H$ NMR (500 MHz, $CDCl_3$): δ2.56–2.63 (m, 1H), 2.80 (dd, J=4.3, 9.4, 1H), 2.91–2.98 (m, 2H), 3.05 (dd, J=6.9, 9.6, 1H), 3.27 (dd, J=5.0, 10.7, 1H), 3.44 (dd, J=5.5, 10.8, 1H), 3.62 (q, J=9.0, 1H), 3.76 (ABq, J=24.2, 2H), 7.22–7.40 (10H). Mass Spectrum ($NH_3$-CI): m/z 268 (M+1).

Step C: 3-(SR)-Hydroxymethyl-4-(SR)-phenylpyrrolidine

A mixture of 302 mg (1.1 mmol) of 1-benzyl-3-(SR)-hydroxymethyl-4-(SR)-phenylpyrrolidine (from Example 1, Step B) and 154 mg of 20% Pd(OH)2/C was hydrogenated at 40 psi on a Paar apparatus for 1 h. The catalyst was filtered and the filtrate was concentrated in vacuo to afford 196 mg (98%) of the title compound as an oil. 1H NMR (500 MHz, CDCl$_3$): δ2.53–2.57 (m, 2H), 3.06–3.60 (6H), 7.24–7.35 (5H). Mass Spectrum (NH3-CI): m/z 178 (M+1).

Step D: 1-(Benzenesulfonyl)-3-(SR)-benzenesulfonyloxymethyl-4-(SR)-phenylpyrrolidine A solution of 196 mg (1.1 mmol) of 3-(SR)-hydroxymethyl-4-(SR)-phenylpyrrolidine (from Example 1, Step C) and 27 mg (0.2 mmol) of 4-(N,N-dimethylamino)pyridine in 5 mL of pyridine at 0 °C. was treated with 488 mg (2.8 mmol) of benzenesulfonyl chloride. The cooling bath was removed and the resulting mixture was stirred at rt for 1 h. The reaction mixture was treated with an additional 290 mg of benzenesulfonyl chloride and the resulting mixture was stirred at rt for 1 h. The reaction mixture was partitioned between 50 mL of ether and 20 mL of sat'd CuSO$_4$ and the layers were separated. The organic layer was washed with 30 mL of H$_2$O, 30 mL of sat'd NaCl, dried over MgSO$_4$ and concentrated in vacuo. Flash chromatography on 30 g of silica gel using 3:2 v/v hexanes/ether afforded 340 mg (67%) of the title compound as a solid. $^1$H NMR (500 MHz, CDCl$_3$): δ2.65–2.72 (m, 1H), 3.21 (dd, J=7.8, 10.3, 1H), 3.44–3.67 (6H), 6.94–7.90 (15H). Mass Spectrum (NH3-CI): m/z 458 (M+1).

Step E: 1-(Benzenesulfonyl)-3-(SR)-iodomethyl-4-(SR)-phenylpyrrolidine

A solution of 234 mg (0.51 mmol) of 1-(benzenesulfonyl)-3-(SR)-benzenesulfonyloxymethyl-4-(SR)-phenylpyrrolidine (from Example 1, Step D) and 1.1 g (7.7 mmol) of sodiuim iodide in 8 mL of acetone was heated at reflux for 20 h. The reaction mixture was partitioned between 50 mL of ether and 30 mL of H$_2$O and the layers were separated. The organic layer was washed with 30 mL of sat'd NaCl and dried over MgSO$_4$. The aqueous layers were combined and extracted with 30 mL of ether. The extract was dried; the organic layers were combined. and concentrated in vacuo. Flash chromatography on 25 g of silica gel using 3:2 v/v hexanes/ether as the eluant afforded 211 mg (96%) of the title compound as an oil. $^1$H NMR (500 MHz, CDCl$_3$): δ2.43 (t, J=9.8, 1H), 2.64–2.74 (m, 2H), 3.30 (dd, J=2.5, 7.8, 1H), 3.47 (q, J=6.7, 1H), 3.67–3.74 (3H), 7.05–7.95 (1OH). Mass Spectrum (NH3-CI): m/z 428 (M+1).

Step F: 1-Benzenesulfonyl-3-(RS)-(spiro[2,3-dihydrobenzo-thiophene-3,4'-piperidin-1'-yl])methyl-4-(SR)-phenylpyrrolidine A solution of 86 mg (0.2 mmol) of 1-(benzenesulfonyl)-3-(SR)-iodomethyl-4-(SR)-phenylpyrrolidine (from Example 1, Step E) and 124 mg (0.6 mmol) of spiro[2,3-dihydrobenzothiophene]-3,4'-piperidine in 2 mL of isobutyrnitrile was heated at 100 °C. for 48 h. The reaction mixture was cooled and partitioned between 50 mL of ether and 25 mL of sat'd NaHCO3 and the layers were separated. The organic layer was dried over MgSO4 and concentrated in vacuo. Flash chromatography on 15 g of silica gel using 2:1 v/v hexanes/ether afforded 57 mg (56%) of the title compound as an oil. $^1$H NMR (500 MHz, CDCl$_3$): δ1.45–3.74 (19H), 7.02–7.96 (14H). Mass Spectrum (NH3-CI): m/z 505 (M+1).

EXAMPLE 2

1-Benzenesulfonyl-3-(RS)-(spiro[2,3-dihydrobenzothiophene-3,4'-piperidin-1'-yl])methyl-4-(SR)-phenylpvrrolidine7 S-oxide A solution of 34 mg (0.07 mmol) of 1-benzenesulfonyl-3-(RS)-(spiro [2,3-dihydrobenzothiophene-3,4'-piperidin-1'-yl])methyl-4-(SR)-phenylpyrrolidine (from Example 1) in 2 mL of THF at 0 OC was treated with a solution of 45 mg (0.07 minol) of oxone in 1 mL of H20 and the resulting mixture was stirred cold for 3 min. The reaction was quenched with 2 mL of 1:1 v/v sat'd NaHSO$_3$/sat'd NaHCO$_3$ and extracted with 4×20 mL of CH2C12. The extracts were dried over MgSO4 and concentrated in vacuo. Flash chromatography on 15 g of silica gel using 49:1 v/v CH2C12/MeOH as the eluant afforded 26 mg (74%) of the title compound as an oil. 1H NMR (500 MHz, CDCl$_3$): δ1.27–3.78 (19H), 7.01–7.96 (14H). Mass Spectrum (NH$_3$-CI): 521 (M+1).

EXAMPLE 3

1-Benzenesulfonyl-3-(RS)-(spiro[2,3-dihydrobenzothiophene-3,4'-piperidin-1'-yl])methyl-4-(SR)-phenylpyrrolidine, S,S-dioxide A solution of 12 mg (0.02 mmol) of 1-benzenesulfonyl-3-(RS)-(spiro[2,3-dihydrobenzothiophene-3,4'-piperidin-1'-yl])methyl-4-(SR)-phenylpyrrolidine (from Example 1) in 2 mL of THF at 0 °C. was treated with a solution of 32 mg (0.05 mmol) of oxone in 1 mL of H$_2$O. The cooling bath was removed and the resulting solution was stirred at rt for 30 min. The reaction was quenched with 2 mL of 1:1 v/v sat'd NaHSO$_3$/sat'd NaHCO$_3$ and extracted with 4×20 mL of CH$_2$Cl$_2$. The extracts were dried over MgSO$_4$ and concentrated in vacuo. Flash chromatography on 10 g of silica gel using 3:2 v/v hexanes/EtOAc as the eluant afforded 8 mg (60%) of the title compound as an oil. Mass Spectrum (NH$_3$-CI): 537 (M+1).

EXAMPLE 4

1-Benzenesulfonyl-3-(SR)-(spiro[2,3-dihydrobenzothiophene-3,4'-piperidin-1'-yl])methyl-4-(SR)-phenylpyrrolidine The title compound was prepared in 6 steps from methyl (Z)-cinnamate using procedures analogous to those described in Example 1. $^1$H NMR (500 MHz, CDCl$_3$): δ1.45–3.76 (m, 19H), 7.10–7.92 (m, 14H). Mass Spectrum (NH$_3$-CI): 505 (M+1).

EXAMPLE 5

1-Benzenesulfonyl-3-(SR)-(spiro[2,3-dihydrobenzothiophene-3,4$^1$-piperidin-1'-yl])methyl-4-(SR)-phenylpyrrolidine, S-oxide The title compound was prepared from 1-benzenesulfonyl-3-(SR)-(spiro[2,3-dihydrobenzothiophene-3,4'-piperidin-1'-yl])methyl-4-(SR)-phenylpyrrolidine (from Example 4) using a procedure analogous to that described in Example 2. $^1$H NMR (500 MHz, CDCl$_3$): δ1.25–3.76 (19H), 7.09–7.91 (14H). Mass Spectrum (NH$_3$-CI): 521 (M+1).

EXAMPLE 6

1-Benzenesulfonyl-3-(SR)-(spiro[2,3-dihydrobenzothiophene-3,4'-piperidin-1'-yl])methyl-4-(SR)-phenylpyrrolidine. S,S-dioxide The title compound was prepared from 1-benzenesulfonyl-3-(SR)-(spiro[2,3-dihydrobenzothiophene-3,4'-piperidin-1'-yl])methyl-4-(SR)-phenylpyrrolidine (from Example 4) using a procedure analogous to that described in Example 3. Mass Spectrum (NH$_3$-CI): 537 (M+1).

EXAMPLE 7
1-Benzenesulfonyl-3-(RS)-((4-phenyl)piperidin-1-yl)methyl-4-(SR)-phenylpyrrolidine The title compound was prepared in 6 steps from methyl (Z)-cinnamate using procedures analogous to those described in Example 1. 4-(Phenyl)piperidine was substituted for spiro[2,3-dihydrobenzo-thiophene]-3,4'-piperidine in Step 6. $^1$H NMR (500 MHz, CDCl$_3$): 67 1.69–3.73 (17H), 7.03–7.96 (15H). Mass Spectrum (NH$_3$-CI): 461 (M+1).

EXAMPLE 8
1-Benzenesulfonyl-3-(SR)-((4-phenyl)piperidin-1-yl)methyl-4-(SR)-phenylpyrrolidine The title compound was prepared in 6 steps from methyl (E)-cinnamate using procedures analogous to those described in Example 1. 4-(Phenyl)piperidine was substituted for spiro[2,3-dihydrobenzothiophene]-3,4'-piperidine in Step 6. 1H NMR (500 MHz, CDCl$_3$): δ1.29–3.75 (17H), 7.12–7.92 (15H). Mass Spectrum (NH$_3$-CI): 461 (M+1).

EXAMPLE 9
1-Phenylmethyl -3-(SR)-((4-phenyl)piperidin-1-yl)methyl-4-(SR)-phenylpyrrolidine Step A: I-Phenylmethyl-3-(RS)-formyl-4-(SR)-phenylpyrrolidine A solution of 0.87 mL (10.0 mmol) of oxalyl chloride in 50 mL of CH$_2$Cl$_2$ at −75° C. was treated with 1.10 mL (15.0 mmol) of DMSO maintaining the internal temperature below −65 ° C. The resulting mixture was stirred cold for 10 min and then 1.34 g (5.0 mmol) of 1-phenylmethyl -3-(RS)-hydroxymethyl-4-(SR)-phenylpyrrolidine (from Example 4) was added in one portion as a solid. The resulting mixture was stirred cold for 30 min and then 8.70 mL (50 mmol) of DIEA was added maintaining the internal temperature below −60 ° C. The cooling bath was removed and the reaction was allowed to warm to 0° C. The reaction was quenched with 50 mL of H$_2$O; the resulting mixture was diluted with 100 mL of CH$_2$Cl$_2$ and 50 mL and the layers were separated. The organic layer was washed with 50 mL of H$_2$O, dired over MgSO$_4$ and concentrated in vacuo. Flash chromatography on 70 g of silica gel using 4:1 v/v hexanes/ether afforded 1.00 g (75%) of the title compound as an oil.
1H NMR (300 MHz, CDCl$_3$): δ2.61 (dd, J=9.0, 7.6, 1H), 2.86 (app t, J=8.6), 2.99–3.06 (m, 1H), 3.10–3.20 (m, 2H), 3.62–3.69 (m, 1H), 3.66 and 3.69 (ABq, J=15.6, 2H), 7.23–7.40 (10H), 9.73 (d, J=1.8, 1H).

Step B: 1-Phenylmethyl -3-(SR)-((4-phenyl) piperidin-1-yl)methyl-4-(SR)-phenylpyrrolidine A solution of 680 mg (2.6 mmol) of 1-phenylmethyl -3-(RS)-formyl -4-(SR)-phenylpyrrolidine (from Example 9, Step B) and 420 mg (2.6 mmol) of (4-phenyl)piperidine in 25 mL of dichloroethane at 0° C. was treated with 635 mg (3.0 mmol) of sodium triacetoxy-borohydride. The cooling bath was removed and the resulting mixture was stirred at rt for 2h. The reaction mixture was partitioned between 100 mL of EtOAc and 50 mL of sat'd NaHCO3 and the layers were separated. The organic layer was washed with 50 mL of sat'd NaCl, dried over MgSO4 and concentrated in vacuo. Flash chromatography on 50 g of silica gel using 10:1 v/v hexanes/EtOAc+1% TEA as the eluant afforded 1.01 g of the title compound as an oil. $^1$H NMR (500 MHz, CDCl$_3$): δ1.65–2.02 (6H.), 2.42–3.03 (11H), 3.72 (AB q, J=35.4, 2H), 7.20–7.43 (m, 15H). Mass Spectrum (NH$_3$-CI): 411 (M+1).

The compounds in Examples 10–29 were prepared using procedures analogous to those described in Example 9 substituting the appropriate secondary amine for (4-phenyl) piperidine in Example 9, Step B.

EXAMPLE 10
1-Phenylmethyl-3-(SR)-(spiro[(indan-1-one-3,4'-piperidin-1'-yl])methyl-4-(SR)-phenylpyrrolidine
$^1$H NMR (500 MHz, CDCl$_3$): δ1.35 (dd, J=2.2, 12.8, 1H), 1.45 (d, J=10.8, 1H), 1.89–2.09 (4H), 2.50–2.74 (9H), 2.92–3.02 (3H), 3.72 (AB q, J=34.8, 2H), 7.19–7.41 (11H), 7.53 (d, J=7.7, 1H), 7.64 (t, J=7.3, 1H), 7.71 (d, J=7.6, 1H). Mass Spectrum (NH$_3$-CI): 451 (M+1).

EXAMPLE 11
1-Phenylmethyl -3-(RS)-(spiro[2,3-dihydrobenzothiophene-3,4'-piperidin-1'-Yll )methyl-4-(SR)-phenylpyrrolidine $^1$H NMR (500 MHz, CDCl$_3$): δ1.66–2.08 (8H), 2.49–3.01 (8H), 3.22 (s, 2H), 3.72 (AB q, J=35.9, 2H), 7.08–7.41 (14H). Mass Spectrum (NH$_3$-CI): 455 (M+1).

EXAMPLE 12
1-Phenylmethyl-3-(RS)-((4-(N-methoxycarbonyl-N-cyclohexylmethyl)-amino)piperidin-1-yl)methyl-4-(SR)-phenylpyrrolidine 1H NMR (500 MHz, CDCl$_3$): δ7.23–7.49 (10H), 3.98 (s, 2H), 3.67 (s, 3H), 3.28–3.30 (2H). 3.09–3.11 (m, 2H), 2.91–2.96 (5H). 2.80 (d, J=9.9, 1H). 2.62–2.70 (1H). 2.52–2.60 (1H). 2.45–2.47 (1H). 1.53–2.06 (1OH). 1.17–1.28 (3H). 0.85–0.91 (3H). Mass Spectrum (NH$_3$-CI): 504 (M+1).

EXAMPLE 13
1-Benzyl-3-(SR)-(4-benzylpiperidin-1-ylmethyl)-4-(SR)-phenyl-pyrrolidine The title compound was prepared from 22 mg of 1-Benzyl-3-(SR)-formyl-4-(SR)-phenylpyrrolidine, 0.013 mL of 4-benzyl-piperidine and 24 mg of sodium triacetoxy-borohydride using a procedure analogous to that described in Example 9 to provide 14 mg of the title compound. RF: 0.39 (50% EtOAc in hexanes). 1H NMR (300 MHz, CDCl$_3$): δ1.2–1.9 (m, 8H), 2.3–3.0 (m, 11H), 3.7 (ABq, 2H), 7.1–7.4 (m, 15H). Mass Spectrum (NH$_3$-CI): 425.3 (M+H).

EXAMPLE 14
1-Benzyl-3-(SR)-(4-hydroxypiperidin-1-ylmethyl)-4-(SR)-phenyl-pyrrolidine The title compound was prepared from 500 mg of 1-Benzyl-3-(SR)-formyl-4-(SR)-phenylpyrrolidine, 196 mg of 4-hydroxypiperidine and 597 mg of sodium triacetoxy-borohydride using a procedure analogous to that described in Example 9, Step B to provide 348 mg of the title compound. R$_F$: 0.16 (5% MeOH in CH$_2$Cl$_3$). $^1$H NMR (300 MHz, CDCl$_3$): δ1.35–1.54 (m, 2H), 1.69–1.83 (m, 2H), 1.93–2.05 (m, 2H), 2.36–2.71 (m, 7H), 3.89–3.01 (m, 3H), 3.55–3.72 (m, 3H), 7.14–7.38 (m, 10H). Mass Spectrum (NH$_3$-CI): 351.3 (M+H).

EXAMPLE 15
1-Benzyl-3-(SR)-(1,2-diphenyl-3-(SR)-methyl-4-methylamino-2-(SR)-butanol-N-ylmethyl)-4-(SR)-phenylpyrrolidine The title compound was prepared from 103 mg of 1-Benzyl-3-(SR)-formyl-4-(SR)-phenylpyrrolidine, 105 mg of 1,2-diphenyl-3-(SR)-methyl-4-methylamino-2-(SR)-butanol-hydrochloride and 120 mg of sodium triacetoxy-borohydride using a procedure analogous to that described in Example 9, Step B to provide 76 mg of the title compound. R$_F$: 0.53 (50% Acetone in hexanes). $^1$H NMR (300 MHz, CDCl$_3$): δ0.98–1.12 (m, 3H), 1.98–2.62 (m, 9H), 2.79–3.24 (m, 5H), 3.39 (ABq, J =13 Hz, 2H), 3.60–3.72 (m, 3H), 7.06–7.45 (m, 20H). Mass Spectrum (NH$_3$-CI): 519.3 (M+H).

EXAMPLE 16
1-Benzyl-3-(SR)-(4-oxopiperidin-1-ylmethyl)-4-(SR)-phenylpyrrolidine To a solution of 0.14 mL of oxalylchloride in 3 mL of $CH_2Cl_2$ at −70° C. was added 0.16 mL of DMSO. After 5 min 270 mg of 1-Benzyl-3-(SR)-(4-hydroxypiperidin-1-ylmethyl)-4-(SR)-phenylpyrrolidine (from Example 14) in 3 mL of CH2Cl2 was added. After stirring for 10 min, the reaction was warmed to 0 OC for 45 min. The reaction was quenched with H20 and partitioned between 100 mL H20 and 100 mL CH2C-2. After separating phases, the aqueous layer was extracted with 100 mL CH2C-2. The combined organic layers were washed with 100 mL brine, dried over Na2SO4 and concentrated under vacuum. The residue was purified by flash chromatography eluting with 2% MeOH in CH2C12 to provide 256 mg of the title compound as a light yellow oil. $R_F$: 0.40 (5% MeOH in $CH_2Cl_2$). $^1$H NMR (300 MHz, $CDCl_3$): δ2.2–2.4 (m, 4H), 2.4–2.7 (m, 9H), 2.9–3.1 (m, 3H), 3.7 (ABq, 2H), 7.1–7.4 (m, 10H). Mass Spectrum (ESI): 349.3 (M+H).

EXAMPLE 17
1-Benzyl-3(SR)-(4-(N-(benzyloxycarbonyl)-N-sec-butylamino)-piperidin-1-ylmethyl)-4-(SR)-phenylpyrrolidine The title compound was prepared from 20 mg of 1-Benzyl-3-(SR)-formyl-4-(SR)-phenylpyrrolidine, 24 mg of 4-(N-(benzyloxycarbonyl)-N-secbutylamino)piperidine-hydrochloride, 0.013 mL of DIEA and 24 mg of sodium triacetoxyborohydride using a procedure analogous to that described in Example 9, Step B to provide 32 mg of the title compound. HPLC (YMC "Octyl" 4.6×250 mm column, 60:40 v/v $H_2O/CH_3CN$+0.5% TFA, 1.5 mL/min, 200 nm): Retention Time: 12.99 min. $^1$H NMR (300 MHz, $CDCl_3$): δ0.70–0.82 (m, 3H), 1.16 (t, J =6.4 Hz, 3H), 1.37–1.95 (m, 10H), 2.34–2.66 (m, 6H), 2.83–2.99 (m, 4H), 3.69 (ABq, J =13 Hz, 2H), 5.11 (s, 2H), 7.14–7.39 (m, 15H). Mass Spectrum (ESI): 540.6 (M+H).

EXAMPLE 18
1-Benzyl-3(SR)-(4-(N-(benzyloxycarbonyl)-N-isopropylamino)-piperidinylmethyl)-4-(SR)-phenylpyrrolidine The title compound was prepared from 20 mg of 1-Benzyl-3-(SR)-formyl-4-(SR)-phenylpyrrolidine, 23 mg of 4-(N-(benzyloxy-carbonyl)-N-isopropylamino) piperidine-hydrochloride, 0.013 mL of DIEA and 26 mg of sodium triacetoxyborohydride using a procedure analogous to that described in Example 9, Step B to provide 31 mg of the title compound. HPLC (YMC "Octyl" 4.6×250 mm column, 60:40 v/v $H_2O/CH_3CN$+0.5% TFA, 1.5 mL/min, 200 nm): Retention Time: 9.99 min. $^1$H NMR (300 MHz, $CDCl_3$): δ1.17–2.00 (m, 14H), 2.34–2.72 (m, 6H), 2.82–3.01 (m, 4H), 3.68 (ABq, J=13 Hz, 2H), 5.12 (s, 2H), 7.13–7.42 (m, 15H). Mass Spectrum (ESI): 526.2 (M+H).

EXAMPLE 19
1-Benzyl-3-(SR)-(1,1-diphenyl-3-methylamino-1-propanol-N-ylmethyl)-4-(SR)-phenylpyrrolidine The title compound was prepared from 21 mg of 1-Benzyl-3-(SR)-formyl-4-(SR)-phenylpyrrolidine, 24 mg of 1,1-diphenyl-3-methyl-amino-1-propanol-hydrochloride, 0.013 mL of DIEA and 24 mg of sodium triacetoxyborohydride using a procedure analogous to that described in Example 9, Step B to provide 32 mg of the title compound. HPLC (YMC "Octyl" 4.6×250 mm column, 60:40 v/v $H_2O/CH_3CN$+0.5% TFA, 1.5 mL/min, 200=m): Retention Time: 7–74 min. $^1$H NMR (300 MHz, $CDCl_3$): δ2.07–2.96 (m, 16H), 3.67 (s, 2H), 7.13–7.50 (m, 20H). Mass Spectrum (ESI): 491.3 (M+H).

EXAMPLE 20
1-Benzyl-3-(SR)-(4-(2-tolyl)-piperidin-1-ylmethyl)-4-(SR)-phenylpyrrolidine The title compound was prepared from 21 mg of 1-Benzyl-3-(SR)-formyl-4-(SR)-phenylpyrrolidine, 16 mg of 4-(2-tolyl)-piperidine-hydrochloride, 0.013 mL of DIEA and 23 mg of sodium triacetoxy-borohydride using a procedure analogous to that described in Example 9, Step B to provide 27 mg of the title compound. HPLC (YMC "Octyl" 4.6×250 mm column, 60:40 v/v $H_2O/CH_3CN$+0.5% TFA, 1.5 mL/min, 200 nm): Retention Time: 6.69 min. $^1$H NMR (300 MHz, $CDCl_3$): δ1.58–1.74 (m, 6H), 1.91–1.99 (m, 2H), 2.28 (s, 3H), 2.47–2.82 (m, 6H), 2.98–3.00 (m, 3H), 3.70 (ABq, J=13 Hz, 2H), 7.04–7.40 (m, 14H). Mass Spectrum (ESI): 425.2 (M+H).

EXAMPLE 21
1-Benzyl-3(SR)-(4-(N-(isopropyloxycarbonyl)-N-methylenecyclohexyl-amino)piperidin-1-ylmethyl)-4-(SR)-phenylpyrrolidine The title compound was prepared from 22 mg of 1-Benzyl-3-(SR)-formyl-4-(SR)-phenylpyrrolidine, 23.5 mg of 4-(N-(isopropyloxy-carbonyl)-N-methylenecyclohexylamino)piperidine-hydrochloride, 0.013 mL of DIEA and 23 mg of sodium triacetoxyborohydride using a procedure analogous to that described in Example 9, Step B to provide 28 mg of the title compound. $R_F$: 0.34 (50% EtOAc in hexanes). $^1$H NMR (300 MHz, $CDCl_3$): δ0.82–0.92 (m, 2H), 1.10–1.25 (m, 9H), 1.44–1.89 (m, 13H), 2.35–2.52 (m, 4H), 2.62–2.68 (m, 2H), 2.83–2.98 (m, 6H), 3.65 (ABq, J=13 Hz, 2H), 4.84–4.91 (m, 1H), 7.16–7.37 (m, 10H). Mass Spectrum (ESI): 532.3 (M+H).

EXAMPLE 22
1-Benzyl-3-(SR)-(4-phenyl-1, 2, 3, 6-tetrahydropyridin-1-ylmethyl)-4-(SR)-phenylpyrrolidine The title compound was prepared from 20 mg of 1-Benzyl-3-(SR)-formyl-4-(SR)-phenylpyrrolidine, 16 mg of 4-phenyl-1, 2, 3, 6-tetrahydropyridine-hydrochloride, 0.013 mL of DIEA and 23 mg of sodium triacetoxyborohydride using a procedure analogous to that described in Example 9, Step B to provide 24 mg of the title compound. RF: 0.37 (50% EtOAc in hexanes). $^1$H NMR (300 MHz, $CDCl_3$): δ2.40–2.71 (m, 9H), 2.91–3.16 (m, 5H), 3.67 (ABq, J=13 Hz, 2H), 5.98–6.00 (m, 1H ), 7.07–7.41 (m, 15H). Mass Spectrum (ESI): 409.1 (M+H).

EXAMPLE 23
1-Benzyl-3-(SR)-(4-phenyl-piperazin-1-ylmethyl)-4-(SR)-phenylpyrrolidine The title compound was prepared from 20 mg of 1-Benzyl-3-(SR)-formyl-4-(SR)-phenylpyrrolidine, 0.013 mL of 4-phenyl-piperazine and 23 mg of sodium triacetoxyborohydride using a procedure analogous to that described in Example 9, Step B to provide 28 mg of the title compound. RF: 0.42 (50% EtOAc in hexanes) $^1$H NMR (300 MHz, $CDCl_3$): o 2.36–2.54 (m, 8H), 2.62–2.67 (m, 1H), 2.90–3.08 (m, 7H), 3.66 (ABq, J=13 Hz, 2H), 6.79–6.88 (m, 3H), 7.14–7.38 (m, 12H). Mass Spectrum (ESI): 412.2 (M+H).

EXAMPLE 24
1-Benzyl-3-(SR)-(1,2,3,4-tetrahydroisoquinolin-2-ylmethyl)-4-(SR)-phenylpyrrolidine The title compound was prepared from 20 mg of 1-Benzyl-3-(SR)-formyl-4-(SR)-phenylpyrrolidine, 0.010 mL of 1, 2, 3, 4-tetrahydro-isoquinoline and 25 mg of sodium triacetoxyborohydride using a procedure analogous to that described in Example 9, Step B to provide 25 mg of the title compound. $R_F$: 0.51 (50% EtOAc in hexanes). $^1$H NMR (300 MHz, CDCl$_3$): δ2.51–2.78 (m, 9H), 2.94–3.00 (m, 3H), 3.40–3.69 (m, 4H), 6.91–6.94 (m, 1H), 7.02–7.38 (m, 13H). Mass spec. (ESI): 383.2 (M+H).

EXAMPLE 25

1-Benzyl-3-(SR)-(2, 3, 4, 5-tetrahydro-1H-benzo[d]-azepin-3-ylmethyl)-4-(SR)-phenylpyrrolidine The title compound was prepared from 20 mg of 1-Benzyl-3-(SR)-formyl-4-(SR)-phenylpyrrolidine, 28 mg of 2, 3, 4, 5-tetrahydro-1H-benzo[d]-azepine-picrate salt, 0.013 mL of DIEA and 24 mg of sodium triacetoxyborohydride using a procedure analogous to that described in Example 9, Step B to provide 14.5 mg of the title compound. $R_F$: 0.53 (50% EtOAc in hexanes). $^1$H NMR (300 MHz, CDCl$_3$): δ2.42–3.02 (m, 16H), 3.67 (ABq, J=13 Hz, 2H), 7.00–7.38 (m, 14H). Mass Spectrum (ESI): 397.1 (M+H).

EXAMPLE 26

1-Benzyl-3-(SR)-(4-phenyl-perhydro-azepin-1-ylmethyl)-4-(SR)-phenylpyrrolidine

The title compound was prepared from 20 mg of 1-Benzyl-3-(SR)-formyl-4-(SR)-phenylpyrrolidine, 13 mg of 4-phenyl-perhydro-azepine and 25 mg of sodium triacetoxyborohydride using a procedure analogous to that described in Example 9, Step B to provide 18.5 mg of the title compound. $R_F$: 0.37 (50% EtOAc in hexanes). $^1$H NMR (300 MHz, CDCl$_3$): δ1.48–1.83 (m, 6H), 2.37–2.69 (m, 10H), 2.88–3.01 (m, 3H), 3.67 (ABq, J=13 Hz, 2H), 7.09–7.39 (m, 15H). Mass Spectrum (CI): 425.3 (M+H).

EXAMPLE 27

1-Benzyl-3-(SR)-(4-carboethoxy-piperidin-1-ylmethyl)-4-(SR)-phenylpyrrolidine

The title compound was prepared from 400 mg of 1-Benzyl-3-(SR)-formyl-4-(SR)-phenylpyrrolidine, 0.24 mL of ethyl isonipecotate and 480 mg of sodium triacetoxyborohydride using a procedure analogous to that described in Example 9, Step B to provide 363 mg of the title compound. $R_F$: 0.31 (50% EtOAc in hexanes). $^1$H NMR (300 MHz, CDCl$_3$): δ1.22 (t, J=7.1 Hz, 3H), 1.54–1.89 (m, 6H), 2.13–2.21 (m, 1H), 2.33–2.64 (m, 6H), 2.77–2.97 (m, 4H), 3.65 (ABq, J=13 Hz, 2H), 4.09 (q, J=7.1 Hz, 2H), 7.14–7.37 (m, 10H). Mass Spectrum (CI): 407.3 (M+H).

EXAMPLE 28

1-Benzyl-3-(SR)-(4-(2,3-naphthalenecarboxamid)-piperidin-1-ylmethyl)-4-(SR)-phenylpyrrolidine To a solution of 35 mg of 1-Benzyl-3-(SR)-(4-hydroxy-piperidin-1-ylmethyl)-4-(SR)-phenylpyrrolidine, 23 mg of 2, 3-naphthalenecarboximide and 31 mg of triphenylphosphine in 0.2 mL of THF at room temperature was added 0.019 mL of diethylazodicarboxylate. After 7 h the reaction was diluted with 10 mL of brine and extracted with 2×10 mL Et$_2$O. The combined organic layers were dried over MgSO$_4$ and concentrated under vacuum. The residue was purified by flash chromatography eluting with a gradient of 0 to 4% MeOH in CH$_2$Cl$_2$ to give 12 mg of the title compound. $R_F$: 0.36 (5% MeOH in CH$_2$Cl$_2$). $^1$H NMR (300 MHz, CDCl$_3$): δ1.49–1.70 (m, 4H), 1.91–2.01 (m, 2H), 2.36–2.78 (m, 7H), 2.92–3.03 (m, 3H), 3.68 (ABq, J=13 Hz, 2H), 4.07–4.15 (m, 1H), 7.14–7.40 (m, 10H), 7.65–7.70 (m, 2H), 8.01–8.06 (m, 2H), 8.30 (s, 2H). Mass Spec (CI): 530.3 (M+H).

EXAMPLE 29

1-Phenylmethyl-3-(SR)-(4-(2-keto-benzimidazol-1-yl) piperidin-1-yl)methyl-4-(SR)-phenylpyrrolidine $^1$H NMR (500 MHz, CDCl$_3$): δ1.59–3.03 (16H), 3.67–3.72 (m, 2H), 4.24–4.30 (m, 1H), 7.04–7.39 (14H), 9.27 (s, 1H). Mass Spectrum (NH$_3$-CI): 467 (M+1). HPLC (YMC "Octyl" 4.6×250 mm column, 60:40 v/v H$_2$O/CH$_3$CN+0.5% TFA, 1.5 mL/min, 200 nn): 3.4 min.

EXAMPLE 30

1-(4-Chloro)benzenesulfonyl-3-(SR)-((4-phenyl) piperidin-1-yl)methyl-4-(SR)-phenylpyrrolidine Step A: 3-(SR)-((4-Phenyl)piperidin-1-yl)methyl-4-(SR)-phenylpyrrolidine A mixture of 232 mg (0.6 mmol) of 1-phenylmethyl-3-(SR)-((4-phenyl) piperidin-1-yl)methyl-4-(SR)-phenylpyrrolidine (from Example 9, Step B), 894 mg (14.1 mmol) of ammonium formate and 116 mg of 20% Pd(OH)$_2$ on carbon in 10 mL of MeOH was heated at reflux for 1 h. The reaction mixture was cooled and filtered througha pad of Celite. The reaction flask and filtered solids were rinsed with 50 mL of EtOAc and the filtrate was concentrated in vacuo. The residue was partitioned between 50 mL of EtOAc and 30 mL of sat'd NaHCO$_3$ and the layers were separated. The organic layer was dried over MgSO$_4$. The aqueous layer was extracted with 50 mL of EtOAc; the extract was dried and the organic layers were combined and concentrated in vacuo to afford 190 mg (95%) of the title compound as an oil. $^1$H NMR (500 MHz, CDCl$_3$): δ1.63–1.80 (m, 4H), 1.93–2.05 (m, 2H), 2.39–2.53 (m, 5H), 2.83 (d, J=10.7, 1H), 2.93–3.02 (m, 2H), 3.08 (t, J=9.6, 1H), 3–47–3.53 (m, 1H), 5.19 (br s, 1H), 7.19–7.38 (1OH). Mass Spectrum (NH$_3$-CI): 321 (M+1).

Step B: 1-(4-Chloro)benzenesulfonyl-3-(SR)-((4-phenyl) piperidin-1-yl)methyl-4-(SR)-phenylpyrrolidine A mixture of 16 mg (0.05 mmol) of 3-(SR)-((4-phenyl)-piperidin-1-yl)methyl-4-(SR)-phenylpyrrolidine (from Example 30, Step A) in 2 mL EtOAc and 1 mL of sat'd NaHCO$_3$ was treated with 21 mg (0.95 mmol) of (4-chloro) benzenesulfonyl chloride. After 30 min, the mixture was partitioned between 20 mL of EtOAc and 10 mL of sat'd NaHCO$_3$ and the layers were separated. The organic layer was washed with 10 mL of sat'd NaCl, dried over MgSO$_4$ and concentrated in vacuo. Flash chromatography on 15 g of silica gel using 4:1 v/v, then 2:1 v/v hexanes/ether as the eluant afforded 14 mg (56%) of the title compound as an oil. $^1$H NMR (500 MHz, CDCl$_3$): δ1.45–3.73 (17H), 7.13–7.33 (1OH), 7.56 (d, J=8.5, 2H), 7.84 (d, J=8.4, 2H). Mass Spectrum (NH$_3$-CI): 495 (M+1).

The compounds in Examples 31–35 were prepared using procedures analogous to those described in Example 30 substituting the appropriate aryl sulfonyl chloride for (4-chloro)benzenesulfonyl chloride in Example 30, Step B.

EXAMPLE 31

1-(2-Thiophene)sulfonyl-3-(SR)-((4-phenyl) piperidin-1-yl)methyl-4-(SR)-phenylpyrrolidine $^1$H NMR (500 MHz, CDCl$_3$): δ1.74–3.81 (17H), 7.14–7.33 (12H), 7.67 (m, 1H). Mass Spectrum (NH$_3$-CI): 467 (M+1).

EXAMPLE 32

1-(1-Napthalene)sulfonyl-3-(SR)-((4-phenyl) piperidin-1-yl)methyl-4-(SR)-phenylpyrrolidine $^1$H NMR (500 MHz, CDCl$_3$): δ1.64–2.85 (12H), 3.00 (q, J=8.5, 1H), 3.32 (t, J=9.4, 1H), 3.40 (t, J=8.7, 1H), 3.82 (t, J=10.1, 1H), 3.87 (br t, J=9.0, 1H), 7.10–7.33 (1OH), 7.57–7.72 (m, 3H), 7.97 (d, J=8.2, 1H), 8.11 (d, J=8.2, 1H), 8.31 (d, J=7.4, 1H), 8.90 (d, J=8.5, 1H). Mass Spectrum (NH$_3$-CI): 511 (M+1).

EXAMPLE 33
1-(2-Napthalene)sulfonyl-3-(SR)-((4-phenyl) piperidin-1-yl)methyl-4-(SR)-phenylpyrrolidine
$^1$H NMR (500 MHz, CDCl$_3$): δ1.64–2.86 (m, 12H), 2.92 (q, J=8.5, 1H), 3.26 (t, J=8.0, 1H), 3.38 (t, J=8.7, 1H), 3.78–3.84 (m, 2H), 7.10–7.33 (11H), 7.64–7.71 (m, 2H), 7.91–8.05 (m, 3H), 8.49 (s, 1H ). Mass Spectrum (NH$_3$-CI): 511 (M+1).

EXAMPLE 34
1-(8-Quinoline)sulfonyl-3-(SR)-((4-phenyl) piperidin-1-yl)methyl-4-(SR)-phenylpyrrolidine
$^1$H NMR (500 MHz, (DC13): δ1.64–2.87 (12H), 2.96 (q, J=9.2, 1H1), 3.41 (t, J=9.2, 1H), 3.58 (t, J=9.4, 1H), 4.26–4.32 (m, 2H), 7.10–7.32 (1OH), 7.58 (dd, J=4.3, 8.2, 1H), 7.66 (t, J=8.0, 1H), 8.07 (d, J=8.2, 1H), 8.29 (d, J=8.2, 1H), 8.56 (d, J=7.4, 1H), 9.12 (d, J=3.8, 1H). Mass Spectrum (NH$_3$-CI): 512 (M+1).

EXAMPLE 35
1-(4-Biphenyl)sulfonyl-3-(SR)-((4-phenyl) piperidin-1-yl)methyl-4-(SR)-phenylpyrrolidine
$^1$H NMR (500 MHz, CDCl$_3$): δ1.64–2.89 (12H), 2.97 (q, J=8.5, 1H), 3.24 (t, J=9.6, 1H), 3.36 (t, J=8.7, 1H), 3.75–3.79 (m, 2H), 7.14–7.33 (14H), 7.46 (m, 1H ), 7.52 (m, 1H ), 7.66 (m, 1H ), 7.80 (m, 1H ), 7.97 (m, 1H ). Mass Spectrum (NH$_3$-CI): 537 (M+1).

The compounds in Examples 36–62 were prepared using procedures analogous to those described in Example 30, 59, or 63 substituting the appropriate aromatic or aliphatic acid chloride for (4-chloro)benzenesulfonyl chloride in Example 30, Step B, the appropriate aromatic or aliphatic carboxylic acid for 1-fluorene carboxylic acid in Example 59 or the appropriate aromatic or aliphatic acid chloride for nicotinoyl chloride·HCl in Example 63.

EXAMPLE 36
1-Benzoyl-3-(SR)-((4-phenyl)piperidin-1-yl)methyl-4-(SR)-phenyl-pyrrolidine
$^1$H NMR (500 MHz, CDCl$_3$): δ1.64–4.21 (17H), 7.17–7.62 (15H). Mass Spectrum (NH$_3$-CI): 425 (M+1).

EXAMPLE 37
1-(2-Chloro)benzoyl-3-(SR)-((4-phenyl)piperidin-1-yl)methyl-4-(SR)-phenylpyrrolidine
$^1$H NMR (500 MHz, CDCl$_3$): δ1.27–4.27 (17H), 7.17–7.47 (14H). Mass Spectrum (NH$_3$-CI): 459 (M+1).

EXAMPLE 38
1-(3-Chloro)benzoyl-3-(SR)-((4-phenyl)piperidin-1-yl)methyl-4-(SR)-phenylpyrrolidine
$^1$H NMR (500 MHz, CDCl$_3$): 81.27–4.20 (17H), 7.17–7.59 (14H). Mass Spectrum (NH$_3$-CI): 459 (M+1).

EXAMPLE 39
1-(4-Chloro)benzoyl-3-(SR)-((4-phenyl)piperidin-1-yl)methyl-4-(SR)-phenylpyrrolidine
$^1$H NMR (500 MHz, CDCl$_3$): δ1.27–4.20 (17H), 7.17–7.58 (14H). Mass Spectrum (NH$_3$-CI): 459 (M+1). HPLC (YMC "Octyl" 4.6×250 mm column, 60:40 v/v H$_2$O/ CH$_3$CN +0.5% TFA, 1.5 mL/min, 200 nm): 7.2 min.

EXAMPLE 40
1-(2-Methoxy)benzoyl-3-(SR)-((4-phenyl)piperidin-1-yl)methyl-4-(SR)-phenylpyrrolidine
$^1$H NMR (500 MHz, CDCl$_3$): δ1.66–4.24 (20H), 3.87 (s, 3H), 6.90–7.41 (14H). Mass Spectrum (NH$_3$-CI): 455 (M+1).

EXAMPLE 41
1-(3-Methoxy)benzoyl-3-(SR)-((4-phenyl)piperidin-1-yl)methyl-$^4$-(SR)-phenylpyrrolidine
$^1$H NMR (500 MHz, CDCl$_3$): δ1.50–4.20 (20H), 3.83 (s, 3H), 6.94–7.38 (14H). Mass Spectrum (NH$_3$-CI): 455 (M+1).

EXAMPLE 42
1-(4-Methoxy)benzoyl-3-(SR)-((4-phenyl)piperidlin-1-yl)methyl-4-(SR)-phenvipyrrolidine
Mass Spectrum (NH$_3$-CI): 455 (M+1). HPLC (YMC "Octyl" 4.6×250 mm column, 60:40 v/v H$_2$O/ CH$_3$CN+ 0.5% TFA, 1.5 mL/min, 200 nm): 9.8 min.

EXAMPLE 43
1-(3,5-Dichloro)benzoyl-3-(SR)-((4-phenyl)piperidin-1-yl)methyl-$^4$-(SR)-phenylpyrrolidine
$^1$H NMR (500 MHz, CDCl$_3$): δ1.60–3.17 (12H), 3.85 (t, J=8.7, 1H), 3.50–3.58 (m, 1H ), 3.74 (dd, J=9.3, 12.3, 1H), 3.81 (dd, J=7.6, 10.6, 1H), 4.11–4.19 (m, 1H ), 7.18–7.47 (13H). Mass Spectrum (NH$_3$-CI): 492 (M+1).

EXAMPLE 44
1-(3,4-Dichloro)benzoyl-3-(SR)-((4-phenyl)piperidin-1-yl)methyl-4-(SR)-phenylpyrrolidine
$^1$H NMR (500 MHz, CDCl$_3$): δ1.60–3.16 (12H), 3.42 (br t, 1H), 3.55 (q, J=12.9, 1H), 3.83 (dd, J=9.6, 12.3, 1H), 4.11–4.19 (m, 1H ), 7.18–7.72 (13H). Mass Spectrum (NH$_3$-CI): 492 (M+1). HPLC (YMC "Octyl" 4.6×250 mm column, 60:40 v/v H$_2$O/ CH$_3$CN+0.5% TFA, 1.5 mL/min, 200 nm): 19.5 min.

EXAMPLE 45
1-(2,6-Dichloro)benzoyl-3-(SR)-((4-phenyl)piperidin-1-yl)methyl-4-(SR)-phenylpyrrolidine
$^1$H NMR (500 MHz, CDCl$_3$): δ1.60–3.25 (11H), 3.34 (t, J=9.4, 1H), 3.57–3.61 (m, 2H), 3.81 (dd, J=8.0, 12.6, 1H), 4.20–4.26 (m, 2H), 7.18–7.39 (13H). Mass Spectrum (NH$_3$-CI): 492 (M+1).

EXAMPLE 46
1-(2,4-Dichloro)benzoyl-3-(SR)-((4-phenyl)piperidin-1-yl)methyl-4-(SR)-phenylpyrrolidine
$^1$H NMR (500 MHz, CDCl$_3$): δ1.60–3.02 (9H), 3.09–3.20 (m, 2H), 3.34 (t, J=9.8, 1H), 3.51–3.61 (m, 2H), 3.73 (dd, J=8.7, 12.6, 1H), 4.17–4.25 (m, 2H), 7.18–7.49 (13H). Mass Spectrum (NH$_3$-CI): 492 (M+1). HPLC (YMC "Octyl" 4.6×250 mm column, 60:40 v/v H$_2$O/CH$_3$CN+0.5% TFA, 1.5 mL/min, 200 nm): 16.9 min.

EXAMPLE 47
1-(2,3-Dichloro)benzoyl-3-(SR)-((4-phenyl)piperidin-1-yl)methyl-4-(SR)-phenylpyrrolidine
$^1$H NMR (500 MHz, CDCl$_3$): δ1.60–4.24 (17H), 7.17–7.55 (13H). Mass Spectrum (NH$_3$-CI): 492 (M+1).

EXAMPLE 48
1-(2,5-Dichloro)benzoyl-3-(SR)-((4-phenyl)piperidin-1-yl)methyl-4-(SR)-phenylpyrrolidine
$^1$H NMR (500 MHz, CDCl$_3$): δ1.60–3.20 (12H), 3.37 (br t, J=9.8, 1H), 3.53 (dd, J=8.7, 12.4, 1H), 3.62 (t, J=10.1, 1H), 3.73 (dd, J=8.9, 12.3, 1H), 4.17–4.25 (m, 2H), 7.17–7.40 (13H). Mass Spectrum (NH$_3$-CI): 492 (M+1). HPLC (YMC "Octyl" 4.6×250 mm column, 60:40 v/v H$_2$O/ CH$_3$CN+ 0.5% TFA, 1.5 mL/min, 200 nm): 15.4 min

EXAMPLE 49
1-(2-Trifluoromethyl)benzoyl-3-(SR)-((4-phenyl)piperidin-1-yl)methyl-4-(SR)-phenylpyrrolidine
$^1$H NMR (500 MHz, CDCl$_3$): δ1.46–2.14 (5H), 2.32–3.19 (6H), 3.26 (t, J=10.3, 1H), 3.52–3.58 (m, 2H), 3.76 (dd, J=8.7, 12.6, 1H), 4.19–4.27 (m, 2H), 7.17–7.77 (14H). Mass Spectrum (NH$_3$-CI): 493 (M+1). HPLC (YMC "Octyl" 4.6×250 mm column, 60:40 v/v H$_2$O/ CH$_3$CN+0.5% TFA, 1.5 ml/min, 200 nm): 12.7 min

EXAMPLE 50
1-(2-Methoxycarbonyl)benzoyl-3-(SR)-((4-phenyl)piperidin-1-yl)methyl-4-(SR)-phenylpyrrolidine $^1$H NMR (500 MHz, CDCl$_3$): δ1.63–2.12 (5H), 2.34–3.27 (10H), 3.40–3.52 (3H), 3.69–3.79 (3H), 4.09–4.17 (m, 2H), 7.14–7.48 (14H). Mass Spectrum (NH$_3$-CI): 483 (M+1).

EXAMPLE 51
1-(2-Methyl)benzoyl-3-(SR)-((4-phenyl)piperidin-1-yl)methyl-4-(SR)-phenylpyrrolidine
$^1$H NMR (500 MHz, CDCl$_3$): δ1.67–3.77 (18H), 2.35–2.40 (3H), 4.18–4.29 (2H), 7.16–7.40 (14H). Mass Spectrum (NH$_3$-CI): 439 (M+1). HPLC (YMC "Octyl" 4.6×250 mm column, 60:40 v/v H$_2$O/ CH$_3$CN+0.5% TFA, 1.5 mL/min, 200 nm): 9.3 min

EXAMPLE 52
1-(2-Fluoro)benzoyl-3-(SR)-((4-phenyl)piperidin-1-yl)methyl-4-(SR)-phenylpyrrolicdine
$^1$H NMR (500 MHz, CDCl$_3$): δ1.71–2.20 (6H), 2.40–2.80 (4H), 2.98–3.17 (3H), 3.35–3.84 (3H), 4.17–4.28 (m, 1H ), 7.00–7.48 (14H). Mass Spectrum (NH$_3$-CI): 443 (M+1). HPLC (YMC "Octyl" 4.6×250 mm column, 60:40 v/v H$_2$O/ CH$_3$CN+0.5% TFA, 1.5 mL/min, 200 nm): 8.6 min

EXAMPLE 53
1-(2-Bromo)benzoyl-3-(SR)-((4-phenyl)piperidin-1-yl)methyl-4-(SR)-phenylpyrrolidine
$^1$H NMR (500 MHz, CDCl$_3$): δ0.91–3.78 (15H), 4.21–4.26 (2H), 7.17–7.64 (14H). Mass Spectrum (NH$_3$-CI): 503 (M+1).

EXAMPLE 54
1-(Cyclohexanoyl)-3-(SR)-((4-phenyl)piperidin-1-yl)methyl-4-(SR)-phenylpyrrolidine
$^1$H NMR (500 MHz, CDCl$_3$): δ1.22–2.11 (16H), 2.29–2.65 (5H), 2.88–3.54 (5H), 3.94–4.09 (2H), 7.19–7.39 (1OH). Mass Spectrum (NH$_3$-CI): 431 (M+1). HPLC (YMC "Octyl" 4.6×250 mm column, 60:40 v/v H$_2$O/ CH$_3$CN +0.5% TFA, 1.5 mL/min, 200 n-m): 11.8 min.

EXAMPLE 55
1-(Cyclopentanoyl)-3-(SR)-((4-phenyl)piperidin-1-yl)methyl-4-(SR)-phenylpyrrolidine
$^1$H NMR (500 MHz, CDCl$_3$): δ1.50–3.56 (24H), 3.80–4.09 (2H), 7.19–7.38 (10H). Mass Spectrum (NH$_3$-CI): 417 (M+1).

EXAMPLE 56
1-(3-Methoxycarbonyl)benzoyl-3-(SR)-((4-phenyl)piperidin-1-yl)methyl-4-(SR)-phenylpyrrolidine
$^1$H NMR (500 MHz, CDCl$_3$): δ1.50–3.16 (12H), 3.39–4.22 (11H), 7.16–8.27 (14H). Mass Spectrum (NH$_3$-CI): 483 (M+1). HPLC (YMC "Octyl" 4.6×250 mm column, 60:40 v/v H$_2$O/ CH$_3$CN+0.5% TFA, 1.5 mL/min, 200 nm): 8.6 min.

EXAMPLE 57
1-(Phenylacetyl)-3-(SR)-((4-phenyl)piperidin-1-yl)methyl-4-(SR)-phenylpyrrolidine
$^1$H NMR (500 MHz, CDCl$_3$): δ1.71–4.15 (19H), 7.21–7.37 (15H). Mass Spectrum (NH$_3$-CI): 439 (M+1).

EXAMPLE 58
1-(Isonicotinoyl)-3-(SR)-(($^4$-phenyl)piperidin-1-yl)methyl-4-(SR)-phenylpyrrolidine
$^1$H NMR (500 MHz, CDCl$_3$): δ7.16–8.78 (9H), 1.27–4.19 (22H). Mass Spectrum (NH$_3$-CI): 426 (M+1).

EXAMPLE 59
1-(Nicotinoyl)-3-(SR)-((4-phenyl)piperidin-1-yl)methyl-4-(SR)-phenylpyrrolidine
A solution of 20 mg (0.06 mmol) of 3-(RS)-((4-phenyl)-piperidin-1-yl)methyl-4-(SR)-phenylpyrrolidine (from Example 30, Step A), 19 mg (0.19 mmol) of TEA and 6 mg (0.05 mmol) of 4-DMAP in 2 mL of CH$_2$Cl$_2$ (2 mL) was treated with 28 mg (0.16 mmol) of nicotinoyl chloride·HCl and was stirred at rt for 2 h. The reaction was concentrated in Vacuo. Preparative thin layer chromatography (silica gel GF, 20×20 cm, 1000 microns) using 92:8 v/v MeOH/ CH$_2$Cl$_2$+0.5% NH$_4$OH as the eluant afforded 20 mg (71%) of the title compound as a yellow foam. $^1$H NMR (500 MHz, CDCl$_3$): δ7.17–8.88 (9H), 1.27–4.24 (22H). Mass Spectrum (NH$_3$-CI): 426 (M+1).

EXAMPLE 60
1-(2-Thiophenecarbonyl)-3-(SR)-((4-phenyl)piperidin-1-yl)methyl-4-(SR)-phenylpyrrolidine
$^1$H NMR (500 MHz, CDCl$_3$): δ7.05–7.75 (13H), 1.80–4.52 (17H). Mass Spectrum (NH$_3$-CI): 426 (M+1).

EXAMPLE 61
1-(1-Naphthoyl)-3-(RS)-((4-phenyl)piperidin- 1-yl)methyl-4-(SR)-phenylpyrrolidine
$^1$H NMR (500 MHz, CDCl$_3$): δ7.12–7.98 (17H), 1.28–4.37 (17H). Mass Spectrum (NH$_3$-CI): 475 (M+1).

EXAMPLE 62
1-(2-Naphthoyl)-3-(RS)-((4-phenyl)piperidin-1-yl)methyl-4-(SR)-phenylpyrrolidine
$^1$H NMR (500 MHz, CDCl$_3$): δ7.12–7.98 (17H), 1.28–4.37 (17H). Mass Spectrum (NH$_3$-CI): 475 (M+1).

EXAMPLE 63
1-(1-Fluorenecarbonyl)-3-(RS)-((4-phenyl)piperidin-1-yl)methyl-4-(SR)-phenylpyrrolidine
A solution of 10 mg (0.03 mnmol) of 3-(RS)-((4-phenyl)piperidin-1-yl)methyl-4-(SR)-phenylpyrrolidine (from Example 30, Step A), 10 mg (0.07 mmol) of DIEA and 10 mg (0.04 mmol) of bis (2-oxo-3-oxazolidinyl)phosphinic chloride (BOP-Cl) in 2 mL of CH$_2$Cl$_2$ (2 mL) at 0° C. was treated with 7 mg (0.16 mmol) of 1-fluorene carboxylic acid. The cooling bath was removed; the reaction was stirred at rt for 2 h and then was concentrated in vacuo . Preparative thin layer chromatography (silica gel GF, 20×20 cm, 1000 microns) using 95:5 v/v MeOH/CH$_2$Cl$_2$ as the eluant afforded 14 mg (88%) of the title compound as a foam. $^1$H NMR (500 MHz, CDCl$_3$): δ7.12–7.87 (17H), 1.28–4.13 (19H). Mass Spectrum (NH$_3$-CI): 513 (M+1).

EXAMPLE 64
1-(9-Fluorenecarbonyl)-3-(RS)-((4-phenyl)piperidin-1-yl)methyl-4-(SR)-phenylpyrrolidine
$^1$H NMR (500 MHz, CDCl$_3$): δ6.92–7.82 (17H), 1.28–5.13 (19H). Mass Spectrum (NH$_3$-CI): 513 (M+1). HPLC (YMC "Octyl" 4.6×250 mm column, 60:40 v/v H₂O/CH₃CN+0.5% TFA, 1.5 mL/min, 200 nm): 21.5 min.

EXAMPLE 65
1-(4-Fluorenecarbonyl)-3-(RS)-((4-phenyl)piperidin-1-yl) methyl-4-(SR)-phenylpyrrolidine
$^1$H NMR (500 MHz, CDCl₃): δ7.11–7.79 (17H), 1.28–4.43 (19H). Mass Spectrum (NH₃-Cl): 513 (M+1).

EXAMPLE 66
1-(1-Adamantanecarbonyl)-3-(RS)-((4-phenyl)piperidin-1-yl)methyl-4-(SR)-phenylpyrrolidine
$^1$H NMR (500 MHz, CDCl₃): δ7.21–7.38 (1OH), 1.74–4.08 (32H). Mass Spectrum (NH₃-Cl): 483 (M+1). HPLC (YMC "Octyl" 4.6×250 mm column, 60:40 v/v H₂O/ CH₃CN+ 0.5% TFA, 1.5 mL/min, 200 nm): 26.2 min.

The compounds described in Examples 67–71 were prepared using procedures analogous to those described in Examples 1 and 9 substituting the appropriately substituted (E)-cinnamate for methyl (Z)-cinnamate in Example 1, Step A.

EXAMPLE 67
1-Phenylmethyl-3-(SR)-((4-phenyl)piperidin-1-yl)methyl-4-(SR)-(2-chloro)phenylpyrrolidine
$^1$H NMR (500 MHz, CDCl₃): δ1.52–1.76 (m, 4H), 1.95–2.04 (m, 2H), 2.39–2.60 (m, 5H), 2.67 (t, J=8.4, 1H), 2.81 (d, J=11.2, 1H), 3.00 (t, J=8.7, 2H), 3.11 (t, J=7.3, 1H), 3.61 (q, J=6.6, 1H), 3.72 (ABq, J=48.3, 2H), 7.11–7.41 (13H), 7.57 (d, J=7.8, 1H). Mass Spectrum (NH₃-Cl): 445 (M+1).

EXAMPLE 68
1-Phenylmethyl-3-(SR)-((4-phenyl)piperidin-1-yl:)methyl-4-(SR)-(3-chloro)phenylpyrrolidine
$^1$H NMR (500 MHz, CDCl₃): δ1.62–1.82 (m, 4H), 1.93–1.97 (m, 1H ), 2.01–2.05 (m, 1H ), 2.42–2.49 (m, 5H), 2.70–2.73 (m, 1H ), 2.75–2.80 (m, 1H ), 2.93–3.02 (m, 4H), 3.70 (A-Bq, J=12.8, 2H), 7.17–7.43 (14H). Mass Spectrum (NH₃-Cl): 445 (M+1). HPLC (YMC "Octyl" 4.6×250 mm column, 60:40 v/v H₂O/CH₃CN+0.5% TFA, 1.5 mLlmin, 200 nm): 11.0 min.

EXAMPLE 69
1-Phenylmethyl-3-(SR)-((4-phenyl)piperidin-1-yl)methyl-4-(SR)-(3-chloro)phenylpyrrolidine
$^1$H NMR (500 MHz, CDCl₃): δ1.58–1.82 (ma, 4H), 1.97 (q, J=11.5, 2H), 2.42–2.53 (m, 5H), 2.68 (t, J=6.5, 1H), 2.79 (d, J=11.0, 1H), 2.93–3.04 (m, 4H), 3.70 (ABq, J=36.6, 2H), 7.22–7.41 (14H). Mass Spectrum (NH₃-Cl): 445 (M+1). HPLC (YMC "Octyl" 4.6×250 mm column, 60:40 v/v H₂O/ CH₃CN +0.5% TFA, 1.5 mL/min, 200 nm): 9.0 min.

EXAMPLE 70
1-Phenylmethyl-3-(SR)-((4-phenyl)piperidin-1-yl)methyl-4-(SR)-(3-bromo)phenylpyrrolidine
$^1$H NMR (500 MHz, CDCl₃): δ1.60–2.03 (7H), 2.38–3.04 (10H), 3.68 (ABq, J=36.6, 2H), 7.14–7.57 (14H). Mass Spectrum (NH₃-Cl): 489 (M+1).

EXAMPLE 71
1-Phenylmethyl-3-(SR)-(spiro [indan-1-one-3,4'-piperidin-1'-yl]methyl)-4-(SR)-(3 4-di-chloro)phenylpyrrolidine The title compound was prepared using procedures analogous to those described in Example 1, Steps A and B (employing methyl (Z)-(3,4-dichlorophenyl)propenoic acid in place of methyl (Z)-cinnamate) and Example 9, Steps A and B (employing spiro[indan-1-one-3,4'-piperidine] in place of 4-phenylpiperidine). Mass Spectrum (ESI) m/e 519 (M+1).

The compounds in Examples 72–76 were prepared from 1-phenylmethyl-3-(RS)-((4-(N-methoxycarbonyl-N-cyclohexyl-methyl)amino)piperidin-1-yl)methyl-4-(SR)-phenylpyrrolidine (from Example 12) using procedures analogous to those described in Example 30 substituting the appropriate acid chloride for (4-chloro)benzene-sulfonyl chloride in Example 30, Step B.

EXAMPLE 72
1(1-Naphthoyl)-3-(RS)-((4-(N-methoxycarbonyl-N-cyclohexyl-methyl)amino)piperidin-1-yl)methyl-4-(SR)-phenylpyrrolidine
$^1$H NMR (500 MHz, CDCl₃): 5 7.13–7.97 (12H), 0.89–4.34 (33H). Mass Spectrum (NH₃-Cl): 568 (M+1).

EXAMPLE 73
1-Cyclohexanoyl-3-(RS)-((4-(N-methoxycarbonyl-N-cyclohexyl-methyl)amino)piperidin-1-yl)methyl-4-(SR)-phenylpyrrolidine
$^1$H NMR (500 MHz, CDCl₃): δ7.20–7.37 (5H), 0.88–4.05 (44H). Mass Spectrum (NH₃-Cl): 524 (M+1). HPLC (YMC "Octyl" 4.6×250 mm column, 60:40 v/v H₂O/CH₃CN+0.5% TFA, 1.5 mL/min, 200 nm): 21.1 min.

EXAMPLE 74
1-Cyclopentanoyl-3-(RS)-((4-(N-methoxycarbonyl-N-cyclohexyl-methyl)amino)piperidin-1-yl)methyl-4-(SR):phenylpyrrolidine
$^1$H NMR (500 MHz, CDCl₃): δ7.21–7.37 (5H), 0.89–4.11 (42H). Mass Spectrum (NH₃-Cl): 510 (M+1). HPLC (YMC "Octyl" 4.6×250 mm column, 60:40 v/v H₂O/ CH₃CN+ 0.5% TFA, 1.5 mL/min, 200 nm): 15.9 min.

EXAMPLE 75
1-(2-Chlorobenzoyl)-3-(RS)-((4-(N-methoxycarbonyl-N-cyclohexyl-methyl)amino)piperidin-1-yl)methyl-4-(SR)-phenylpyrrolidine
$^1$H NMR (500 MHz, CDCl₃): δ7.19–7.46 (9H), 0.89–4.21 (33H). Mass Spectrum (NH₃-Cl): 552 (M+1). HPLC (YMC "Octyl" 4.6×250 mm column, 60:40 v/v H₂O/ CH₃CN+ 0.5% TFA, 1.5 mL/min, 200 nm): 16.9 min.

EXAMPLE 76
1-Benzoyl-3-(RS)-((4-(N-methoxycarbonyl-N-cyclohexylmethyl)-amino)piperidin-1-yl)methyl-4-(SR)-phenylpyrrolidine
$^1$H NMR (500 MHz, CDCl₃): δ7.20–7.59 (1OH), 0.89–4.15 (33H). Mass Spectrum (NH₃-Cl): 518 (M+1). HPLC (YMC "Octyl" 4.6×250 mm column, 60:40 v/v H₂O/ CH₃CN+ 0.5% TFA, 1.5 mL/min, 200 nm): 13.5 min.

EXAMPLE 77
1-Phenylmethyl-3-(SR)-((4-phenyl)piperidin-1-yl)methyl-4-(SR)-(3-biphenyl)psrrolidine A mixture of 34 mg (0.07 mmol) of 1-phenylmethyl -3-(SR)-((4-phenyl)piperidin-1-yl)methyl-4-(SR)-(3-bromo)phenylpyrrolidine (from Example 70), 19 mg (0.09 mmol) of benzene boronic acid, 32 mg (0.30 mmol) of Na₂CO₃ and 5.0 mg (0.004 mmol) of tetrakis(triphenyl-phosphine)palladium(0) in 3 mL of 2:1 v/v toluene/EtOH was stirred in an oil bath set at 95° C. for 20 h. The reaction mixture was partitioned between 20 mL of ether and 10 mL of H₂O and the layers were separated. The organic layer was washed with 10 mL of 0.5 N KHS04, 10 mL of sat'd NaHCO₃, 10 mL of sat'd NaCl, dried over MgSO₄ and concentrated in vacuo. Flash chromatography on 15 g of silica gel using 2:1 v/v, then 1:1 v/v hexanes/ether as the eluant afforded 15 mg (44%) of the title compound as a solid. $^1$H NMR (500 MHz, CDCl$_3$): δ1.22–4.20 (19H), 7.01–8.20 (19H). Mass Spectrum (NH$_3$-CI): 487 (M+1).

EXAMPLE 78

1-Phenylmethyl-3-(SR)-((4-phenyl)piperidin-1-yl)methyl-4-(SR)-(3-methyl)phenylpyrrolidine A mixture of 42 mg (0.08 mmol) of 1-phenylmethyl-3-(SR)-((4-phenyl)piperidin-1-yl)methyl-4-(SR)-(3-bromo)phenylpyrrolidine (from Example 70), 46 mg (0.26 mmol) of tetramethyltin and 6 mg (0.09 mmol) of bis(triphenylphosphine)palladium dichloride in 2 mL of DMF was heated at 100° C. for 24 h. The reaction mixture was cooled and partitioned between 20 mL of ether and 10 mL of H$_2$O and the layers were separated. The organic layer was washed with 10 mL of sat'd NaHCO$_3$, 10 mL of sat'd NaCl, dried over MgSO$_4$ and concentrated in vacuo. Flash chromatography on 16 g of silica gel using 3:2 v/v hexanes/ether as the eluant afforded 22 mg (61%) of the title compound as an oil. $^1$H NMR (500 MHz, CDCl$_3$): δ1.65–1.78 (m, 3H), 1.94–2.02 (m, 2H), 2.38 (s, 3H), 2.42–3.03 (m, 12H), 3.72 (ABq, J=13.0, 2H), 7.02–7.42 (m, 14H). Mass Spectrum (NH$_3$-CI): 425 (M+1). HPLC (YMC "Octyl" 4.6×250 mm column, 60:40 v/v H20/CH$_3$CN+0.5% TFA, 1.5 mL/min, 200 nm): 6.9 min.

EXAMPLE 79

1-Phenylmethyl-3-(SR)-((4-phenyl)piperidin-1-yl)methyl-4-(SR)-(3-methoxvcarbonyl)phenylpyrrolidine Carbon monoxide gas was bubbled through a mixture of 42 mg (0.08 mmol) of 1-phenylmethyl-3-(SR)-((4-phenyl)piperidin-1-yl)methyl-4-(SR)-(3-bromo)phenylpyrrolidine (from Example 70), 24 ,L (0.17 mmol) of TEA and 40 mg (0.03 mmol) of tetrakis(triphenyl-phosphine)palladium(0) in 2.5 mL of 4:1 v/v DMF/MeOH and the resulting mixture was stirred under an atmosphere of CO at 70 ° C. for 12 h. The reaction mixture was cooled, filtered and the filtrate was concentrated in vacuo. The residue was partitioned between 20 mL of EtOAc and 10 mL of sat'd NaHCO$_3$ and the layers were separated. The organic layer was washed with 10 mL of sat'd NaCl, dried over MgSO$_4$ and concentrated in vacuo. Flash chromatography on 10 g of silica gel using 4:1 v/v hexanes/EtOAc as the eluant afforded 15 mg (38%) of the title compound as an oil. $^1$H NMR (500 MHz, CDCl$_3$): δ1.54–3.11 (17H), 3.71 (ABq, J=39.6, 2H), 3.94 (s, 3H), 7.19–7.42 (11H), 7.59 (d, J=7.8, 1H), 7.88 (d, J=7.8, lH), 8.08 (s, 1H ). Mass Spectrum (NH$_3$-CI): 469 (M+1).

EXAMPLE 80

1-(2-Chlorobenzoyl)-3-(RS)-((4-(N-phenylmethoxycarbonyl-N-ethyl)amino)piperidin-1-l)methyl-4-(SR)-phenylpyrrolidine Step A: 1-(2-Chloro)benzoyl-3-(RS)-hydroxymethyl-4-(SR)-phenylpyrrolidine A mixture of 290 mg (1.6 mmol) of 3-(RS)-hydroxymethyl-4-(SR)-phenylpyrrolidine (from Example 4) in 10 mL of EtOAc and 5 mL of sat'd NaHCO$_3$ was treated with 0.25mL (2.0 mmol) of (2-chloro)-benzoyl chloride and stirred at rt for 20 min. The mixture was diluted with 25 mL of EtOAc and 10 mL of H$_2$O and the layers were separated. The organic layer was washed with 15 mL of 2 N HCl, 15 mL of sat'd NaHCO$_3$, 15 mL of sat'd NaCl, dried over MgSO$_4$ and concentrated in vacuo. Flash chromatography on 12 g of silica gel using 2:1 v/v CH$_2$Cl$_2$/EtOAc as the eluant afforded 146 mg of the title compound as an oil. $^1$H NMR (500 MHz, CDCl$_3$): δ1.69 (br s, 1H ), 2.50–2.63 (1H), 3.20–3.74 (6H), 4.09–4.22 (1H ), 7.20–7.42 (9H).

Step B: 1-(2-Chloro)benzoyl-3-(RS)-formyl -4-(SR)-phenylpyrrolidine

The title compound was prepared from 1-(2-chloro)benzoyl-3-(RS)-hydroxymethyl-4-(SR)-phenylpyrrolidine (from Example 80, Step A) using a procedure analogous to that descibed in Example 9, Step A. Mass Spectrum (NH$_3$-CI): 314 (M+1).

Step C: 1-(2-Chlorobenzoyl) -3-(RS)-((4-(N-phenylmethoxy-carbonyl-N-ethyl)amino)piperidin-1-yl) methyl-4-(SR)-phenylpyrrolidine A mixture of 80 mg (0.25 mmol) of 1-(2-chloro)benzoyl-3-(RS)-formyl -4-(SR)-phenylpyrrolidine (from Example 90, Step B) and 90 mg (0.30 mmol) 4-(N-phenylmethoxycarbonyl-N-ethylamino)-piperidine HCl and 45 μL (0.32 mmol) of TEA in 2 mL of dichloroethane was treated with 105 mg (0.5 mmol) of sodium triacetoxyborohydride and the. resulting mixture was stirred at rt for 3 h. The reaction mixture was partitioned between 30 mL of ether and 10 mL of 1 N NaOH and the layers were separated. The organic layer was washed with 10 mL of sat'd NaCl, dried over MgSO$_4$ and concentrated in vacuo. Flash chromatography on 8 g of silica gel using 1:1 v/v hexanes/EtOAc +1% TEA as the eluant afforded 110 mg (77%) of the title compound as an oil. Mass Spectrum (NH$_3$-CI): 561 (M+1). HPLC (YMC "Octyl" 4.6×250 mm column, 60:40 v/v H$_2$O/CH$_3$CN+0.5% TFA, 1.5 mL/min, 200 nm): 11.3 min.

The compounds described in Examples 81–84 were prepared using procedures analogous to those described in Example 80 substituting the appropriate acid chloride for (2-chloro)benzoyl chloride in Example 80, Step A.

EXAMPLE 81

1-(Benzoyl)-3-(RS)-((4-(N-phenylmethoxycarbonyl-N-ethyl)amino)-piperidin-1-yl)methyl-4-(SR)-phenylpyrrolidine
$^1$H NMR (500 MHz, CDCl$_3$): δ1.02–4.40 (22H), 5.10–5.16 (2H), 7.00–8.15 (15H).

EXAMPLE 82

1-( 1-Napthoyl)-3-(RS)-((4-(N-phenylmethoxycarbonyl-N-ethyl)amino)-piperidin-1-yl)methyl-4-(SR)-phenylpyrrolidine
$^1$H NMR (500 MHz, CDCl$_3$): δ1.05–4.50 (22H), 5.10–5.16 (2H), 7.12–7.97 (17H).

EXAMPLE 83

1-(Cyclohexanoyl)-3-(RS)-((4-(N-phenylmethoxycarbonyl-N-ethyl)amino)-piperidin-1-yl)methyl-4-(SR)-phenylpyrrolidine
$^1$H NMR (500 MHz, CDCl$_3$): δ1.11–4.02 (33H), 5.14 (app s, 2H), 7.20–7.36 (10H).

EXAMPLE 84

1-(Cyclopentanoyl)-3-(RS)-((4-(N-phenylmethoxycarbonyl-N-ethyl)amino)-piperidin-1-yl)methyl-4-(SR)-phenylpyrrolidine
$^1$H NMR (500 MHz, CDCl$_3$): δ1.11–4.48 (31H), 5.13 (app s, 2H), 7.20–7.36 (10H).

EXAMPLE 85

1-(2-Phenylethyl)-3-(SR)-((4-phenyl)piperidin-1-yl) methyl-4-(SR)-phenylpyrrolidine A mixture of 50 mg (0.16 mmol) 3-(SR)-((4-phenyl) piperidin-1-yl)methyl-4-(SR)-phenylpyrrolidine (from Example 30, Step A) and 37 mg (0.31 mmol) of phenylacetaldehyde and 100 mg 4 A powdered molecular sieves in 3 mL of MeOH was treated with 18 mg (0.28 mmol) of sodium cyanoborohydride and 2 drops of HOAc and stirred at rt for 18 h. The mixture was filtered onto a pad of Celite; the pad and flask were rinsed well with MeOH (25 mL). The filtrate was concentrated in vacuo and the residue was partitioned between 25 mL of EtOAc and 15 mL of sat'd NaHCO$_3$ and the layers were separated. The organic layer was dried over MgSO$_4$ and concentrated in vacuo. Flash chromatography on 15 g of silica gel using 2:1 v/v hexanes/EtOAc afforded 32 mg (48%) of the title compound as an oil. $^1$H NMR (500 MHz, CDCl$_3$): δ1.66–2.04 (6H), 2.42–3.13 (15H), 7.20–7.37 (15H). Mass Spectrum (NH$_3$-CI): 427 (M+1).

The compounds described in Examples 86–88 were prepared using a procedure analogous to that described in Example 85 substituting the appropriate aldehyde for phenylacetaldehyde.

EXAMPLE 86
1-(3-Phenylpropyl)-3-(SR)-((4-phenyl)piperidin-1-yl) methyl-4-(SR)-phenylpyrrolidine
$^1$H NMR (500 MHz, CDCl$_3$): δ1.65–2.03 (7H), 2.41–3.05 (16H), 7.21–7.37 (15H). Mass Spectrum (NH$_3$-CI): 439 (M+1). HPLC (YMC "Octyl" 4.6×250 mm column, 60:40 v/v H$_2$O/CH$_3$CN+0.5% TFA, 1.5 mL/min, 200 nm): 11.9 min.

EXAMPLE 87
1-(Cyclohexylmethyl)-3-(SR)-((4-phenyl)piperidin-1-yl) methyl-4-(SR)-phenylpyrrolidine
$^1$H NMR (500 MHz, CDCl$_3$): δ7.19–7.36 (17H), 1.03–3.04 (30H). Mass Spectrum (NH$_3$-CI): 417 (M+1). HPLC (YMC "Octyl" 4.6×250 mm column, 60:40 v/v H$_2$O/ CH$_3$CN+ 0.5% TFA, 1.5 mL/min, 200 nm): 7.2 min.

EXAMPLE 88
1-((1-Napthyl)methyl)-3-(SR)-((4-phenyl)piperidin-1-yl) methyl-4-(SR)-phenlpvrrolidine
$^1$H NMR (500 MHz, CDCl$_3$): δ7.18–8.40 (17H), 1.28–4.14 (19H). Mass Spectrum (NH$_3$-CI): 461 (M+1). HPLC (YMC "Octyl" 4.6×250 mm column, 60:40 v/v H$_2$O/ CH$_3$CN+ 0.5% TFA, 1.5 mL/min, 200 nm): 8.4 min.

EXAMPLE 89
1-((N-Phenylcarbamoyl)-3-(SR)-((4-phenyl)piperidin-1-yl) methyl-4-(SR)-phenylpyrrolidine A solution of 50 mg (0.16 mmol) of 3-(SR)-((4-phenyl)-piperidin-1-yl)methyl-4-(SR)-phenylpyrrolidine (from Example 30, Step A) and 43 gL (0.25 mmol) of DIEA in 2 mL of CH$_2$Cl$_2$ was treated with 34 μL (0.31 mmol) of phenyl isocyanate and stirred at rt for 2 h. The reaction mixture was partitioned between 20 mL of EtOAc and 10 mL of H$_2$O and the layers were separated. The organic layer was dried over MgSO$_4$ and concentrated in vacuo. Flash chromatography on 15 g of silica gel using 2:1 v/v hexanes/EtOAc as the eluant afforded 39 mg (57%) of the title compound as an oil. $^1$H NMR (500 MHz, CDCl$_3$): δ1.70–1.83 (4H), 1.93–1.97 (m, 1H ), 2.09–2.13 (m, 1H ), 2.40–2.49 (3H), 2.68–2.73 (m, 1H ), 2.91 (d, J=11.0, 1H), 3.04 (d, J=11.0, 1H), 3.12 (q, J=9.2, 1H), 3.37 (t, J=9.0, 1H), 3.54 (t, J=9.6, 1H), 3.95–4.01 (m, 2H), 6.31 (s, 1H ), 7.03–7.48 (15H). Mass Spectrum (NH$_3$-CI): 440 (M+1).

EXAMPLE 90
1-((1-(RS)-Phenylethyl)-3-(SR)-((4-phenyl)piperidin-1-yl) methyl-4-(SR)-phenylpyrrolidine A solution of 54 mg (0.17 mmol) of 3-(SR)-((4-phenyl)-piperidin-1-yl)methyl-4-(SR)-phenylpyrrolidine (from Example 30, Step A), 62 mg (0.34 mmol) of (+)-(1-phenyl) ethyl bromide and 53 JIL (0.30 mmol) of DIEA in 3 mL of CH$_3$CN was heated at reflux for 1 h. The reaction mixture was cooled and partitioned between 25 mL of ether and 10 mL of sat'd NaHCO$_3$ and the layers were separated. The organic layer was dried over MgSO$_4$ and concentrated in vacuo. Flash chromatography on 15 g of silica gel using 3:2 v/v hexanes/EtOAc as the eluant afforded 46 mg (64%) of the title compounds as a mixture of inseparable racemic diastereomers. Mass Spec (NH$_3$-CI): 425 (M+1).

EXAMPLE 91
1-(Benzothiazol-2-yl)-3-(SR)-((4-phenyl)piperidin-1-yl) methyl-4-(SR)-phenylpyrrolidine A mixture of 54 mg (0.16 mmol) of 3-(SR)-((4-phenyl) piperidin-1-yl)methyl-4-(SR)-phenylpyrrolidine (from Example 30, Step A), 53 mg (0.31 mmol) of (2-chloro) benzothiazole and 65 mg (0.47 mmol) of K$_2$CO$_3$ in 3 mL of DMF was heated at 80° C. for 1 h. The reaction mixture was cooled, partitioned between 25 mL of ether and 15 mL of H$_2$O and the layers were separated. The organic layer was dried over MgSO$_4$ and concentrated in vacuo. Flash chromatography on 15 g of silica gel using 1:1 v/v hexnaes/EtOAc as the eluant afforded 16 mg (23%) of the title compound as an oil. $^1$H NMR (500 MHz, CDCl$_3$): δ1.79–3.04 (12H), 3.29 (q, J=8.9, 1H), 3.55 (t, J=9.0, 1H), 3.69 (t, J=9.6, 1H), 4.03–4.11 (m, 2H), 7.07–7.64 (14H). Mass Spectrum (NH$_3$-CI): 454 (M+.1).

EXAMPLE 92
1-(Benzoxazol-2-yl)-3-(SR)-((4-phenyl)piperidin-1-yl) methyl-4-(SR)-phenylpyrrolidine The title compound was prepared using a procedure analogous to that described in Example 91 substituting (2-chloro)benzoxazole for (2-chloro)benzothiazole. $^1$H NMR (500 MHz, CDCl$_3$): δ1.61–3.28 (12H), 3.25 (q, J=8.7, 1H), 3.59 (t, J=9.6, 1H), 3.75 (t, J=9.0, 1H), 4.16 (dd, J=7.8, 10.5, 2H), 7.01–7.41 (14H). Mass Spectrum (NH$_3$-CI): 438 (M+1).

EXAMPLE 93
1-Benzyl-3-(SR)-(4-(N-methoxy, N-methyl-carboxamide)-piperidin-1-ylmethyl)-4-(SR)-phenylpyrrolidine To a solution of 225 mg of 1-benzyl-3-(SR)-(4-carboethoxy-piperidin-1-ylmethyl)-4-(SR)-phenylpyrrolidine (from Example 27) and 83 mg of N-methoxy-methylamine hydrochloride in 1.5 mL of THF at −20° C. was added 0.83 mL of isopropylmagnesium chloride (2M in THF). The reaction was allowed to warm to 0° C. over 30 min. The reaction was quenched with 1N NaHCO$_3$. The mixture was partitioned between 50 mL of EtOAc and 50 mL of IN NaHCO$_3$. After separating layers, the organic phase was washed with 50 mL of brine, dried over Na2SO$_4$ and concentrated under vacuum. The residue was purified by flash chromatography eluting with a 2.5% MeOH in CH$_2$Cl$_2$ to give 159 mg of the title compound. R$_F$: 0.26 (5% MeOH in CH$_2$Cl$_2$). $^1$H NMR (300 MHz, CDCl$_3$): δ1.52–1.90 (m, 6H), 2.34–2.71 (m, 7H), 2.88–3.02 (m, 4H), 3.15 (s, 3H), 3.59–3.71 (m, 5H), 7.13–7.38(m, 10H). Mass Spectrum (CI): 422.3 (M+H).

EXAMPLE 94
1-Benzyl-3-(SR)-(4-(N-methyl-N-phenyl-carboxamide)-piperidin-l-ylmethyl)-4-(SR)-phenylpyrrolidine The title compound was prepared from 35 mg of 1-benzyl-3-(SR)-(4-carboethoxy-piperidin-1-ylmethyl)-4-(SR)-phenylpyrrolidine (from Example 29), 0.015 mL of N-methylaniline and 0.070 mL of isopropylmagnesium chloride (2M in THF) using a procedure analogous to that described in Example 93 to provide 12 mg of the title compound. R$_F$: 0.30 (5% MeOH in CH$_2$Cl$_2$). $^1$H NMR (300 MHz, CDCl$_3$): δ1.36–1.86 (m, 6H), 2.02–2.94 (m, 11H), 3.22 (s, 3H), 3.63 (ABq, J=13 Hz, 2H), 7.10–7.41 (m, 15H). Mass Spectrum (CI): 468.3 (M+H).

EXAMPLE 95
1-Benzyl-3-(SR)-(4-(N-benzyl-N-methyl-carboxamide)-piperidin-l-ylmethyl)-4-(SR)-phenylpyrrolidine The title compound was prepared from 35 mg of 1-benzyl-3-(SR)-(4-carboethoxy-piperidin-1-ylmethyl)-4-(SR)-phenylpyrrolidine (from Example 29), 0.017 mL of N-benzyl-N-methylamine and 0.070 mL of isopropylmagnesium chloride (2M in THF) using a procedure analogous to that described in Example 93 to provide 7.5 mg of the title compound. R$_F$: 0.25 (5% MeOH in CH$_2$Cl$_2$). 1-H NMR (300 MHz, CDCl$_3$): δ1.49–1.90 (m, 6H), 2.30–2.51 (m, 5H), 2.60–2.73(m, 2H), 2.84–3.02 (m, 7H), 3.59–3.72 (m, 2H), 4.51, 4.57 (2S, 2H), 7.10–7.37 (m, 16H). Mass Spectrum (CI): 482.4 (M+H).

EXAMPLE 96
1-Benzyl-3-(SR)-(4-(N-benzyl-N-ethyl-carboxamide)-piperidin-1-ylmethyl)-4-(SR)-phenylpyrrolidine The title compound was prepared from 30 mg of 1-benzyl-3-(SR)-(4-carboethoxy-piper idin- 1-y-methyl)-4-(SR)-phenylpyrrolidine, 0.022 mL of N-benzyl-N-methylamine and 0.075 mL of isopropyl-magnesium chloride (2M in THF) using a procedure analogous to that described in Example 93 to provide 16 mg of the title compound. R$_F$: 0.30 (5%.MeOH in CH$_2$Cl$_2$). $^1$H NMR (300 MHz, CDCl$_3$): δ1.04–1.13 (m, 3H), 1.44–1.94 (m, 6H), 2.27–3.01 (m, 11H), 3.23,3.37 (2q, J=7.1 Hz, 2H), 3.58–3.72 (m, 2H), 4.49, 4.57 (2s, 2H), 7.11–7.37 (m, 15H). Mass Spectrum (CI): 496.3 (M+H).

EXAMPLE 97
1-Benzyl-3-(SR)-(4-(N-methyl-N-phenethyl-carboxamide)-piperidin-1-ylmethyl)-4-(SR)-phenylpyrrolidine The title compound was prepared from 37.5 mg of 1-benzyl-3-(SR)-(4-carboethoxy-piperidin-1-ylmethyl)-4-(SR)-phenylpyrrolidine, 0.020 mL of N-methyl-N-phenethylamine and 0.070 mL of isopropyl-magnesium chloride (2M in THF) using a procedure analogous to that described in Example 93 to provide 25.5 mg of the title compound. RF: 0.20 (5% MeOH in CH$_2$Cl$_2$). $^1$H NMR (300 MHz, CDCl$_3$): δ1.20–1.97 (m, 7H), 2.27–2.49 (m, 4H), 2.61–2.70 (m, 2H), 2.78–3.00 (m, 9H), 3.46–3.71 (m, 4H), 7.09–7.37 (m, 15H). Mass Spectrum (CI): 496.3 (M+H).

EXAMPLE 98
1-Benzyl-(SR)-[3-methyl-3-((4-phenyl)piperidin-1-yl) methyl] -4-(SR)-phenylpyrrolidine Step A: 1-Benzyl-(RS)-[3-methyl-3-formyl]-4-(SR)-phenylpyrrolidine A solution of 150 mg (1.0 mmol) of α-methyl cinnamaldehyde, 400 mg (1.67 mmol) of N-(methoxymethyl)-N-6 (trimethylsilylmethyl) benzylamine and 25 mg (0.2 mmol) of titanium tetrafluoride in 5 mL of CH$_3$CN was stirred at 50° C. for 18 h. The reaction mixture was cooled and concentrated in vacuo. The residue was partitioned between 50 mL of ether and 25 mL of 50% sat'd NaCl and the layers were separated. The orgainc layer was dried over MgSO$_4$. The aqueous layer was extracted with 50 mL of ether; the extract was dried, combined with the original organic layer and concentrated in vacuo. Flash chromatography on 12 g of silica gel using 10:1 v/v hexanes/ether as the eluant afforded 203 mg (75%) of the title compound as an oil. $^1$H NMR (500 MHz, CDCl$_3$): δ0.72 (s, 3H), 2.40 (d, J=.12.0, 1H), 2.88 (t, J=9.5, 1H), 3.19–3.22 (m, 2H), 3.68 and 3.76 (ABq, J=40.5, 2H), 7.20–7.39 (1OH), 9.65 (s, b 10H ).

Step B: 1-Benzyl-(SR)-[3--methyl-3-((4-phenyl)piperidin-1-yl)methyl]-4-(SR)-phenylpyrrolidine The title compound was prepared from 1-benzyl-(RS)-[3-methyl-3-formyl]-4-(SR)-phenylpyrrolidine (from Example 98, Step A) and(4-phenyl)piperidine using a procedure analogous to that described in Example 9. 1H NMR (500 MHz, CDCl$_3$): δ0.69 (s, 3H), 1.72–1.79 (4H), 2.25–2.45 (4H), 2.35 and 2.79 (ABq, J=220.0, 2H), 2.89 (t, J=8.5, 1H), 2.90–2.95 (m, 1H ), 3.05 (app t, J=9.0, 1H), 3.17 (app t, J=8.0, 1H), 3.62 and 3.74 (ABq, J=60.5, 2H), 7.17–7.39 (15H).

EXAMPLE 99
1-Benzyl-3-(SR)-(1-(RS)-((4-phenyl)piperidin-1-yl)ethyl)-4-(SR)-phenylpyrrolidine and 1-Benzyl-3-(SR)-(1-(SR)-((4-phenyl)piperidin-1-yl)ethyl)-4-(SR)-phenylpyrrolidine Step A: 1-Benzyl-3-(RS)-acetyl-4-(SR)-phenylpyrrolidine The title compound was prepared from (E)-4-phenyl-3-butan-2-one using a procedure analogous to that described in Example 1, Step A. $^1$H NMR (400 MHz, CDCl$_3$): δ2.07 (s, 3H), 2.72 (m, 1H ), 2.83–2.87 (m, 1H ), 2.97–3.02 (2H), 3.21 (app q, J=8.4, 1H), 3.58 (app q, J=6.8, 1H), 3.64–3.68 (2H), 7.20–7.38 (15H); Mass Spectrum (NH$_3$-CI): 280 (M+1).

Step B: 1-Benzyl-3-(SR)-(1-(RS)-((hydroxy)ethyl)-4-(SR)-phenylpyrrolidine and 1-Benzyl-3-(SR)-(1-(RS)-(hydroxy)ethyl)-4-(SR)-phenylpyrrolidine A solution of 750 mg (2.7 mmol) of 1-benzyl-3-(RS)-acetyl-4-(SR)-phenylpyrrolidine (from Example 99, Step A) in 10 mL of MeOH at 0° C. was treated with 150 mg of NaBH4 and was stirred cold for 30 min. The reaction was quenched with 5 mL of sat'd NaHCO3 and -concentrated in vacuo. The residue was partitioned between 50 mL of ether and 25 mL of H$_2$O and the layers were separated. The organic layer was washed with 25 mL of sat'd NaCl, dried over MgSO$_4$ and concentrated in vacuo. Flash chromtography on 35 g of silica gel using 4:1 v/V, then 2:1 v/v hexanes/EtOAc afforded 375 mg of (+)-Diastereomer B1 and 159 mg of (±)-Diastereomer B2 (70% total yield). For (±)-Diastereomer B2 $^1$H NMR (300 MHz, CDCl$_3$): d 1.11 (d, J=6.4, 3H), 2.19–2.25 (m, 1H ), 2.34 (app t, J=8.8, 1H), 2.79 (dd, J=7.0, 9.2, 1H), 2.90 (dd, J=r2.4, 9.4), 3.03 (app t, J=8.8, 1H), 3.44–3.51 (m, 1H ), 3.65 (app s, 2H), 3.93–4.00 (m, 1H ), 7.17–7.33 (1OH). For (+)-Diastereomer B2: 1H NMR (300 MHz, CDCl$_3$): d 1.12 (d, J=6.4, 3H), 2.19–2.25 (m, 1H ), 2.39–2.43 (m, 1H ), 2.71 (app t, J=10.6, 1H), 3.07 (dd, J=3.2, 9.6, 1H), 3.22–3.33 (2H), and 3.65 and 3.72 (ABq, J=20.0, 2H), 3.85–3.91 (m, 1H ), 7.17–7.33 (1OH).

Step C: 1-Benzyl-3-(SR)-(1-(RS)-((azido)ethyl)-4-(SR)-phenyl-pyrrolidine and 1-Benzyl-3-(SR)-(1-(RS)-(azido)ethyl)-4-(SR)-phenylpyrrolidine A mixture of 147 mg (0.52 mmol) of (+)-Diastereomer B-(from Example 99, Step B), 262 mg (1.0 mmol) of triphenylphosphine, 68 mg (1.0 mmol) of imidazole and 231 mg (0.75 mmol) of zinc azide, bis(pyridine) complex in 3 mL of CH$_2$Cl$_2$ at 0° C. was treated with a solution of 174 mg (1.0 mmol) of diethylazodicarboxylate in 1 mL of CH2Cl2. The cooling bath was removed and the reaction was stirred at rt for 1 h. The reaction was filtered through a pad of Celite and the filtrate was concentrated in vacuo. Flash chromatography on 12 g of silica gel using 17:3 v/v hexanes/ether as the eluant afforded 129 mg (81%) of one of the title compounds (Diatereomer Cl) as an oil: $^1$H NMR (300 MHz, CDCl$_3$): δ1.18 (d, J=6.4, 3H), 2.26–2.35 (m, 1H ), 2.63–2.69 (m, 2H), 2.86–3.09 (3H), 3.49–3.58 (m, 1H ), 3.63 and 3.70 (ABq, J=21.4, 2H), 7.18–7.38 (1OH); IR (cm-1, neat) 2104.

(±)-Diastereomer B2 was reacted similarly to afford Diastereomer C2 as an oil: $^1$H NMR (500 MHz, CDCl$_3$): d 1.22 (d, J=6.5, 3H), 2.33–2.42 (2H), 2.66–2.70 (m, 1H ), 2.88–2.93 (m, 2H), 3.17 (app q, J=6.5, 1H), 3.47–3.52 (m, 1H ), 3.61 and 3.66 (ABq, J=26.0, 2H), 7.15–7.35 (1OH).
Step D: 1-Benzyl-3-(SR)-(1-(RS)-((4-phenyl)piperidin-lyl)ethyl)-4-(SR)-phenylpyrrolidine and 1-Benzyl-3-(SR)-(1-(SR)-((4-phenyl)piperidin-1-yl)ethyl)-4-(SR)-phenylpyrrolidine A mixture of 20 mg of 10% palladium on carbon and 128 mg (0.42 mmol) of (±)-Diastereomer Cl (from Example 99, Step B) in 4 mL of methanol was stirred under an atmosphere of H2 for 20 h. The reaction mixture was filtered through a pad of Celite and the filtrate was concentrated in vacuo. The residue, 181 mg (0.37 mmol) of (±)-1,5-bis(4-toluenesulfonyloxy)-3-phenylpentane and 175 mL (1.0 mmol) of DIEA were dissolved in 5 mL of isobutyrylnitrile and the mixture was stirred at 100° C. for 20 h. The reaction mixture was cooled and partitioned between 50 mL of CH$_2$Cl$_2$ and 20 mL of 1.0 N NaOH and the layers were separated. The organic layer was dried over MgSO$_4$ and concentrated in vacuo. Flash chromatography on 8 g of silica gel using 40:1 v/v hexanes/EtOAc +1.5% TEA as the eluant afforded 70 mg of impure product. Flash chromatography of this material on 8 g of silica gel using 100:1:0.1 v/v/v CH$_2$Cl$_2$/MeOH/NH$_{40}$H as the eluant afforded 54 mg (30%) of one of the title compounds (Diastereomer Dl) as an oil: $^1$H NMR (500 MHz, CDCl$_3$): δ0.82 (d, J=6.5, 3H), 1.53–1.61 (m, 1H ), 1.71–1.77 (3H), 2.08 (app t, J=11.0, 1H), 2.36–3.00 (11H), 3.58 and 3.74 (ABq, J=78.5, 2H), 7.15–7.45 (15H); Mass Spectrum (NH$_3$-CI): 425 (M+1). (±)-Diastereomer C2 was reacted similarly to afford (±)-Diastereomer D2 as an oil: $^1$H NMR (500 MHz, CDCl$_3$): δ0.87 (d, J=6.5, 3H), 1.03–1.11 (m, 1H ), 1.31–1.34 (m, 1H ), 1.67–1.77 (2H), 1.93 (dt, J=2.0, 11.5, 1H), 2.18–2.22 (m, 1H ), 2.26–2.38 (3H), 2.50 (dt, J=3.0, 11.0, 1H), 2.54–2.60 (m, 1H ), 2.65–2.68 (m, 1H ), 2.73–2.76 (m, 1H ), 2.84 (app t, J=8.5, 1H), 2.92 (app t, J=8.0, 1H), 3.27–3.30 (m, 1H ), 3.59 and 3.67 (ABq, J=38.0, 2H), 7.11–7.35 (15H);); Mass Spectrum (NH$_3$-CI): 425 (M+1). HPLC (YMC "Octyl" 4.6×250 mm column, 60:40 v/v H$_2$O/ CH$_3$CN+0.5% TFA, 1.5 ml/min, 200 nm): 6.0 min.

EXAMPLE 100
1-(2-Chloro)benzoyl-3-(SR)-(1-(RS)-((4-phenyl)piperidin-1-yl)ethyl)-4-(SR)-phenylpyrrolidine or 1-(2-chloro)benzoyl-3-(SR)-(1-(SR)-((4-phenyl)piperidin-1-yl)ethyl)-4-(SR)-phenylpyrrolidine The title compound was prepared from (±)-Diastereomer D2 (from Example 99, Step D) using procedures analogous to those described in Example 9, Step B and Example 37: 1H NMR (500 MHz, CDCl$_3$): δ0.80–1.00 (4H), 1.22–1.64 (5H), 1.98–2.67 (6H), 3.28–3.54 (3H), 4.03–4.11 (m, IH), 7.02–7.43 (m, 14H); Mass Spectrum (NH$_3$-CI): 473 (M+1). HPLC (YMC "Octyl" 4.6×250 mm column, 60:40 v/v H$_2$O/ CH$_3$CN+0.5% TFA, 1.5 mL/min, 200 nm): 10.7 min.

EXAMPLE 101
N-Benzyl-3-(SR)-phenl-4-(SR)-(4-phenlpiperidin-1-ylmethyl)-piperidine
Step A: N-Benzyl-4-trifluoromethanesulfonyl-1, 2, 5, 6-tetrahydropyridine To a solution of N-benzyl-4-piperidone in 27 mL of THF at −78 ° C. was added 6.0 mL of lithium bis(trimethylsilyl) amide (1.0M in THF). After stirring at −78° C. for 25 min, the reaction was warmed to 0° C. for 5 min, then recooled to −78° C. After adding 2.54 g of 2-EN, N-bis(trifluoromethyl-sulfonyl)amino]-5-chloropyridine, the reaction was stirred for 1 h at −78° C., quenched with 1N NaHCO$_3$ and warmed to room temperature. The reaction was partitioned between 100 mL of 1N NaHCO$_3$ and 100 mL of Et$_2$O. After separating phases, the aqueous layer was extracted with 100 mL of Et$_2$O. The combined organic layers were dried over Na2SO$_4$ and concentrated under vacuum. The residue was purified by flash chromatography eluting with 10% EtOAc in hexanes to provide 737 mg of the title compound: $^1$H NMR (300 MHz, CDCl$_3$): δ2.4 (m, 2H), 2.7 (t, 2H), 3.1 (m, 2H), 3.6 (s, 2H), 5.7 (m, 1H ), 7.2–7.4 (m, 5H). R$_F$: 0.52 (20% EtOAc in hexanes).
Step B: N-Benzyl-4-carbomethoxy-1, 2, 5, 6-tetrahydropyridine To a solution of 253 mg of triflate (from Example 101, Step A) and 0.21 mL of TEA in 1.2 mL of MeOH and 7.8 mL of DMF was added 367 mg of tetrakis (triphenylphosphine)palladium(0). After bubbling carbon monoxide through the solution for 20 min, the reaction was warmed to 65° C. under 1 atm of CO for 7.5 h. After cooling to room temperature, the reaction was concentrated under vacuum. The residue was dissolved in 100 mL of EtAOc and washed with 100 mL 1N NaHCO$_3$. After separating layers the aqueous phase was extracted with 100 EtAOc. The combined organic layers were dried over Na2SO$_4$ and concentrated under vacuum. The residue was purified by flash chromatography eluting with 20% EtOAc in hexanes to provide 125 mg of the title compound: $^1$H NMR (300 MHz, CDCl$_3$): δ2.4 (m, 2H), 2.6 (t, 2H), 3.1 (m, 2H), 3.6 (s, 2H), 3.7 (s, 3H), 6.9 (m, 1H ), 7.2–7.4 (m, 5H). R$_F$: 0.56 (50% EtOAc in hexanes).
Step C: N-Benzyl-4-carbomethoxv-3-phenyl-piperidine To a suspension of 59 mg of ester (from Example 101, Step B), 4.4 mg of CuBr2 and 0.096 mL of TMSCI in 2.5 mL of Et$_2$O at −45° C. was added 0.125 mL of phenylmagnesium bromide (3.OM in Et$_2$O). After stirring at −45° C. for 1 h, the reaction was quenched with 10% NH$_{40}$H. The reaction was partitioned between 10 mL of H$_2$O and 10 mL of Et$_2$O. After separating layers, the aqueous phase was extracted with 10 mL of Et$_2$O. The combined organic layers were dried over MgSO$_4$ and concentrated under vacuum. The residue was purified by flash chromatography eluting with 20% Et$_2$O in hexanes to provide 12 mg of the title compound: $^1$H NMR (300 MHz, CDCl$_3$): δ1.8–1.9 (m, 1H ), 2.0–2.1 (m, 1H ), 2.3–2.4 (m, 1H ), 2.6–2.7 (m, 1H ), 2.8–2.9 (m, 2H), 3.1–3.2 (m, 1H ), 3.2–3.3 (m, 1H ), 3.4 (s, 3H), 3.6 (s, 2H), 7.2–7.4 (m, 8H), 7.4–7.5 (m, 2H). R$_F$: 0.40 (50% Et$_2$O in hexanes).
Step D: N-Benzyl-4-(4-phenylpiperidinecarboxamide)-3-phenylpiperidine To a solution 12 mg of methyl ester (from Example 101, Step C) and 9 mg of 4-phenylpiperidine in 0.5 mL of THF at −20° C. was added 0.030 mL isopropylmagnesium chloride (2M in THF). The reaction was stirred at −20° C. for 1 h, then warmed to room temperature. The reaction was quenched with saturated NaCl and partitioned between 10 mL of brine and 10 mL of EtOAc. After separating layers the aqueous phase was extracted with 10 mL EtOAc. The combined organic layers were dried over Na$_2$SO$_4$ and concentrated under vacuum. The residue was purified by flash chromatography eluting with 100% EtOAc to provide 8 mg of the title compound: $^1$H NMR (300 MHz, CDCl$_3$): δ1.4–2.1 (m, 6H), 2.3–2.8 (m, 4H), 2.9–3.4 (m, 5H), 3.6–3.9 (m, 3H), 4.6–4.8 (m, 1H), 6.9–7.4 (m, 15H); Mass Spectrum (CI): 439.2 (M+H). R$_F$: 0.28 (100% EtOAc).
Step E: N-Benzyl-3-(SR)-phenyl-4-(SR)-(4-phenylpiperidin-1-ylmethyl)-piperidine To a solution of 8 mg of amide (from Example 101, Step D) in 1 mL of THF at 0° C. was added 3 mg of lithium aluminumhydride. After 2 h at 0 OC the reaction was quenched with saturated Rochelle salts and partitioned between 10 mL of Rochelle salts and 10 mL of EtOAc. After separating layers the aqueous phase was extracted with 10 mL EtOAc. The combined organic layers were dried over $Na_2SO_4$ and concentrated under vacuum. The residue was purified by flash chromatography eluting with 25% EtOAc in hexanes to provide 3 mg of the title compound: $^1$H NMR (300 MHz, $CDCl_3$): δ1.5–2.1 (m, 6H), 2.1–2.6 (m, 5H), 2.7–3.2 (m, 7H), 3.4–3.6 (m, 3H), 7.1–7.4 (m, 13H), 7.7–7–8 (m, 2H); Mass Spectrum (CI): 425.2 (M+H). $R_F$: 0.47 (50% EtOAc in hexanes).

EXAMPLE 102

N-Tertbutoxycarbonyl-4-(SR)-phenyl-3-(SR)-(4-phenylpiperidin-l-ylmethyl)-piperidine
Step A: N-Tertbutoxycarbonyl-4-phenyl-3-(4-phenylpipericline-carboxamide)-1, 2, 5, 6-tetrahydropyrdine To a solution of 14.4 mg 4-phenylpiperidine in 1.6 mL $CH_2Cl_2$ at 0° C. was added 0.035 mL of DIEA, 26.5 mg of 1-(t-butoxycarbonyl)-4-phenyl-1,2,5,6-tetrahydronicotinic acid and 26,5 mg of BOP-Ci (Bis(2-oxo-3-oxazolidinyl)-phosphinic chloride). After 4 h at 0° C. and I h at room temperature, the reaction was diluted with 50 mL of EtOAc and washed with 50 mL $H_2O$, 50 mL 1N $NaHCO_3$, 50 mL $H_2O$ and 50 mL brine. The organic phase was dried over $Na_2SO_4$ and concentrated under vacuum. The residue was purified by flash chromatography eluting with 35% EtOAc in hexanes to provide 22 mg of the title compound: $^1$H NMR (300 MHz, $CDCl_3$): δ1.5–1.8 (m, 13H ), 2.1–2.6 (m, 3H), 2.8–3.0 (m, 2H ), 3.6–4.5 (m, 5H ), 4.6–4.8 (m, 1H ), 6.8 (br d, 1H ), 7.1–7.5 (m, 9H ). $R_F$: 0.47 (50% EtOAc in hexanes).
Step B: N-Tertbutoxycarbonyl-4-phenyl-3-(4-phenylpiperidine-carboxamide)piperidine To a solution of 11 mg of amide (from Example 102, Step A) in 0.5 mL MeOH at room temperature was added 26 mg of magnesium turnings. After 3 h at room temperature the reaction was concentrated under vacuum. The residue was suspended in 10 mL of EtOAc and washed with 10 mL of brine. After separating the layers, the aqueous phase was extracted with 10 mL EtOAc. The combined organic layers were dried over $Na_2SO_4$ and concentrated under vacuum. The residue was taken on to Step C without further purification.
Step C: N-Tertbutoxycarbonyl-4-phenyl-3-(4-phenylpiperidin-1-ylmethyl)-piperidine To a solution of the amide (from Example 102, Step B) at 0° C. in 0.5 mL of THF was added 0.3 mL $AlH_3$ (0.2M in THF). After 1.5 h at 0° C. the reaction was quenched with brine. The reaction was partitioned between 10 mL of EtOAc and 10 mL of brine. After separating the layers, the aqueous phase was extracted with 10 mL EtOAc. The combined organic layers were dried over $Na_2SO_4$ and concentrated under vacuum. The residue was purified by flash chromatography eluting with 30% EtOAc in hexanes to provide 4 mg of the title compound: $^1$H NMR (300 MHz, $CDCl_3$): δ1.4–2.1 (m, 19H), 2.2–3.1 (m, 7H), 4.2–4.6 (m, 2H), 7.1–7.4 (m, 10H); Mass Spectrum (ESI): 435.5 (M+H). $R_F$: 0.60 (50% EtOAc in hexanes).

EXAMPLE 103

N-Sulfonyl-4-(SR)-phenyl-3-(SR)-(4-phenylpiperidin-1-ylmethyl)-ipiperidine
Step A: 4-(SR)-Phenyl-3-(SR)-(4-phenylpiperidin-1-ylmethyl)-piperidine To a solution of 5.5 mg of carbamate (from Example 102, Step C) in 0.6 mL of $CH_2Cl_2$ at room temperature was added 0.4 mL trifluoroacetic acid. After 1 h at room temperature, volatiles were removed under vacuum. The crude product taken onto Step B without further purification.
Step B: N-Sulfonyl-4-(SR)-phenyl-3-(SR)-(4-phenylpiperidin-1-ylmethyl)-piperidine To a solution of the above deprotected amine (from Example 103, Step A) in 1 mL of $CH_2Cl_2$ was added 0.014 mL of DIEA, 0.002 mL of benzenesulfonyl chloride and a catalytic amount of dimethylaminopyridine. After stirring at room temperature for 20 h, the reaction was diluted with 25 mL of $CH_2Cl_2$ and washed with 25 mL of 1N $NaHCO_3$. After separating layers, the organic phase was dried over $Na_2SO_4$ and concentrated under vacuum. The residue was purified by flash chromatography eluting with 20% EtOAc in hexanes to provide 3 mg of the title compound: $^1$H NMR (300 MHz, $CDCl_3$): δ1.5–2.9 (m, 17H), 4.0–4.2 (m, 2H), 7.1–7.4 (m, 12H), 7.5–7.7 (m, 2H), 7.8–7.9 (m, 1H ); Mass spec. (ESI): 475.3 (M+H). $R_F$: 0.44 (50% EtOAc in hexanes).

EXAMPLE 104

N-Sulfonyl-4-(SR)-phenyl-3-(SR)-(4-phenylpiperidin)-piperidine
Step A: N-Tertbutoxycarbonyl-4-phenyl-3-(carbomethoxy)-1, 2, 5, 6-tetrahydropyridine To a solution of 153 mg of 1-(t-butoxycarbonyl)-4-phenyl-1,2,5,6-tetrahydronicotinic acid in 1 mL of THF and 1 mL of MeOH was added 0.6 mL of TMSCHN2 (2M in hexanes). The reaction was stirred at room temperature for 2 h and concentrated under vacuum. The residue was purified by flash chromatography eluting with 20% EtOAc in hexanes to provide 116 mg of the title compound: $^1$H NMR (300 MHz, $CDCl_3$): δ1.5 (s, 9H), 2.5–2.6 (m, 2H), 3.5 (s, 3H), 3.6 (t, 2H), 4.2–4.3 (m, 2H), 7.1–7.2 (m, 2H), 7.2–7.4 (m, 3H). $R_F$: 0.68 (50% EtOAc in hexanes).
Step B: N-Tertbutoxycarbonyl-4-phenyl-3-(carbomethoxy)-piperidine To a solution of 110 mg of ester (from Example 104, Step A) in 5 mL of MeOH at room temperature was added 345 mg of magnesium turnings. After 1.5 h at room temperature the reaction became exothermic and was cooled with an ice bath. The reaction was warmed to room temperature overnight. The reaction was filtered through a pad of celite. The filtrate was concentrated uner vacuum. The residue was suspended in 25 mL of EtOAc and washed with 25 mL of brine. After separating the layers, the aqueous phase was extracted with 25 mL EtOAc. The combined organic layers were dried over $Na_2SO_4$ and concentrated under vacuum to give 89 mg of a residue which was taken onto Step C without further purification: $^1$H NMR (300 MHz, $CDCl_3$): δ 1.4–1.9 (m, 11H), 2.6–3.3 (m, 4H), 3.5 (s, 3H), 4.2–4.6 (m, 2H), 7.1–7.4 (m, 5H).
Step C: N-Tertbutoxycarbonyl-4-phenyl-3-(carboxy)-piperidine To a solution of 89 mg of methyl ester (from Example 104, Step B) in 1.5 mL EtOH was added 1.0 mL of 0.5N NaOH. After 36 h the reaction was concentrated under vacuum. The residue was dissolved in 25 mL $H_2O$ and washed with 25 mL $Et_2O$. After separating layers, the aqueous phase was acidified to pH 2 using 0.5N $KHSO_4$. The aqueous phase was extracted with 3×25 mL of $CH_2Cl_2$. The combined extracts were dried over $Na_2SO_4$ and concentrated under vacuum to give 58 mg of a white foam which was taken on without further purification.
Step D: N-Tertbutoxycarbonyl-4-phenyl-3-(aminobenzyloxy-carbonyl)-piperidine To a solution of 58 mg of carboxylic acid (from Example 104, Step C) in THF at −10° C. was added 0.029 mL of NMM and 0.034 mL of isobutylchloroformate. After stirring at room temperature for 50 min, the reaction was cooled to −10° C. and 68 mg of NaN$_3$ in 0.35 mL of H$_2$O was added. After stirring an additional 20 min at −10° C., the reaction was partitioned between 10 mL of Et$_2$O and 10 mL of H20. After separating layers, the organic phase was washed with 10 mL of brine and dried over Na$_2$SO$_4$ and concentrated under vacuum to give the crude acyl azide (IR 2135 cm$^{-1}$). A solution of the acyl azide in 1 mL of toluene was warmed to 80° C. for 40 min to produce an isocyanate (IR 2256 cm$^{-1}$). To the solution of the isocyanate was added 0.044 mL of benzyl alcohol. After warming to 80° C. for 2 h, the reaction was partitioned between 25 mL of Et$_2$O and 10 mL of 1N NaOH. After separating layers, the organic phase was washed with 10 mL of brine, dried over Na$_2$S04 and concentrated under vacuum. The residue was purified by flash chromatography eluting with 50% Et$_2$O in hexanes to provide 35 mg of the title compound: $^1$H NMR (300 MHz, CDCl$_3$): δ1.4–1.9 (m, 11H), 2.5–2.8 (m, 2H), 3.7–3.8 (m, 1H ), 4.1–4.6 (m, 3H), 4.8–5.0 (m, 2H), 7.1–7.4 (m, 10H). R$_F$: 0.17 (50% Et$_2$O in hexanes).

Step E: N-Tertbutoxvcarbonyl-4-phenyl-3-amino-piperidine

A solution of 35 mg of benzyl carbamate (from Example 104, Step D) in 1 mL of EtOH containing 6 mg of 10% Pd-C was stirred under 1 Atm of H2 for 24 h. The reaction mixture was filtered through a pad of celite and concentrated under vacuum to give 24 mg of a residue which was taken onto Step F without further purification.

Step F: N-Tertbutoxycarbonyl-4-(SR)-phenyl-3-(SR)-(4-phenylpiperidin-1-yl)-piperidine To a solution of amine (from Example 104, Step E) and (±) -1, 5-dibromo, 3-phenyl-pentane in 0.5 mL of isobutylnitrile was added 0.080 mL of DIEA and a catalytic amount of tetrabutyl-ammonium iodide. After warming the reaction to 95° C. for 22 h, the mixture was partitioned between 10 mL of CH$_2$Cl$_2$ and 10 mL 1N NaOH. After separating layers, the aqueous phase was extracted with 10 mL of CH$_2$Cl$_2$. The combined organic layers were dried over Na$_2$SO$_4$ and concentrated under vacuum. The residue was purified by flash chromatography eluting with 10% EtOAc in hexanes to provide 10 mg of the title compound: $^1$H NMR (300 MHz, CDCl$_3$): δ1.2–1.9 (m, 16H), 2.1–2.4 (m, 2H), 2.6–3.0 (m, 6H), 4.0–4.4 (m, 2H), 7.0–7.4 (m, 10H). R$_F$: 0.45 (20% EtOAc in hexanes).

Step G: 4-(SR)-Phenyl-3-(SR)-(4-phenylpiperidin-1-yl)-piperidine

To a solution of 10 mg of tert-butylcarbamate (from Example 104, Step F) in 0.6 mL of CH$_2$Cl$_2$ at room temperature was added 0.4 mL trifluoroacetic acid. After 2 h at room temperature, volatiles were removed under vacuum. The crude product taken onto Step H without further purification.

Step H: N-Sulfonyl-4-(SR)-phenyl-3-(SR)-(4-phenylpiperidin)-piperidine

To a solution of the amine (from Example 104, Step G) in 1 mL of CH$_2$Cl$_2$ was added 0.028 mL of DIEA, 0.004 mL of benzenesulfonyl chloride and a catalytic amount of dimethylamino-pyridine. After stirring at room temperature overnight, the reaction was diluted with 25 mL of CH$_2$Cl$_2$ and washed with 25 mL of 1N NaHCO$_3$. After separating layers, the organic phase was dried over Na$_2$SO$_4$ and concentrated under vacuum. The residue was purified by flash chromatography eluting with 20% EtOAc in hexanes to provide 8 mg of the title compound: $^1$H NMR (300 MHz, CDCl$_3$): δ1.2–1.7 (m, 4H), 1.8–2.1 (m, 3H), 2.2–2.3 (m, 3H), 2.5–2.8 (m, 4H), 3.0–3.1 (m, 1H ), 3.8–3.9 (m, 1H ), 4.0–4.1 (m, 1H ), 7.0–7.3 (m, l0H), 7.5–7.7 (m, 3H), 7.8–7.9 (m, 2H); Mass Spectrum (EI): 461.2 (M+H). R$_F$: 0.36 (50% EtOAc in hexanes).

The 1-benzyl pyrrolidine derivatives in Examples 105 - 124 were prepared using procedures analogous to those described in Example 1 Steps A and B 9 and in Example 9. What is varied is the cinnamate selected to prepare the pyrrolidine precursor (Example 1 Step A and B) and the amine selected for the transformation in Example 9. Other Examples are prepared by 1) removal of the benzyl group by procedures described in Example 1, Step C, or Example 30, Step A and 2) by acylation with an acid chloride or carboxylic acid by procedures analogous to Example 30, Step B or Example 63, respectively. In some Examples, the stereoisomers of the racemic title compounds are separated by HPLC chromotography utilizing chiral columns as indicated.

EXAMPLE 105

1-Benzyl-3-(spiro[indan-1-one-3,4'-piperidin-1'-yl]methyl)-4-(3,4-di-chloro)phenylpyrrolidine (Stereoisomers 1 and 2)

The stereoisomers of Example 71 were separated by HPLC (CHIRALPAK AD, 2×25 cm, 2.5% iPrOH: hexanes) to give faster and slower moving isomers.

Stereoisomer 1 Mass Spectrum (ESI) m/e 519 (M+1).
Stereoisomer 2 Mass Spectrum (ESI) m/e 519 (M+1).

EXAMPLE 106

1-Benzyl-3-((4-phenylpiperidin-1-yl)methyl)-4-(3-chloro)phenyl pyrrolidine (Stereoisomers 1 and 2)

The stereoisomers of Example 69 were separated by HPLC (CHIRALCEL OD, 2×25 cm, 5% iPrOH: hexanes) to give faster and slower moving isomers. Stereoisomer 1 Mass Spectrum (ESI) m/e 455 (M+1), [α]$_D$=−24.2 (c.=1.48, CHCl$_3$) Stereoisomer 2 Mass Spectrum (ESI) m/e 455 (M+1), [α]$_D$=+24.6 (c.=1.46, CHCl$_3$)

EXAMPLE 107

1-Benzyl-3-((4-phenylpiperidin- 1-yl)methyl)-4-(4-chloro)phenyl pyrrolidine (Stereoisomers 1 and 2)

The stereoisomers were separated by HPLC (CHIRALCEL OD, 2×25 cm, 5% iPrOH: hexanes) to give faster and slower moving isomers. Stereoisomer 1 Mass Spectrum (ESI) m/e 455 (M+1), [α]D=−27.3 (c.=1.034, CHCl$_3$) Stereoisomer 2 Mass Spectrum (ESI) m/e 455 (M+1), [α]$_D$=+26.8 (c.=0.99, CHCl$_3$)

EXAMPLE 108

1-Benzoyl-3-((4-phenylpiperidin-1-yl)methyl)-4-(3,4-dichloro)phenylpyrrrolidine (Stereoisomers 1 and 2)

The stereoisomers were separated by HPLC (CHIRALPAK AD, 2×25 cm, 10% iPrOH: hexanes) to give faster and slower moving isomers. Stereoisomer I Mass Spectrum (ESI) m/e 493 (M+1). 5Stereoisomer 2 Mass Spectrum (ESI) m/e 493 (M+1).

EXAMPLE 109

1–3,5-Dichlorobenzoyl-3-((4-phenylpiperidin-1-yl)methyl)-4-(3,4-dichloro)phenylpyrrolidine (Stereoisomers 1 and 2)

The stereoisomers were separated by HPLC (CHIRALPAK AD, 2×25 cm, 8% iPrOH: hexanes) to give faster and slower moving isomers. Stereoisomer 1 Mass Spectrum (ESI) m/e 561 (M+1). Stereoisomer 2 Mass Spectrum (ESI) m/e 561 (M+1).

EXAMPLE 110
1-Benzoyl-3-(SR)-((4-phenylpiperazin-1'-yl)methyl)-4-(SR)-phenyl pyrrolidine The title compound was prepared from 1-benzyl-3-(SR)-((4-phenylpiperazin-1'-yl]methyl)-4-(SR)-(3,4-di-chloro) phenylpyrrolidine (Example 23). Mass Spectrum (ESI) m/e 426 (M+1).

EXAMPLE 111
1-Benzyl-3-(SR)-((4-benzylpiperazin- 1-yl)methyl)-4-(SR)-phenyl pyrrolidine
Mass Spectrum (ESI) m/e 426 (M+1).

EXAMPLE 112
1-( 1-Naphthoyl)-3-(SR)-((4-benzylpiperazin-1-yl)methyl)-4-(SR)-phenyl pyrrolidine
Mass Spectrum (ESI) m/e 489 (M+1).

EXAMPLE 113
1-Benzoyl-3-((4-benzylpiperidin-1-yl)methyl)-4-phenylpyrrolidine (Stereoisomers 1 and 2)

The stereoisomers were separated by HPLC (CHIRALPAK AD, 2×25 cm, 15% iPrOH: hexanes) to give faster and slower moving isomers. Stereoisomer 1 Mass Spectrum ($NH_3$-CI) m/e 439 (M+1) Stereoisomer 2 Mass Spectrum (N-3- CI) ml e 439 (M+1)

EXAMPLE 114
1-Benzoyl-3-((4-(2-phenyleth-1-yl)piperidin- 1-yl)metliyl)-4-phenylpvrolidine (Stereoisomers 1 and 2)

The stereoisomers were separated by HPLC (CHIRALPAK AD, 2×5 cm, 10% iPrOH: hexanes) to give faster and slower moving isomers. Stereoisomer 1 Mass Spectrum ($NH_3$-CI) m/e 4 53 (M+l ) Stereoisomer 2 Mass Spectrum ($NH_3$-CI) nile 453 (M+1)

EXAMPLE 115
1-Benzoyl-3-(SR)-((4-(3-phenylprop-1-yl)piperidin-1-yl)methyl)-4-(SR) phenylpyrrolidine
Mass Spectrum (ESI) m/e 467 (M+-).

EXAMPLE 116
1-Benzyl-3-(SR)-((4-phenylpiperidin-1-yl)methyl)-4-(SR)-(3,4-dimethyl)phenylpyrrolidine
Mass Spectrum (PB-$NH_3$/CI): m/e 439 (M+1)

EXAMPLE 117
1-Benzoyl-3-(SR)-((4-phenylpiperidin-1-yl)methyl)-4-(SR)-(3,4-dimethyl)phenylpyrrolidine
Mass Spectrum (PB-$NH_3$/CI): m/e 453 (M+1).

EXAMPLE 118
1-(1-Naphthoyl)-3-(SR)-((4-phenylpiperidin-1-yl)methyl)-4-(SR)-(3,4-dimethyl)phenylpyrrolidine
Mass Spectrum (PB-$NH_3$/CI): m/e 503 (M+1).

EXAMPLE 119
1-Benzyl-3-(SR)-((4-phenylpiperidin-1-yl)methyl)-4-(SR)-(3,4-difluoro)phenylpyrrolidine
Mass Spectrum Mass Spectrum ($NH_3$/CI): m/e 447 (M+1).

EXAMPLE 120
1-(3,4-dichlorobenzoyl)-3-(SR)-((4-phenylpiperidin-1-yl)methyl)-4-(SR)-(3,4-difluorophenyl)pyrrolidine
Mass Spectrum ($NH_3$/CI): mn/e 529 (M+1).

EXAMPLE 121
1-(2,3-dichlorobenzoyl)-3-(SR)-((4-phenylpiperidin-1-yl)methyl)-4-(SR)-(3,4-difluorophenyl)pyrrolidine
Mass Spectrum ($NH_3$/CI): m/e 529 (M+1).

EXAMPLE 122
1-(1-Naphthoyl)-3-(SR)-((4-phenylpiperidin-1-yl)methyl)-4-(SR)-(3,4-difluorophenyl)pyrrolidine
Mass Spectrum ($NH_3$/CI): m/e 511 (M+1).

EXAMPLE 123
1-(Benzoyl)-3-(SR)-((4-(2-methoxyphenyl)piperidin- 1-yl)methyl)-4-(SR)-phenylpyrrolidine
Mass Spectrum (ESI) m/e 455 (M+1).

EXAMPLE 124
1-(Benzoyl)-3-((4-(2-methoxyphenyl)piperidin-1-yl)methyl)-4-phenylpyrrolidine (Stereoisomers 1 and 2)

The stereoisomers of Example 123 were separated by HPLC (ChiralPAK AD, 2×25 cm, 10% iPrOH: hexanes) to give faster and slower moving isomers. Stereoisomer 1 Mass Spectrum (ESI) m/e 455 (M+1), $[\alpha]_D$=−51 (c.=0.65, $CHCl_3$) Stereoisomer 2 Mass Spectrum (ESI) m/e 455 (M+1), $[\alpha]_D$=+45 (c.=0.64, $CHCl_3$)

EXAMPLE 125
1-(1-Naphthoyl)-3-(SR)-((4-(4-fluoro)phenylpiperidin-1-yl)methyl)-4-(SR)-phenylpyrrolidine Step 1. 1-(1-Naphthoyl)-3-(SR)-hydroxymethyl-4-(SR)-phenylpyrrolidine To a solution of 610 mg (3.47 mmol) of 3-(SR)-hydroxymethyl-4-(SR)-phenylpyrrolidine (Example 1, Step C) in 30 mL of methylene chloride (anhydrous) was added 661 mg (3.47 mmol) of 1-naphthoyl chloride and 795 mg (7.58 mmol) of triethylamine at 0° C. and the reaction mixture was stirred for 2 h. The reaction mixture was partitioned between 100 mL of methylene chloride and 15 mL of aq $NaHCO_3$. The aqueous layer was extracted with methylene chloride (20 mL×3). The combined organic layers were dried over $Na_2SO_4$, filtered, and concentrated. The residue was purified by silica gel chromatography with hexane / acetone=3:1 to afford the title compound as a white solid. $^1$H NMR ($CDCl_3$) δ3.15–3.32 (m, 2H), 3.42–3.56 (m, 2H), 3.82 (m, 1H ), 4.17–4.31 (m, 1H ), 7.10–7.36 (m, 6H), 7.42–7.92 (m, 6H); Mass Spectrum (PB-$NH_3$/CI): m/e 332 (M+1).

Step 2. 1-(1-Naphthoyl)-3-(SR)-formyl-4-(SR)-phenylpyrrolidine

To a solution of 0.45 mL (5.2 mmol) of oxalyl chloride in 20 mL of methylene chloride (anhydrous) was added slowly 0.74 mL (10.4 nimol) of methyl sulfoxide at −78° C. and the solution was stirred for 10 min. To this was added 0.7 g (2.6 mmol) of 1-(1-naphthpyl)-3-(SR)-hydroxymethyl-4-(SR)-phenylpyrrolidine in 10 mL of methylene chloride (anhydrous) and the reaction mixture was stirred at -78 OC for 15 min. To the reaction mixture was then added 1.8 mL (13 mmol) of triethylamine and the reaction mixture was stirred at -78 OC for 10 min. The cooling bath was removed and the reaction was warmed to room temperature for 40 min. The reaction mixture was poured into 100 mL of ether, washed with 30 mL of aq $NaHCO_3$, dried over $Na_2SO_4$, and concentrated to afford the title compound as a colorless oil which was used without further purification. $^1$H NMR ($CDCl_3$) δ7.16–7.59 (m, 9H), 7.86–7.92 (m, 3H), 9.59, 9.77 (s, 1H , two rotamers); Mass Spectrum (PB-$NH_3$/CI): m/e 330 (M+1).

Step 3. 4-(4-Fluorophenyl)piperidine

A mixture of 2.00 g (9.36 mmol) of 4-(4-fluorophenyl)-1,2,3,6-tetrahydropyridine hydrochloride (Aldrich) and 400 mg of palladium (5% on activated carbon) in 40 mL of methanol (anhydrous) was pressurized to 50 psi with hydrogen gas at room temperature for 4 h. The reaction mixture was then filtered through a plug of celite, and the filtrate was washed with a mixture of 5: 1 methylene chloride / ammonia (2M in MeOH) and concentrated. The residue was partitioned between 100 mL of methylene chloride and 15 mL of aq. NaHCO$_3$. The aqueous layer was extracted with methylene chloride (20 mL×3). The combined organic layers were dried over Na$_2$SO$_4$ and concentrated to give the title compound as a white solid. $^1$H NMR (CDCl$_3$) δ2.03 (m, 2H), 2.23 (m, 2H), 2.76 (m, 1H ), 3,04 (m, 2H), 3.64 (m, 2H), 7.00 (t, 2H, J=8Hz), 7.21 (m, 2H); Mass Spectrum (PB-NH$_3$/CI): m/e 180 (M+1).

Step 4. 1-(1-Naphthoyl)-3-(SR)-((4-(4-fluoro)phenylpiperidin-1-yl)methyl)-4-(SR)-phenylpyrrolidine To a solution of 20 mg (0.063 mmol) of 1-(1-naphthoyl)-3-formyl-4-(SR)-phenylpyrrolidine and 26.7 mg of sodium triacetoxyborohydride in 5 mL of 1,2-dichloroethane (anhydrous) was added 22.7 mg (0.126 mmol) of 4-(4-fluorophenyl)piperidine and the reaction mixture was stirred at room temperature for 3 h. The reaction mixture was partitioned between 30 mL of methylene chloride and 5 mL of aq NaHCO$_3$. The aqueous layer was extracted with methylene chloride (10 mL x 3). The combined organic layer was dried over Na$_2$SO$_4$ and concentrated. The residue was purified by silica gel chromatography with hexane / acetone=3:1 to afford the title compound. $^1$H NMR (CDCl$_3$) δ1.60–1.79 (m, 3H), 1.90–2.18 (m, 2H), 2.26–2.57 (m, 2H), 2.68–2.93 (m, 2H), 6.94–7.38 (m, 6H), 7.40–7.60 (m, 3H); Mass Spectrum (PB-NH$_3$/CI): m/e 493 (M+1).

EXAMPLE 126

1-(1-Naphthoyl)-3-(SR)-((4-benzylpiperidin-1-yl)methyl)-4-(SR)-phenyl pyrrolidine The title compound was prepared as described in Example 125. Mass Spectrum (PB-NH$_3$/CI): m/e 489 (M+1).

EXAMPLE 127

1-(1-Naphthoyl)-3-(SR)-((4-(3-phenylprop-1-yl)piperidin-1-yl)methyl)-4-(SR)-phenylpyrrolidine The title compound was prepared as described in Example 125. Mass Spectrum (PB-NH$_3$/CI): m/e 517 (M+1).

EXAMPLE 128

1-(3,4-dichlorobenzoyl)-3-(SR)-((4-(4-fluoro)phenylpiperidin-1-yl)methyl)-4-(SR)-phenylpyrrolidine The title compound was prepared from 3-(SR)-hydroxymethyl-4-(SR)-phenylpyrrolidine according to procedures described in Example 125 using 3,4-dichlorobenzoyl chloride in place of 1-naphthoyl chloride. Mass Spectrum (PB-NH$_3$/CI): m/e 511 (M+1).

EXAMPLE 129

1-(3,4-Dichlorobenzoyl)-3-(SR)-((4-(3-phenylprop-1-yl)piperidin-1-yl)methyl)-4-(SR)-phenylpyrrolidine The title compound was prepared as described in Examples 125 and 126. Mass Spectrum (PB-NH$_3$/CI): m/e 535 (M+1).

Examples 130 –134 were prepared from 3-(SR)-(spiro [indan-1-one-3,4'-piperidin-1'-yl]methyl)-4-(SR)-phenylpyrrolidine (from deprotection of Example 10) by acylation with an acid chloride or carboxylic acid by procedures analogous to Example 30, Step B or Example 63, respectively.

EXAMPLE 130

1-(1-Naphthoyl)-3-(SR)-(spiro [indan-1-one-3,4'-piperidin-1'-yl]methyl)-4-(SR)-phenylpyrrolidine
Mass Spectrum (PB-NH$_3$/CI): m/e 515 (M+1).

EXAMPLE 131

1-(2-Naphthoyl)-3-(SR)-(spiro [indan-1-one-3,4'-piperidin-1'-yl]methyl)-4-(SR)-phenylpyrrolidine
Mass Spectrum (PB-NH$_3$/CI): m/e 515 (M+1).

EXAMPLE 132

1-Benzoyl-3-(SR)-(spiro [indan-1-one-3,4'-piperidin-1'-yl] methyl)-4-(SR)-phenylpyrrolidine
Mass Spectrum (PB-NH$_3$/CI): m/e 465 (M+1).

EXAMPLE 133

1-(3,4-Dichlorobenzoyl)-3-(SR)-(spiro [indan-1-one-3,4'-piperidin-1'-yl]methyl)-4-(SR)-phenylpyrrolidine
Mass Spectrum (PB-NH$_3$/CI): m/e 533 (M+1) (35Cl), 535 (37Cl).

EXAMPLE 134

1-(2,3-Dichlorobenzoyl)-3-(SR)-(spiro [indan-1-one-3,4'-piperidin-1'-yl]methyl)-4-(SR)-phenylpyrrolidine
Mass Spectrum (PB-NH$_3$/CI): m/e 533 (M+1) (35C1), 535 (37Cl).

Examples 135–137 were prepared by procedures analogous to those described in Example 85 substituting the appropriate aldehyde for phenylacetaldehyde.

EXAMPLE 135

1-(1-Naphthylmethyl)-3-(SR)-(spiro [indan-1-one-3,4'-piperidin-1'-yl]methyl)-4-(SR)-phenylpyrrolidine Mass Spectrum (PB-NH$_3$/CI): m/e 501 (M+1).

EXAMPLE 136

1-(2-Naphthylmethyl)-3-(SR)-(spiro[indan-1-one-3,4'-piperidin-1'-yl]methyl)-4-(SR)-phenylpyrrolidine
Mass Spectrum (PB-NH$_3$/CI): m/e 501 (M+1).

EXAMPLE 137

1-(3,4-Dichlorobenzyl)-3-(SR)-(4-phenylpiperidin-1-yl) methyl)-4-(SR)-phenylpyrrolidine
Mass Spectrum (PB-NH$_3$/CI): m/e 479 (M+1).

Examples 138–148 were prepared from 3-(SR)-((4-phenylpiperidin-1'-yl)methyl)-4-(SR)-phenyl pyrrolidine (Example 30, Step A) by acylation with an acid chloride or carboxylic acid by procedures analogous to Example 30, Step B or Example 63, respectively. In some Examples, the stereoisomers of the racemic title compounds are separated by HLPC chromotography ustilizing chiral columns as indicated.

EXAMPLE 138

1-(2-Methylnaphth1-oyl)-3-(SR)-((4-phenylpipeiidin-1-yl)methyl)-4-(SR)-phenylpyrrolidine
Mass Spectrum (PB-NH$_3$/CI): m/e 489 (M+1).

EXAMPLE 139

1-(2-Ethoxynaphth-1-oyl)-3-(SR)-((4-phenylpiperidin-1-yl)methyl)-4-(SR)-phenylpyrrolidine
Mass Spectrum (PB-NH$_3$/CI): m/e 519 (M+1).

EXAMPLE 140

1-(4-Trifluoromethylbenzoyl)-3-(SR)-((4-phenylpiperidin-1-yl)methyl)-4-(SR)-phenylpyrrolidine
Mass Spectrum (PB-NH$_3$/CI): m/e 493 (M+1).

EXAMPLE 141
1-(4-Bromobenzoyl)-3-(SR)-((4-phenylpiperidin-1-yl)methyl)-4-(SR)-phenylpyrrolidine
Mass Spectrum (PB-NH$_3$/CI): m/e 503 (M+1), (79 Br), 505 (81 Br).

EXAMPLE 142
1-(4-Phenylbenzoyl)-3-(SR)-((4-phenylpiperidin-1-yl)methyl)-4-(SR)-phenylpyrrolidine
Mass Spectrum (PB-NH$_3$/CI): m/e 501 (M+1).

EXAMPLE 143
1-(4-Methylbenzoyl)-3-(SR)-((4-phenylpiperidin-1-yl)methyl)-4-(SR)-phenylpyrrolidine
Mass Spectrum (PB-NH$_3$/CI): m/e 439 (M+1).

EXAMPLE 144
1-(3-Phenyl-n-propion- 1-oyl)-3-(SR)-((4-phenylpiperidin-1-yl)methyl)-4-(SR)-phenylpyrrolidine
Mass Spectrum (PB-NH$_3$/CI): m/e 453 (M+1).

EXAMPLE 145
1-(4-Iodobenzoyl)-3-(SR)-((4-phenylpiperidin-1-yl)methyl)-4-(SR)-phenylpyrrolidine
Mass Spectrum (PB-NH$_3$/CI): m/e 551 (M+1).

EXAMPLE 146
1-(4-Fluorobenzoyl)-3-(SR)-((4-phenylpiperidin-1-yl)methyl)-4-(SR)-phenylpyrrolidine
Mass Spectrum (PB-NH$_3$/CI): m/e 443 (M+1).

EXAMPLE 147
1-(3-Bromobenzoyl)-3-(SR)-((4-phenylpiperidin- 1-yl)methyl)-4-(SR)-phenylpyrrolidine
Mass Spectrum (PB-NH$_3$/CI): m/e 503 (M+1), (79 Br), 505 (81 Br).

EXAMPLE 148
1-(2-hydroxybenzoyl)-3-(SR)-((4-phenylpiperidin-1-yl)methyl)-4-(SR)-phenylpyrrolidine
Mass Spectrum (PB-NH$_3$/CI): m/e 441 (M+1).

EXAMPLE 149
1-Phenylmethyl-3-(S)-((4-phenylpiperidin-1-yl)methyl)-4-(S)-phenylpyrrolidine [(SS)-stereoisomer of Example 9]
Step 1. (S)-N-Cinnamoyl-4-benzyl-2-oxazolidinone To a solution of 10 g of cinnamic acid (67.5 mmol) in 200 mL of THF was added 11.3 mL of triethylamine (81 mmol). The solution was cooled to −78° C. under nitrogen and to this was added a solution of 9.1 mL of pivaloyl chloride (74.2 mmol) in 100 mL THF. The reaction mixture was allowed to warm to 0° C. over 1 h, then was cooled to −78° C.

Meanwhile, a solution of 12.0 g (67.2 mmol) of (S)-benzyl-2-oxazolidinone in 100 mL of THF was cooled to −78° C. under nitrogen. To this was added 46.5 mL of nbutyllithium (1.62M, mmol) and the solution was stirred for 30 min at −78 ° C. This was added via cannula to the first solution. After addition was complete, the solution was allowed to warm to room temperature for 2 h.

The reaction was quenched by addition of saturated aqueous NH$_4$Cl and the mixture was extracted with ethyl acetate. The organic layer was washed with brine, dried over MgSO$_4$, and filtered. The solution was concentrated and the residue was purified by chromatography on silica gel using ethyl acetate-hexane (4:1) to afford the title compound; $^1$H NMR (CDCl$_3$) δ 2.86 (d, AB, J=9.5 Hz, 1H), 2.88 (d, AB, J=9.5 Hz, 1H), 3.38 (d, AB, J=3 Hz, 1H), 3.41 (d, AB, J=3 Hz, 1H), 4.2–4.3 (m, 2H), 4.82 (m, 1H), 7.25–7.46 (m, 8H), 7.65(m, 1H), 7.95 (dd, AB, J=15.5 Hz, 18 Hz, 2H); Mass spectrum (ESI) m/e=308 (M+1).

Step 2. (S)-N-(1-Benzyl-4-(S)-phenyl-3-(R)-pyrrolidinylcarbonyl)-4-benzyl-2-oxazolidinone and (S)-N-(1-Benzyl-4-(R)-phenyl-3-(S)-pyrrolidinylcarbonyl)-4-benzyl-2-oxazolidinone To a solution of 15.0 g of (S)-N-cinnamoyl-4-benzyl-2-oxazolidinone (Step 1, 48.8 mmol) in 150 mL of CH$_2$Cl$_2$ at −10° C. was added 23 g (97.6 mmol) of N-(methoxymethyl-N-trimethylsilylmethyl-benzylamine. Then 1 mL of trifluoroacetic acid was added and the solution was stirred at room temperature for 1 h. The solution was poured into saturated NaHCO$_3$ solution and the layers were separated. The aqueous layer was washed with CH$_2$Cl$_2$ and the combined organic extracts were washed with brine, dried over MgSO$_4$, filtered, and concentrated. The residue was purified by chromatography on silica gel using ethyl acetate-hexane (4:1) to afford the title compound (S)-N-[(1-Benzyl)-4-(S)-phenyl-3-(R)-pyrrolidinylcarbonyl]-4-benzyl-2-oxazolidinone. $^1$H NMR (CDCl$_3$) δ 2.76 (m, 1H), 2.85 (m, 1H), 2.96 (m, 1H), 3.25–3.4 (m, 3H), 3.72 (d, AB, J=13 Hz, 1H), 3.85 (d, AB, J=13 Hz, 1H), 4.05–4.24 (m, 4H), 4.66 (m, 1H), 7.20–7.45 (m, 15H); Mass spectrum (ESI) m/e=441 (M+1); [α]$_D$=+106 (c. 1.03, CHCl$_3$)

Futher elution of the above column using ethyl acetate-hexane (4:1) afforded the title compound (S)-N-[(1-benzyl)-4-(R)-phenyl-3-(S)-pyrrolidinylcarbonyl]-4-benzyl-2-oxazolidinone; $^1$H NMR (CDCl$_3$) δ 2.78 (m, 2H), 2.85 (m, 1H), 3.19 (dd, J=2.5 Hz, 13.5 Hz, 1H), 3.25–3.35 (m, 3H), 3.71 (d, AB, J=13 Hz, 1H), 3.81 (d, AB, J=13 Hz, 1H), 4.15–4.24 (m, 4H), 4.36 (m, 1H), 4.72 (m, 1H) 7.1 (m, 1H), 7.20–7.45 (m, 14H); Mass spectrum (ESI) m/e=441 (M+1); [α]$_D$=+1.4 (c.=4.366, CHCl$_3$)

Step 3. 1-Benzyl-3-(R)-hydroxymethyl-4-(S)-phenylpyrrolidine

To a solution of 5.34 gm of (S)-N-[(1-benzyl)-4-(S)-phenyl-3-(R)-pyrrolidinylcarbonyl]-4-benzyl-2-oxazolidinone (Step 2, 12.12 mmol)) in 50 mL of tetrahydrofuran was added 25 mL of a solution of LiAlH$_4$ in tetrahydrofuran (1.02 M, 25 mmol). The solution was stirred at room temperature for 18 h, then was quenched by addition of aqueous KOH solution. The mixture was filtered and the residue was washed with ether. The combined organic filtrate was dried over MgSO$_4$, filtered, and concentrated. The residue was purified by chromatography on silica gel using ethyl acetate-hexane (1:1) to afford the title compound. $^1$H NMR (CDCl$_3$) δ 2.4–2.6 (m, 2H), 2.8–3.0 (m, 2H), 3.10–3.5 (m, 3H), 3.6–3.85 (m, 4H), 7.20–7.45 (m, 10H); Mass spectrum (ESI) m/e=267 (M+1); [α]$_D$=+8.74 (c.=1.42, CHCl$_3$)

Step 4. 1-Benzyl-3-(R)-formyl-4-(S)-phenylpyrrolidine

A solution of 1.31 mL (15 mmol) of oxalyl chloride in 20 mL of dry CH$_2$Cl$_2$ was cooled to −78° C. under nitrogen. To this was added 1.78 mL (25 mmol) of dimethyl sulfoxide and the mixture was stirred at −78° C. for 15 min. A solution of 2.67 g (10 mmol) of 1-benzyl-3-(R)-hydroxymethyl-4-(S)-phenylpyrrolidine in 10 mL of dry CH$_2$Cl$_2$ was added and the mixture was stirred at −78° C. for 1 h. Then 4.88 mL (35 mmol) of triethylamine were added and the solution was allowed to warm to room temperature over 1 h. The reaction mixture was diluted with 100 mL of ether, poured onto 200 mL of water and the layers were separated. The aqueous layer was washed with ether and the combined organic extracts were washed with 0.1 M HCl saturated NaHCO$_3$ solution and brine. The ethereal solution was dried over MgSO$_4$, filtered, and concentrated to afford the title compound, which was used directly in the next step. Mass Spectrum (ESI) m/e 265 (M+1).

Step 5. 1-Benzyl-3-(S)-((4-phenylpiperidin-1-yl)methyl)-4-(S)-phenylpyrrolidine

To a solution of 2.68 g (10 mmol) of 1-benzyl-3-(R)-formyl-4-(S)-phenylpyrrolidine in 10 mL of 1,2-dichlorethane was added 2.0 g (12 mmol) of 4-phenylpiperidine. To this was added 3.2 g (15 mmol) of sodium triacetoxyborohydride and the solution was stirred at room temperature for 1 h. The reaction was poured into 50 mL of saturated NaHCO$_3$ solution and the mixture was extracted with three portions of ethyl acetate. The combined organic extracts were washed with brine, dried over MgSO$_4$, filtered and concentrated. The residue was purified by chromatography on silica gel using ethyl acetate-hexane (1:1) to afford the title compound. $^1$H NMR (CDCl$_3$) δ 1.6–1.85 (m, 4H), 1.98 (dq, J=7 Hz, J=2 Hz, 2H), 2.4–2.56 (m, 4H), 2.62 (m, 1H), 2.72 (m, 1H), 2.83 (m, 1H), 3.04 (m, 4H), 3.69 (d, AB, J=7 Hz, 1H), 3.77 (d, AB, J=7 Hz, 1H), 7.2–7.6 (m, 15H); Mass Spectrum (ESI) m/e 411 (M+1); $[\alpha]_D$=+26.0 (c.=1.56, CHCl$_3$)

EXAMPLE 150

1-(1-Benzyl)-3-(R)-((4-phenylpiperidin-1-yl) methyl)-4-(R)-phenylpyrrolidine [(RR)-stereoisomer of Example 9]

Step 1. 1-Benzyl-3-(S)-hydroxymethyl-4-(R)-phenylpyrrolidine

To a solution of 6.55 gm of (S)-N-[(1-Benzyl)-4-(R)-phenyl-3-(S)-pyrrolidinylcarbonyl]-4-benzyl-2-oxazolidinone (Example 1E, Step 2, 14.87 mmol) ) in 50 mL of tetrahydrofuran was added 30 mL of a solution of LiAlH$_4$ in tetrahydrofuran (1.02M, 30 mmol). The solution was stirred at room temperature for 18h, then was quenched by addition of aqueous KOH solution. The mixture was filtered and the residue was washed with ether. The combined organic filtrate was dried over MgSO$_4$, filtered, and concentrated. The residue was purified by chromatography on silica gel using ethyl acetate-hexane (1:1) to afford the title compound. $^1$H NMR (CDCl$_3$) δ 2.4–2.6 (m, 2H), 2.8–3.0 (m, 2H), 3.10–3.5 (m, 3H), 3.6–3.85 (m, 4H), 7.20–7.45 (m, 10H); Mass spectrum (ESI) m/e=267 (M+1); $[\alpha]_D$=−8.90 (c.=1.39, CHCl$_3$)

Step 2. 1-Benzyl-3-(S)-formyl-4-(R)-phenylpyrrolidine

A solution of 1.31 mL (15 mmol) of oxalyl chloride in 20 mL of dry CH$_2$Cl$_2$ was cooled to −78° C. under nitrogen. To this was added 1.78 mL (25 mmol) of dimethyl sulfoxide and the mixture was stirred at −78° C. for 15 min. A solution of 2.67 g (10 mmol) of 1-benzyl-3-(S)-hydroxymethyl-4-(R)-phenylpyrrolidine in 10 mL of dry CH$_2$Cl$_2$ was added and the mixture was stirred at −78° C. for 1 h. Then 4.88 mL (35 mmol) of triethylamine was added and the solution was allowed to warm to room temperature over 1 h. The reaction mixture was diluted with 100 mL ether, poured into 200 mL of water, and the layers were separated. The aqueous layer was washed with ether and the combined organic extracts were washed with 0.1 M HCl, saturated NaHCO$_3$ solution and brine. The ethereal solution was dried over MgSO$_4$, filtered, and concentrated to afford the title compound, which was used directly in the next step. Mass Spectrum: (ESI) m/e 265 (M+H)

Step 3. 1-Benzyl-3-(R)-((4-phenylpiperidin-1-yl)methyl)-4-(R)-phenylpyrrolidine

To a solution of 2.68 g (10 mmols) of 1-Benzyl-3-(S)-formyl-4-(S)-phenylpyrrolidine in 10 mL of 1,2-dichlorethane was added 2.0 g (12 mmol) of 4-phenylpiperidine. To this was added 3.2 g (15 mmol) of sodium triacetoxyborohydride and the solution was stirred at room temperature for 1 h. The reaction was poured into 50 mL of saturated NaHCO$_3$ solution and the mixture was extracted with three portions of ethyl acetate. The combined organic extracts were washed with brine, dried over MgSO$_4$, filtered and concentrated. The residue was purified by chromatography on silica gel using ethyl acetate-hexane (1:1) to afford the title compound. $^1$H NMR (CDCl$_3$) d 1.6–1.85 (m, 4H), 1.98 (dq, J=7 Hz, J=2 Hz, 2H), 2.4–2.56 (m, 4H), 2.62 (m, 1H), 2.72 (m, 1H), 2.83 (m, 1H), 3.04 (m, 4H), 3.69 (d, AB, J=7 Hz, 1H), 3.77 (d, AB, J=7 Hz, 1H), 7.2–7.6 (m, 15H); Mass Spectrum: (ESI) m/e 411 (M+1); $[\alpha]_D$=−26.0 (c.=1.56, CHCl$_3$)

EXAMPLE 151

1-(1-Naphthoyl)-3-(R)-((4-phenyl)piperidin-1-yl) methyl)-4-(R)-phenylpyrrolidine [(RR)-stereoisomer of Example 61]

The title compound was prepared from 3-(S)-hydroxymethyl-4-(R)-phenylpyrrolidine (Example 150) according to procedures described in Example 150).

Mass Spectrum (ESI) m/e 475 (M+1), $[\alpha]_D$=−39.6 (c.=1.10, CHCl$_3$)

EXAMPLE 152

1-(1-Naphthoyl)-3-(S)-((4-phenyl)piperidin-1-yl) methyl)-4-(S)-phenylpyrrolidine [(SS)-stereoisomer of Example 61]

The title compound was prepared from 3-(R)-hydroxymethyl-4-(S)-phenylpyrrolidine (Example 150) according to procedures described in Example 149).

Mass Spectrum (ESI) m/e 475 (M+1), $[\alpha]_D$=+39.4 (c.=1.10, CHCl$_3$)

EXAMPLE 153

1-(1-Naphthoyl)-3-(S)-((4-(4-fluoro)phenyl) piperidin-1-yl)methyl)-4-(S)-phenylpyrrolidine [(SS)-stereoisomer of Example 1A]

The title compound was prepared from 3-(R)-hydroxymethyl-4-(S)-phenylpyrrolidine (Example 149) according to procedures described in Example 125).

Mass Spectrum (PB-NH3/CI): m/e 491 (M+1). $[\alpha]_D$=+19.5° (c.=0.60, CHCl$_3$)

EXAMPLE 154

1-(1-Naphthoyl)-3-(R)-((4-(4-fluoro)-phenyl) piperidin-1-yl)methyl)-4-(R)-phenylpyrrolidine [(RR)-stereoisomer of Example 1A]

The title compound was prepared from 3-(S)-hydroxymethyl-4-(R)-phenylpyrrolidine (Example 150) according to procedures described in Example 125).

Mass Spectrum (PB-NH$_3$/CI): m/e 491 (M+1). $[\alpha]_D$=−21.25° (c.=0.60, CHCl$_3$)

EXAMPLE 155

1-Benzoyl-3-(S)-((4-phenyl)piperidin-1-yl)methyl-4-(R)-phenylpyrrolidine and 1-Benzoyl-3-(R)-((4-phenyl)piperidin-1-yl)methyl-4-(S)-phenylpyrrolidine Resolution of 20 mg of 1-benzoyl-3-(SR)-((4-phenyl) piperidin-1-yl)methyl-4-(RS)-phenylpyrrolidine (from Example 36) was carried out via semi-preparative HPLC using a Chiralpak AD 2×25 cm column with 70/30 v/v hexanes/iPrOH as the eluant at a flow rate of 9.0 ml/min and detection at 220 nM to afford 8.4 mg of 1-benzoyl-3-(S)-((4-phenyl)piperidin-1-yl)methyl-4-(R)-phenylpyrrolidine and 8.2 mg of 1-Benzoyl-3-(S)-((4-phenyl)piperidin-1-yl) methyl-4-(R)-phenylpyrrolidine. Analytical HPLC: Chiralpak AD 4.6×250 mm column, 70/30 v/v hexanes/iPrOH, 0.5 mL/min, 220 nm. Retention times: 3-(S), 4-(R), 14.8 min; 3-(R), 4-(S), 24.0 min.

EXAMPLE 156

1-(2-Chlorobenzoyl)-3-(R)-((4-(N-phenylmethoxycarbonyl-N-ethyl)amino)piperidin-1-yl)methyl-4-(S)-phenylpyrrolidine and 1-(2-Chlorobenzoyl)-3-(S)-((4-(N-phenylmethoxycarbonyl-N-ethyl)amino)piperidin-1-yl)methyl-4-(R)-phenylpyrrolidine Resolution of 15 mg of 1-(2-chlorobenzoyl)-3-(RS)-((4-(N-phenylmethoxycarbonyl-N-ethyl)amino)piperidin-1-yl) methyl-4-(SR)-phenylpyrrolidine (from Example 80) was carried out via semi-preparative HPLC using a Chiralcel OD 2×25 cm column with 60/40 v/v hexanes/EtOH as the eluant at a flow rate of 9.0 ml/min and detection at 240 nM to afford 4.1 mg of 1-(2-chlorobenzoyl)-3-(R)-((4-(N-phenylmethoxycarbonyl-N-ethyl)amino)piperidin-1-yl) methyl-4-(S)-phenylpyrrolidine and 6.2 mg of 1-(2-chlorobenzoyl)-3-(S)-((4-(N-phenylmethoxycarbonyl-N-ethyl)amino)piperidin-1-yl)methyl-4-(R)-phenylpyrrolidine. Analytical HPLC: Chiralcel OD 4.6×250 mm column, 60/40 v/v hexanes/EtOH, 0.5 mL/min, 220 nm. Retention times: 3-(R), 4-(S), 14.7 min; 3-(S), 4-(R), 24.1 min.

Examples 157 and 158 were prepared in a manner analogous to Examples 36–62.

EXAMPLE 157

1-(2-Methyl)propionyl-3-(SR)-((4-phenyl)piperidin-1-yl)methyl-4-(SR)-phenylpyrrolidine $^1$H NMR (500 MHz, CDCl$_3$): δ 1.64–4.21 (17H), 7.17–7.62 (15H). Mass Spectrum (NH$_3$-CI): 391 (M+1).

EXAMPLE 158

1-(2-Ethyl)butanonyl-3-(SR)-((4-phenyl)piperidin-1-yl)methyl-4-(SR)-phenylpyrrolidine Mass Spectrum (NH$_3$-CI): 419 (M+1).

EXAMPLE 159

1-Benzyl-3-(SR)-(4-(N-methyl-N-(3-phenylpropyl)-carboxamide)-piperidin-1-ylmethyl)-4-(SR)-phenylpyrrolidine The title compound was prepared from 35 mg of N-benzyl-3-(SR)-(4-carboethoxy-piperidin-1-ylmethyl)-4-(SR)-phenylpyrrolidine, 30 mg of N-methyl-N-(3-phenylpropyl)amine and 0.090 mL of isopropylmagnesium chloride (2M in THF) using a procedure analogous to that described in Example 93 to provide 29.5 mg of the title compound.

R$_F$: 0.15 (5% MeOH in CH$_2$Cl$_2$). $^1$H NMR (300 MHz, CDCl$_3$): δ 1.35–2.15 (m, 10H), 2.3–2.75 (m, 8H), 2.8–3.1 (m, 6H), 3.2 (m, 1H), 3.4 (m, 1H), 3.6–3.8 (m, 2H), 7.1–7.4 (m, 15H). Mass Spectrum (CI): 510.7 (M+H).

EXAMPLE 160

1-Benzyl-3-(SR)-(4-(N-methyl-N-(4-phenylbutyl)-carboxamide)-piperidin-1-ylmethyl)-4-(SR)-phenylpyrrolidine The title compound was prepared from 52 mg of N-benzyl-3-(SR)-(4-carboethoxy-piperidin-1-ylmethyl)-4-(SR)-phenylpyrrolidine, 37 mg of N-methyl-N-(4-phenylbutyl)amine and 0.13 mL of isopropylmagnesium chloride (2M in THF) using a procedure analogous to that described in Example 93 to provide 23 mg of the title compound. R$_F$: 0.25 (5% MeOH in CH$_2$Cl$_2$). $^1$H NMR (300 MHz, CDCl$_3$): δ 1.4–1.9 (m, 10H), 2.25–2.75 (m, 9H), 2.85–3.1 (m, 7H), 3.2 (m,1H), 3.4 (m, 1H), 3.65 (ABq, 2H), 7.1–7.4 (m, 15H). Mass Spectrum (CI): 524.3 (M+H).

EXAMPLE 161

1-Benzyl-3-(SR)-(4-(N-(3-phenylpropyl)-carboxamide)-piperidin-1-ylmethyl)-4-(SR)-phenylpyrrolidine The title compound was prepared from 151 mg of N-benzyl-3-(SR)-(4-carboethoxy-piperidin-1-ylmethyl)-4-(SR)-phenylpyrrolidine, 0.105 mL of 3-phenylpropylamine and 0.55 mL of isopropylmagnesium chloride (2M in THF) using a procedure analogous to that described in Example 93 to provide 94.5 mg of the title compound. R$_F$: 0.20 (5% MeOH in CH$_2$Cl$_2$). $^1$H NMR (300 MHz, CDCl$_3$): δ 1.4–2.0 (m, 9H), 2.35–2.7 (m, 8H), 2.85–3.0 (m, 4H), 3.2–3.3 (m, 2H), 3.4 (m, 1H), 3.65 (ABq, 2H), 7.1–7.4 (m, 15H). Mass Spectrum (CI): 496.8 (M+H).

EXAMPLE 162

1-Benzoyl-3-(SR)-(4-(2-tolyl)-piperidin-1-ylmethyl)-4-(SR)-phenylpyrrolidine

Step A: 3-(SR)-(4-(2-tolyl)-piperidin-1-ylmethyl)-4-(SR)-phenylpyrrolidine

The title compound was prepared from 15 mg of 1-Benzoyl-3-(SR)-(4-(2-tolyl)-piperidin-1-ylmethyl)-4-(SR)-phenylpyrrolidine (from Example 20), 35 mg of ammonium formate and 8 mg of 10% Pd on carbon in 1.5 mL of MeOH using a procedure analogous to that described in Example 30, Step A (except Pd on carbon was substituted for 20% Pd(OH)$_2$) to provide the title compound, which was taken onto Step B without further purification.

Step B: 1-Benzoyl-3-(SR)-(4-(2-tolyl)-piperidin-1-ylmethyl)-4-(SR)-phenylpyrrolidine The title compound was prepared from 3-(SR)-(4-(2-tolyl)-piperidin-1-ylmethyl)-4-(SR)-phenylpyrrolidine (Step A), 0.014 mL of DIEA, 12.5 mg of BOP-Cl and 5 mg of benzoic acid in 0.5 mL of CH$_2$Cl$_2$ using a procedure analogous to that described in Example 63 to provide the title compound. R$_F$: 0.45 (5% MeOH in CH$_2$Cl$_2$). $^1$H NMR (300 MHz, CDCl$_3$): δ 1.4–4.5 (m, 20H), 7.05–7.6 (m, 14H). Mass Spectrum (CI): 439.4 (M+H).

Examples 163 to 169 were prepared by the general procedures given Example 1, substituting the appropriate acyl chloride or carboxylic acid (in the presence of EDAC and hydroxybenzotriazole) for benzenesulfonyl chloride in Step D, and substituting the appropriate piperidine derivative for spiro[2,3-dihydrobenzothiophene]-3,4'-piperidine in step F. Alternatively, these compounds can be prepared as described in Example 9, using 3-(SR)-hydroxymethyl-4-(SR)-phenylpyrrolidine, the intermediate from Example 1, Step C.

EXAMPLE 163

1-(Cyclobutanoyl)-3-(SR)-(4-phenylpiperidin-1-ylmethyl)-4-(SR)-phenylpyrrolidine Mass Spectrum (NH$_3$-CI): 403 (M+1).

EXAMPLE 164

1-(2-Furanoyl)-3-(SR)-(4-phenylpiperidin-1-ylmethyl)-4-(SR)-phenylpyrrolidine

Mass Spectrum (NH$_3$-CI): 415 (M+1).

EXAMPLE 165

1-(3-Furanoyl)-3-(SR)-(4-phenylpiperidin-1-ylmethyl)-4-(SR)-phenylpyrrolidine

Mass Spectrum (NH$_3$-CI): 415 (M+1).

EXAMPLE 166

1-(2-(SR)-(2, 3, 4, 5-Tetrahydrofuranoyl))-3-(SR)-(4-phenylpiperidin-1-ylmethyl)-4-(SR)-phenylpyrrolidine Mass Spectrum (NH$_3$-CI): 419 (M+1).

EXAMPLE 167

1-Benzyl-3-(SR)-(4-phenylpiperidin-1-ylmethyl)-4-(SR)-(3-fluorophenyl)pyrrolidine The compound was prepared using procedures analogous to those described in Examples 1 and 9 substituting the appropriately substituted (E)-cinnamate for methyl (Z)-cinnamate in Example 1, Step A. Mass Spectrum (NH$_3$-CI): 429 (M+1).

EXAMPLE 168

1-(2-Phenyl)benzoyl-3-(SR)-(4-phenylpiperidin-1-ylmethyl)-4-(SR)-phenylpyrrolidine Mass Spectrum (NH$_3$-CI): 501 (M+1).

EXAMPLE 169

1-Benzyl-3-(SR)-(4-(N-(benzyloxycarbonyl)-N-ethylamino)-piperidin-1-ylmethyl)-4-(SR)-phenylpyrrolidine Mass Spectrum (NH$_3$-CI): 512 (M+1).

Examples 170 to 174 were prepared as described in Ex. 63.

EXAMPLE 170

1-((2-methyl)cyclohexancarbonyl)-3-(RS)-((4-phenyl)piperidin-1-yl)methyl-4-(SR)-phenylpyrrolidine Mass Spectrum (NH$_3$-CI): 445 (M+1).

EXAMPLE 171

1-((2-carbomethoxy)benzoyl)-3-(RS)-((4-phenyl)piperidin-1-yl)methyl-4-(SR)-phenylpyrrolidine Mass Spectrum (NH$_3$-CI): 489 (M+1).

EXAMPLE 172

1-(indol-4-ylcarbonyl)-3-(RS)-((4-phenyl)piperidin-1-yl)methyl-4-(SR)-phenylpyrrolidine Mass Spectrum (NH$_3$-CI): 464 (M+1).

EXAMPLE 173

1-(indol-3-ylcarbonyl)-3-(RS)-((4-phenyl)piperidin-1-yl)methyl-4-(SR)-phenylpyrrolidine Mass Spectrum (NH$_3$-CI): 464 (M+1).

EXAMPLE 174

1-(indol-7-ylcarbonyl)-3-(RS)-((4-phenyl)piperidin-1-yl)methyl-4-(SR)-phenylpyrrolidine Mass Spectrum (NH$_3$-CI): 464 (M+1).

EXAMPLE 175

1-((4-fluoro)napthalene-1-carbonyl)-3-(RS)-((4-phenyl)piperidin-1-yl)methyl-4-(SR)-phenylpyrrolidine The title compound was prepared as described in Example 59 using the acid chloride as an intermediate. Mass Spectrum (NH$_3$-CI): 493 (M+1).

EXAMPLE 176

1-(3,4,4a,5,6,7,8,8a octahydro-napthalene-1-carbonyl)3-(RS)-((4-phenyl)piperidin-1-yl)methyl 4-(SR)-phenylpyrrolidine Step A: 1-Trifluoromethanesulfonyl-3,4,4a,5,6,7,8,8a octahydronapthal-1-ene To a solution of 155 mg (1.02 mmol) of decalone in 3 mL of THF at −78° C. was added 1.43 mL (1.43 mmol) of lithium bis(trimethylsilyl)amide (1.0 M in THF). After stirring at −78° C. for 1 hour, 560 mg (1.43 mmol) of 2-[N,N-bis(trifluoromethyl-sulfonyl)amino]-5-chloropyridine was added. After stirring for an additional 2 hours the reaction was warmed to −20° C. and quenched with a saturated solution of ammonium chloride (10 mL). The reaction mixture was diluted with H$_2$O (50 mL), and extracted with CH$_2$Cl$_2$ (3×30 mL). The combined organic extracts were washed with brine, dried (Na$_2$SO$_4$), and concentrated in vacuo. The residue was purified by flash chromatography eluting with 0–15% EtOAc in hexanes to afford the triflate (90 mg, 30%) as a colorless oil. $^1$H NMR (CDCl$_3$, 500 MHz) δ 5.69–5.71 (m, 1H), 2.21–2.29 (m, 2H), 2.07–2.29 (m, 2H), 1.57–1.88 (m, 4H), 1.27–1.45 (m, 4H), 1.10–1.18(m, 2H) ppm.

Step B: 1-Carboxylic acid-3,4,4a,5,6,7,8,8a octahydro-napthal-1-ene

To a solution of 90 mg (0.32 mmol) of triflate (from Step A) in 2 mL of DMF was added 126 mg (1.28 mmol) of potassium acetate followed by 12 mg (0.016 mmol) of Pd(PPh$_3$)$_2$(OAc)$_2$. After bubbling carbon monoxide through the solution for 5 min, the reaction was stirred at room temperature. After 3 hours the reaction was diluted with H$_2$O (50 mL), 0.5N HCl solution to a pH of 3 and extracted with CH$_2$Cl$_2$ (3×30 mL). The combined organic extracts were washed with brine, dried (Na$_2$SO$_4$), and concentrated in vacuo to yield a black oil. The oil was purified using flash chromatography (7 g of silica gel 60, 40% v/v ethyl acetate/hexanes) to afforded 33 mg (53%) of the title compound as a yellow crystalline solid.$^1$H NMR (CDCl$_3$, 500 MHz) δ 6.92–6.93 (m, 1H), 2.37–2.40 (m, 1H), 2.23–2.27 (m, 2H), 2.02–2.03 (m, 1H)1.60–1.81 (m, 4H), 1.17–1.45 (m, 5H), 0.90–0.93 (m, 1H) ppm.

Step C: 1-(3,4,4a,5,6,7,8,8a octahydro-napthalene-1-carbonyl)3-(RS)-((4-phenyl) piperidin-1-yl)methyl 4-(SR)-phenylpyrrolidine The title compound was prepared using 3,4,4a,5,6,7,8,8a octahydro-napthal-1-ene-1-carboxylic acid (from Step B) and procedures analogous to those described in Example 63. Mass Spectrum ($NH_3$-CI): 483 (M+1).

EXAMPLE 177

1-(3,4 dihydro-napthalene-1-carbonyl)-3-(RS)-((4-phenyl)piperidin-1-yl)methyl 4-(SR)-phenylpyrrolidine Step A: 1-Trifluoromethanesulfonyl-3,4 dihydro-napthalene The title compound was prepared using alpha-tetralone and procedures analogous to those described in Example 176, Step A. $^1$H NMR ($CDCl_3$, 500 MHz) δ 7.19–7.38 (m, 4H), 6.04 (t, 1H, J=4.8 Hz), 2.89 (t, 2H, J=8.2 Hz), 2.51–2.56 (m, 2H) ppm.

Step B: 3,4 Dihydro-napthalene-1-carboxylic acid

The title compound was prepared using the triflate from Step A and procedures analgous to those described in Example 176, Step B. $^1$H NMR ($CDCl_3$, 500 MHz) δ 7.92 (d, 1H, J=7.6 Hz), 7.41 (t, 1H, J=4.8 Hz), 7.18–7.28 (m, 3H), 2.81 (t, 2H, J=7.8 Hz), 2.45–2.49 (m, 2H) ppm.

Step C: 1-(3,4 dihydro-napthalen-1-carbonyl)3-(RS)-((4-phenyl) piperidin-1-yl)methyl 4-(SR)-phenylpyrrolidine The title compound was prepared using 1-carboxylic acid-3,4 dihydro-napthal-1-ene (from Step B) and procedures analgous to those described in Example 63. Mass Spectrum ($NH_3$-CI): 477 (M+1).

EXAMPLE 178

1-(5,6,7,8 tetrahydronapthalen-1-carbonyl)-3-(RS)-((4-phenyl)piperidin-1-yl)methyl 4-(SR)-phenylpyrrolidine Step A: 1-Trifluoromethanesulfonyl-5,6,7,8 tetrahydronapthalene To a solution of 5,6,7,8 tetrahydro-1-napthol (155 mg, 1.02 mmol) in 3 mL of $CH_2Cl_2$ at 0° C. was added triethylamine (257 mg, 2.54 mmol) followed by 900 mg (2.54 mmol) of 2-[N,N-bis(trifluoromethylsulfonyl)amino]-5-chloropyridine. The reaction was allowed to warm to room temperature. After stirring overnight the reaction was diluted with $H_2O$ (50 mL), and extracted with $CH_2Cl_2$ (3×30 mL). The combined organic extracts were washed with brine, dried ($Na_2SO_4$), and concentrated in vacuo. The residue was purified by flash chromatography eluting with 0–15% EtOAc in hexanes to afford the triflate (281 mg, 60%) as a colorless oil.$^1$H NMR ($CDCl_3$, 500 MHz) δ 7.06–7.18 (m, 3H), 2.80–2.84 (m, 4H), 1.80–1.96 (m, 4H) ppm.

Step B: 5,6,7,8 Tetrahydronapthalene-1-carboxylic acid

The title compound was prepared using the triflate from Step A and procedures analogous to those described in Example 176, Step B. $^1$H NMR ($CDCl_3$, 500 MHz) δ 7.85 (d, 1H, J=7.8 Hz), 7.28–7.30 (m, 1H), 7.19 (t, 1H, J=7.6 Hz), 3.15–3.18 (m, 2H), 2.84–2.87 (m, 2H), 1.82–1.83 (m, 4H) ppm.

Step C: 1-(5,6,7,8 tetrahydro-napthalene-1-carbonyl)-3-(RS)-((4-phenyl)piperidin-1-yl)methyl 4-(SR)-phenylpyrrolidine The title compound was prepared using 5,6,7,8 tetrahydro napthalene-1-carboxylic acid (from Step B) and procedures analogous to those described in Example 63. Mass Spectrum ($NH_3$-CI): 479 (M+1).

EXAMPLE 179

1-((Adamant-1-yl)methyl)-3-(RS)-((4-phenyl)piperidin-1-yl)methyl-4-(SR)-phenylpyrrolidine To a solution of 1-(1-adamantanecarbonyl)-3-(RS)-((4-phenyl)piperidin-1-yl)methyl-4-(SR)-phenylpyrrolidine (10 mg, 0.021 mmol) in 2 mL of THF was added lithium aluminum hydride (2 mg, 0.042 mmol). The reaction was heated to reflux. After 2 hours the reaction was quenched with $H_2O$ (0.5 mL), 15% NaOH solution (0.5 mL), $H_2O$ (1.0 mL) and diluted with a saturated solution of Rochelle salts (50 mL) and $CH_2Cl_2$ (50 mL). After stirring for 1 hour the mixture was extracted with $CH_2Cl_2$ (3×50 mL). The combined organic extracts were washed with brine, dried ($Na_2SO_4$), and concentrated in vacuo to yield 9 mg of the title compound. Mass Spectrum ($NH_3$-CI): 469 (M+1).

EXAMPLE 180

1-((7-indole)methyl)-3-(RS)-((4-phenyl)piperidin-1-yl)methyl-4-(SR)-phenylpyrrolidine The title compound was prepared using 1-(indol-7-carbonyl)-3-(RS)-((4-phenyl)piperidin-1-yl)methyl-4-(SR)-phenylpyrrolidine (from Example 174) and procedures analogous to those described in Example 179. Mass Spectrum ($NH_3$-CI): 450 (M+1).

EXAMPLE 181

1-(2(R)-phenyl-cyclohexyl-1(S)-methyl)-3-(RS)-((4-phenyl)piperidin-1-yl)methyl-4-(SR)-phenylpyrrolidine The title compound was prepared using 1-((2R)-phenylcyclohexane-1-(S)-carbonyl)-3-(RS)-((4-phenyl)piperidin-1-yl)methyl-4-(SR)-phenylpyrrolidine (from Example 183) and procedures analogous to those described in Example 179. Mass Spectrum ($NH_3$-CI): 493 (M+1).

EXAMPLE 182

1-(2(R)-phenyl-cyclohex-3-ene-1(S)-carbonyl)-3-(RS)-((4-phenyl)piperidin-1-yl)methyl 4-(SR)-phenylpyrrolidine Step A: 1(R)-phenyl-cyclohex-5-ene-2(S)-carbonyl chloride To a solution of 155 mg (1.02 mmol) of 1(R)-phenyl-2 (S)-carboxy cyclohex-5-ene (See U.S. Pat. No. 5,750,549, Example 158, Step B) in 3 mL of $CH_2Cl_2$ at 0° C. was added oxalyl chloride (100 uL) followed by DMF (1 drop). The reaction was allowed to warm to room temperature. After stirring 1 hour the reaction was concentrated in vacuo, redissolved in $CH_2Cl_2$ and concentrated to a yellow solid which was used directly in the next step.

Step B: 1-(2(R)-phenyl-cyclohex-3-ene-1(S)-carbonyl)-3-(RS)-((4-phenyl)piperidin-1-yl)methyl 4-(SR)-phenylpyrrolidine The title compound was prepared using the acid chloride from Step A and procedures analogous to those described in Example 59. Mass Spectrum ($NH_3$-CI): 493 (M+1).

EXAMPLE 183

1-(2(R)-phenyl-cyclohexane-1(S)-carbonyl)-3-(RS)-((4-phenyl)piperidin-1-yl)methyl-4-(SR)-phenylpyrrolidine To a solution of 14 mg (0.03 mmol) of 1-(2(R) phenylcyclohex-3-ene-1(S)-carbonyl)-3-(RS)-((4-phenyl) piperidin-1-yl)methyl 4-(SR)-phenylpyrrolidine (from Example 182, Step B) in 2 mL of MeOH was added 10% Pd/C (7.0 mg). The reaction mixture was hydrogenated at 50 psi on a Parr apparatus for 4 hrs. The reaction was filtered thru Celite, washed with MeOH and the filtrate was concentrated in vacuo to afford 10 mg of the title compound as an oil. Mass Spectrum ($NH_3$-CI): 507 (M+1).

EXAMPLE 184

1-(2(S)-phenyl-cyclohex-3-ene-1(R)-carbonyl)-3-(RS)-((4-phenyl)piperidin-1-yl)methyl 4-(SR)-phenylpyrrolidine The title compound was prepared using 1(S)-phenyl-2(R)-carboxy-cyclohex-5-ene and procedures analogous to those described in Example 182, Steps A and B. Mass Spectrum (NH$_3$-CI): 505 (M+1).

EXAMPLE 185

1-(2(S)-phenyl-cyclohexane-1(R)-carbonyl)-3-(RS)-((4-phenyl)piperidin-1-yl)methyl-4-(SR)-phenylpyrrolidine The title compound was prepared using 1-(2(S)-phenylcyclohex-3-ene-1(R)-carbonyl)-3-(RS)-((4-phenyl)piperidin-1-yl)methyl 4-(SR)-phenylpyrrolidine (from Example 184) and procedures analogous to those described in Example 183. Mass Spectrum (NH$_3$-CI): 507 (M+1).

EXAMPLE 186

1-(2(R)-phenyl) cyclohex-3-ene-1(R)-carbonyl)-3-(RS)-((4-phenyl)piperidin-1-yl)methyl 4-(SR)-phenylpyrrolidine Step A: 1(R)-phenyl-2(S)-carbomethoxy-cyclohex-5-ene To a solution of 900 mg (4.45 mmol) of 1(R)-phenyl-2(S)-carboxy cyclohex-5-ene (See U.S. Pat. No. 5,750,549, Example 158, Step B) in a 4:1 solution of MeOH/THF was added trimethylsilyldiazomethane until a yellow color persisted. After stirring at room temperature for 3 hour the reaction was concentrated in vacuo and the residue was purified by flash chromatography eluting with 0–15% EtOAc in hexanes to afford the ester (300 mg) as a colorless oil. $^1$H NMR (CDCl$_3$, 500 MHz) δ 7.19–7.30 (m, 5H), 5.98–6.01 (m, 1H), 5.76–5.79 (m, 1H),3.89 (s, 1H),3.50 (s, 3H), 2.95–2.98 (m, 1H), 2.16–2.32 (m, 2H),1.80–1.87 (m, 2H) ppm.

Step B: 1(R)-phenyl-2(S)-hydroxymethyl-cyclohex-5-ene

A solution of 300 mg (1.38 mmol) of 1(R)-phenyl-2(S)-carbomethoxy-cyclohex-5-ene (from Step A) in 30 mL of CH$_2$Cl$_2$ at 0° C. was treated with 2.3 mL of 1.5 M diisobutylaluminum hydride solution in toluene. After stirring for 30 minutes the reaction was quenched with 50 mL of sat'd sodium potassium tartrate solution, diluted with 100 mL of ether and stirred at rt for 20 h. The layers were separated and the organic layer was washed with 75 mL of H$_2$O, dried over MgSO$_4$ and concentrated in vacuo. Flash chromatography on 100 g of silica gel using 5–25% v/v EtOAc/hexanes as the eluant afforded 185 mg (72%) of the title compound as an oil. $^1$H NMR (CDCl$_3$, 500 MHz) δ 7.23–7.34 (m, 5H), 5.95–5.97 (m, 1H), 5.77–5.79 (m, 1H),3.66 (s, 1H), 3.23–3.32 (m, 2H), 2.14–2.25 (m, 3H),1.51–1.62 (m, 3H) ppm.

Step C: 1(R)-phenyl-2(S)-carboxaldehyde-cyclohex-5-ene

A solution of 0.09 mL (1.0 mmol) of oxalyl chloride in 4 mL of CH$_2$Cl$_2$ at −75° C. was treated with 0.142 mL (2.0 mmol) of DMSO maintaining the internal temperature below −65° C. The resulting mixture was stirred cold for 10 min and then 75 mg (0.40 mmol) of 1(R)-phenyl-2(S)-hydroxymethyl-cyclohex-5-ene (from Step B) was added in one portion. The resulting mixture was stirred cold for 30 min and then 0.547 mL (4.0 mmol) of DIEA was added maintaining the internal temperature below −60° C. The cooling bath was removed and the reaction was allowed to warm to room temperature and stirred for 45 minutes. The reaction was quenched with 50 mL of H$_2$O; the resulting mixture was extracted with CH$_2$Cl$_2$ (3×50 mL). The combined organic extracts were washed with brine, dried (Na$_2$SO$_4$), and concentrated in vacuo. The residue was purified with flash chromatography (70 g of silica gel; 0–25% v/v ethyl acetate/hexanes) afforded 67 mg (90%) of the title compound as an oil. $^1$H NMR (CDCl$_3$, 500 MHz) δ 9.52 (d, 1H, J=1.8 Hz), 7.23–7.34 (m, 5H), 5.99–6.03 (m, 1H), 5.84–5.87 (m, 1H),3.99 (s, 1H), 2.77–2.81 (m, 1H), 2.28–2.34 (m, 1H), 2.16–2.22 (m, 1H), 1.59–1.91 (m, 2H) ppm.

Step D: 1(R)-phenyl-2(R)-carboxaldehyde-cyclohex-5-ene

The aldehyde 67 mg (from Step E) was taken up in MeOH (2 mL) and treated with NaOMe (0.5 mL of 0.32 M in MeOH) at room temp for 3 hours. The reaction mixture was quenched with H$_2$O (50 mL) and extracted with EtOAc (3×30 mL). The combined organic extracts were washed with brine, dried (Na$_2$SO$_4$), and concentrated in vacuo to afford the epimerized aldehyde (54 mg, 81%) as a colorless oil. $^1$H NMR (CDCl$_3$, 500 MHz) δ 9.71 (d, 1H, J=1.3 Hz), 7.23–7.35 (m, 5H), 5.92–5.95 (m, 1H), 5.70–5.73 (m, 1H), 3.79–3.81 (m, 1H), 2.61–2.64 (m, 1H), 2.20–2.22 (m, 2H), 1.76–1.99 (m, 2H) ppm.

Step E: 1(R)-phenyl-2(R)-carboxy-cyclohex-5-ene

To a solution of the aldehyde (from Step D) 54 mg (2.36 mmol) in THF (3 mL) at 0° C. was added sulfamic acid (430 uL, 1M aq.), NaH$_2$PO$_4$ (160 uL, 2.7M aq.), and NaClO$_2$ (430 uL, 1M aq.). The reaction mixture was allowed to warm to room temp and stirred for 18 h. The reaction mixture was then quenched by addition of H$_2$O (50 mL), and extracted with CH$_2$Cl$_2$ (3×30 mL). The combined organic extracts were washed with brine, dried (Na$_2$SO$_4$), and concentrated in vacuo. The residue was purified with flash chromatography (70 g of silica gel;25% v/v ethyl acetate/hexanes with 0.5% acetic acid ) to afford 31 mg (54%) of the carboxylic acid. $^1$H NMR (CDCl$_3$, 500 MHz) δ 7.23–7.33 (m, 5H), 5.88–5.92 (m, 1H), 5.65–5.68 (m, 1H), 3.75–3.78 (m, 1H), 2.62–2.67 (m, 1H), 1.88–2.24 (m, 4H) ppm.

Step F 1-(2(R)-phenyl-cyclohex-3-ene-1(R)-carbonyl)-3-(RS)-((4-phenyl)piperidin-1-yl)methyl-4-(SR)-phenylpyrrolidine The title compound was prepared using 1(R)-phenyl-2(R)-carboxy-cyclohex-5-ene (from Step E) and procedures analogous to those described in Example 63. Mass Spectrum (NH$_3$-CI): 505 (M+1).

EXAMPLE 187

1-(2(R)-phenyl-cyclohexane-1(R)-carbonyl)-3-(RS)-((4-phenyl)piperidin-1-yl)methyl-4-(SR)-phenylpyrrolidine The title compound was prepared using 1-(2(R)-phenyl-cyclohex-3-ene-1(R)-carbonyl)-3-(RS)-((4-phenyl)piperidin-1-yl)methyl 4-(SR)-phenylpyrrolidine (from Example 186) and procedures analogous to those described in Example 14. Mass Spectrum (NH$_3$-CI): 507 (M+1).

EXAMPLE 188

1-(2(S)-phenyl-cyclohex-3-ene-1(S)-carbonyl)-3-(RS)-((4-phenyl)piperidin-1-yl)methyl 4-(SR)-phenylpyrrolidine The title compound was prepared starting with 1(S)-phenyl-2(R)-carboxy-cyclohex-5-ene and procedures analogous to those described in Example 186, Steps A–F. Mass Spectrum (NH$_3$-CI): 505 (M+1).

EXAMPLE 189

1-(2(S)-phenyl-cyclohexane-1(S)-carbonyl)-3-(RS)-((4-phenyl)piperidin-1-yl)methyl-4-(SR)-phenylpyrrolidine The title compound was prepared using 1-((2(S) phenyl) cyclohex-3-ene-1(S)-carbonyl)3-(RS)-((4-phenyl)piperidin- 1-yl)methyl 4-(SR)-phenylpyrrolidine (from Example 188) and procedures analogous to those described in Example 183. Mass Spectrum (NH₃-CI): 507 (M+1).

The compounds in Examples 190 to 218 were prepared according to the procedures given in Example 220 (carried out in single compounds format, wherein the mixing and archiving steps are omitted). Example 219 was prepared by coupling of 4-(3-phenylpropyl)-piperidine with 3-(RS)-carboxy-4-(SR)-phenylpyrrolidine followed by reduction with BMS as in examples 190–218. Acylation of the pyrrolidine nitrogen with cyclohexane carbonyl chloride provided the final product.

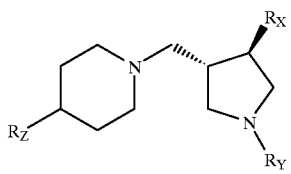

| EXAMPLE | Rx | Ry | Rz | Spectral Data |
|---|---|---|---|---|
| 190 | Ph | COc-Hex | benzyl N-methyl carbamate | MS: 518 (M + 1) |
| 191 | Ph | COc-Hex | benzyl N-propyl carbamate | MS: 546 (M + 1) |
| 192 | Ph | COc-Hex | benzyl N-butyl carbamate | MS: 560 (M + 1) |
| 193 | Ph | COc-Hex | benzyl N-(cyclopropylmethyl) carbamate | MS: 558 (M + 1) |
| 194 | Ph | COc-Hex | benzyl N-(1-cyclopropylethyl) carbamate | MS: 558 (M + 1) |

-continued

| | | | | MS: |
|---|---|---|---|---|
| 195 | 4-F—Ph | COc-Hex | [benzyl N-ethyl carbamate group] | 550 (M + 1) |
| 196 | Ph | [2-thienyl sulfonyl] | [methyl N-hexyl carbamate group] | MS: 548 (M + 1) |
| 197 | Ph | CH₂-c-Hex | [3-phenylpropyl group] | MS: 459 (M + 1) |
| 198 | Ph | [2-thienyl sulfonyl] | [3-phenylpropyl group] | MS: 509 (M + 1) |

[Structure: pyrrolidine with Rx, Ry, and CH₂-piperidine-Rz substituents]

| EXAMPLE | $R_x$ | $R_y$ | $R_z$ | HPLC (Method)[a] | MS (M + 1) |
|---|---|---|---|---|---|
| 199 | Ph | PhSO₂— | Ph | 8.19 min (A) | 461.3 |
| 200 | Ph | 4-methylphenylsulfonyl | Ph | 8.43 min (A) | 475.4 |
| 201 | Ph | 3-(CF₃)phenylsulfonyl | Ph | 8.75 min (A) | 529.4 |
| 202 | Ph | 2-methylphenylsulfonyl | Ph | 8.48 min (A) | 475.4 |

| | | | | | |
|---|---|---|---|---|---|
| 203 | Ph | 2-fluorophenyl-SO$_2$- | Ph | 8.27 min (A) | 479.3 |
| 204 | Ph | 3-fluorophenyl-SO$_2$- | Ph | 8.33 min (A) | 479.3 |
| 205 | Ph | 2-chlorophenyl-SO$_2$- | Ph | 8.45 min (A) | 495.1 |
| 206 | Ph | 3-chlorophenyl-SO$_2$- | Ph | 8.61 min (A) | 495.1 |
| 207 | Ph | 3-methylphenyl-SO$_2$- | Ph | 8.46 min (A) | 475.4 |
| 208 | Ph | cyclohexylmethyl- | 2-methylphenyl- | 4.60 min (B) | 431.3 |
| 209 | Ph | cyclohexylmethyl- | PhCH$_2$OC(O)N(Et)- | 4.18 min (B) | 518.4 |
| 210 | 3-MeO-phenyl- | benzyl- | PhCH$_2$CH$_2$CH$_2$- | 4.88 min (B) | 483.5 |
| 211 | Ph | benzyl- | PhCH$_2$CH$_2$CH$_2$- | 6.21 min (C) | 453.3 |
| 212 | Ph | phenethyl- | PhCH$_2$CH$_2$CH$_2$- | 5.61 min (C) | 467.3 |
| 213 | Ph | ethyl- | PhCH$_2$CH$_2$CH$_2$- | 5.82 min (C) | 391.3 |
| 214 | Ph | 2-thienylmethyl- | PhCH$_2$CH$_2$CH$_2$- | 6.21 min (C) | 459.3 |

-continued

| | | | | | |
|---|---|---|---|---|---|
| 215 | Ph | 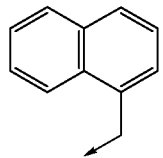 | 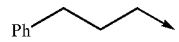 | 6.52 min (C) | 503.3 |
| 216 | Ph | 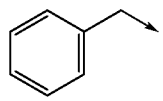 | 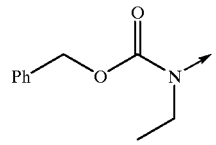 | 5.53 min (C) | 496.4 |
| 217 | Ph | 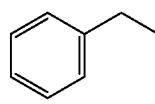 | 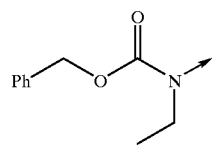 | 6.29 min (C) | 542.4 |
| 218 | Ph | 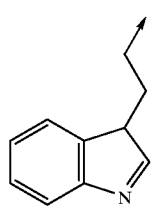 | 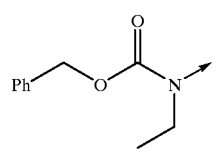 | 4.88 min (C) | 565.4 |
| 219 | Ph | 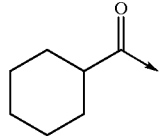 | 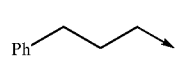 | 5.25 min (C) | 473.1 |

[a]HPLC Column: Zorbax SB-C8 4.6 × 75 mm, 3.5 micron. Conditions: A; 10 → 100% CH3CN/H2O w/0.1% TFA over 10 min. B; 10 → 100% CH$_3$CN/H2O w/0.1% TFA over 7.5 min. C; 10 → 100% CH3CN/H2O w/0.1% TFA over 7.5 min.

EXAMPLE 220

Preparation of 21×19 Combinatorial Library

Commercially available 4-sulfamylbenzoyl polystyrene resin (4.2 g /4.8 mmol), 1-(t-butoxycarbonyl)-3-(RS)-carboxy-4-(SR)-phenylpyrrolidine (29 mmol, 6 equiv), diisopropylethylamine (DIEA; 15 mmol, 3 equiv) and DMAP (1.2 mmol, 0.25 equiv) were suspended in 40 mL of 1/1 methylene chloride/THF. Diisopropylcarbodiimide (15 mmol, 3 equiv) was added and the mixture was agitated by rotary stirring overnight. The resin was then washed sequentially with 1/1 methylene chloride/THF, THF and methylene chloride (4×40 mL each). The resin was split into 22 equal portions and each was washed with methylene chloride (3×5 mL). Each of the 21 pools was treated with 40% TFA/methylene chloride for 30 min then washed with methylene chloride (5×5 mL). To each of the 21 pools of resin, 5 mL of a 0.4 M methylene chloride solution in the Y subunit (2 mmol, 5.3 equiv; see structures below) was added followed by DIEA (3 mmol, 8 equiv). The mixtures were shaken and let stand for 30 min. The resin was washed with methylene chloride, THF and 1/1 methylene chloride/THF (4×5 mL each). 80 mg of resin from each pool was archived for deconvolution and the remaining resin in the 22 flasks was then combined in 7/3 dichloroethane/DMF and mixed for 2h. The combined resin was split into 19 equal portions and each portion was washed with THF (3×1 mL). A solution of trimethylsilyldiazomethane (1.0 M in 1/1 THF/Hexane, 1.5 mL) was added, the mixtures were shaken and let stand for 2 h. The resin in each pool was washed with 1 mL of THF and treated with trimethylsilyldiazomethane as above. The resin was washed with THF, methylene chloride and ether, then dried under nitrogen and transferred to a flask containing the Z subunit (2 equiv; see structures below) in 0.35 mL THF. The suspension was heated to 50° C. overnight. To each of the 19 library pools was added 250 mg of scavenging resin (see below) and the mixtures were let stand overnight. The resin was filtered off and the samples were concentrated. A solution of borane-methylsulfide (0.5 M in dioxane, 0.5 mL) was added and the pools were heated to 50° C. for 3 h. The solvent was removed and the residue was dissolved in 2 mL of 1% HCl/methanol and heated to 50° C. overnight. The solvent was removed and the pools were redissolved in 2 mL of 1% HCl/methanol then concentrated again. This was repeated a second time. The samples were then lyophilized from acetonitrile/water to give the 19 pools indexed by their Z subunits as light brown solids.

Scavenging resin was prepared by reacting commercially available aminomethyl polystyrene (10 grams) with a solution of pentafluorophenyl chlorothionoformate and DIEA (50 mL of 0.5 M in each reagent, in methylene chloride). After 30 min the resin was washed with methylene chloride and treated with a 0.5 M solution of DIEA in DMF. After washing with DMF, THF, methylene chloride and ether (3×50 mL each) the scavenging resin was dried under nitrogen.
Y Subunits:
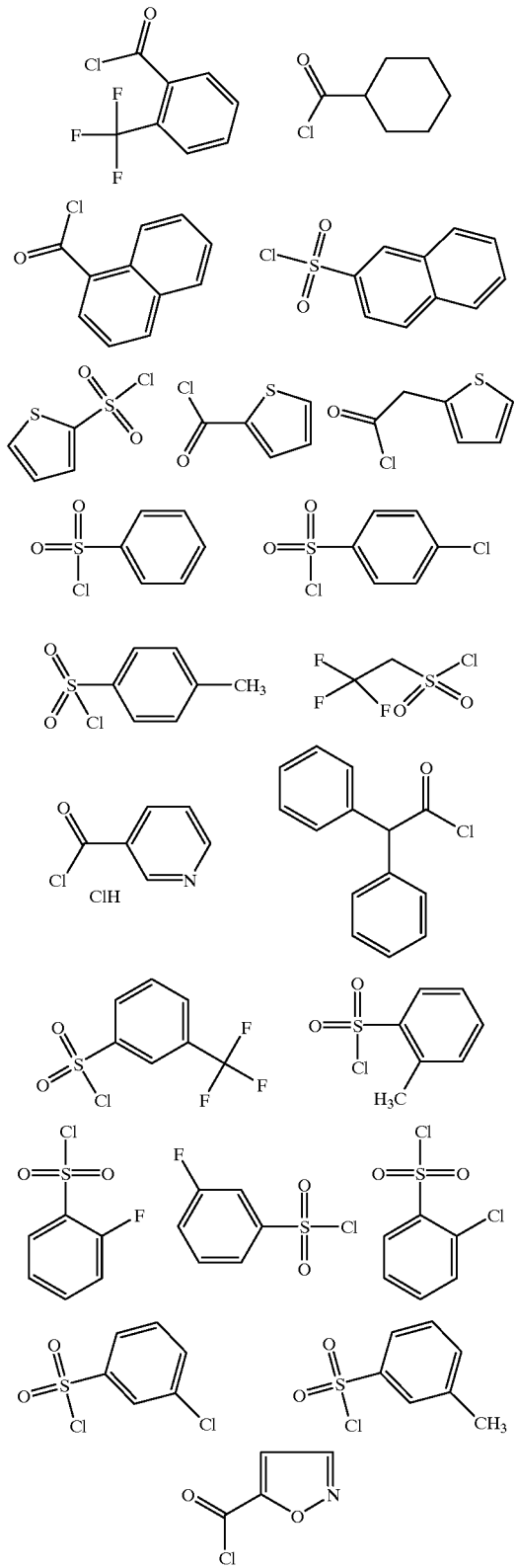
Z Subunits:
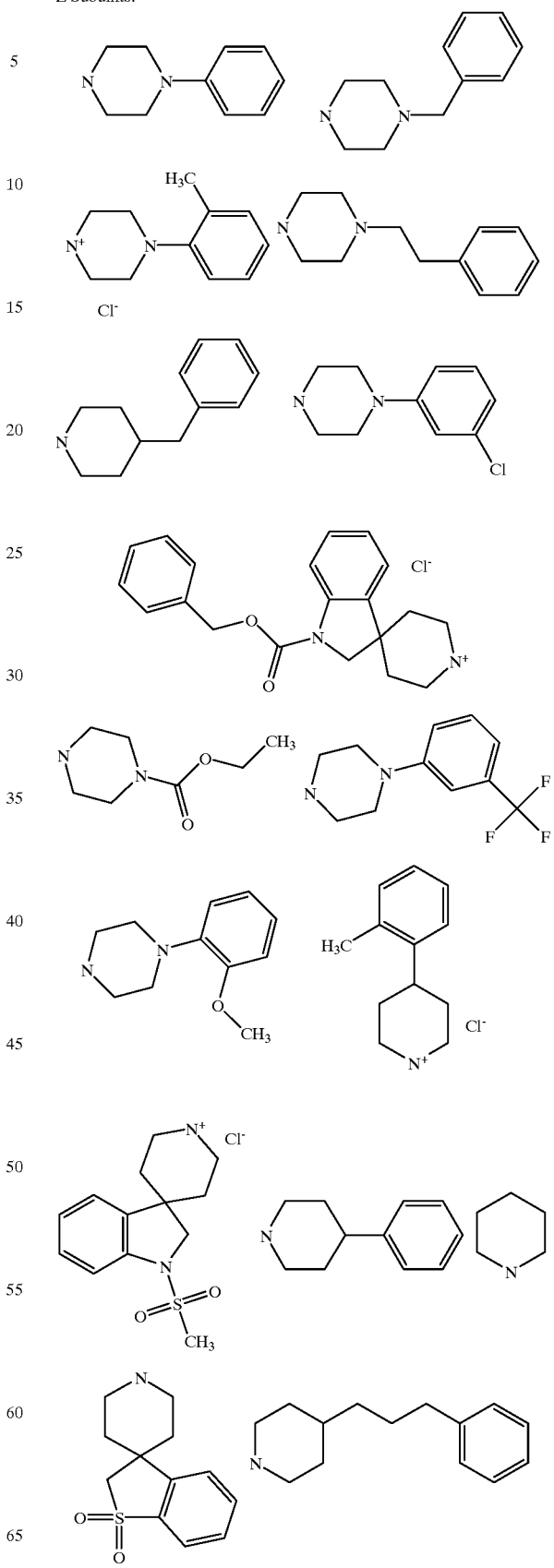
-continued -continued

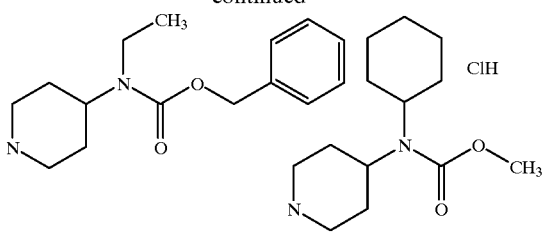

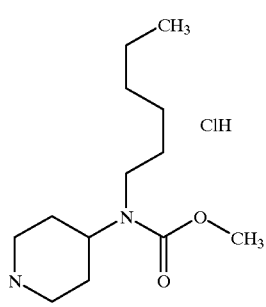

The compounds in Examples 221 and 222 were prepared from 4-carboxy-3-phenylpiperidine (which can be obtained from N-benzyl-4-carbomethoxy-3-phenyl-piperidine (from Example 101, Step C) by hydrolysis with aqueous sodium hydroxide followed by hydrogenolysis in ethanol with 10% palladium on carbon and hydrogen gas) followed by reaction with cyclohexanecarbonyl chloride to provide 1-cyclohexylcarbonyl-4-carboxy-3-phenylpiperidine. Treatment of the latter compound with the appropriate secondary amine in the presence of EDC followed by reduction of both amides with borane-methyl sulfide then provided the indicated final compounds.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the mammal being treated for any of the indications with the compounds of the invention indicated above. Likewise, the specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A compound of the formula I:

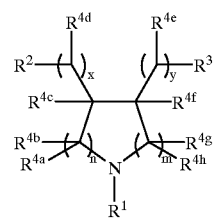

wherein:

$R^1$ is —X—$R^8$, wherein X is selected from the group consisting of:

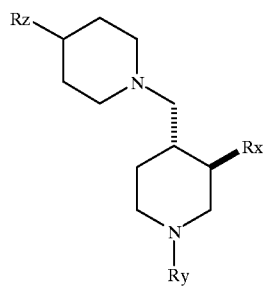

| EXAMPLE | $R_x$ | $R_y$ | $R_z$ | HPLC (Method)$^a$ | MS (M + 1) |
|---|---|---|---|---|---|
| 221 | Ph | cyclohexylmethyl | Ph-propyl | 4.27 min | 473.4 |
| 222 | Ph | cyclohexylmethyl | Ph-CH₂-O-C(O)-N(Et)- | 4.11 min | 532.4 |

(1) —CH₂—,
(2) —CH₂CH₂—,
(3) —CH₂CH₂CH₂—,
(4) —CH(C₁₋₆ alkyl)—,
(5) —CO—,
(6) -SO₂—,
(7) —CONH₂—, and
(8) —CONH(C₁₋₆ alkyl)—, and wherein R⁸ is a selected from:
  phenyl, naphthyl, biphenyl, fluorenyl, dihydronaphthyl, tetrahydronaphthyl, octahydronaphthyl, C₁₋₆ alkyl, C₅₋₈ cycloalkyl, cyclohexenyl, adamantyl, and heteroaryl, which may be unsubstituted or substituted, where the substituents are independently selected from:
  (a) hydroxy,
  (b) C₁₋₃alkyl,
  (c) —O—C₁₋₃alkyl,
  (d) halogen,
  (e) trifluoromethyl,
  (f) phenyl
  (g) —CO₂(C₁₋₆ alkyl), and
  (h) —CONH₂;

R² is selected from the group consisting of:

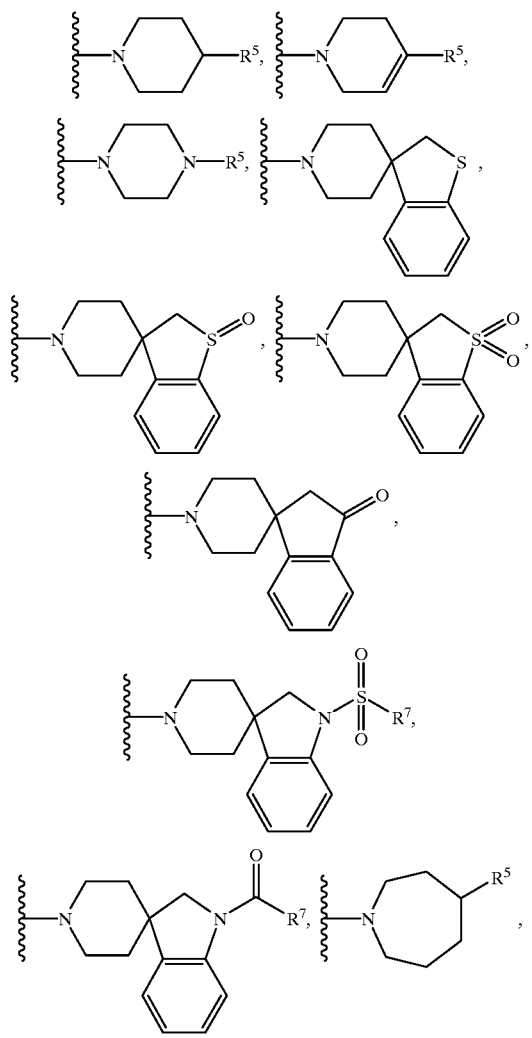

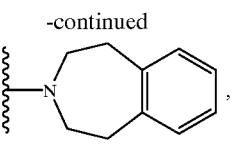

wherein R⁵ is a selected from:
  (1) —NR⁶CO—O—R⁷, wherein R⁶ is hydrogen, C₁₋₆ alkyl or C₁₋₆ alkyl-C₅₋₆ cycloalkyl, and R⁷ is C₁₋₆ alkyl, C₅₋₆ cycloalkyl, benzyl or phenyl, which is unsubsituted or substituted with halo, C₁₋₃alkyl, C₁₋₃alkoxy or trifluoromethyl,
  (2) —phenyl, which is unsubsituted or substituted with halo, C₁₋₃alkyl, C₁₋₃alkoxy or trifluoromethyl,
  (3) —C₁₋₆alkyl-phenyl, which is unsubsituted or substituted with halo, C₁₋₃alkyl, C₁₋₃alkoxy or trifluoromethyl,
  (4) —O—C₁₋₆alkyl-phenyl, which is unsubsituted or substituted with halo, C₁₋₃alkyl, C₁₋₃alkoxy or trifluoromethyl,
  (5) —C₁₋₄alkyl—O—C₁₋₄alkyl-phenyl, which is unsubsituted or substituted with halo, C₁₋₃alkyl, C₁₋₃alkoxy or trifluoromethyl,
  (6) —hydrogen,
  (7) —C₁₋₆alkyl,
  (8) —OH,
  (9) —CO₂(C₁₋₆ alkyl), and
  (10) —CO—NR⁶—(C₀₋₃ alkyl)—R⁷;

R³ is selected from the group consisting of:
  phenyl, naphthyl, biphenyl, fluorenyl, dihydronaphthyl, tetrahydronaphthyl, octahydronaphthyl, C₁₋₆ alkyl, C₅₋₈ cycloalkyl, cyclohexenyl, adamantyl, and heteroaryl, which may be unsubstituted or substituted, where the substituents are independently selected from:
  (a) hydroxy,
  (b) C₁₋₃alkyl,
  (c) —O—C₁₋₃alkyl,
  (d) halogen,
  (e) trifluoromethyl,
  (f) phenyl
  (g) —CO₂(C₁₋₆ alkyl), and
  (h) —CONH₂;

R⁴ᵃ, R⁴ᵇ, R⁴ᶜ, R⁴ᵈ, R⁴ᵉ, R⁴ᶠ, R⁴ᵍ, and R⁴ʰ are independently selected from the group consisting of:
  (1) hydrogen, and
  (2) C₁₋₆ alkyl;
m is 1 and n is 1;
x is an integer selected from 0, 1, 2 and 3;
y is an integer selected from 0, 1 and 2;
and pharmaceutically acceptable salts thereof and individual diastereomers thereof.

2. The compound of claim 1 of formula Ib:

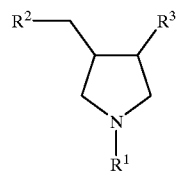

Ib wherein:
  R¹ is —X—R⁸, wherein X is selected from the group consisting of:

(1) —CH₂—,
(2) —CH₂CH₂—,
(3) —CH(C₁₋₆ alkyl)—,
(4) —CO—,
(5) —SO₂—,
(6) —CONH₂—, and
(7) —CONH(C₁₋₆ alkyl)—, and wherein R⁸ is a selected from:
  phenyl, naphthyl, biphenyl, fluorenyl, dihydronaphthyl, tetrahydronaphthyl, octahydronaphthyl, C₁₋₆ alkyl, C₅₋₈ cycloalkyl, cyclohexenyl, adamantyl, and heteroaryl, which may be unsubstituted or substituted, where the substituents are independently selected from:
    (a) hydroxy,
    (b) C₁₋₃alkyl,
    (c) —O—C₁₋₃alkyl,
    (d) halogen,
    (e) trifluoromethyl,
    (f) phenyl
    (g) —CO₂(C₁₋₆ alkyl), and
    (h) —CONH₂;

R² is selected from the group consisting of:

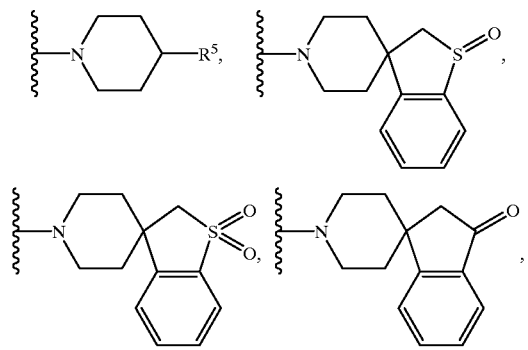

wherein R⁵ is a selected from:
  (1) —NR⁶CO—O—R⁷, wherein R⁶ is hydrogen, C₁₋₆ alkyl or C₁₋₆ alkyl-C₅₋₆ cycloalkyl, and R⁷ is C₁₋₆ alkyl, C₅₋₆ cycloalkyl, benzyl or phenyl, which is unsubsituted or substituted with halo, C₁₋₃alkyl, C₁₋₃alkoxy or trifluoromethyl,
  (2) —phenyl, which is unsubsituted or substituted with halo, C₁₋₃alkyl, C₁₋₃alkoxy or trifluoromethyl,
  (3) —C₁₋₆alkyl-phenyl, which is unsubsituted or substituted with halo, C₁₋₃alkyl, C₁₋₃alkoxy or trifluoromethyl,
  (4) —hydrogen,
  (5) —C₁₋₆alkyl,
  (6) —OH,
  (7) —CO₂(C₁₋₆ alkyl), and
  (8) —CO—NR⁶—(C₀₋₃ alkyl)—R⁷;

R³ is selected from the group consisting of:
  phenyl, naphthyl, biphenyl, fluorenyl, dihydronaphthyl, tetrahydronaphthyl, octahydronaphthyl, C₁₋₆ alkyl, C₅₋₈ cycloalkyl, cyclohexenyl, adamantyl, and heteroaryl, which may be unsubstituted or substituted, where the substituents are independently selected from:
    (a) hydroxy,
    (b) C₁₋₃alkyl,
    (c) —O—C₁₋₃alkyl,
    (d) halogen,
    (e) trifluoromethyl,
    (f) phenyl
    (g) —CO₂(C₁₋₆ alkyl), and
    (h) —CONH₂;

and pharmaceutically acceptable salts thereof and individual diastereomers thereof.

3. A compound of the formula Ic:

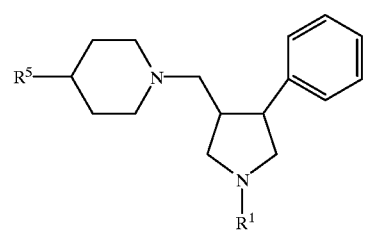

Ic wherein
  R¹ is —X—R⁸, wherein X is selected from the group consisting of:
    (1) —CH₂—, and
    (2) —CO—,
  and wherein R⁸ is a selected from cyclohexyl, cyclopentyl, naphthyl, unsubstituted phenyl or substituted phenyl, where the substituents on phenyl are independently selected from halogen and methyl;
  R⁵ is a selected from:
    (1) —phenyl, which is unsubsituted or substituted with halo, C₁₋₃alkyl, C₁₋₃alkoxy or trifluoromethyl, and
    (3) —C₁₋₆alkyl-phenyl, which is unsubsituted or substituted with halo, C₁₋₃alkyl, C₁₋₃alkoxy or trifluoromethyl;

and pharmaceutically acceptable salts thereof and individual diastereomers thereof.

4. The compound of claim 3 of the formula Id:

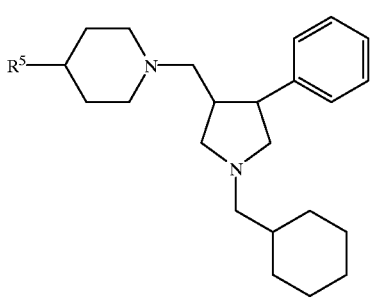

Id wherein R⁵ is a selected from:
  (1) —phenyl, which is unsubsituted or substituted with halo, C₁₋₃alkyl, C₁₋₃alkoxy or trifluoromethyl, and
  (3) —C₃₋₄alkyl-phenyl, which is unsubsituted or substituted with halo, C₁₋₃alkyl, C₁₋₃alkoxy or trifluoromethyl.

5. The compound of claim 1 wherein:
  R¹ is —X—R⁸, wherein X is selected from the group consisting of:
    (1) —CH₂—,
    (2) —CH₂CH₂—,
    (3) —CH(C₁₋₆ alkyl)—,
    (4) —CO—,
    (5) —SO₂—,
    (6) —CONH₂—, and
    (7) —CONH(C₁₋₆ alkyl)—, and wherein $R^8$ is a selected from:
  phenyl, naphthyl, biphenyl, fluorenyl, dihydronaphthyl, tetrahydronaphthyl, octahydronaphthyl, $C_{1-6}$ alkyl, $C_{5-8}$ cycloalkyl, cyclohexenyl, adamantyl, and heteroaryl, which may be unsubstituted or substituted, where the substituents are independently selected from:
  (a) hydroxy,
  (b) $C_{1-3}$alkyl,
  (c) —O—$C_{1-3}$alkyl,
  (d) halogen,
  (e) trifluoromethyl,
  (f) phenyl
  (g) —$CO_2$($C_{1-6}$ alkyl), and
  (h) —$CONH_2$.

6. The compound of claim 1 wherein:
$R^1$ is —X—$R^8$, wherein X is selected from the group consisting of:
  (1) —$CH_2$—, and
  (2) —CO—,
and wherein $R^8$ is a selected from:
  phenyl, naphthyl, $C_{1-6}$ alkyl, cyclohexyl, cyclopentyl, pyridyl, quinolyl, thiophenyl, indolyl, benzoxazolyl and benzthiazolyl, which may be unsubstituted or substituted, where the substituents are independently selected from:
  (a) chloro,
  (b) fluoro,
  (c) —O—$CH_3$,
  (d) —$CH_3$,
  (e) trifluoromethyl,
  (f) —$CO_2CH_3$, and
  (g) —$CONH_2$.

7. The compound of claim 1 wherein:
$R^1$ is selected from the group consisting of:
  (1) —$CH_2$—phenyl,
  (2) —CO—phenyl,
  (3) —$CH_2$—(2-chlorophenyl),
  (4) —CO—(2-chlorophenyl),
  (5) —$CH_2$—(2-naphthyl),
  (6) —CO—(2-naphthyl);
  (7) —$CH_2$—cyclopentyl,
  (8) —CO—cyclopentyl,
  (9) —$CH_2$—cyclohexyl, and
  (10) —CO—cyclohexyl.

8. The compound of claim 1 wherein:
$R^2$ is selected from the group consisting of:

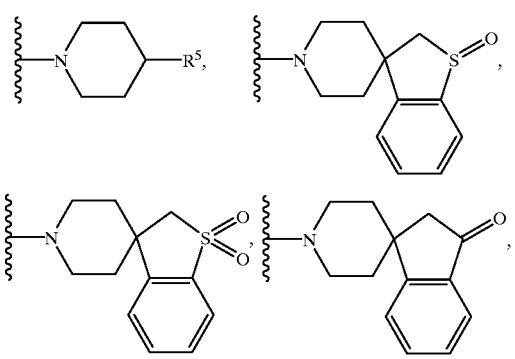

wherein $R^5$ is a selected from:
  (1) —$NR^6CO$—O—$R^7$, wherein $R^6$ is hydrogen, $C_{1-6}$ alkyl or $C_{1-6}$ alkyl-$C_{5-6}$ cycloalkyl, and $R^7$ is $C_{1-6}$ alkyl, $C_{5-6}$ cycloalkyl, benzyl or phenyl, which is unsubsituted or substituted with halo, $CF_3$, $C_{1-3}$alkyl, $C_{1-3}$alkoxy or trifluoromethyl,
  (2) —phenyl, which is unsubsituted or substituted with halo, $CF_3$, $C_{1-3}$alkyl, $C_{1-3}$alkoxy or trifluoromethyl,
  (3) —$C_{1-6}$alkyl,
  (4) —$C_{1-6}$alkyl-phenyl, which is unsubsituted or substituted with halo, $CF_3$, $C_{1-3}$alkyl, $C_{1-3}$alkoxy or trifluoromethyl,
  (5) —$CO_2$($C_{1-6}$ alkyl), and
  (6) —CO—$NR^6$—($C_{0-3}$ alkyl)—$R^7$.

9. The compound of claim 1 wherein:
$R^2$ is:

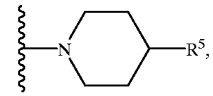

wherein $R^5$ is selected from:
  (1) —$NR^6CO$—O—$R^7$, wherein $R^6$ is hydrogen, $C_{1-6}$ alkyl or $C_{1-6}$ alkyl-$C_{5-6}$ cycloalkyl, and $R^7$ is $C_{1-6}$ alkyl, $C_{5-6}$ cycloalkyl, benzyl or phenyl, which is unsubsituted or substituted with halo, $CF_3$, $C_{1-3}$alkyl, $C_{1-3}$alkoxy or trifluoromethyl,
  (2) —phenyl, which is unsubsituted or substituted with halo, $CF_3$, $C_{1-3}$alkyl, $C_{1-3}$alkoxy or trifluoromethyl,
  (3) —$C_{1-6}$alkyl-phenyl, which is unsubsituted or substituted with halo, $CF_3$, $C_{1-3}$alkyl, $C_{1-3}$alkoxy or trifluoromethyl, and
  (4) —CO—$NR^6$—($C_{0-3}$ alkyl)—$R^7$.

10. The compound of claim 1 wherein:
$R^2$ is:

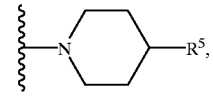

wherein $R^5$ is selected from:
  (1) —phenyl, which is unsubsituted or substituted with halo, $CF_3$, $C_{1-3}$alkyl, $C_{1-3}$alkoxy or trifluoromethyl, and
  (2) —$C_{1-6}$alkyl-phenyl, which is unsubsituted or substituted with halo, $CF_3$, $C_{1-3}$alkyl, $C_{1-3}$alkoxy or trifluoromethyl.

11. The compound of claim 1 wherein:
$R^2$ is:

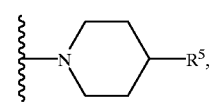

wherein $R^5$ is a selected from:
  (1) —phenyl, which is unsubsituted or substituted with halo, $C_{1-3}$alkyl, $C_{1-3}$alkoxy or trifluoromethyl, and
  (3) —$C_{3-4}$alkyl-phenyl, which is unsubsituted or substituted with halo, $C_{1-3}$alkyl, $C_{1-3}$alkoxy or trifluoromethyl.

12. The compound of claim 1 wherein:
$R^3$ is selected from the group consisting of:
  phenyl, naphthyl, biphenyl, fluorenyl, dihydronaphthyl, tetrahydronaphthyl, octahydronaphthyl, $C_{1-6}$ alkyl; $C_{5-8}$ cycloalkyl, cyclohexenyl, adamantyl, and thienyl, which may be unsubstituted or substituted, where the substituents are independently selected from:
(a) hydroxy,
(b) $C_{1-3}$alkyl,
(c) —O—$C_{1-3}$alkyl,
(d) halogen,
(e) trifluoromethyl,
(f) phenyl
(g) —$CO_2$($C_{1-6}$ alkyl), and
(h) —$CONH_2$.

13. The compound of claim 1 wherein:
$R^3$ is phenyl or thienyl, which may be unsubstituted or substituted, where the substituents are independently selected from:
(a) chloro,
(b) fluoro,
(c) bromo,
(d) trifluoromethyl, and
(e) —O—$CH_3$.

14. The compound of claim 1 wherein:
$R^3$ is phenyl or thienyl.

15. The compound of claim 1 wherein:
$R^{4a}$, $R^{4b}$, $R^{4c}$, $R^{4e}$, $R^{4f}$, $R^{4g}$, and $R^{4h}$ are each hydrogen and wherein $R^{4d}$ is selected from the group consisting of:
(1) hydrogen, and
(2) $CH_3$.

16. The compound of claim 1 wherein:
x is 1 and y is 0.

17. The compound of claim 1 which is of the stereochemical configuration:

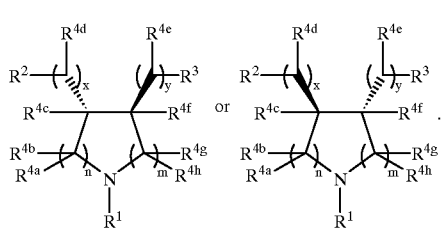

18. A compound which is selected from the group consisting of:

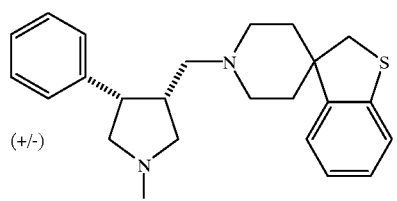

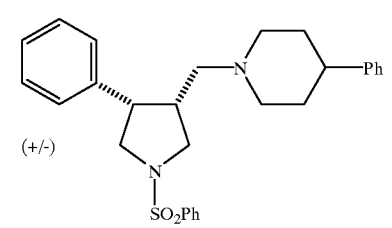

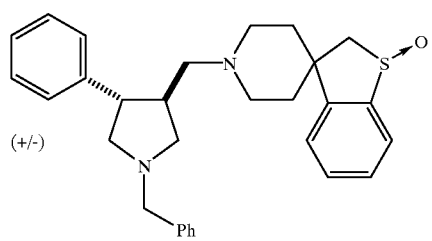

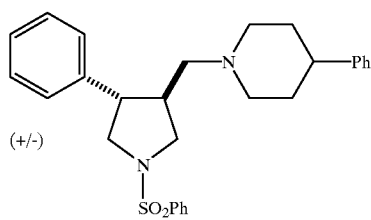

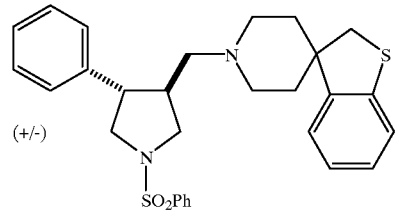

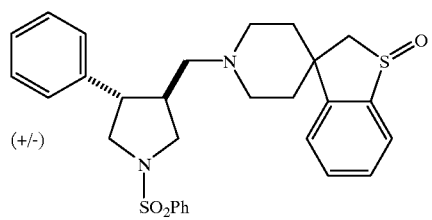

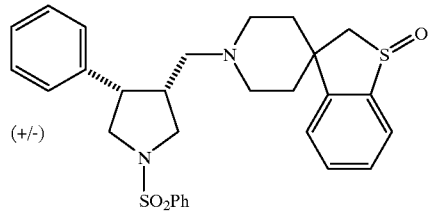

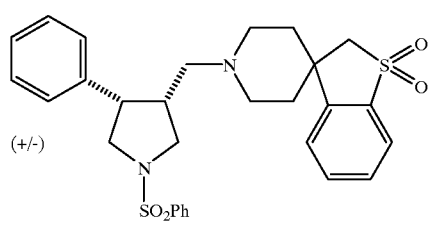

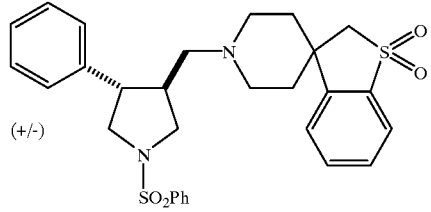

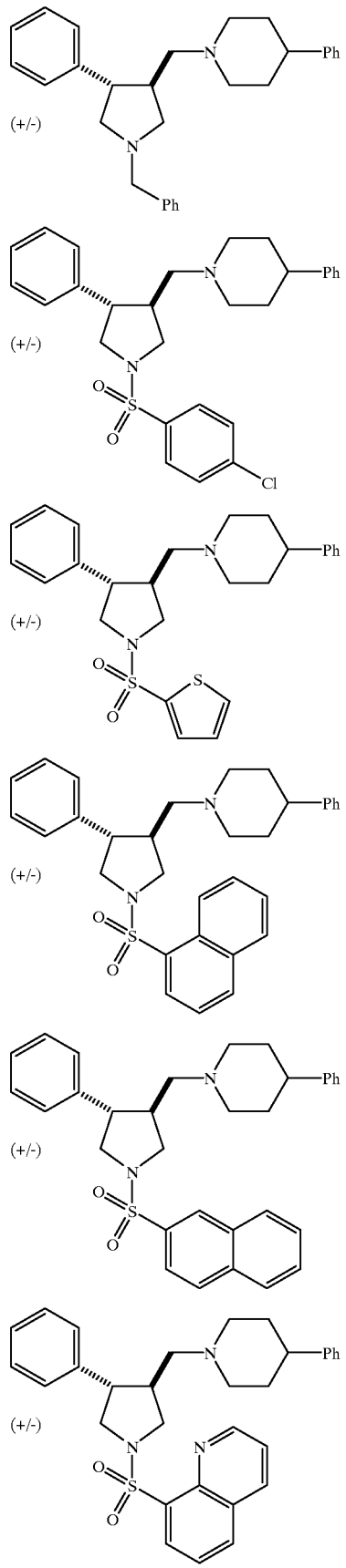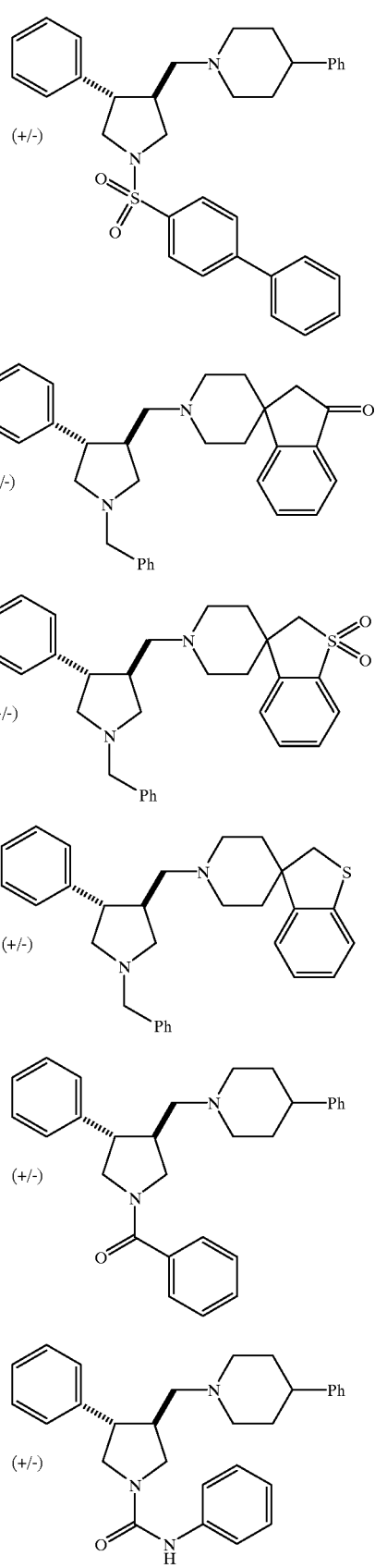

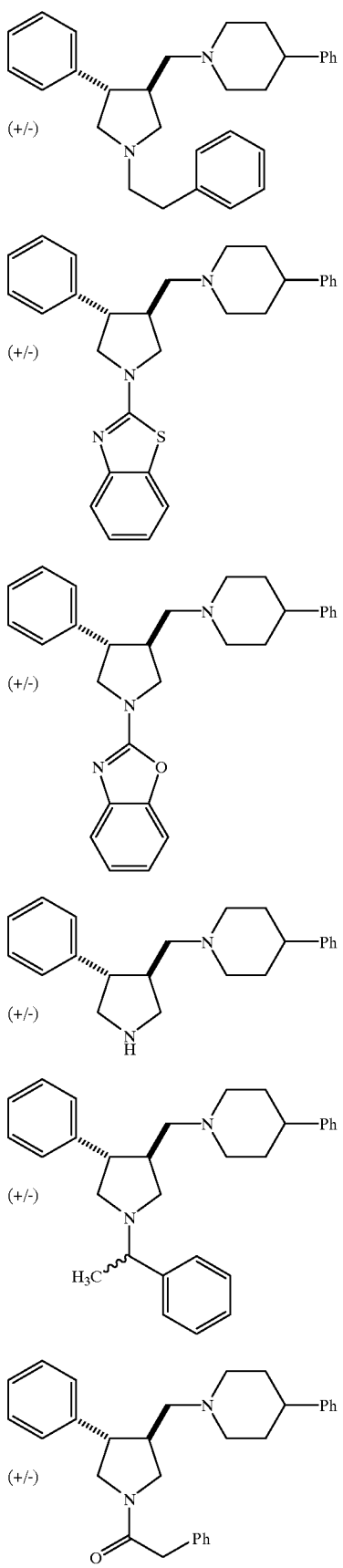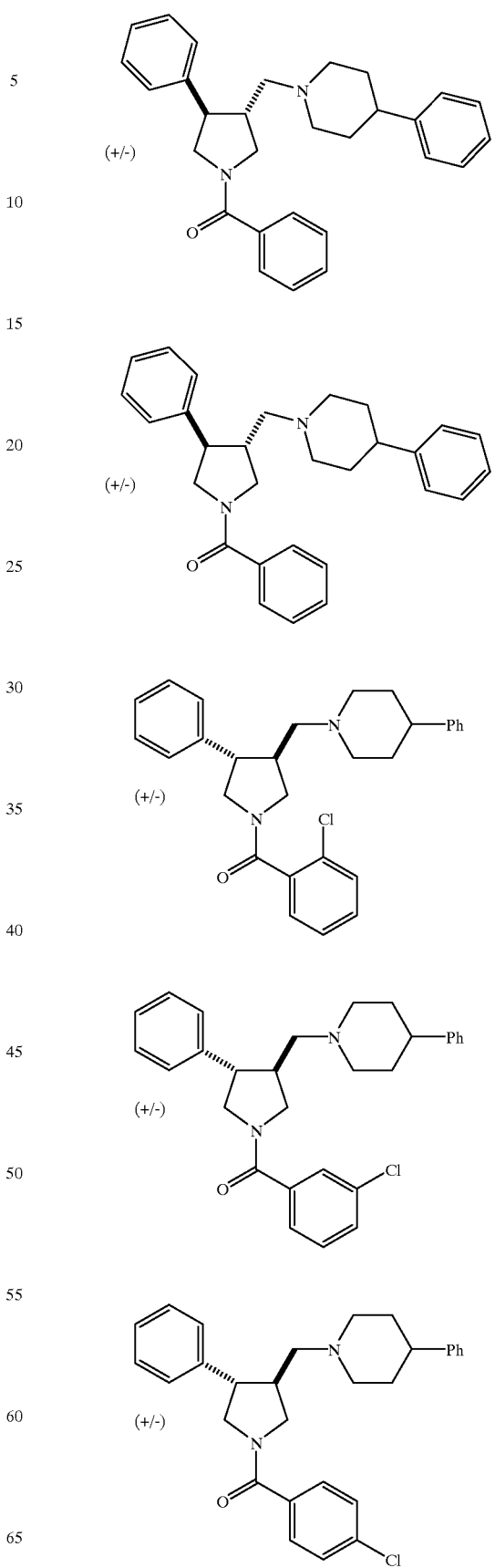

161
-continued
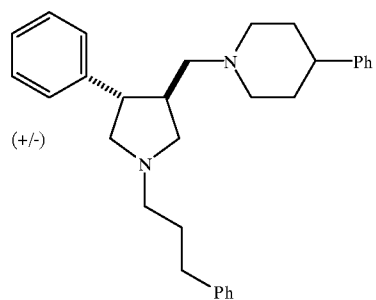
(+/-)
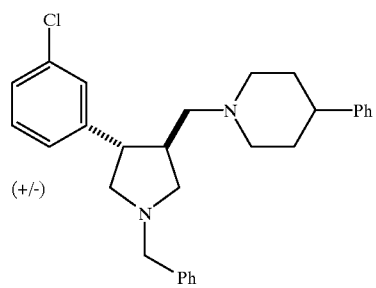
(+/-)
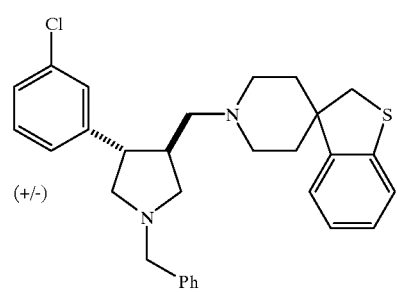
(+/-)
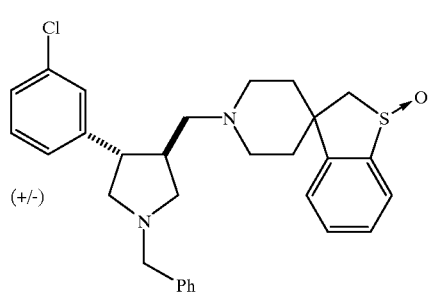
(+/-)
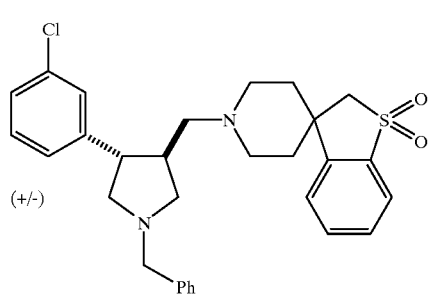
(+/-)
162
-continued
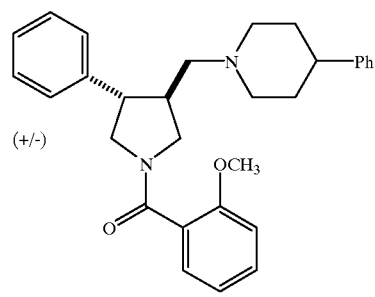
(+/-)
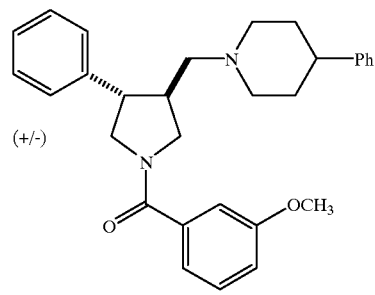
(+/-)
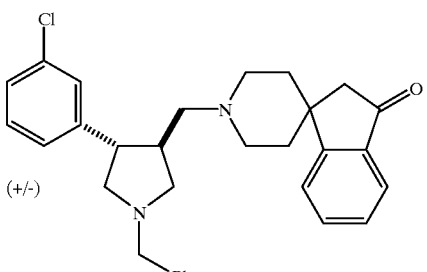
(+/-)
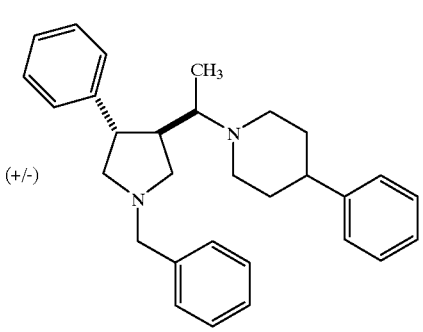
(+/-)
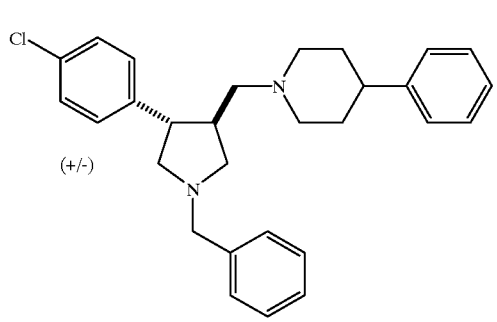
(+/-)

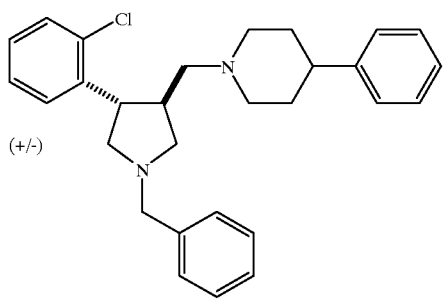
(+/-)
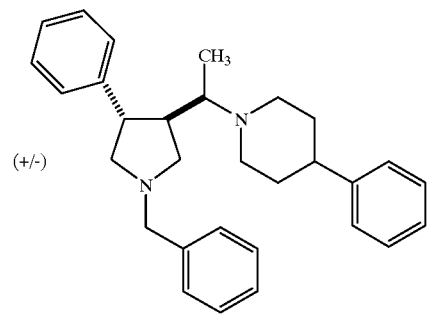
(+/-)
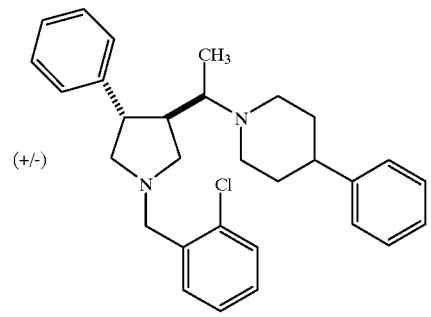
(+/-)
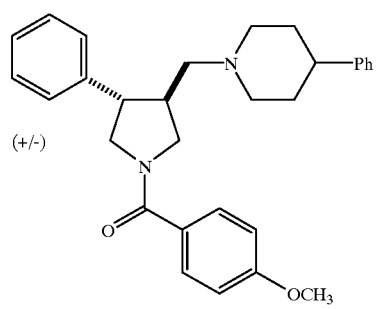
(+/-)
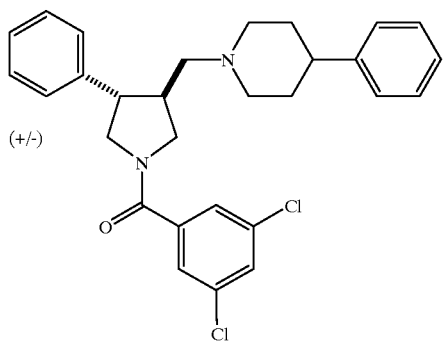
(+/-)
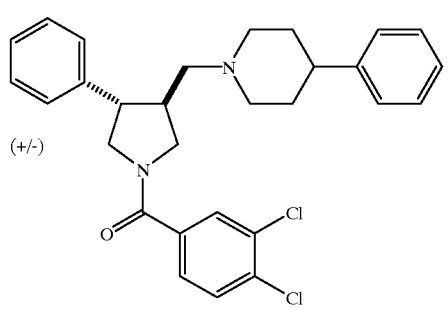
(+/-)
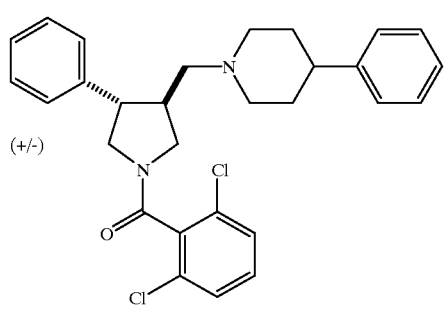
(+/-)
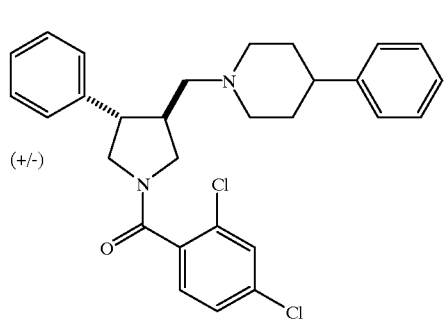
(+/-)
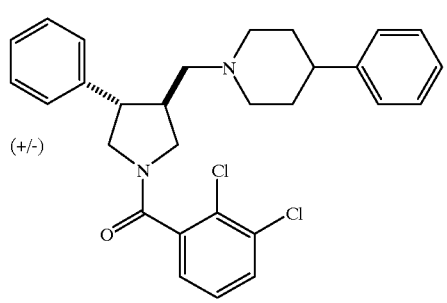
(+/-)
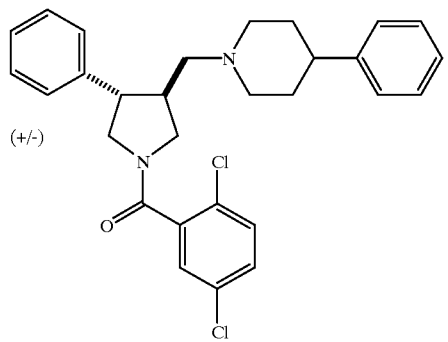
(+/-)

-continued
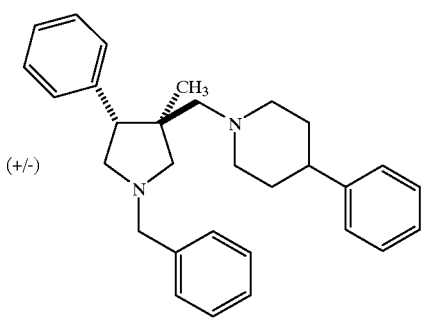
(+/-)
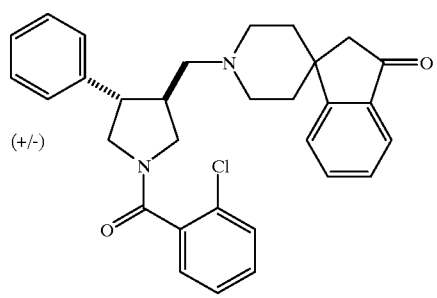
(+/-)
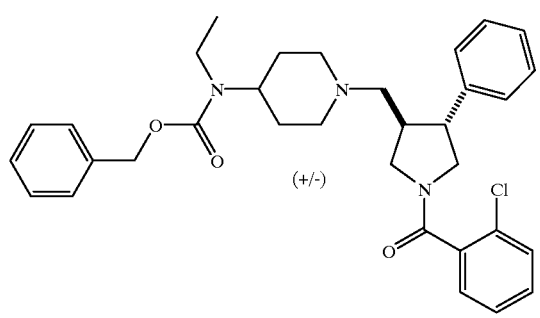
(+/-)
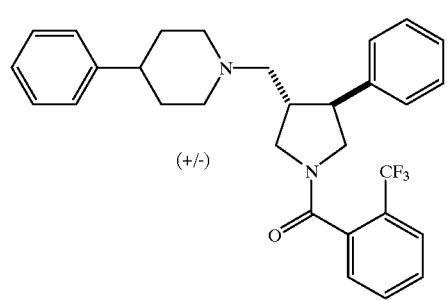
(+/-)
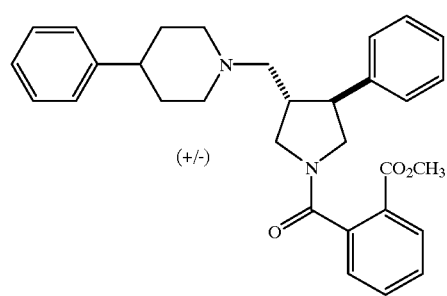
(+/-)
-continued
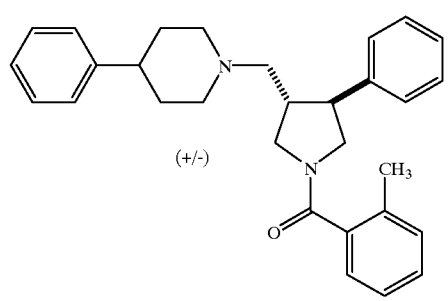
(+/-)
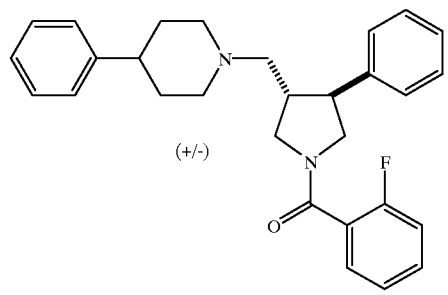
(+/-)
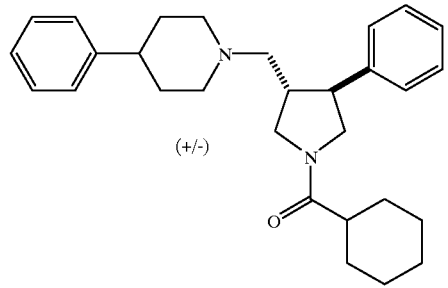
(+/-)
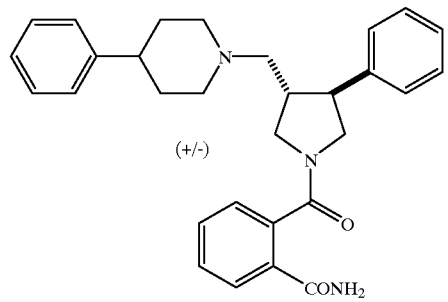
(+/-)
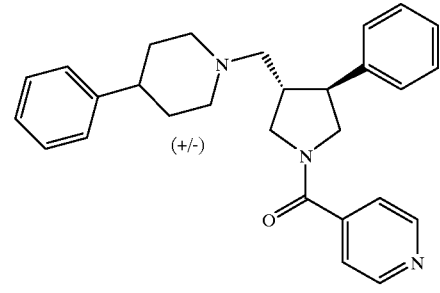
(+/-)

167
-continued
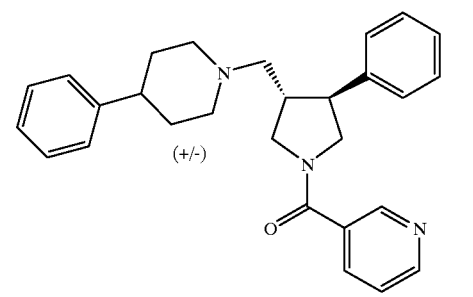
(+/-)
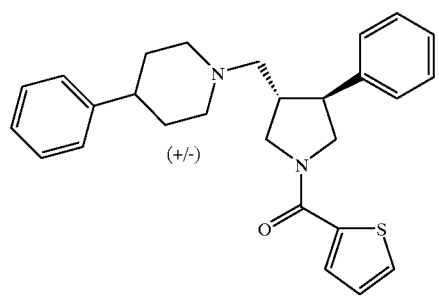
(+/-)
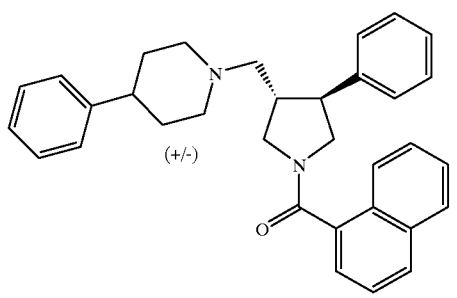
(+/-)
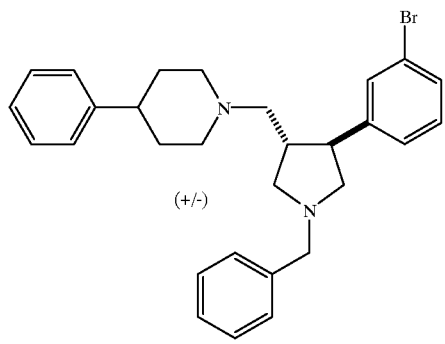
(+/-)
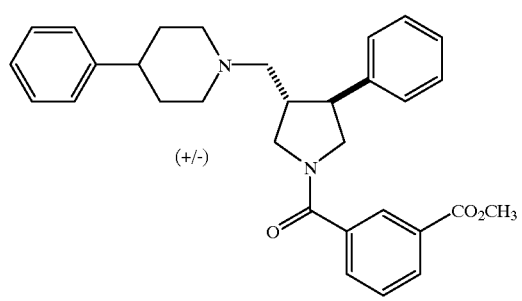
(+/-)
168
-continued
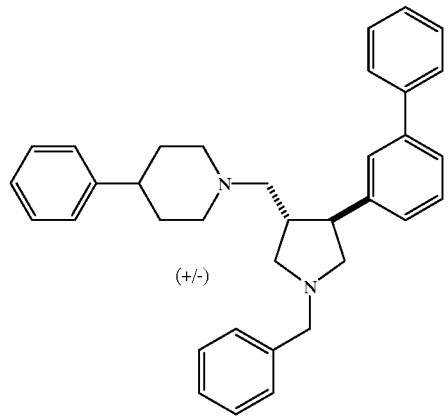
(+/-)
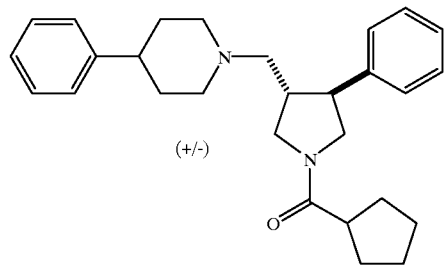
(+/-)
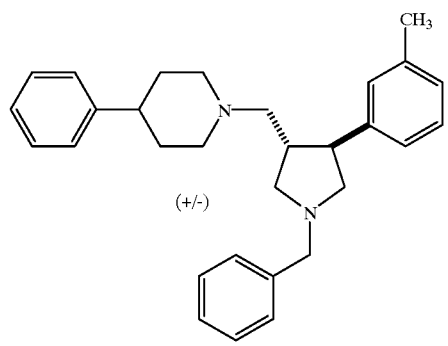
(+/-)
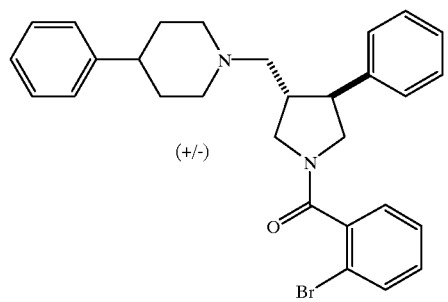
(+/-)

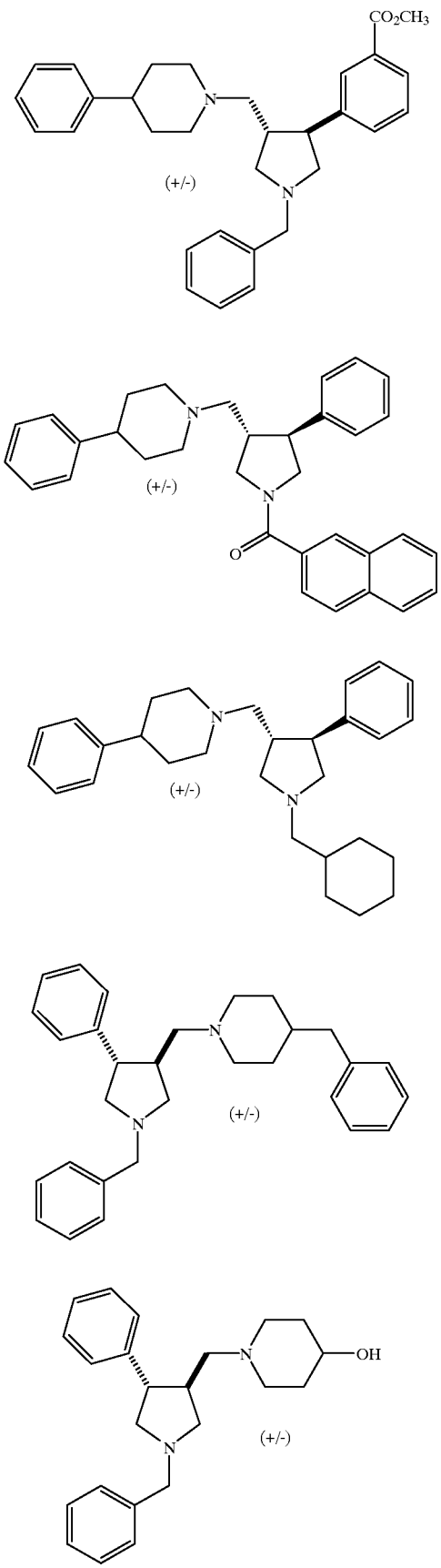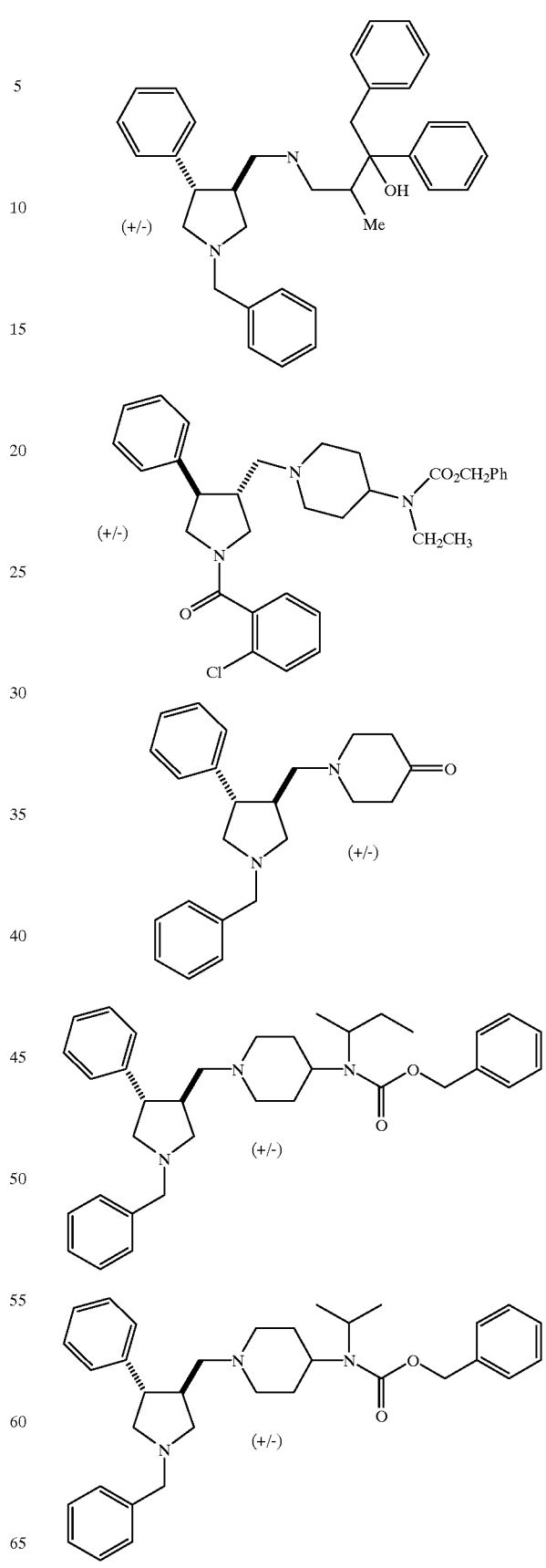

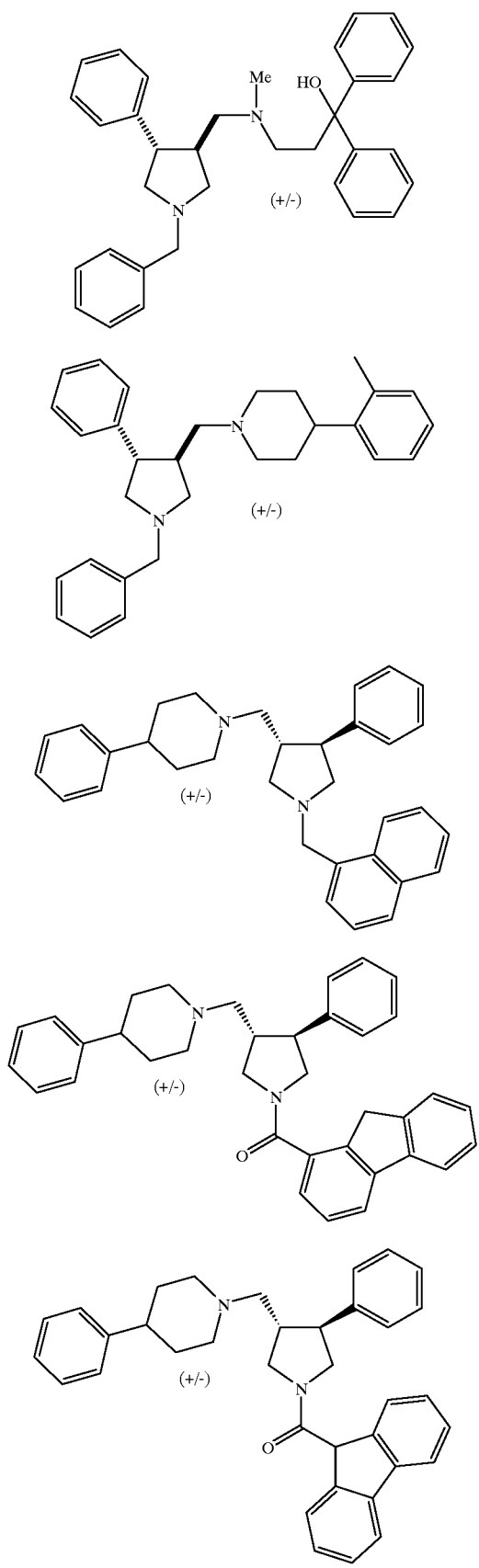
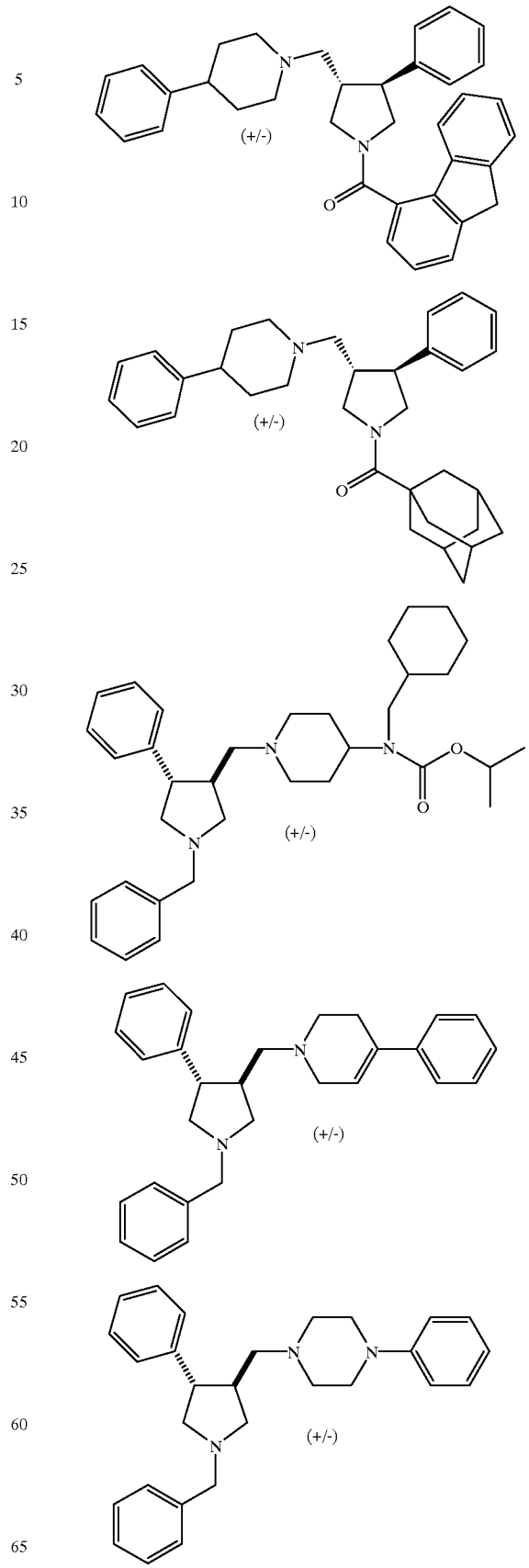

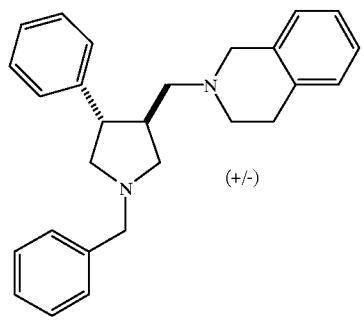
(+/-)
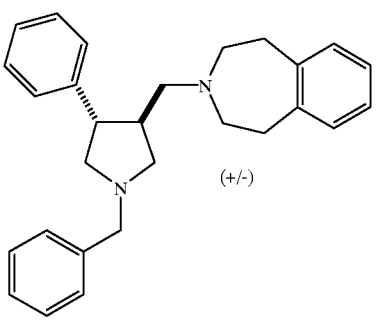
(+/-)
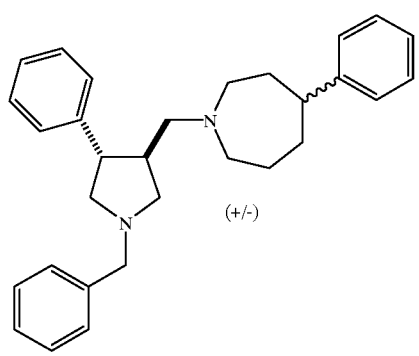
(+/-)
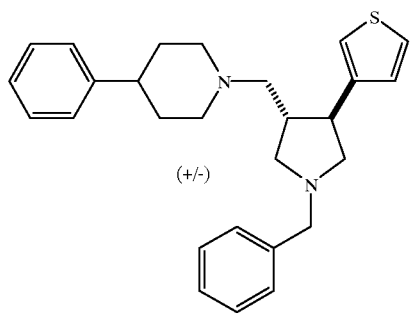
(+/-)
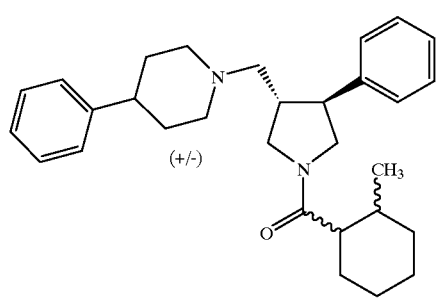
(+/-)
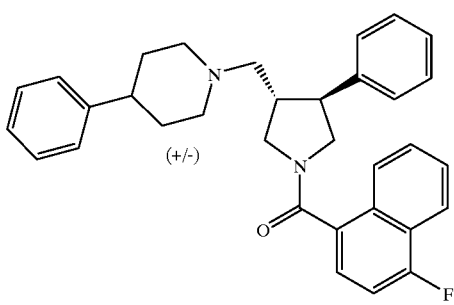
(+/-)
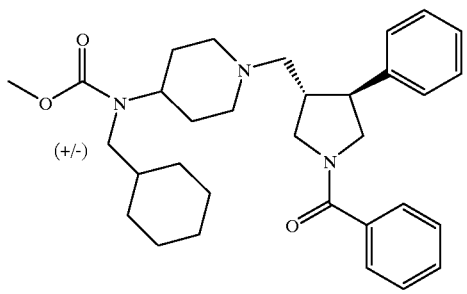
(+/-)
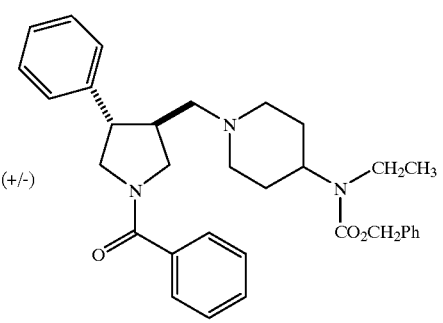
(+/-)
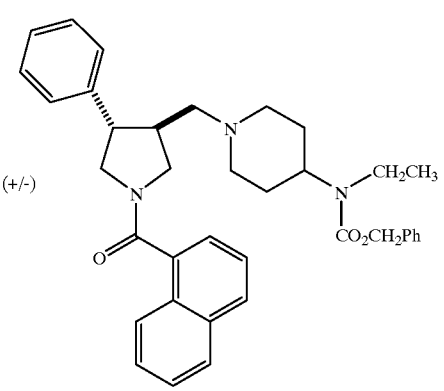
(+/-)
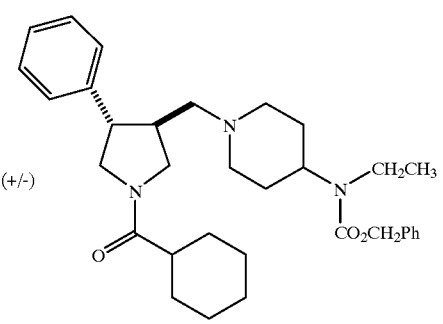
(+/-)

175
-continued
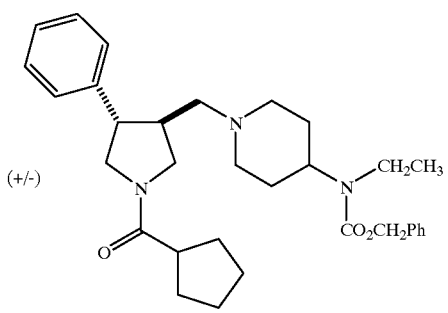
(+/-)
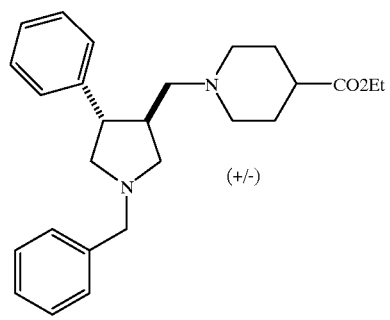
(+/-)
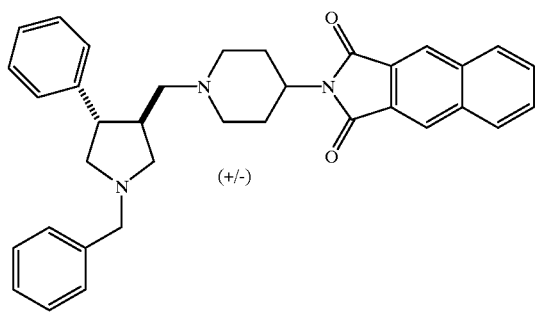
(+/-)
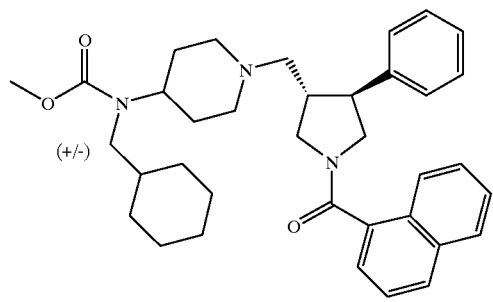
(+/-)
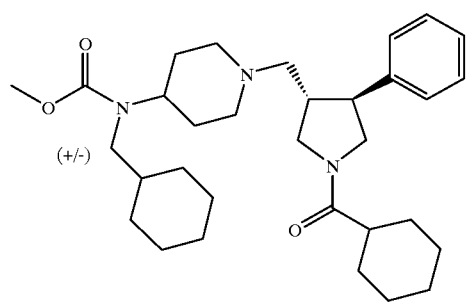
(+/-)
176
-continued
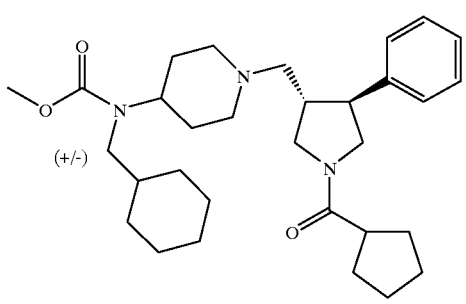
(+/-)
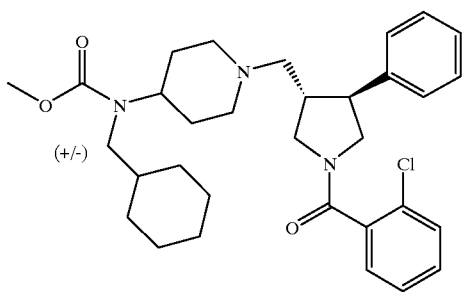
(+/-)
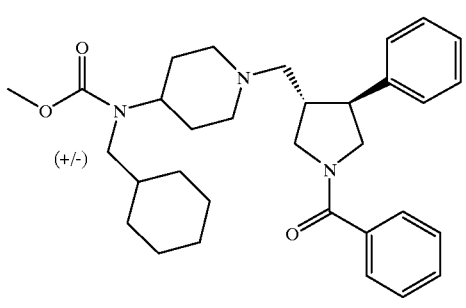
(+/-)
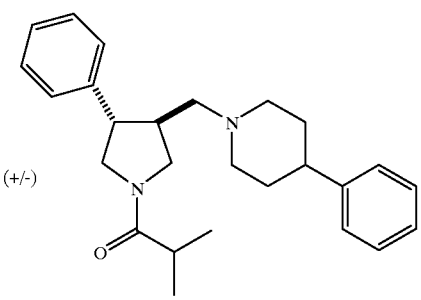
(+/-)
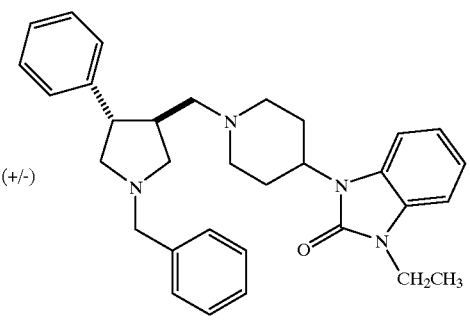
(+/-)

177
-continued
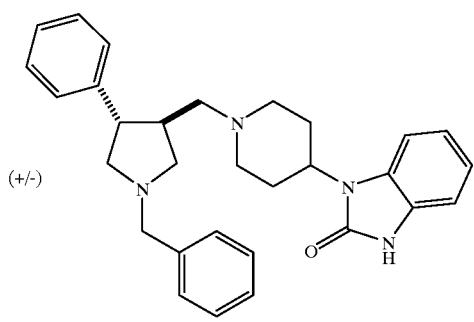
(+/-)
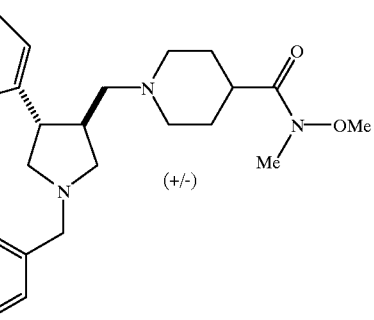
(+/-)
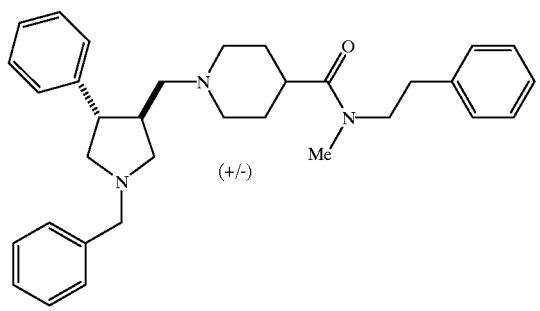
(+/-)
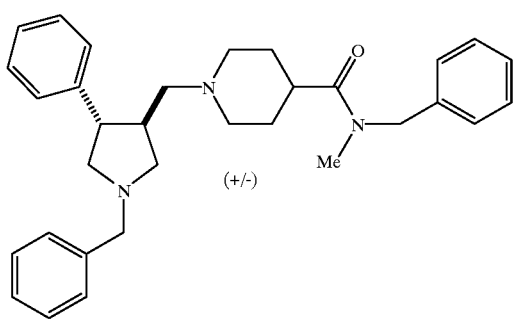
(+/-)
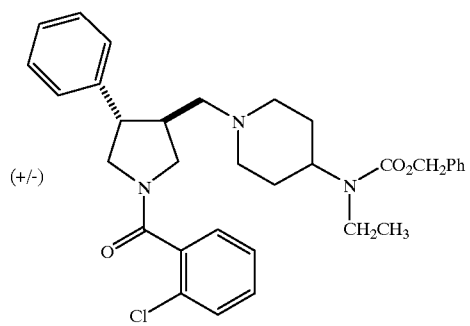
(+/-)
178
-continued
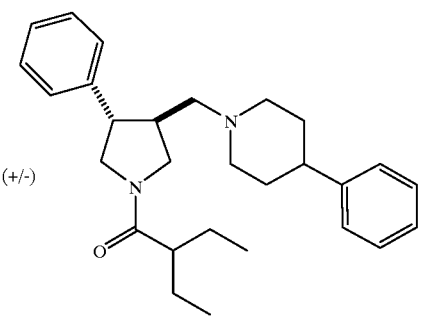
(+/-)
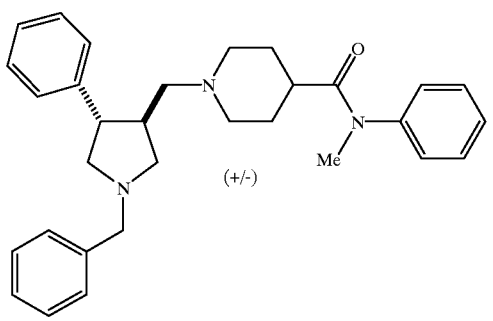
(+/-)
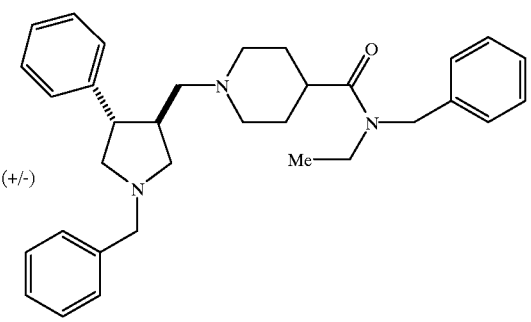
(+/-)
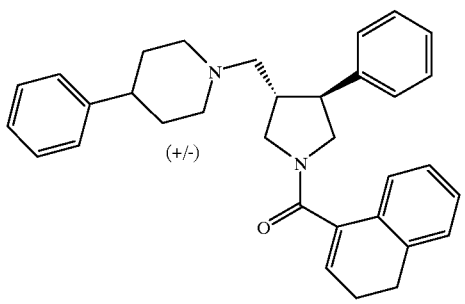
(+/-)
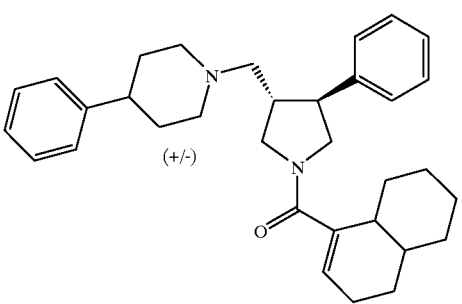
(+/-)

179
-continued
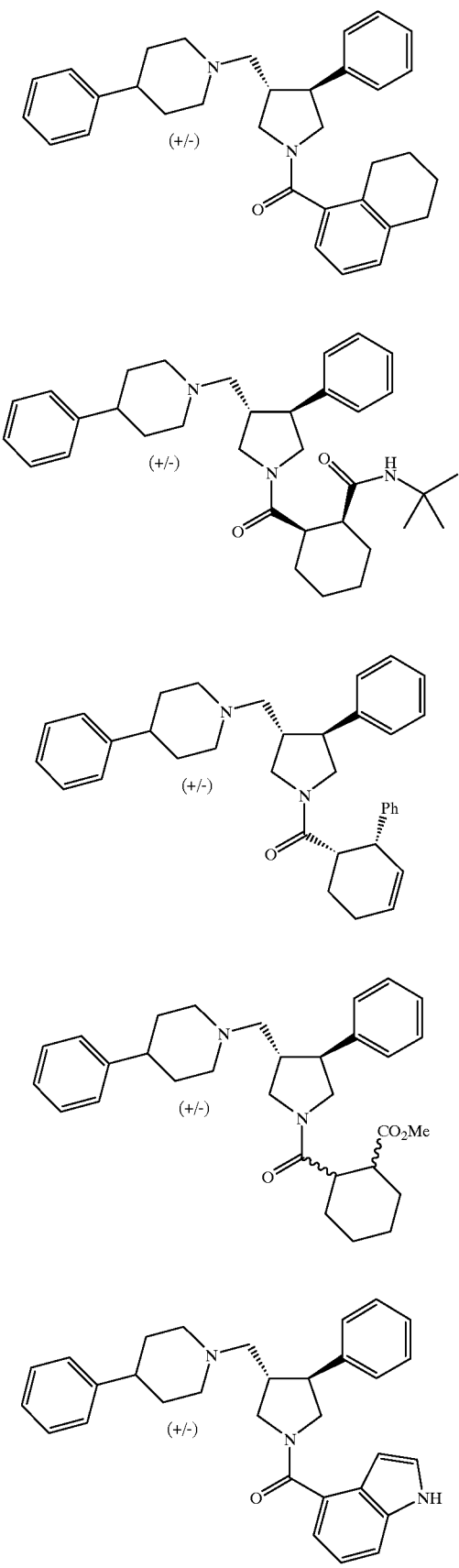
180
-continued
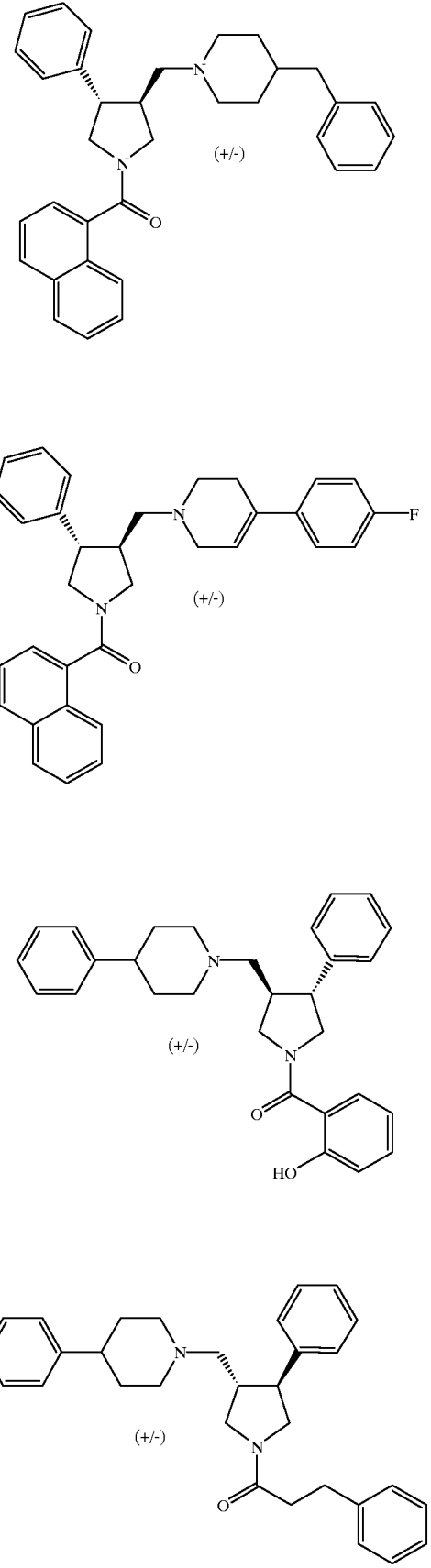

181
-continued
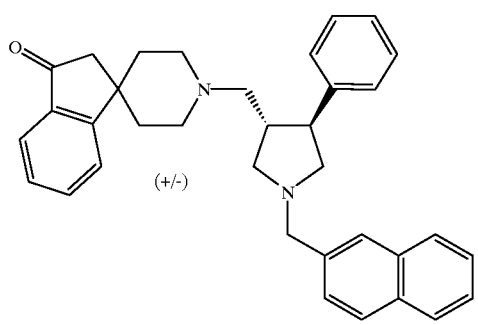
(+/-)
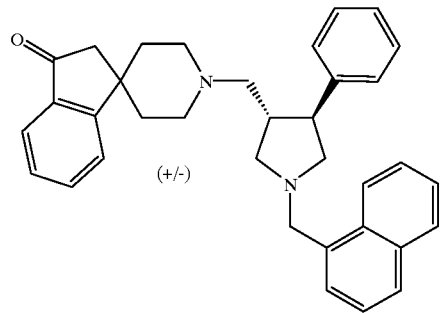
(+/-)
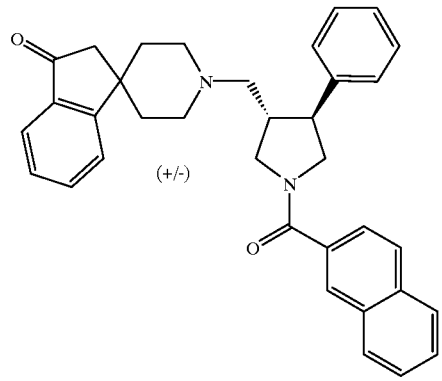
(+/-)
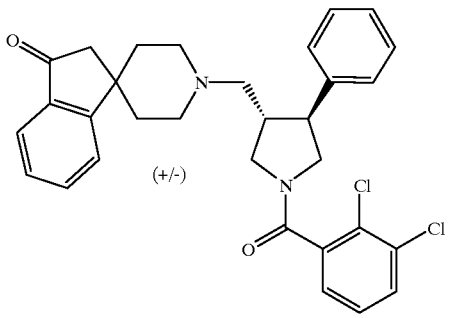
(+/-)
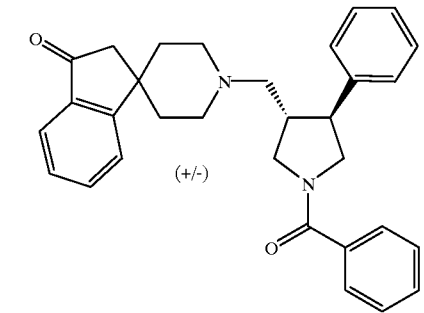
(+/-)
182
-continued
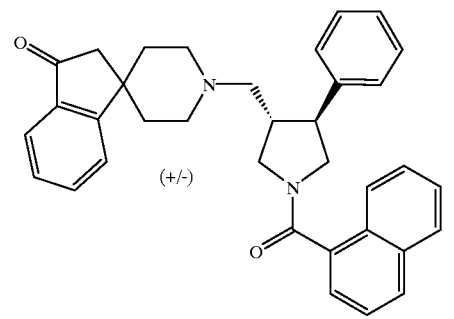
(+/-)
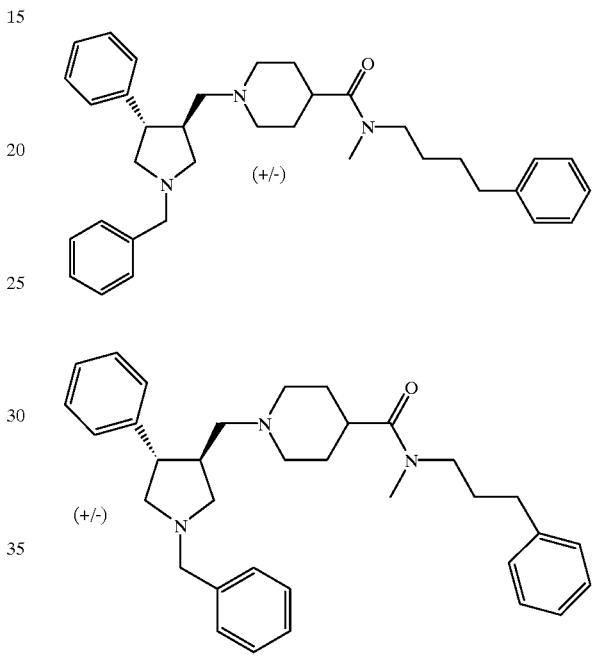
(+/-)
(+/-)
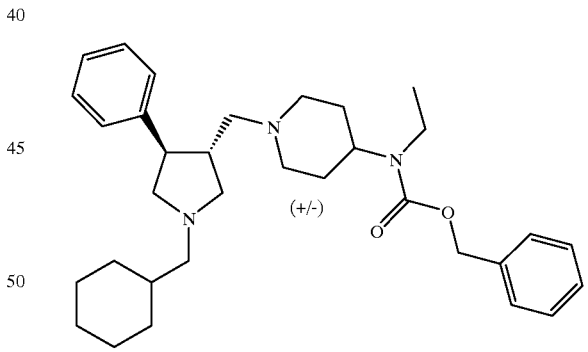
(+/-)
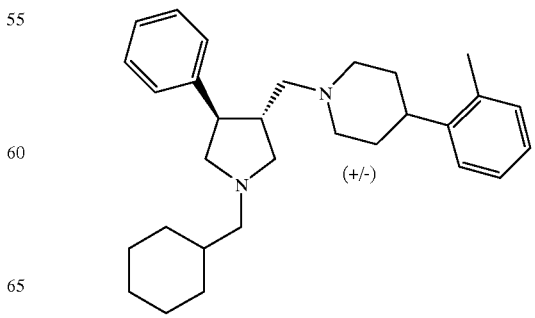
(+/-)

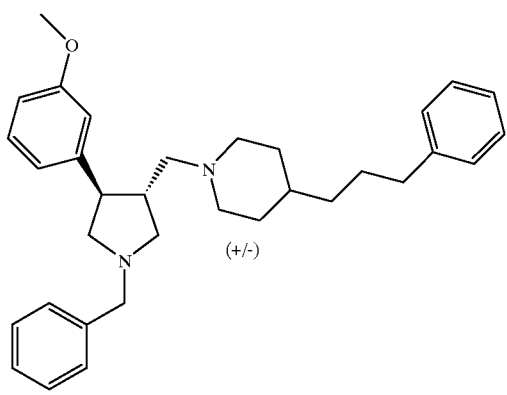
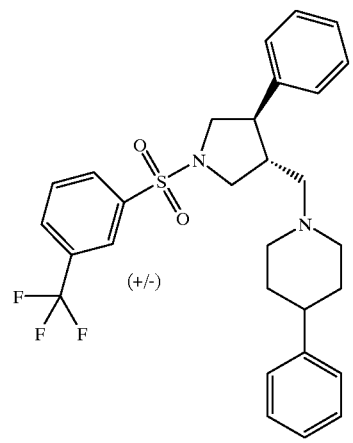
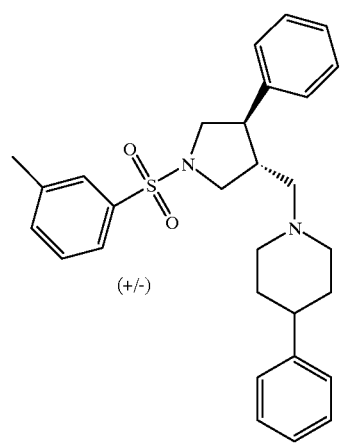
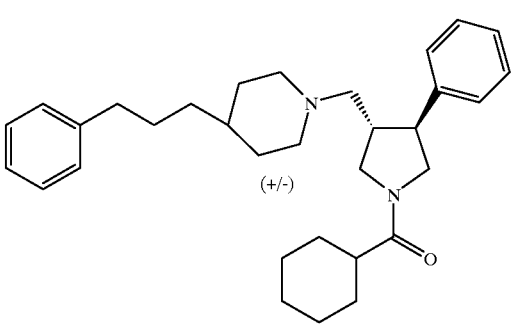
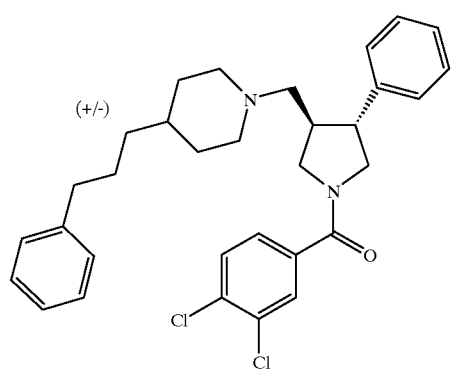
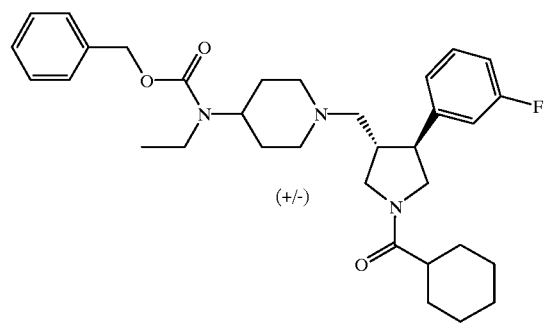

185
-continued
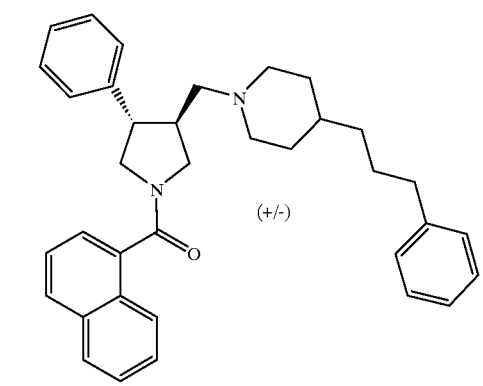
(+/-)
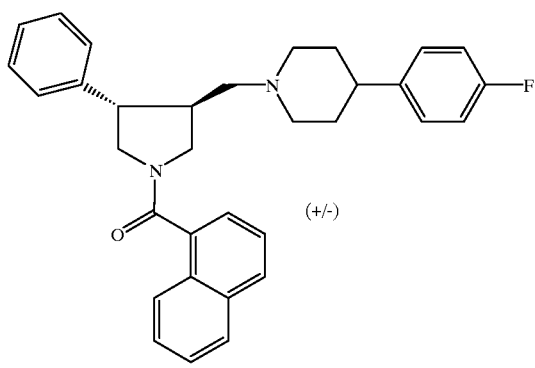
(+/-)
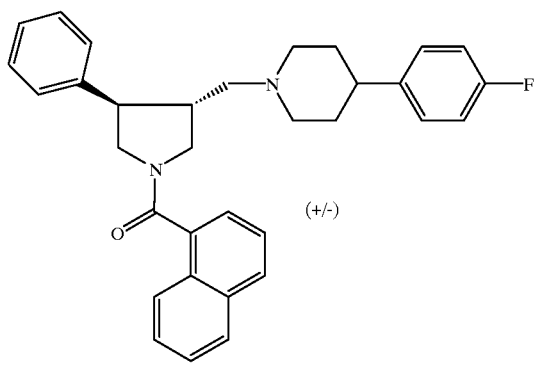
(+/-)
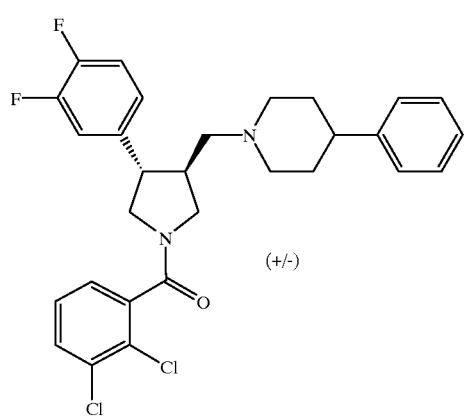
(+/-)
186
-continued
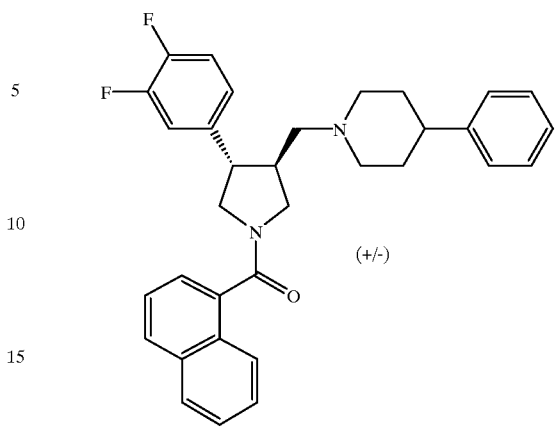
(+/-)
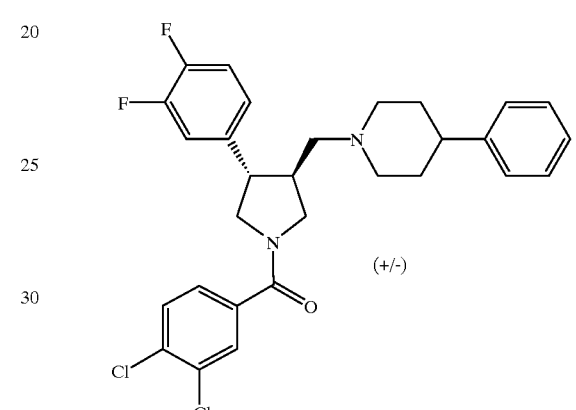
(+/-)
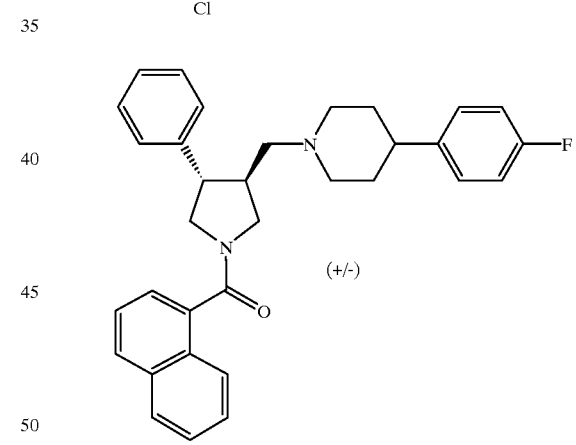
(+/-)
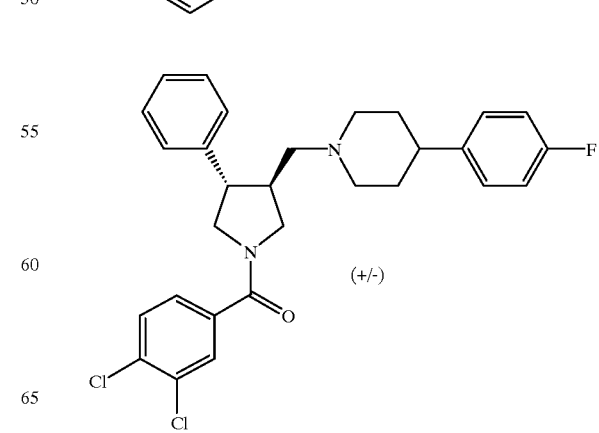
(+/-)

187
-continued
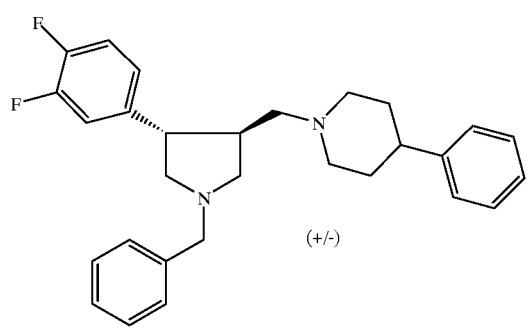
(+/−)
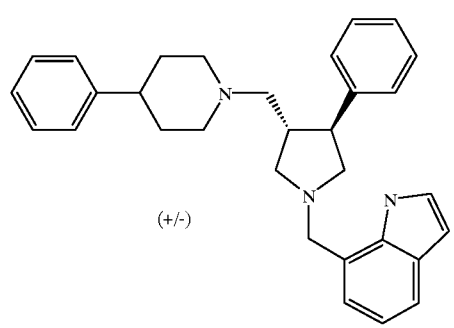
(+/−)
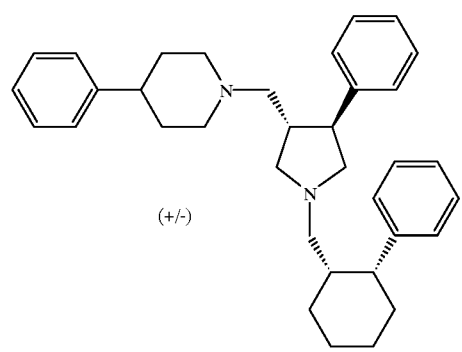
(+/−)
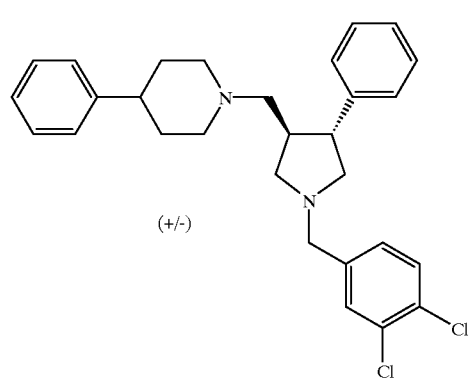
(+/−)
188
-continued
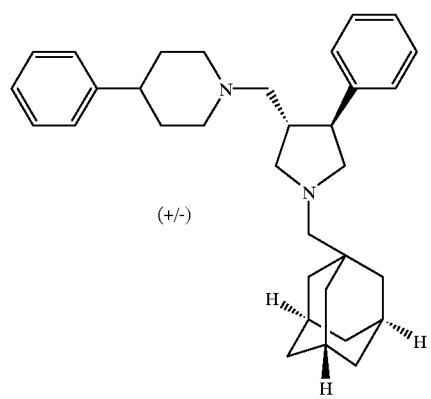
(+/−)
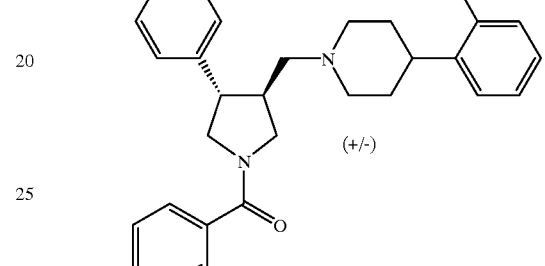
(+/−)
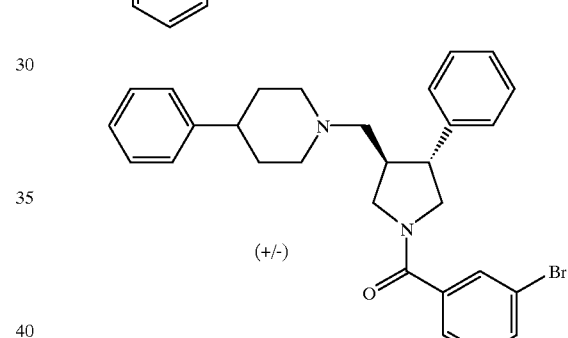
(+/−)
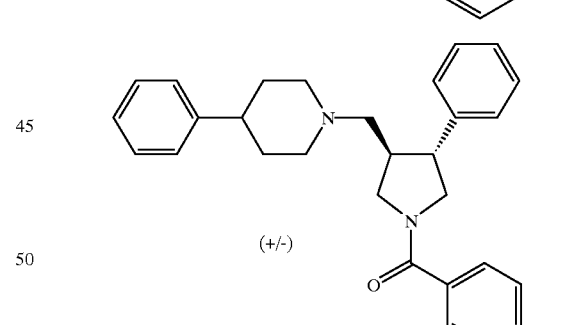
(+/−)
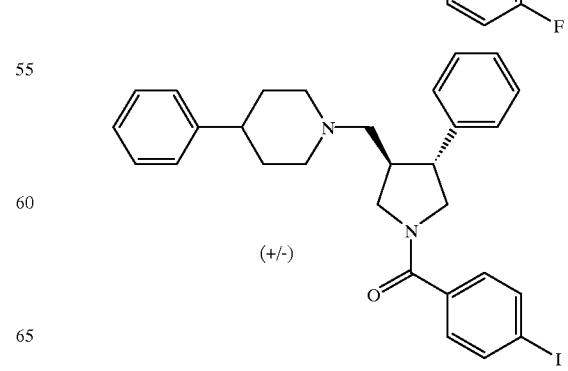
(+/−)

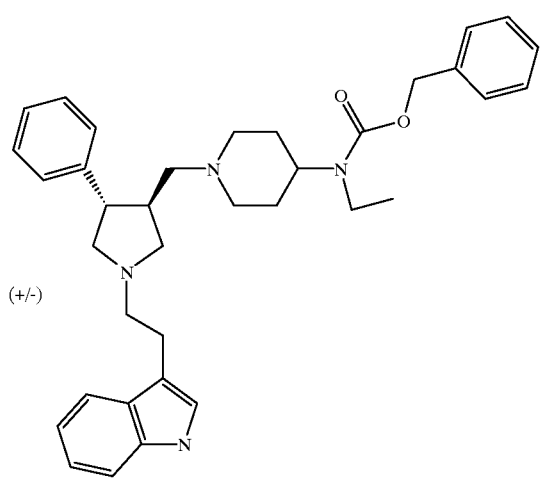
(+/-)
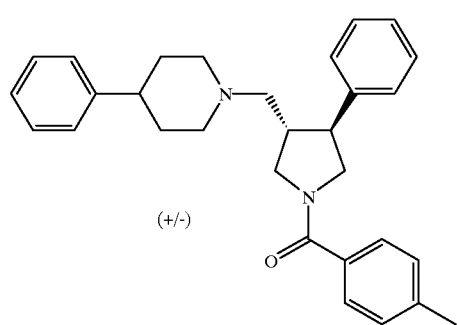
(+/-)
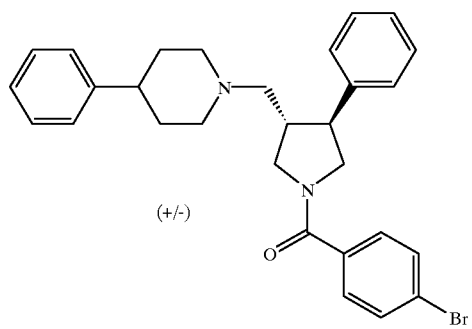
(+/-)
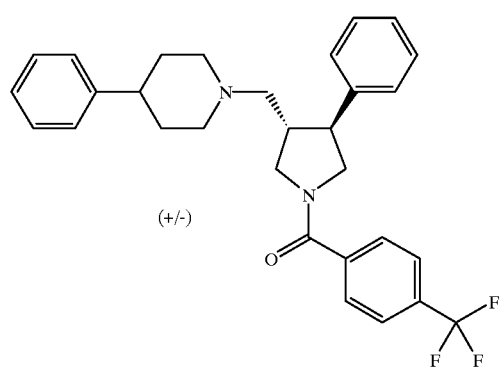
(+/-)
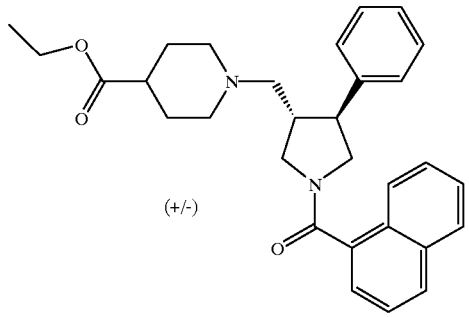
(+/-)
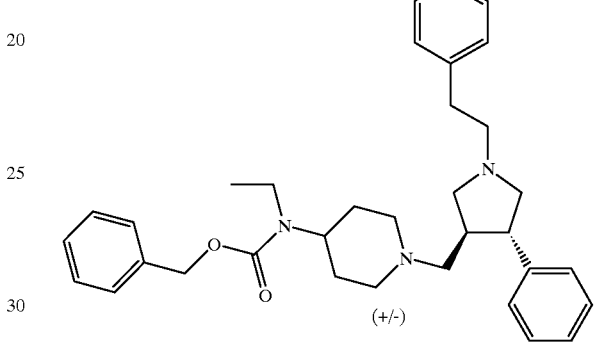
(+/-)
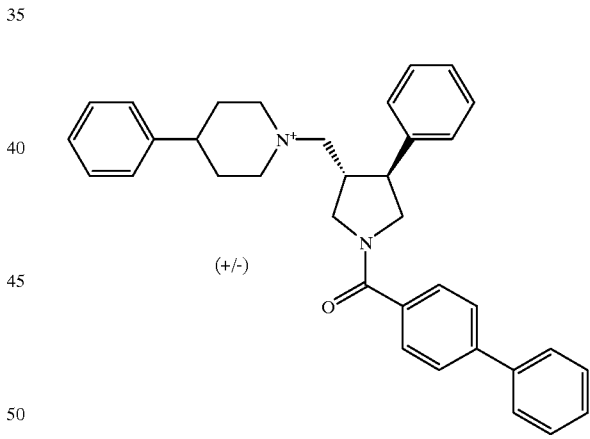
(+/-)
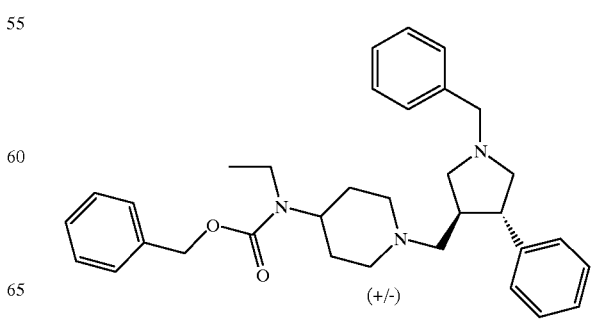
(+/-)

191
-continued
192
-continued
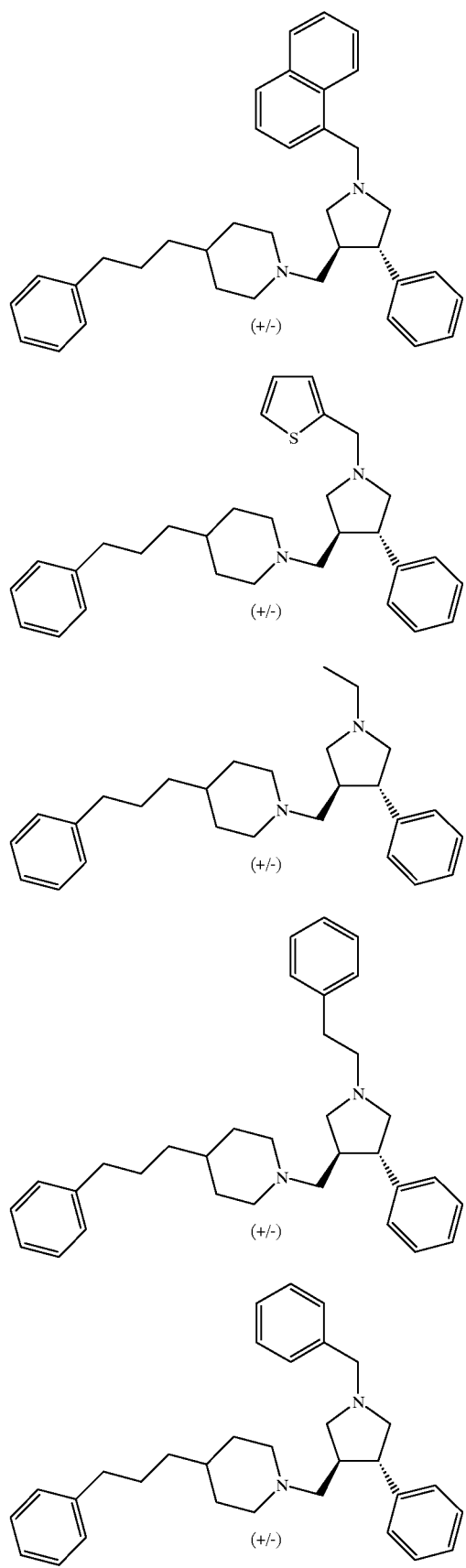
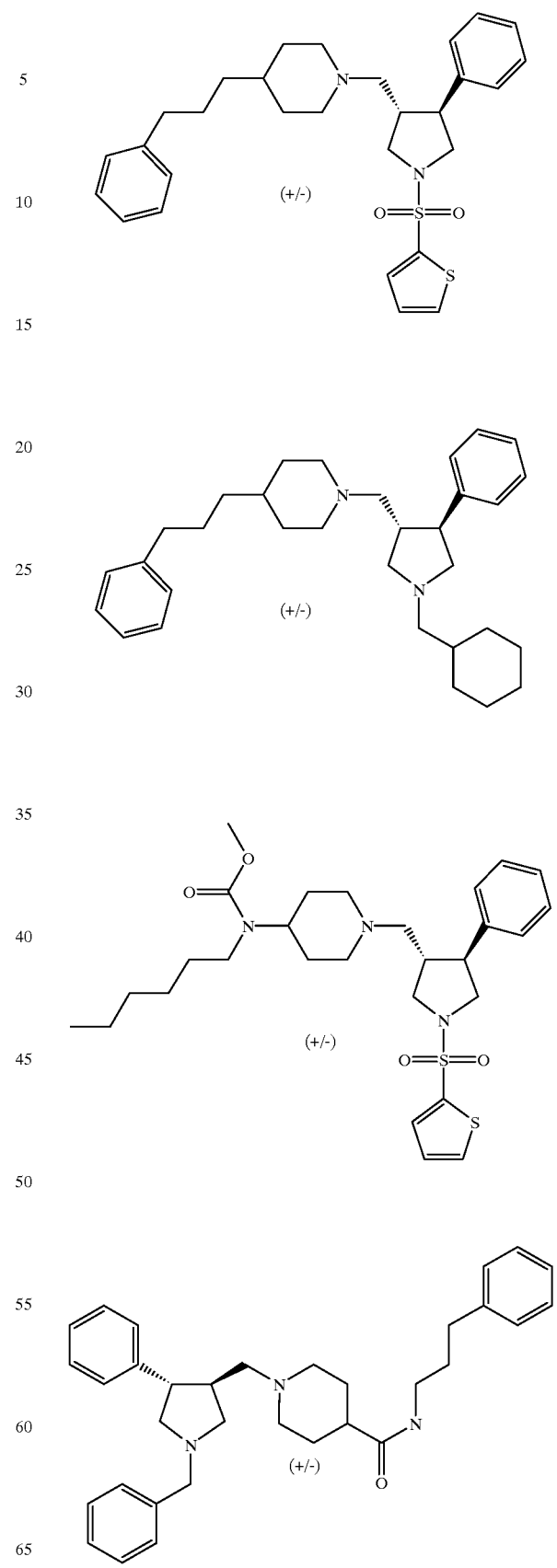

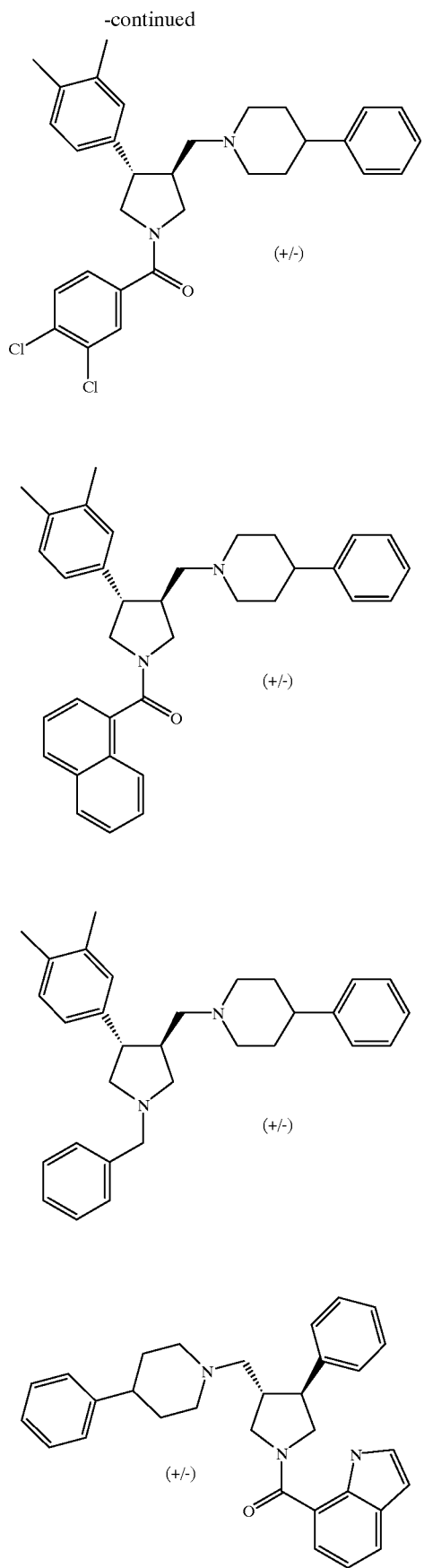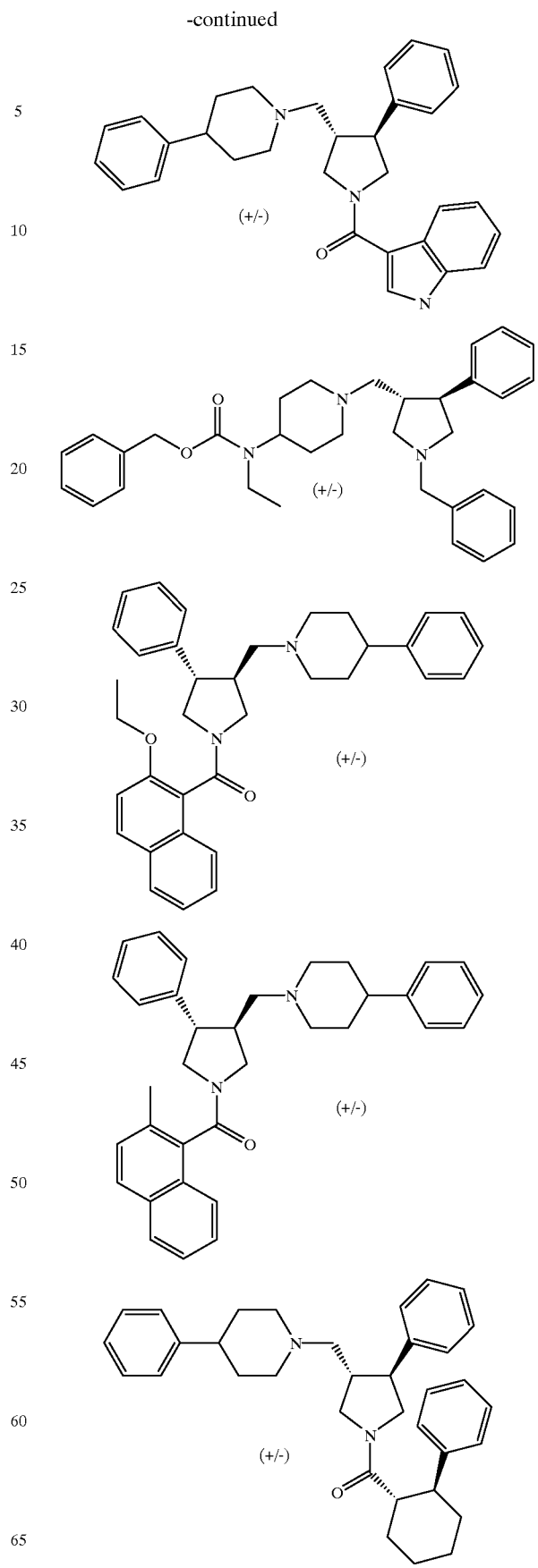

195
-continued
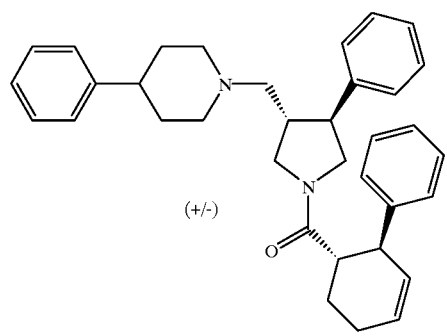
(+/-)
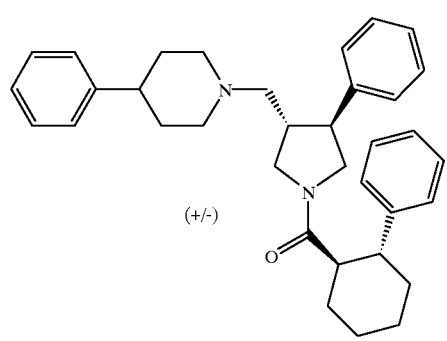
(+/-)
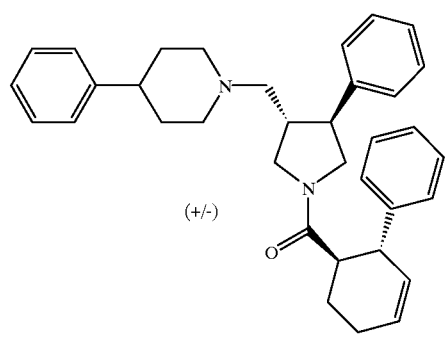
(+/-)
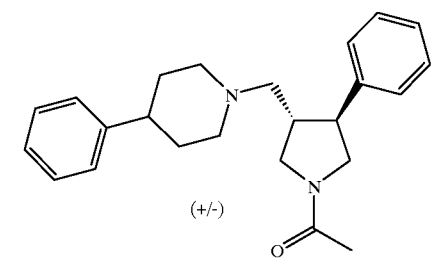
(+/-)
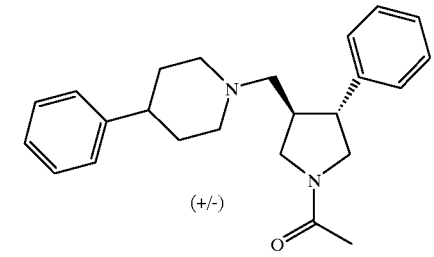
(+/-)
196
-continued
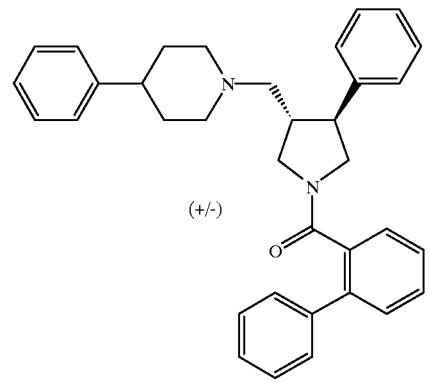
(+/-)
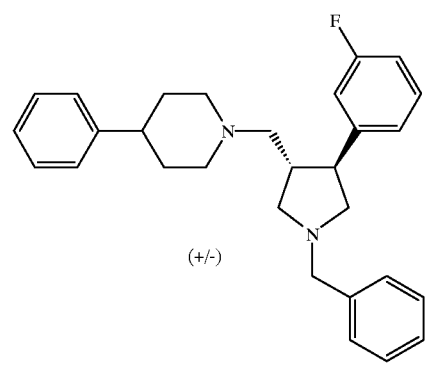
(+/-)
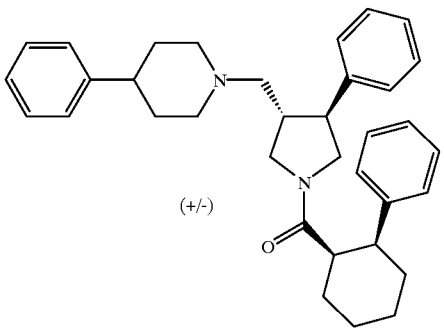
(+/-)
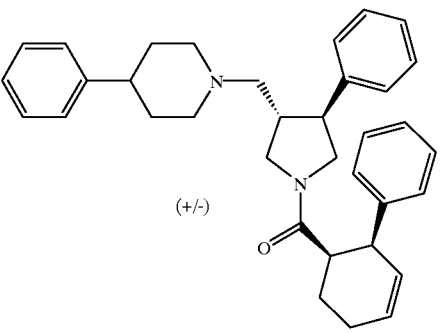
(+/-)

197
-continued
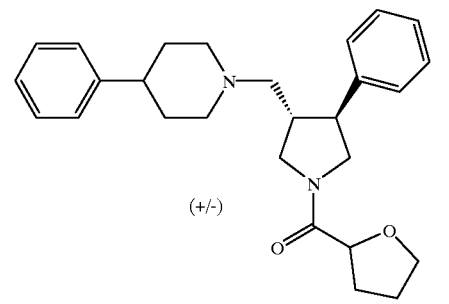
(+/-)
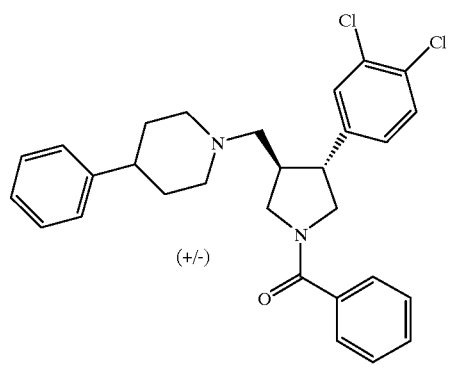
(+/-)
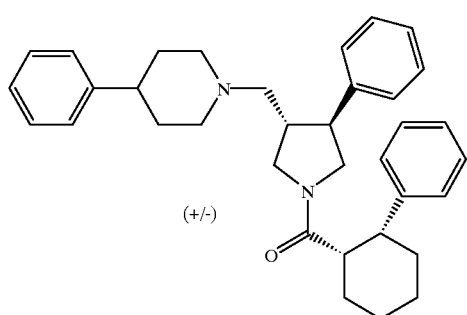
(+/-)
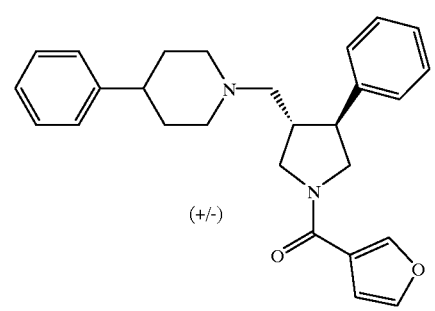
(+/-)
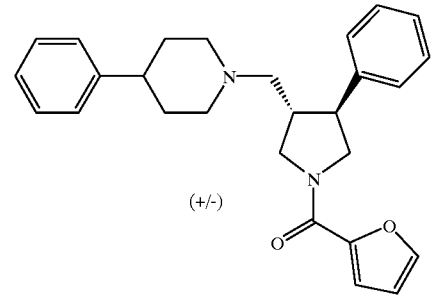
(+/-)
198
-continued
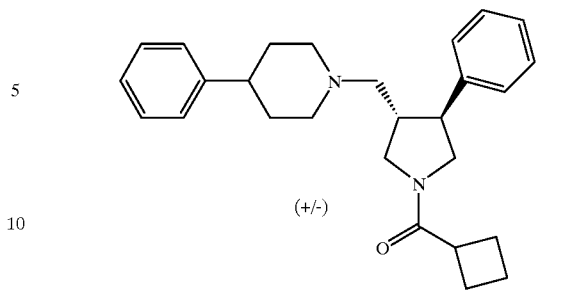
(+/-)
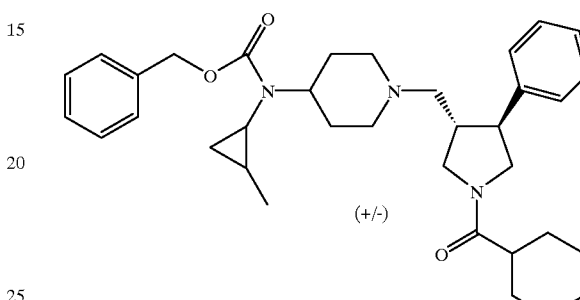
(+/-)
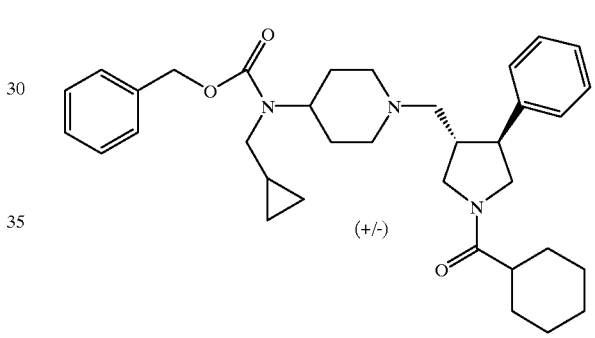
(+/-)
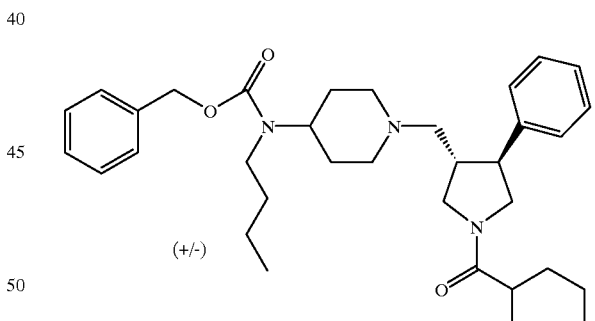
(+/-)
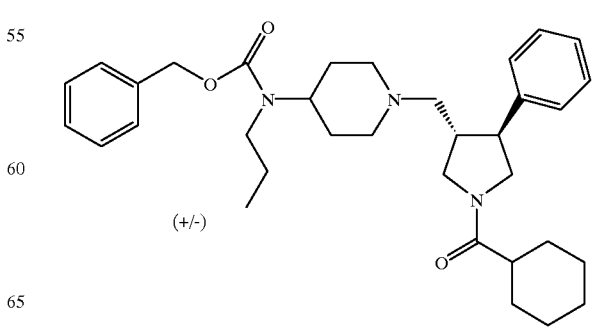
(+/-)

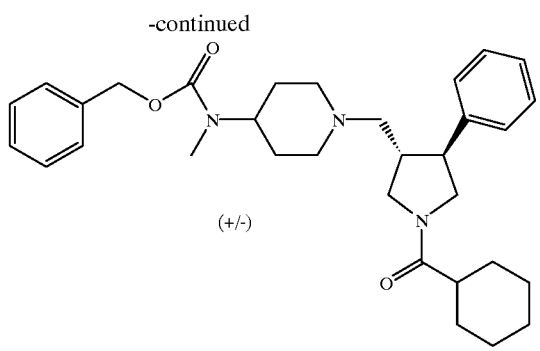
(+/-)
and pharmaceutically acceptable salts thereof and individual diastereomers thereof.
19. A compound which is selected from the group consisting of:
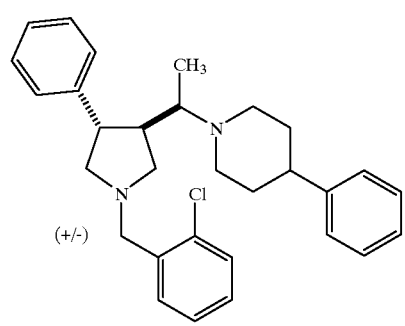
(+/-)
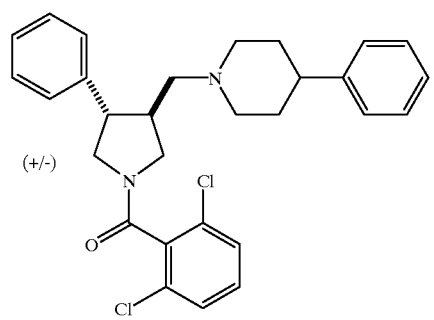
(+/-)
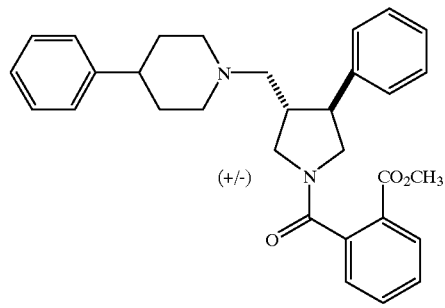
(+/-)
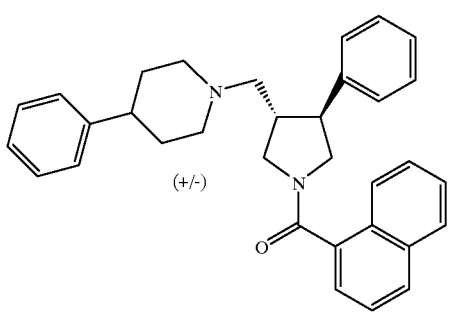
(+/-)
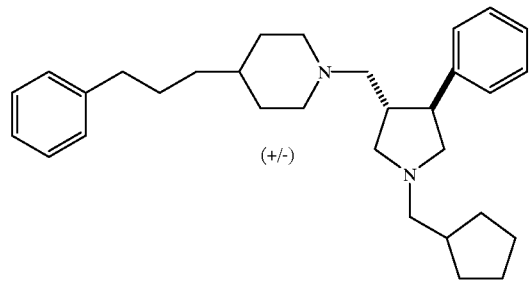
(+/-)
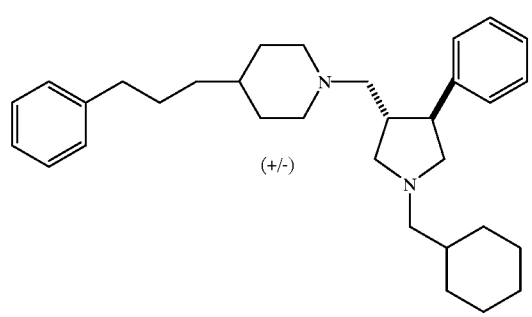
(+/-)
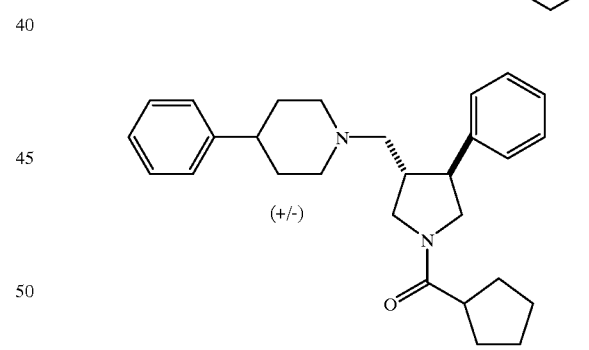
(+/-)
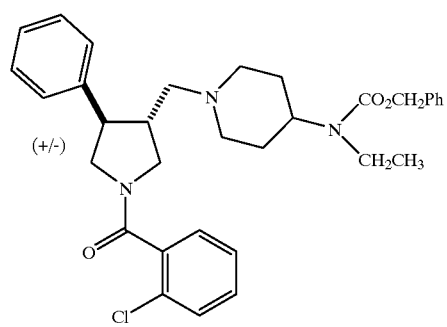
(+/-)

201
-continued

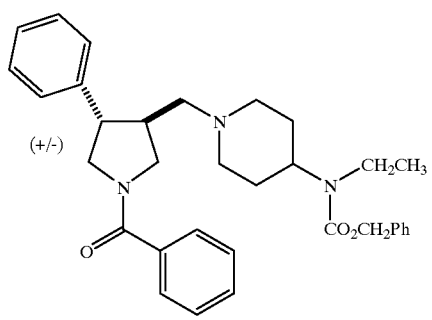

202
-continued

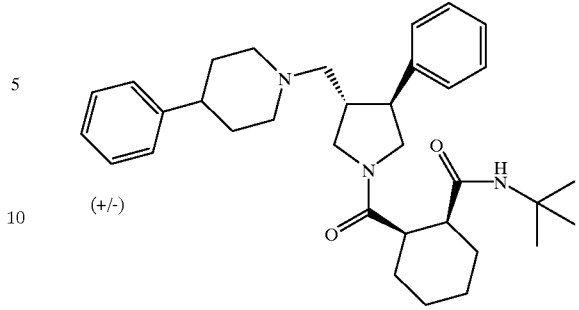

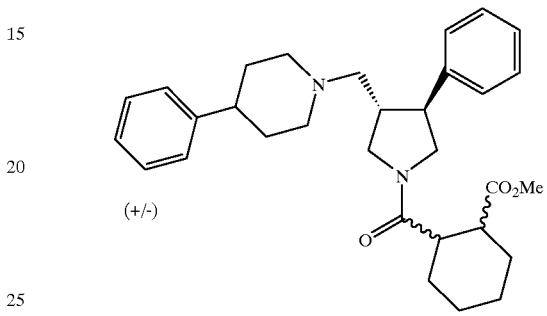

and pharmaceutically acceptable salts thereof and individual diastereomers thereof.

20. A pharmaceutical composition which comprises an inert carrier and a therapeutically effective amount of compound of claim 1.

21. A method for blocking the entry of HIV into target cells of a patient comprising administering to the patient in need thereof the compound of claim 1 in an amount effective to block HIV from binding to surface receptors of the target cells.

22. The method of claim 21 wherein blocking the entry of HIV into target cells prevents infection of the patient by HIV.

23. The method of claim 21 wherein blocking the entry of HIV into target cells prevents infectious spread of HIV in the patient.

24. The method of claim 21 wherein blocking the entry of HIV into target cells delays the onset of AIDS in the patient.

25. The method of claim 21 wherein blocking the entry of HIV into target cells treats the pathological conditions of AIDS in the patient.

* * * * *